US007223833B1

(12) United States Patent
Nielsen et al.

(10) Patent No.: US 7,223,833 B1
(45) Date of Patent: May 29, 2007

(54) PEPTIDE NUCLEIC ACID CONJUGATES

(75) Inventors: Peter Nielsen, Kokkedal (DK); Ole Buchardt, Vaerlose (DK); Soren Holst Sonnechsen, Tastrup (DK); Jesper Lohse, Copenhagen (DK); Michael Egholm, Lexington, MA (US); Muthiah Manoharan, Carlsbad, CA (US); John Kiely, San Diego, CA (US); Michael Griffith, San Diego, CA (US); Kelly Sprankle, Vista, CA (US)

(73) Assignees: Isis Pharmaceuticals, Inc., Carlsbad, CA (US); Peter E. Nielsen, Frederiksberg (DK)

( * ) Notice: Subject to any disclaimer, the term of this patent is extended or adjusted under 35 U.S.C. 154(b) by 0 days.

(21) Appl. No.: 08/319,411

(22) Filed: Oct. 6, 1994

Related U.S. Application Data

(63) Continuation-in-part of application No. 08/108,591, filed as application No. PCT/EP92/01219 on May 22, 1992, now Pat. No. 6,395,474, application No. 08/319,411, which is a continuation-in-part of application No. 08/275,951, filed on Jul. 15, 1994, now Pat. No. 6,451,968, and a continuation-in-part of application No. 08/088,658, filed on Jul. 2, 1993, now Pat. No. 5,641,625, and a continuation-in-part of application No. 08/088,661, filed on Jul. 2, 1993.

(30) Foreign Application Priority Data

| May 24, 1991 | (DK) | ........................... 986/91 |
| May 24, 1991 | (DK) | ........................... 987/91 |
| Apr. 15, 1992 | (DK) | ........................... 510/92 |

(51) Int. Cl.
C12Q 1/68 (2006.01)
C07K 5/00 (2006.01)

(52) U.S. Cl. .............. 530/300; 530/323; 530/350; 536/23.1; 536/24.1; 536/24.3; 536/24.31; 536/24.32; 536/24.33; 536/25.3; 935/77; 935/78

(58) Field of Classification Search .............. 435/6, 435/7.2, 890; 436/501; 530/300, 350, 323; 536/22.1, 23.1, 24.31–24.33, 25.3; 514/2, 514/44; 935/77, 78
See application file for complete search history.

(56) References Cited

U.S. PATENT DOCUMENTS

| 4,711,955 | A | * | 12/1987 | Ward et al. ................... 536/29 |
| 4,879,220 | A | * | 11/1989 | Mrsny et al. ............... 435/7.21 |
| 4,917,800 | A | * | 4/1990 | Lonsdale et al. ............ 210/940 |
| 5,134,066 | A |   | 7/1992 | Rogers et al. ................. 435/91 |
| 5,142,047 | A |   | 8/1992 | Summerton et al. ........ 544/118 |
| 5,166,315 | A | * | 11/1992 | Summerton et al. ........ 528/406 |
| 5,234,579 | A | * | 8/1993 | Pasternak ..................... 208/308 |
| 5,324,483 | A |   | 6/1994 | Cody et al. .................. 422/131 |
| 5,539,082 | A | * | 7/1996 | Nielsen et al. .............. 530/300 |
| 5,623,049 | A | * | 4/1997 | Lobberding et al. ........ 530/300 |
| 5,705,333 | A | * | 1/1998 | Shah et al. ...................... 435/6 |
| 5,719,262 | A | * | 2/1998 | Buchardt et al. ............ 530/300 |
| 5,773,571 | A | * | 6/1998 | Nielsen et al. .............. 530/300 |
| 5,786,461 | A | * | 7/1998 | Buchardt et al. ............ 536/18.7 |
| 5,834,607 | A | * | 11/1998 | Manoharan et al. ......... 536/22.1 |
| 6,395,474 | B1 | * | 5/2002 | Buchardt et al. .............. 435/6 |

FOREIGN PATENT DOCUMENTS

| WO | WO 86/05518 | * | 9/1986 |
| WO | WO 86/05519 |   | 9/1986 |
| WO | WO 90/02749 |   | 3/1990 |
| WO | WO 92/20702 |   | 11/1992 |
| WO | WO 92/20703 |   | 11/1992 |
| WO | WO 93/05180 |   | 3/1993 |
| WO | WO 93/07883 |   | 4/1993 |
| WO | WO 93/12129 |   | 6/1993 |
| WO | WO A93/12129 |   | 6/1993 |
| WO | WO 93/18052 |   | 9/1993 |
| WO | WO 94/06815 |   | 3/1994 |
| WO | WO 95/16202 |   | 6/1995 |
| WO | WO 95/32305 |   | 11/1995 |

OTHER PUBLICATIONS

Suvityer et al., Biochemistry, vol. 32, No. 39, pp. 10489-10496, 1993.*
Saito et al., Journal of the American Chemical Society, vol. 105, No. 23, pp. 6989-6991, 1983.*
Finle et al., Analytical Biochemistry, vol. 108, pp. 394-401, 1980.*
Soon et al., Biochemistry, vol. 26, pp. 7113-7121, 1987.*
Mechanic et al., Biochimica et Biophysica Acta, vol. 393, pp. 419-425 (1975).*
Fujii et al., FEBS Letters, vol. 97, No. 1, pp. 193-195 (1979).*
Lehninger [Published by Worth Publishers, Inc., 70 Fifth Avenue, New York, NY 10011 (1970)], pp. 204 and 272.*
Affinity Chromatography—A practical Approach, P.D.g. Dean, W.S. Johnson and F.A. Middle, eds., IRL Press Ltd., Oxford 1986.
Agrawal, S. and Tang, "Site-Specific Funcitonalization of Oligodeoxynucleotides for Non-Radioactive Labelling", *Tetrahedron Letters* 1990, 31 (11), 1543-1546.
Akashi, et al., "New Aspects of Polymer Drugs", *Adv. Polym. Sci.* 1990, 97, 108-146.
Aldrich Technical Bulletin Number AL-180, "Diazald®, MNNG and Diazomethane Generators", 1990.

(Continued)

Primary Examiner—Michael Borin
(74) Attorney, Agent, or Firm—Woodcock Washburn LLP

(57) ABSTRACT

A novel class of peptide nucleic acids are described which include a conjugate attached thereto. The peptide nucleic acids generally comprise ligands such as naturally occurring DNA bases attached to a peptide backbone through a suitable linker.

3 Claims, 6 Drawing Sheets

OTHER PUBLICATIONS

Anderson et al., "t-Butyloxycarbonylamino Acids and Their Use in Peptide Synthesis", *J. Am. Chem. Soc.* 1957, 79, 6180-6183.

Atherton et al., "The Fluorenylmethoxycarbonyl Amino Protecting Group", The Peptides 9, 1987 1-38.

Atherton et al., "A Physically Supported Gel Polymer for Low Pressure, Continuous Flow Solid Phase Reactions. Application to Solid Phase Peptide Synthesis", *J. Chem. Soc. Chem. Commun* 1981, 1151-1152.

Atherton et al., "Polyamide Supports for Polypeptide Synthesis", *J. Am. Chem. Soc* 1975, 50, 6584-6585.

Atherton et al., "Peptide Synthesis. Part 2. Procedures for solid-phase Synthesis Using Nα—Fluorenylmethoxycarbonylamino-acids on Polyamide Supports. Synthesis of Substance P and of Acyl Carrier Protein 65-74 Decapeptide", *J. C. S. Perkin* 1981, I, 538-546.

Atherton, E. et al., "The Polyamide Method of Solid Phase Peptide and Oligonucleotide Synthesis" *Bioorg. Chem.* 1979, 8, 351-370.

Baker, B., "Decapitation of a 5-capped oligoribonucleotide by o-phenanthroline:Cu (II) ", *J. Am. Chem. Soc.* 1993, 115, 3378-3379.

Barany et al., "Solid-phase Peptide Synthesis: a Silver Anniversary Report", *Int. J. Peptide Protein Res.* 1987, 30, 705-739.

Barany and Merrified in "The Peptides" vol. 2, Academic Press, N.Y., 1979, pp. 1-284.

Barany et al., "A New Amino Protecting Group Removable by Reduction. Chemistry of the Dithiasuccinoyl (Dts) Function", *J. Am. Chem. Soc.* 1977, 99, 7363-7365.

Barton et al., "Solid-Phase Synthesis of Selectively Protected Peptides for Use as Building Units in the Solid-Phase Synthesis of Large Molecules", *J. Am. Chem. Soc.* 1973, 95, 4501-4506.

Bayer and Jung, "A New Support for Polypeptide Synthesis in Columns", *Tetrahedron Lett* 1970, 51, 4503-4505.

Beaucage and Caruthers, "Deoxynucleoside Phosphoramidites-A New Class of Key Intermediates for Deoxypolynucleotide Synthesis" *Tetrahedron Lett.* , 1981, 22, 1859-1862.

Bearn, Milošet al., "Substituted ω—(4-Oxo-3, 4-Dihydro-5-Pyrimidinyl) Alkanoic Acids, Their Derivatives and Analogues" *Collect. Czech. Chem. Commun.* 1983, 48, 292-298.

Berg et al., "Long-Chain Polystyrene-Grafter Polyethylene Film Matrix: A New Support for Solid-Phase Peptide Synthesis", *J. Am. Chem. Soc* 1989, 111, 8024-8026.

Blackwell, T. K. et al., "Sequence-Specific DNA Binding by the c-Myc protein," *Science* 1990, 250, 1149-1151.

Bodánzsky, "Synthesis of Peptides by Aminolysis of Nitrophenyl Esters", *Nature* 1955, 175, 685.

Bodanszky et al., "Active Esters and Resins in Peptide Synthesis", *Chem. Ind.* 1964, 1423-1424.

Bodanzsky, "Principles of Peptide Synthesis", Springer Verlag, Berlin-New York 1984.

Brady et al., "Large-Scale Synthesis of a Cyclic Hexapeptide Analogue of Somatostatin," *J. Org. Chem.* 1987, 52, 764-769.

Brady et al., "Some Novel, Acid-Labile Amine Protecting Groups", *J. Org. Chem.* 1977, 42, 143-146.

Buttrey et al., "Synthetic Analogues of Polynucleotides-XIII: The Resolution of DL-β—(Thymin-1-YL)Alanine and Polymerisation of the β—(Thymin-1-YL)Alanines", *Tetrahedron* 1975, 31, 73-75.

Carpino, "New Amino-Protecting Groups in Organic Synthesis", *Acc. Chem. Res.* 1973, 6, 191-198.

Carpino "The 9-Fluorenylmethoxycarbonyl Amino-Protecting Group" *J. Org. Chem.* , 1972, 37, 3404-3409.

Carpino, "Oxidative Reactions of Hydrazines. IV. Elimination of Nitrogen from 1, 1-Disubstituted-2-arenesulfonhydrazides[1-4]", *J. Am. Chem. Soc.* 1957, 79, 4427-4431.

Carpino and Han, "The 9-Fluorenylmethoxycarbonyl Function, a New Base-Sensitive Amino-Protecting Group", *J. Am. Chem. Soc.* 1970, 92, 5748-5749.

Carpino et al., "((9-Fluorenylmethyl) oxy) carbonyl (FMOC) Amino Acid Fluorides. Convenient New Peptide Coupling Reagents Applicable to the FMOC/tert-Butyl Strategy for Solution and Solid-Phase Syntheses", *J. Am. Chem. Soc.* 1990, 112. 9651-9652.

Caruthers, Marvin H., "Gene Synthesis Machines: DNA Chemistry and Its Uses" *Science*, 1985, 232, 281-285.

Chiang et al., "Antisense Oligonucleotides Inhibit Intercellular Adhesion Molecule 1 Expression by Two Distinct Mechanisms", *J.Biol.Chem.* , 1991, 266:18162-18171.

Corey et al., "Generation of a Hybrid Sequence-Specific Single-Stranded Deoxyribonuclease", *Science*, 1987, 238:1401-1403.

Cullen, B., "The HIV-1 Tat Protein: An RNA Sequence-Specific Processivity Factor?" *Cell* 1990, 63, 655-657.

Daniels et al., "Membranes as Solid Supports for Peptide Synthesis", *Tetrahedron Lett.* 1989, 30, 4345-4348.

Delgado et al., "The Uses and Properties of PEG-Linked Proteins", *Critical Reviews in Therapeutic Drug Carrier Systems.* 1992, 9, 249-304.

Demidov, V. et al., "Sequence Selective Double Strand DNA Cleavage by Peptide Nucleic Acid (PNA) Targeting Using Nuclease S1" *Nucl. Acids Res.* 1993 21(19), 2103-2107.

Depto et al., "Regulated Expression of the Human Cytomegalovirus pp65 Gene: Octamer Sequence in the Promoter Is Required for Activation by Viral Gene Products," *J. Virol.* 1989, 63, 1232-1238.

Dizio et al., "Progestin-Rhenium Complexes: Metal-Labled Steroids with High Receptor Binding Affinity, Potential Receptor-Directed Agents for Diagnostic Imaging or Therapy", *Bioconjugate Chem.* , 1991, 2, 353-366.

Doel et al., "An Approach to the Synthesis of Peptide Analogues of Oligonucleotides (Nucleopeptides) ", *Tetrahedron Letters* 1969, 27, 2285-2288.

Doel et al., "The Synthesis of Peptides Containing Purine and Pyrimidine Derivatives of DL-Alanine", *Tetrahedron* 1974, 30, 2755-2759.

Dreyer and Dervan, "Sequence-specific cleavage of single-stranded DNA: Oligodeoxynucleotide-EDTA-Fe (II) ", *Proc.Natl.Acad.Sci. USA* 82, 1985, 968-972.

Dubochet et al., "A New Preparation Method for Dark-Field Electron Microscopy of Biomacromolecules," *J. Ultrastruct. Res.* 1971, 35, 147-167.

Eckstein, ed., *Oligonucleotides and Analogues, A Practical Approach*, IRL Press, 1991..

Egholm, M. "Peptide nucleic acids (PNA). Oligonucleotide analogues with an achiral peptide backbone", *J. Am. Chem. Soc.* 1992, 114, 1895-1897.

Egholm, M. et al., "Peptide Nucleic Acids Containing Adenine and Guanine Recognize Thymine and Sytosine in Complementary DNA Sequences" *J. Chem. Soc. Chem. Commun.* 1993 800-801.

Egholm et al., "PNA Hybridizes to Complementary Oligonucleotides Obeying the Watson-Crick Hydrogen-Bonding Rules", *Nature* 365 1993 566-568.

Egholm, et al., "Recognition of Guanine and Adenine in DNA by Cytosine and Thymine Containing Peptide Nucleic Acids (PNA)[1,2]", *J. Am. Chem. Soc.* , 1992, 114, 9677-9678.

Egholm et al., "Peptide Nucleic Acids (PNA) : A Novel Approach to Sequence-Selective Recognition of Double-Stranded DNA" *Innovation and Perspectives in Solid Phase Synthesisi Collected Papers (Epton, Ed. by Intercept ltd, Andover, England)* 1992, 325-328.

Eichler et al., "Application of Cellulose Paper as Support Material in Simultaneous Solid Phase Peptide Synthesis", *Collect. Czech. Chem. Commun.* 1989, 54, 1746-1752.

Fissekis, John D. and Sweet, Frederick, "Synthesis of 5-Carboxymethyluridine. A Nucleoside from Transfer Ribonucleic Acid" *Biochemistry* 1970, 9, 3136-3142.

Fodor, Stephen P.A. et al., "Light-Directed, Spatially Addressable Parallel Chemical Synthesis" *Science*, 1991, 251, 767-773.

Franza, Jr., B. R. et al., "Characterization of cellular proteins recognizing the HIV enhancer using a microscale DNA-affinity precipitation assay," *Nature* 1987, 330, 391-395.

Fridkin et al., "A Synthesis of Cyclic Peptides Utilizing High Molecular Weight Carriers", *J. Am. Chem. Soc* 1965, 87, 4646-4648.

Froehler, et al., "Oligodeoxynucleotides Containing C-5 Propyne Analogs of 2'—Deoxyuridine and 2'—Deoxycytidine," *Tetrahedron Letters* 1992, 33, 5307-5310.

Gait, ed., *Oligonucleotide Synthesis, A Practical Approach*, IRL Press, 1984.

Gao, et al., "6—O—(Pentafluorophenyl)—2'—Deoxyguanosine: A Versatile Synthon for Nucleoside and Oligonucleotide Synthesis", *The Journal of Organic Chemistry* 1992, 57:6954-6959.

Gewirtz, "Therapeutic Application of Antisense DNA in the Treatment of Human Leukemia", published in Antisense Strategies vol. 660 178-187 (Oct. 28, 1992). Annals of the New York Academy of Sciences (Baserga & Dehnardt Eds.).

Geysen et al., "Use of Peptide Synthesis to Probe Viral Antigens for Epitopes to a Resolution of a Single Amino Acid", *Proc. Natl. Acad. Sci. USA* 1984, 81: 3998-4002.

Gilham, P. T., "The Covalent Binding of Nucleotides, Polynucleotides, and Nucleic Acids to Cellulose" in *Methods in Enzymology*, Chapter 10, L. Grossmann and K. Moldave, eds. 1971, 21, part D, 191-197, Academic Press, N.Y. and London.

Gilmore, T. D. and Temin, H. M., "Different Localization of the Product of the v-rel Oncogene in Chicken Fibroblasts and Spleen Cells Correlates with Transformation by REV-T", *Cell* 1986 44 791-800.

Goodman and Levine, "Peptide Synthesis *via* Active Esters. IV. Racemization and Ring-Opening Reactions of Optically Active Oxazolones", *J. Am. Chem. Soc.* 1964, 86, 2918-2922.

Gorman, Jeffrey, "An Apparatus for Simultaneous Manual Solid-Phase Synthesis of Multiple Peptide Analogs", *Anal. Biochem* 1984 136 397-406.

Greene and Wuts, *Protective Groups in Organic Synthesis*, 2d ed. John Wiley & Sons, New York, 1991.

Greenfield et al., Thiol-Containing Cross-Linking, *Bioconjugate Chem.*, 1990, 1, 400-410.

Hahn et al., "Design and Synthesis of a Peptide Having Chymotrypsin-Like Esterase Activity", *Science* 1990, 248, 1544-1547.

Hahn et al., "Molecular cloning and characterization of the HTLV-III virus associated with AIDS," *Nature* 1984, 312, 166-169.

Haas, W.L. et al., "Adamantyloxycarbonyl, a New Blocking Group. Preparation of 1-Adamantyl Chloroformate" *J. Am. Chem. Soc.*, 1966, 88, 1988-1992.

Hanvey et al., "Antisense and Antigene Properties of Peptide Nucleic Acids", *Science* 1992, 258, 1481-1485.

Haralambidis et al., "Preparation of base-modified nucleosides suitable for non-radioactive label attachment and their incorporation into synthetic ologodeoxyribonucleotides", *Nucleic Acids Research*, 15, 1987, 4857-4876.

Harris et al., "New Strategy for the Synthesis", *J. Am. Chem. Soc.*, 1991, 113, 4328-4329.

Heimer, J.P. et al., "Synthesis of Analogs and Oligomers on N—(2-aminoethyl) glycine and Their Gastrointestinal Absorption in the Rat" *Int. J. Pept. Protein Res.*, 1984, 23, 203-211.

Holm and Meldal, "Multiple Column Peptide Synthesis", *"Proceedings of the 20th European Peptide Symposium"*, G. Jung and E. Bayer, eds., Walter de Gruyter & Co., Berlin: 1989, 208-210.

Houghten, "General Method for the Rapid Solid-Phase Synthesis of Large Numbers of Peptides: Specificity of Antigen-Antibody Interaction at the Level of Individual Amino Acids", *Proc. Natl. Acad. Sci. USA* 1985, 82, 5131-5135.

Huang et al., "Acyclic Nucleic Acid Analogues: Synthesis and Oligomerization of γ, 4-Diamino-2-oxo-1 (2H)—pyrimidinepentanoic Acid and σ 4-Diamino-2-oxo-1 (2H)—pyrimidinehexanoic Acid", *J. Org. Chem.* 1991, 56, 6007-6018.

Hyrup et al., "Modification of the Binding Affinity of Peptide Nucleic Acids (PNA). PNA with Extended Backbones Consisting of 2-Aminoethyl-β-Alanine or 3-Aminopropylglycine Units" *J. Chem. Soc. Chem. Commun.* 1993, 518-519.

Inaki et al., "Functionality and Applicability of Synthetic Nucleic Acid Analogs", in *Current Topics in Polymer Science* 1987, Ottenbrite, Utracki, Inoue, Eds., New York : Macmillan Pub. Co., 1, 80-100.

Inaki, Y., "Synthetic Nucleic Acid Analogs", *Prog. Polym. Sci.* 1992, 17, 515-570.

Jenkins, Y. and Barton, "A Sequence-Specific Molecular Light Switch: Tethering of an Oligonucleotide to a Dipyridophonic Complex of Ruthenium (II)", *J. Am. Chem. Soc.* 1992, 114, 8736-8738.

Jeppesen, C. et al., "A Specific and Efficient Photoreaction Between E. coli RNA Polymerase and $T_{+1}$ in the *lac*UV5 or *deo*P1 Promoter", *Nucleic Acids Research* 1988, 16(2), 9545-9555.

Jones, Jr., "Hydrogenation of Protected Leucine Enkephalin from a Resin During Solid Phase Synthesis", *Tetrahedron Lett.* 1977, 33, 2853-2856.

Kent and Merrifield, "Preparation and Properties of tert-Butyloxycarbonylaminoacyl-4-(oxymethyl) phenylacetamidomethyl —(Kel F-g-styrene) Resin, an Insoluble, Noncrosslinked Support for Solid Phase Peptide Synthesis", *Israel J. Chem* 1978, 17, 243-247.

König et al., "Autoregulation of fos: the Dyad Symmetry Element as the Major Target of Repression," *EMBO Journal* 1989, 8, 2559-2566.

König and Geiger, "Racemisierung bei Peptidsynthesen", *Chem. Ber.* 1973, 103, 2024-2033.

Köand Geiger, "Eine Neue Methode Zur Synthese Von Peptiden: Aktivierung Der Carboxylgruppe Mit Dicyclohexylcarbodiimid Und 3-Hydroxy-4-oxo-3.4-dihydro-1.2.3-benzotriazin", *Chem. Ber.* 1973, 103, 2034-2040.

de Koning et al., "Unconventional Nucleotide Analogues V. Derivatives of 6—(1-pyrinidinyl)—and 6—(9-purinyl)—2-aminocaproic acid,", *Recueil* 1971, 90, 874-884.

Kovacs, J. et al., "Glutamic and Aspartic Anhydrides. Rearrangement of N-Carboxyglutamic 1, 5-Anhydride to the Leuchs'Anhydride and Conversion of the Latter to Pyroglutamic Acid" J. Am. Chem. Soc. 1963 85: 1839-1844.

Krchňák et al., "Continuous-Flow Solid-Phase Peptide Synthesis", *Tetrahedron Lett* 1987, 28, 4469-4472.

Krchňák et al., "Multiple Continuous-Flow Solid Phase peptide Synthesis", *Int. J. Peptide protein Res.* 1989, 33, 209-213.

Kypryszewski, "O Estrach Chlorofenylowych Aminokwasow. II. Synteza Peptydow Poprzes Aminolize Aktywnych Estrow 2, 4, 6-Trojchlorofenylowych N-Chronionych Aminokwasow", *Rocz. Chem.* 1961, 35, 595-600.

Lal et al., "Diphenylphosphoryl Azide A Novel Reagent for the Stereospecific Synthesis of Azides from Alcohols, " *Tetrahedron Letters* 1977, 23, 1977-1980.

Lebl, Michal and Eichler, Jutta, "Simulation of Continuous Solid Phase Synthesis: Synthesis of Methionine Enkephalin and its Analogs" *Peptide Research*, 1989, 2, 297-300.

Letsinger, et al., "Synthesis of Thymidine Oligonucleotides by Phosphite Triester Intermediates" *J. Am. Chem. Soc.* 1976, 98, 3655-3661.

Li et al., "The Synthesis of a Protein Possessing Growth-Promoting and Lactogenic Activities", *J. Am. Chem. Soc.* 1970, 92, 7608-7609.

Lu et al., "Synthesis of Polyesters Containing Nucleic Acid Base Derivatives as Pending Side Chains," *J. Polym. Sci.* 1986, *Part A: Polymer Chemistry* 24: 525-536.

Mack, D. P. et al., "Design and Chemical Synthesis of a Sequence-Specific DNA-Cleaving Protein" *J. of Am. Chem. Society* 1988 110 7572-7574.

Mahoharan, *Antisense Research and Applications*, Crooke and Lebleu, eds., CRC Press, Boca Raton, 1993.

McCurdy, et al., "Deoxyoligonucleotides with Inverted Polarity: Synthesis and Use in Triple-Helix Formation," *Nucleosides and Nucleotides* 1991, 10, 287-290.

McKay and Albertson, "New Amine-Masking Groups for Peptide Synthesis", *J. Am. Chem. Soc.* 1957, 79, 4686-4690.

Meier et al., "peptide Nucleic Acids (PNAs)—Unusual Properties of Nonionic Oligonucleotide Analogues", *Angew. Chem. Int. Ed. Engl.* 1992, 31, 1008-1010.

Merrifield, "Solid Phase Peptide Synthesis. I. The Synthesis of a Tetrapeptide", *J. Am. Chem. Soc.* 1963, 85, 2149-2154.

Merrifield, "Solid Phase Synthesis", *Science* 1986, 232, 341-347.

Meyer, et al., "Efficient, Specific Cross-Linking and Cleavage of DNA by Stable, Synthetic Complementary Oligodeoxynucleotides", J. Am. Chem. Soc. 111, 1989 8517-8519.

Mitchell annd Merrifield, "Occurrence of N-Alkylation During the Acidolytic Cleavage of Urethane Protecting Groups[1a,b]", *J. Org. Chem.* 1976, 41, 2015-2019.

Mitchell et al., "Preparation of Aminomethyl-Polystyrene Resin by Direct Amidomethylation", *Tetraherdon Lett.* 1976, 42, 3795-3798.

Mizutaniy Takaharu and Tachibana, Yoshio, "Oligo (dT)—glyceryl Porous Glass, a Better Support for the Preparation of mRNA" *J. Chromatogr*, 1986, 356, 202-205.

Mutter and Bayer, "Rapid Procedure for Liquid-Phase Peptide Synthesis: The Crystallization Method", *Angew. Chem., Int. Ed. Engl.* 1974, 13, 88-89.

Nagae et al., "Functional Monomers and Polymers. CLIV. Application of Nucleic Acid base Containing Polymers to High Performance Liquid Chromatography," *J. Polym. Sci.: Part A: Polymer Chemistry* 1989, 27, 2593-2609.

Nefkens and Tesser, "A Novel Activated Ester in Peptide Synthesis " *J. Am. Chem. Soc.* 1961, 83, 1263.

Nielsen, P. E. et al., "Photochemical Cleavage or DNA by Nitrobenzamides" *Biochem.* 1988, 27, 6338-6343.

Nielsen, et al., "Sequence-Selective Recognition of DNA by Strand Displacement with a Thymine-Substiauted Polyamide," *Science*, 254 1991 1497-1500.

Nisen, P. D. et al., "Enhanced Expression of the N-myc Gene in Wilms'Tumors," *Cancer Research* 1986, 46, 6217-6222.

Nollet et al., "Unconventional Nucleotide Analogues-III, 4—)$N_1$ - Pyrimidyl)—2-Aminobutyric Acids", *Tetrahedron* 1968, 25, 5989-5994.

Nollet et al., "Unconventional Ncleotide Analogues-I, $N_9$-Purinyl α-Amino Acids", *Tetrahedron* 1969, 25, 5971-5981.

Nollet et al., "Unconventional Nucleotide Analogues-II, Synthesis of the Adenyl Analogue of Willardiine", *Tetrahedron* 1969, 25, 5983-5987.

Nollet et al., "Michael Addition of 4—O-Ethyluracil. A Method for Specific $N_1$-Alkylation of hydroxpyrimidines", *Tetrahedron Letters* 1969, 53, 4605-4606.

*Nucleic Acid Hybridization—A Practical Approach*, B. D. Harnes and S. J. Higgins, IRL Press Ltd., Oxford 1987.

Odian, "Principles of Polymerization", McGraw-Hill, N. Y. 1970.

Omura, K. and Swern, "Oxidation of Alcohols by "Activated" Dimethyl Sulfoxide. A Preparative, Steric and Mechanistic Study", *Tetrahedron* 1978, 34, 1651-1660.

Ono, A. et al., "Triplex Formation of Oligonucleotides Containing 2' —O-Methylpseudoisocytidine in Substitution for 2' —Deoycytidine" *J. Am. Chem. Soc.* 1991, 113, 4032-4033.

Ono, Akira et al., "Triplex Formation of an Oligonucleotide Containing 2' —)-Methylpseudoisocytidine with a DNA Duplex at Neutral pH" *J. Org. Chem.* 1992, 57, 3225-3230.

Ouchi, T. et al., "Synthesis and antitumor activity of poly (ethylene glycol)s linked to 5-fluorouracil via a urethane or urea bond", *Drug Design and discovery* 1992, 9, 93-105.

Parr and Grohmann, "Solid-Phase Peptide Synthesis on an Inorganic Matrix having Organic Groups on the Surface", *Angew. Chem. Internal. Ed.* 1972, 11, 314-315.

Petty et al., "Cytochrome Oxidase Models. 2. μ-Bipyrimidyl Mixed-Metal Complexes as Synthetic Models for the Fe/Cu Binuclear Active Site of Cytochrome Oxidase", *J. Am. Chem. Soc.* 1980, 102, 611-620.

Pietta and Marshall, "Amide Protection and Amide Supports in Solid-Phase Peptide Synthesis" *Chemical Communications*, 1970, 650-651.

Pitha et al., "Inhibition of Murine Leukemia Virus Replication by Poly (vinyluracil) and Poly (vinyladenine)", *Proc. Natl Acad. Sci. USA* 1973, 70, 1204-1208.

Pitha, J., "Physiological Activities of Synthetic Analogs of Polynucleotides", *Adv. Polym. Sci.* 1983, 50, 1-16.

Pless et al., Über die Geschwindigkeit der aminolyse von Verschiedenen Neuen, Aktivierten, N-geschützten α-Aminosäurephenylestern, insbesondere 2, 4, 5—Trichlorphenylestern) *Helv. Chim. Acta* 1963, 46, 1609-1625.

Pollack, S. J. et al., "Selective Chemical Catalysis by an Antibody" *Science*, 1986, 234, 1570-1573.

Ravasio, N. and Rossi, M., "Selective Hydrogenations Promoted by Copper Catalysts 1. Chemoselectivity, Regioselectivity, and Stereoselectivity in the Hydrogenation of 3-Substituted Steroids", *J. Org. Chem.* 1991, 56, 4329-4333.

Rich and Gurwara, "Preparation of a New o-Nitrobenzyl Resin for Solid-Phase Synthesis of tert-Butyloxycarbonyl-Protected Peptide Acids". *J. Am. Chem. Soc.* 1975, 97, 1575-1579.

Rivaille et al., "Synthesis of LH-RH Using a New Phenolic Polymer as Solid Support and "BOP" Reagent for Fragment Coupling", *Tetrahedron* 1980, 36, 3413-3419.

Ruth, J., "Oligodeoxynucleotides with Reporter Groups Attached to the Base", in *Oligonucleotides and Analogues: A Practical Approach* 1991, IRL Press, Oxford.

Sági, et al., "Base-Modified Oligodeoxynucleotides. I. Effect of 5-Alkyl, 5—)1-Alkenyl) and 5—(1-Alkynyl) Substitution of teh Pyrimidines on Duplex Stability and Hydrophobicity," *Tetrahedron Letters* 1993, 34, 2191-2194.

Sakakibara, et al., "A New Method for Releasing Oxytocin form Fully-Protected Nona-peptides Using Anhydrous Hydrogen Fluoride" *Bull. Chem. Soc. Jpn.* 1965, 38, 1412-1413.

Schlatter, James M. and Mazur, Robert H., "Hydrogenationin Solid Phase Peptide Synthesis. I. Removal of Product from the Resin" *Tet. Letts.* 1977 33: 2851-2852.

Scott et al., "The Use of Resin Coated Glass Beads in the Form of a Packed Bed for the Solid Phase Synthesis of Peptides", *J. Chromatogr. Sci* 1971, 9, 577-591.

Sheehan, "A New Method of Forming Peptide Bonds", *J. Am. Chem. Soc.* 1955, 77, 1067-1068.

Shemyakin et al., "Synthesis of Peptides in Solution on a Polymeric Support I. Synthesis of Clycylglycyl-L-Leucylglycine", *Tetrahedron Lett* 1965, 27, 2323-2327.

Shokat et al., "A New Strategy for the Generation of Catalytic Antibodies", *Nature* 1989, 338, 269-271.

Sieber and Iselin, "77. Selektive Acidolytische Spaltung von Aralkyloxycarbonyl-Aminoschutzgruppen", *Helv. Chem. Acta.* 1968, 51, 614-622.

Sigman, "Chemical Nucleases", *Biochem.* 1990, 29:9097-9105.

Simon et al., "Peptoids: A modular approach to drug discovery", *Proc. Natl. Acad. Sci. USA* 1992, 89, 9367-9371.

Sluka, J.P. et al., "Reagents and methods for the solid-phase synthesis of protein-EDTA for use in affinity cleaving", *J. Am. Chem. Soc.* 1990, 112, 6369-6374.

Smith-Jones, P. et al., "Antibody Labeling with Copper-67 Using the Bifunctional Macrocyle 4—[ (1, 4, 8, 11-Tetraazacyclotetradec-1-yl)methyl] benzoic Acid", *Bioconjugate Chemistry* 1991, 2, 415-421.

*Solid-Phase Biochemistry—Analytical and Synthetic Aspects*, W.H. Scouten, ed., John Wiley & Sons, N.Y., 1983.

Sproat, B.S. et al., "Highly Efficient Chemical Synthesis of 2' — O-methylioligoribunocleotides and Tetrabiotinylated Derivatives; Novel Probes That are Resistant to Degradation by RNA or DNA Specific Nucleases", *Nucleic Acids Research* 1989, 17 (9), 3373-3386.

Spalholtz et al., "Bovine Papillomavirus Transcriptional Regulation: Localization of the E2-Responsive Elements of the Long Control Region," *J. Virol.* 1987, 61, 2128-2137.

Stenberg et al., "Promoter-Specific trans Activation and Repression by Human Cytomegalovirus Immediate-Early Proteins Involves Common and Unique Protein Domains," *J. Virol.* 1990, 64, 1556-1565.

Stewart and Young, "Solid Phase Peptide Synthesis", 2nd Ed., Pierce Chemical Company, Ill., 1984.

Studer et al., "One Step Synthesis of Mono-*N*-substituted Azamacrocycles with a Carboxylic Group in the Side-Chain and their Complexes with $Cu^{2+}$ and $Ni^{2+}$", Helvetica Chimica Acta 69, 1986 2081-2086.

Takemoto et al., "Synthetic Nucleic Acid Analogs. Preparation and Interacttions", *Adv. Polym. Sci.* 1981, 1-51.

Tam, James P., "A Gradative Deprotection Strategy for the Solid-Phase Synthesis of Peptide Amides Using p—(Acyloxy) benzhydrylamine Resin and the $S_N2$Deprotection Method", *J. Org. Chem.* 1985 50 5291-5298.

Tam et al., "Multi-Detachable Resin Supports for Solid Phase Fragment Synthesis", *Tetrahedron Lett.* 1979, 52, 4935-4938.

Tam et al., "S$_N$2 Deprotection of Synthetic Peptides with a Low Concentration of HF in Dimethyl Sulfide: Evidence and Application in Peptide Synthesis", *J. Am. Chem. Soc.* 1983, 105, 6442-6455.

Tam et al., "Improved Synthesis of 4—(Boc-Minoacyloxymethyl)-phenylacetic Acids for Use in Solid Phase Peptide Synthesis", *Communications* 1979, 955-957.

Tam et al., "Mechanisms for the Removal of Benzyl Protecting Groups in Synthetic Peptides by Trifluoromethanesulfonic Acid-Trifluoroacetic Acid-Dimethyl Sulfide", *J. Am. Chem. Soc.* 1986, 108, 5242-5251.

Tam, "Design and Synthesis of Multidetachable Resin Supports for Solid-Phase Peptide Synthesis", *J. Am. Chem. Soc.* 1980, 102, 6117-6127.

Telser, J. et al., "DNA Oligomers and Duplexes Containing a Covalently Attached Derivative of Tris (2, 2' -bipyridine) ruthenium(II) : Synthesis and Characterization by Thermodynamic annd Optical Specttroscopic Measurements"3, *J. Am. Chem. Soc.* 1989, 111, 7221-7226.

Tibanyenda et al., "The effect of single base-pair mismatches on the duplex stability of d(T-A-T-T-A-A-T-A-T-C-A-A-G-T-T-G) . d(C-A-A-C-T-T-G-A-T-A-T-T-A-A-T-A)," *Eur. J. Biochem.* 1984, 139, 19-27.

Tramontano et al., "Catalytic Antibodies", *Science* 1986, 234, 1566-1570.

Trapane, T.L. et al., "A Proposed Model for Triplex Formation at Single-Stranded Nucleic Acid Target Sites of Unrestricted Sequence", Abstracts Conference on Nucleic Acids Medical Applications, Cancun, Mexico, Jan. 1993.

Trapane, T. et al., "Formation of a purine-purine-pyrimidine triplex with purine oligomers having non-ionic methylphosphonate linkages" *Abstract of J. Biomol. Strul. Struct.*, 1991, 8, from "Seventh Conversation in Biomolecular Stereodynamics" a229..

Trapane, T.L. and Ts'o, P.O.P., "Triplex Formation of Adenine and Thymine Deoxyoligonucleotides and Their Nonionic Methylphosphonate Analogs" *Biophys. J.*, 1992, 61, Abstract 2437.

Tregear, "Graft Copolymers as Insoluble Supports in Peptide Synthesis", *Chemistry and Biology of Peptides* 1972, J. Meienhofer, ed., Ann Arbor Sci. Publ., Ann. Arbor, 175-178.

Uhlmann et al., "Antisense Oligonucleotides: A New Therapeutic Principle", *Chemical Reviews* 1990, 90, 544-583.

van Rietschoten, "Simultaneous Synthesis of Two Peptide Analogs on Different Insoluble Supports", *Peptides* 1974, 1975, Y. Wolman, Ed., Wiley and Sons, New York, pp. 113-116.

Vasseur et al., "Oligonucleosides: Synthesis of a Novel Methylhydroxylamine-Linked Nucleoside Dimer and Its Incorporation into Antisense Sequences," *J. Am. Chem. Soc.* 1992, 114, 4006-4007.

Verber, Daniel F. et al., "Isonicotinyloxycarbonyl, a Novel Amino Protecting Group for Peptide Synthesis", *J. Org. Chem.* 1977, 42 (20), 3286-3288.

Vickers, T. et al., "Inhibition of HIV-LTR gene expression by oligonucleotides targeted to the TAR element," *Nucleic Acids Research* 1991, 19, 3359-3368.

Wagner, R., "Antisense Gene Inhibition by Oligonucleotides Containing C-5 Propyne Pyrimidines", *Science* 1993, 260, 1510-1513.

Wakelin, L. P.G. et al., "Kinetic annd Equilibrium Binding Studies of Amsacrine-4-Carboxamides: A Class of Asymmetrical DNA-Intercalating Agents which Bind by Threading Through the DNA Helix" *J. Med. Chem* 1990, 33, 2039-2044.

Weller et al., "Molecular Modeling of Acyclic Polyamide Oligonucleotide Analogues", *J. Org. Chem.* 1991, 6000-6006.

Wieland et al., "Symmetrical Boc-Amino Acid Anhydrides for Economical Peptide Syntheses on a Solid Phase", *Angew. Chem., Int. Ed. Engl.* 1971, 10, 336.

Yajima et al., "Trifluoromethanesulphonic Acid, as a Deprotecting Reagent in Peptide Chemistry", *J. Chem. Soc., Chem. Comm.* 1974, 107-108.

Zervas et al., "New Methods in Peptide Synthesis. I Tritylsulfenyl and o-Nitrophenylsulfenyl Groups as N-Protecting Groups", *J. Am. Chem. Soc.* 1963, 85, 3660-3666.

Zhang, Z. and McCormick, "Uptake of *N*—(4'—pyridoxyl) amines and Release of Amines by Renal Cells: A Model for Transporter-Enhanced Delivery of Bioactive Compounds", *PNAS USA* 1991, 88, 10407-10410.

Almarsson, et al., "Molecular Mechanics Calculations of the Structures of Polyamide Nucleic Acid DNA Duplexes and Triple Helical Hybrids", *Proc. Natl. Acad. Sci. USA*, 1993, 90(16) : 7518-7522.

Almarsson, et al., "Peptide Nucleic Acid (PNA) Conformation and Polymorphism in PNA-DNA and PNa-RNA Hybrids", *Proc. Natl., Acad. Sci. USA*, 1993, 90(20) : 9542-9546.

Brown, et al., "NMR Solution Structure of a Peptide Nucleic Acid Complexed with RNA", *Science*, 1994, 265:777-780.

Chen, et al., "Molecular Dynamics and NMR Studies of Single-Stranded PNAs", *Tetrahedron Lett.*, 1994, 35 (29) : 5105-5108.

Demidov, et al., "Sequence Selective Double Strand DNa Cleavage by PNA Targeting Using Nuclease S1", *Nucleic Acids Res.*, 1993, 21 (9) : 2103-2107.

Demidov, et al., "Stability of Peptide Nucleic Acids in Human Serum and Cellular Extracts", *Biochem Pharmacol*, 1994, 48 (6) : 1310-1313.

Dueholm, et al., "An Efficient Synthetic Approach to Boc-aminoacetaldehyde and Its Application in the Synthesis of 2-Boc-aminoethylglycine Methyl Ester", *Org. Prep. Proc. Int.*, 1993, 25:457-461.

Dueholm, et al., "Peptide Nucleic Acid (PNA) with a Chiral Backbone Based on Alanine", *Bioorg. Med. Chem. Lett.*, 1994, 48) : 1077-1080.

Dueholm, et al., Synthesis of Peptide Nucleic Acids Monomers Containing the Four Natural Nucleobases: Thymine, Cytosine, Adenine and Guanine, and Their Oligomerization, *J. Org. Chem.*, 1994, 59 (19) :5767-5773.

Egholm, et al., "Peptide Nucleic Acids (PNA). Oligonucleotide Analogues with an Achrial Peptide Backbone", *J. Chem. Soc.*, 1992, 114:1895-1897.

Egholm, et al., "Recognition of Guanine and Adenine in DNA by Cytosine and Thymine Containing Peptide Nucleic Acids (PNA)", *J. Am. Chem. Soc.*, 1992, 114:9677-9678.

Egholm, et al. "Peptide Nucleic Acids Containing Adenine or Guanine Recognize Thymine and Cytosine in Complementary DNA Sequences", *J. Chem. Soc. Comm.*, 1993, p. 800-801.

Flam, F., "Can DNA Mimics Improve on the Real Thing?", *Science*, 1993, 262:1647-1649.

Frank-Kamenetskii, M., "A Change of Backbone", *Nature*, 1991, 354(6354) : 505.

Griffith, et al., Single and Bis Peptide Nucleic Acids as Triplexing Agents: Binding and Stoichiometry, *J. Am. Chem. Soc.*, 1995, 117(2) :831-832.

Hyrup, et al., Modification of the Binding Affinity of Peptide Nucleic Acids (PNA). PNA With Extended Backbones Consisting of 2-aminoethyl—B-alanine or 3-aminopropylglycine Units, *J. Chem. Soc. Chem. Comm.*, 1993, Issue 6;518-519.

Hyrup, et al., "Structure-activity Studies of the Binding of Modified Peptide Nucleic Acids (PNA) to DNA", *J. Am. Chem. Soc.*, 1994, 116 (18) : 7964-7970.

Kosynkina, et al., "A Convenient Synthesis of Chiral Peptide Nucleic Acids (PNA) Monomers", *Tetrahedron Lett.*, 1994, 35 (29) : 5173-5176.

Lagriffoul, et al., "The Synthesis, Co-oligomerization and Hybridization of a Thymine-Thymine Heterodimer Containing PNA", *Bioorg. Med. Chem. Lett.*, 1994, 4 (8) : 1081-1085.

Leijon, et al., "Structural Characterzation of PNA-DNA Duplexes by NMR. Evidence for DNA in a B-like Conformation", *Biochemistry*, 1994, 33 (33) : 9820-9825.

Mollegaard, et al., "Peptide Nucleic Acid-DNA Strand Displacement Loops as Artifical Transcription Promoters", *Proc. Natl. Acad. Sci. USA*, 1994, 91(9) :3892-3895.

Nielsen, et al., "Peptide Nucleic Acids (PNA). Poetntial Anti-Sense and Anti-Gene Agents", *Anticancer Drug Des.*, 1993, 8 (1) :53-56.

Nielsen, P.E., "Peptide Nucleic Acids (PNA) : Potential Antiviral Agents", *Int'l. Antiviral News*, 1993, 1:37-39.

Nielsen, et al., "Peptide Nucleic Acids (PNA). DNA Analogues with a Polymide Backbone", *Antisense Research and Applications*, 1993, p. 363-367.

Nielsen, P.E., "Peptide Nucleic Acid (PNA) : A Model Structure for the Primordial Genetic Material", *Orig. Life Evol. Biosph.*, 1993, 23 (5-6) : 323-327.

Nielsen, et al., "Peptide Nucleic Acid (PNA) . A DNA Mimic with a Peptide Backbone", *Bioconjugate Chem.*, 1994, 5(1) :3-7.

Nielsen, et al., "Sequence-Specific Transcription Arrest by Peptide Nucleic Acid Bound to the DNA Template Strand", *Gene*, 1994, 149 (1) :139-145.

Orum, et al., "Single Base Pair Mutation Analysis by PNA Directed PCR Clamping", *Nucleic Acids Res.*, 1993, 21 (23) :5332-5336.

Peffer, et al., "Strand-Invasion of Duplex DNA by Peptide Nucleic Acid Oligomers", *Proc. Natl. Acad. Sci. USA*, 1993, 90 (22) : 10648-10652.

Rose, D.J., "Characterization of Antisense Binding Properties of Peptide Nucleic Acids by Capillary Gen Electrophoresis", *Anal. Chem.*, 1993, 65 (24) :3545-3549.

Wittung, et al., "DNA-like Double Helix Formed by Peptide Nucleic Acid", *Nature*, 1994, 368 (6471) :561-563.

Heimer, E.P., "Synthesis of analogs and oligomers of N-(2-aminoethyl)glycine and their gastrointestinal absorption in the rat," *Int. J. Peptide Protein Res.*, 1984, 23, 203-211.

\* cited by examiner

A. Diazomethane, MeOH
B. LiBH$_4$, MeOH
C. PPh$_3$, Phthalimide, DEAD
D. TFA, CH$_2$Cl$_2$, NaHCO$_3$, Methyl bromoacetate
E. 1-Thyminylacetylchloride
F. H$_2$NNH$_2$, Boc$_2$O, NaOH, MBHA Lys resin A. Hydrazine, Ethanol
B. Methyl bromoacetate
C. 1-Thyminylacetylchloride A. H₂NNH₂, Boc₂O/NaOH, LiBH₄/MeOH A. Ph3P, DEAD; TFA, TSOH
B. Boc2NH
C. Ethoxycarbonylphthalimide; EtOH, DCC, HOBT
D. TFA, DCM
E. H2NNH2

A. Potassium m-periodate
B. Glacial acetic acid, Sodiumtriacetoxyborohydride
C. N-1-Carboxymethylthymine (Compound 3), 1N NaOH

PEPTIDE NUCLEIC ACID CONJUGATES

CROSS REFERENCE TO RELATED APPLICATIONS

This application is a continuation-in-part of United States application Ser. No. 08/108,591, filed Nov. 27, 1993 that, in turn, is a national phase application of PCT application EP02/01219, filed May 22, 1992, claiming priority to Danish Patent Applications: No. 986/91, filed May 24, 1991, No. 987/91, filed May 24, 1991, and No. 510/92, filed Apr. 15, 1992. In addition, this application is a continuation-in-part to U.S. application Ser. No. 08/088,658, filed Jul. 2, 1993, U.S. application Ser. No. 08/088,661, filed Jul. 2, 1993 and U.S. application Ser. No. 08/275,951, filed Jul. 15, 1994.

The contents of the foregoing patent applications are incorporated herein by reference.

This invention was made subject to a joint research agreement between Isis Pharmaceuticals, University of Copenhagen, Ole Buchardt, Peter Nielsen, Michael Egholm and Rolf Berg.

FIELD OF THE INVENTION

This invention is directed to compounds that are not polynucleotides yet which bind to complementary DNA and RNA strands more strongly than the corresponding DNA. In particular, the invention concerns peptide nucleic acids (PNAs) which are functionalized to include covalently bound conjugates.

BACKGROUND OF THE INVENTION

Oligonucleotides and their analogs have been developed and used in molecular biology in certain procedures as probes, primers, linkers, adapters, and gene fragments. Modifications to oligonucleotides used in these procedures include labeling with non isotopic labels, e.g. fluorescein, biotin, digoxigenin, alkaline phosphatase, or other reporter molecules. Other modifications have been made to the ribose phosphate backbone to increase the resistance to nucleases. These modifications include use of methyl phosphonates, phosphorothioates, phosphorodithioate linkages, and 2'-O-methyl ribose sugar units. Further modifications include those made to modulate uptake and cellular distribution. Phosphorothioate oligonucleotides are presently being used as antisense agents in human clinical trials for the treatment of various disease states, and as antiviral agents.

With the success of these oligonucleotides for both diagnostic and therapeutic uses, there exists an ongoing demand for improved oligonucleotide analogs.

Oligonucleotides can interact with native DNA and RNA in several ways. For example, an oligonucleotide may form a duplex with a single stranded nucleic acid, or form a triplex structure by binding to double stranded DNA. However, to form a triplex structure with a double stranded DNA, the cytosine bases of the oligonucleotide must be protonated. Triplexing is therefore pH dependent. P.O.P. Ts'o and associates have used pseudo isocytosine as a permanently protonated analogue of cytosine in DNA triplexing (see Ono, et al., *J. Am. Chem. Soc.*, 1991, 113, 4032-4033; Ono, et. al., *J. Org. Chem.*, 1992, 57, 3225-3230). Trapane and Ts'o have also suggested the use of pseudo isocytosine for triplex formation with single-stranded nucleic acid targets. (see, Trapane, et. al., *J. Biomol. Strul. Struct.*, 1991, 8, 229; Trapane, et. al., *Biophys. J.*, 1992, 61, 2437; and Trapane, et. al., *Abstracts Conference on Nucleic Acids Medical Applications*, Cancun, Mexico, January 1993). WO 93/05180 discloses substitution of 8-Oxoadenine for protonated cytosine in triplex formation.

Peptide nucleic acids (PNAs) are compounds that in some respects are analogous to oligonucleotides, but which differ in structure. In peptide nucleic acids, the deoxyribose backbone of oligonucleotides has been replaced with a backbone having peptide linkages. Each subunit has attached a naturally occurring or non-naturally occurring base. One such backbone is constructed of repeating units of N-(2-aminoethyl)glycine linked through amide bonds.

PNA binds both DNA and RNA to form PNA/DNA or PNA/RNA duplexes. The resulting PNA/DNA or PNA/RNA duplexes are bound with greater affinity than corresponding DNA/DNA or DNA/RNA duplexes as evidence by their higher melting temperatures (Tm). This high thermal stability has been attributed to the neutrality of the PNA backbone, which does not encounter the charge repulsion present in DNA or RNA duplexes. The neutral backbone of the PNA also renders the Tms of PNA/DNA (RNA) duplexes practically independent of salt concentration. Thus the PNA/DNA duplex offers a further advantage over DNA/DNA duplex interactions which are highly dependent on ionic strength. Homopyrimidine PNAs have been shown to bind complementary DNA or RNA forming $(PNA)_2$/DNA(RNA) triplexes of high thermal stability (see, e.g., Egholm, et al., Science, 1991, 254, 1497; Egholm, et al., J. Am. Chem. Soc., 1992, 114, 1895; Egholm, et al., J. Am. Chem. Soc., 1992, 114, 9677).

In addition to increased affinity, PNA has also been shown to bind to DNA with increased specificity. When a PNA/DNA duplex mismatch is melted relative to the DNA/DNA duplex there is seen an 8 to 20° C. drop in the Tm. This magnitude of a drop in Tm is not seen with the corresponding DNA/DNA duplex with a mismatch present. See Egholm, M., et al., Nature 1993 365 p. 566.

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are in reverse orientation with respect to the 5'-3' direction of the DNA or RNA.

PNAs bind to both single stranded DNA and double stranded DNA. It has been observed that two strands of PNA can bind to dsDNA. While PNA/DNA duplexes are stable in the antiparallel configuration, it was previously believed that the parallel orientation is preferred for $(PNA)_2$/DNA triplexes.

The binding of two single stranded pyrimidine PNAs to a double stranded DNA has been shown to occur via strand displacement, rather than by conventional triple helix formation as observed with triplexing oligonucleotides. When PNA strands invade double stranded DNA, one strand of the DNA is displaced and forms a loop on the side of the $PNA_2$/DNA complex area. The other strand of the DNA is part of the $(PNA)_2$/DNA triplex structure. The single stranded loop area (known as a D loop) is susceptible to cleavage by enzymes that can cleave single stranded DNA.

A further advantage of PNA compared to oligonucleotides is that their polyamide backbone is not recognized by either nucleases or proteases, and are therefore resistant to degradation by enzymes.

Because of their properties, PNAs are known to be useful in several different applications. Since PNAs have stronger binding and greater specificity than oligonucleotides, they are of great utility as probes in cloning, blotting procedures, and in applications such as fluorescence in situ hybridization (FISH). Homopyrimidine PNAs are used for strand displacement in homopurine targets. The restriction sites that overlap with or are adjacent to the D-loop will not be cleaved by restriction enzymes. Additionally, the local triplex inhibits gene transcription. The binding of PNAs to specific restriction sites within a DNA fragment can inhibit cleavage at those sites. This inhibition is useful in cloning and subcloning procedures. Labeled PNAs are also used to directly map DNA molecules by hybridizing PNA molecules having a fluorescent label to complementary sequences in duplex DNA using strand invasion.

PNAs also have been used to detect point mutations in PCR-based assays (PCR clamping). In PCR clamping, PNA is used to detect point mutations in a PCR-based assay, e.g. the distinction between a common wild type allele and a mutant allele, in a segment of DNA under investigation. Typically, a PNA oligomer complementary to the wild type sequence is synthesized and included in the PCR reaction mixture with two DNA primers, one of which is complementary to the mutant sequence. The wild type PNA oligomer and the DNA primer compete for hybridization to the target. Hybridization of the DNA primer and subsequent amplification will only occur if the target is a mutant allele. With this method, the presence and exact identity of a mutant can be determined.

Considerable research is being directed to the application of oligonucleotides and oligonucleotide analogs that bind complementary DNA and RNA strands for use as diagnostics, research reagents and potential therapeutics. For many uses, the oligonucleotides and oligonucleotide analogs must be transported across cell membranes or taken up by cells to express activity.

PCT/EP/01219 describes novel peptide nucleic acid (PNA) compounds which bind complementary DNA and RNA more tightly than the corresponding DNA. It is desirable to append to these compounds groups which modulate or otherwise influence their activity or their membrane or cellular transport. One method for increasing such transport is by the attachment of a pendant lipophilic group. United States application serial number 117,363, filed Sep. 3, 1993, entitled "Amine-Derivatized Nucleosides and Oligonucleosides", describes several alkylamino functionalities and their use in the attachment of such pendant groups to oligonucleosides.

Additionally, U.S. application Ser. No. 07/943,516, filed Sep. 11, 1992, entitled "Novel Amines and Methods of Making and Using the Same" and corresponding -published PCT application- WO 94/06815 describe other novel amine-containing compounds and their incorporation into oligonucleotides for, inter alia, the purposes of enhancing cellular uptake, increasing lipophilicity, causing greater cellular retention and increasing the distribution of the compound within the cell.

U.S. application Ser. No. 08/116,801, filed Sep. 3, 1993, entitled "Thiol-Derivatized Nucleosides and Oligonucleosides" describes nucleosides and oligonucleosides derivatized to include thiolalkyl functionality, through which pendant groups are attached.

There remains a need in the art for stable compounds that bind complementary DNA and RNA to form double-stranded, helical structures which mimic double-stranded DNA, and which are capable of being derivatized to bear pendant groups to further enhance or modulate their binding, cellular uptake, or other activity.

OBJECTS OF THE INVENTION

It is an object of the invention to provide PNAs having at least one conjugate attached thereto.

It is a further object of this invention to provide PNAs which include alkylamino chemical functionality.

It is another object of this invention to provide PNAs which include alkylthio chemical functionality.

It is a further object of the invention to provide PNAs having improved transfer properties across cellular membranes.

It is another object to provide peptide nucleic acids that include intercalators, nucleic acid cleaving agents, cell surface phospholipids, and/or diagnostic agents.

These and other objects will become apparent from the following description and accompanying claims.

SUMMARY OF THE INVENTION

The present invention provides PNA conjugates comprising a PNA backbone and a conjugate bound to the PNA either directly or through a linking moiety. The PNA backbone has an amino end, a carboxyl end, and a plurality of amido groups. Nucleobases are tethered to the backbone through internally located amino groups.

The conjugate is bound through the linking moiety to at least one of the backbone, the tether, or the nucleobase. Preferably, the conjugate is bound to the backbone.

The conjugate can be a reporter enzyme, a reporter molecule, a steroid, a carbohydrate, a terpene, a peptide, a protein, an aromatic lipophilic molecule, a non aromatic lipophilic molecule, a phospholipid, an intercalator, a cell receptor binding molecule, a crosslinking agent, a water soluble vitamin, a lipid soluble vitamin, an RNA/DNA cleaving complex, a metal chelator, a porphyrin, an alkylator, or a polymeric compound selected from polymeric amines, polymeric glycols and polyethers. The conjugate is preferably bound to the peptide nucleic acid backbone, a tether or a nucleobase through a linking moiety.

Also provided are PNA conjugates of the formula:

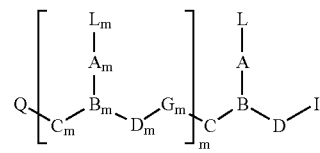

wherein:

m is an integer from 1 to about 50;

L and $L_m$ independently are $R^{12}(R^{13})_a$; wherein:

$R^{12}$ is hydrogen, hydroxy, $(C_1–C_4)$alkanoyl, a naturally occurring nucleobase, a non-naturally occurring nucleobase, an aromatic moiety, a DNA intercalator, a nucleobase-binding group, a heterocyclic moiety, a reporter ligand, or a conjugate;

provided that at least one of $R^{12}$ is a naturally occurring nucleobase, a non-naturally occurring nucleobase, a DNA intercalator, or a nucleobase-binding group;

$R^{13}$ is a conjugate; and a is 0 or 1;

C and $C_m$ independently are $(CR^6R^7)_y$; wherein:

$R^6$ and $R^7$ independently are hydrogen, a side chain of a naturally occurring alpha amino acid, $(C_2-C_6)$ alkyl, aryl, aralkyl, heteroaryl, hydroxy, $(C_1-C_6)$ alkoxy, $(C_1-C_6)$ alkylthio, a conjugate, $NR^3R^4$, $SR^5$ or $R^6$ and $R^7$ taken together complete an alicyclic or heterocyclic system;

wherein $R^5$ is hydrogen, a conjugate, $(C_1-C_6)$alkyl, hydroxy-, alkoxy-, or alkylthio- substituted $(C_1-C_6)$ alkyl; and $R^3$ and $R^4$ independently are hydrogen, a conjugate, $(C_1-C_4)$alkyl, hydroxy- or alkoxy- or alkylthio-substituted $(C_1-C_4)$alkyl, hydroxy, alkoxy, alkylthio or amino;

D and $D_m$ independently are $(CR^6R^6)_z$;

each of y and z is zero or an integer from 1 to 10, wherein the sum y+z is greater than 2 but not more than 10;

$G_m$ is independently —$NR^3CO$—, —$NR^3CS$—, —$NR^3SO$—, or

—$NR^3SO_2$— in either orientation;

each pair of $A-A_m$ and $B-B_m$ are selected such that:

(a) A or $A_m$ is a group of formula (IIa), (IIb) or (IIc) and B or $B_m$ is N or $R^3N^+$; or (b) A or Am is a group of formula (IId) and B or $B_m$ is CH;

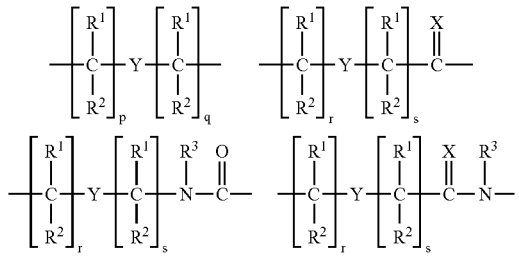

wherein:

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

$R^1$ and $R^2$ independently are hydrogen, $(C_1-C_4)$alkyl, hydroxy-substituted $(C_1-C_4)$alkyl, alkoxy-substituted $(C_1-C_4)$alkyl, alkylthio-substituted $(C_1-C_4)$alkyl, hydroxy, alkoxy, alkylthio, amino, halogen or a conjugate;

I is —$NR^8R^9$ or —$NR^{10}C(O)R^{11}$; wherein:

$R^8$, $R^9$, $R^{10}$ and $R^{11}$ independently are hydrogen, alkyl, an amino protecting group, a reporter ligand, an intercalator, a chelator, a peptide, a protein, a carbohydrate, a lipid, a steroid, a nucleoside, a nucleotide, a nucleotide diphosphate, a nucleotide triphosphate, an oligonucleotide, an oligonucleoside, a soluble polymer, a non-soluble polymer or a conjugate;

Q is —$CO_2H$, —$CO_2R^8$, —$CO_2R^9$, —$CONR^8R^9$, —$SO_2NR^{10}R^{11}$ or an activated derivative of —$CO_2H$ or —$SO_3H$; and wherein at least one of $R^1$, $R^2$, $R^3$, $R^4$, $R^5$, $R^6$, $R^7$, $R^8$, $R^9$, $R^{10}$, $R^{11}$, $R^{12}$ and $R^{13}$ is a conjugate wherein said conjugate is a reporter enzyme, a reporter molecule, a steroid, a carbohydrate, a terpene, a peptide, a protein, an aromatic lipophilic molecule, a non aromatic lipophilic molecule, a phospholipid, an intercalator, a cell receptor binding molecule, a crosslinking agent, a water soluble vitamin, a lipid soluble vitamin, an RNA cleaving complex, a metal chelator, a porphyrin an alkylator, or a polymeric compound selected from polymeric amines, a polymeric glycols and polyethers; and wherein the conjugate optionally includes a linking moiety. The conjugate is preferably bond to the PNA through a linking moiety.

In preferred embodiments at least one group $R^1$, $R^2$, $R^3$, $R^4$, $R^5$, $R^6$, $R^7$, $R^8$, $R^9$, $R^{10}$, $R^{11}$ $R^{12}$ or $R^{13}$ is a conjugate. In other preferred embodiments at least one of group A-Am includes at least one of group $R^1$, $R^2$ or $R^3$.

At least one of groups $B-B_m$ or groups $G-G_m$ preferably include at least one group $R^3$, and at least one of said groups Q or I preferably include at least one of groups $R^8$, $R^9$, $R^{10}$ and $R^{11}$. At least one of said groups $D-D_m$, or $C-C_m$ preferably include at least one of $R^3$, $R^4$, $R^5$, $R^6$ and $R^7$.

In preferred embodiments m is from 1 to about 200, preferably from 1 to about 50, and more preferably from 1 to about 20.

Also provided are compounds having one of the following formulas:

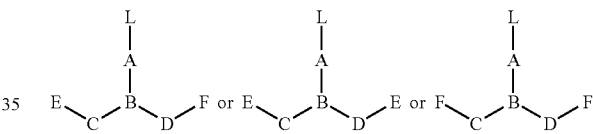

wherein:

L, A, B, C and D are as defined above.

E independently is COOH, CSOH, SOOH, $SO_2OH$ or an activated or protected derivative thereof;

F independently is $NHR^3$ or $NPgR^3$, where Pg is an amino protecting group; and at least one of $R^1$, $R^2$, $R^3$, $R^4$, $R^5$, $R^6$, $R^7$, $R^{12}$, and $R^{13}$ is a conjugate as defined above, and wherein the conjugate is preferably bound through a linking moiety.

In preferred embodiments at least one of $R^3$, $R^4$, $R^5$, $R^6$, and $R^7$ is a conjugate. In other preferred embodiments at least one group $R^3$ is a conjugate. Preferably, $R^{12}$ is a conjugate or $R^{13}$ is a conjugate. In some preferred embodiments at least one group A or group B includes a conjugate, or at least one of said groups C or said groups D include a conjugate.

Also provided are peptide nucleic acid conjugates comprising a plurality of PNA monomers wherein at least one of the PNA monomers has the formula:

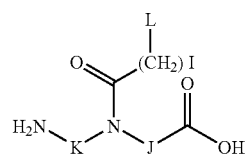

or formula:

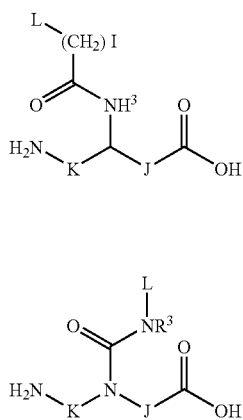

or formula:

wherein:

L is defined as above;

K is $(CR^6R^7)_z$ and J is $(CR^6R^7)_y$ wherein $R^6$, $R^7$, y and z are defined above; 1 is an integer from 1 to 5; and at least one of $R^1$, $R^2$, $R^3$, $R^4$, $R^5$, $R^6$, $R^7$, $R^{12}$, and $R^{13}$ is a conjugate as defined above. Preferably, at least one of group K, group J or $R^3$ includes a conjugate, preferably bound through a linking moiety.

BRIEF DESCRIPTION OF THE FIGURES

The numerous objects and advantages of the present invention may be better understood by those skilled in the art by reference to the accompanying figures, in which.

DETAILED DESCRIPTION OF THE INVENTION

This invention is directed to novel peptide nucleic acids having at least one conjugate group. Each PNA monomer or polymer has a backbone which is the linear portion of the PNA. The backbone is normally defined from an amino (N) terminus or derivative thereof to a carboxyl (C) terminus or derivative thereof. In some preferred embodiments the backbone has an N terminal end, a C terminal end, a number of amide linkages which is equal to one less than the number of monomer units in the PNA, and a number of internal substituted amine groups which is equal to the number of monomers in the PNA.

The N terminal or an internal amide nitrogen of the PNA backbone is separated from the nearest substituted amino group by a number of methylene groups which may bear substituent groups. In preferred embodiments there are two such methylene groups. The substituted amino group is bound to a tether, which is in turn bound to a ligand. The ligand is typically a nucleobase.

The substituted amino group is separated from the C terminal carboxyl group or an internal peptidyl carbonyl group of the PNA backbone by one or more methylene groups which may bear substituent groups. In preferred embodiments there is one such methylene group. Thus, in these preferred embodiments the PNA backbone of n monomeric units has the structure:

H-[HN—$(CH_2)_2$—N(tether-nucleobase)-$(CH_2)$—CO]$_n$—OH wherein the methylene groups optionally bear substituent groups in place of hydrogen.

Monomers and oligomers of the present invention include at least one conjugate attached to the N terminal end, C terminal end, a backbone methylene (inclusive of all methylenes in the backbone), an internal substituted amine, a tether, a ligand or an amide linkage between monomers in an oligomer.

Figure 2:
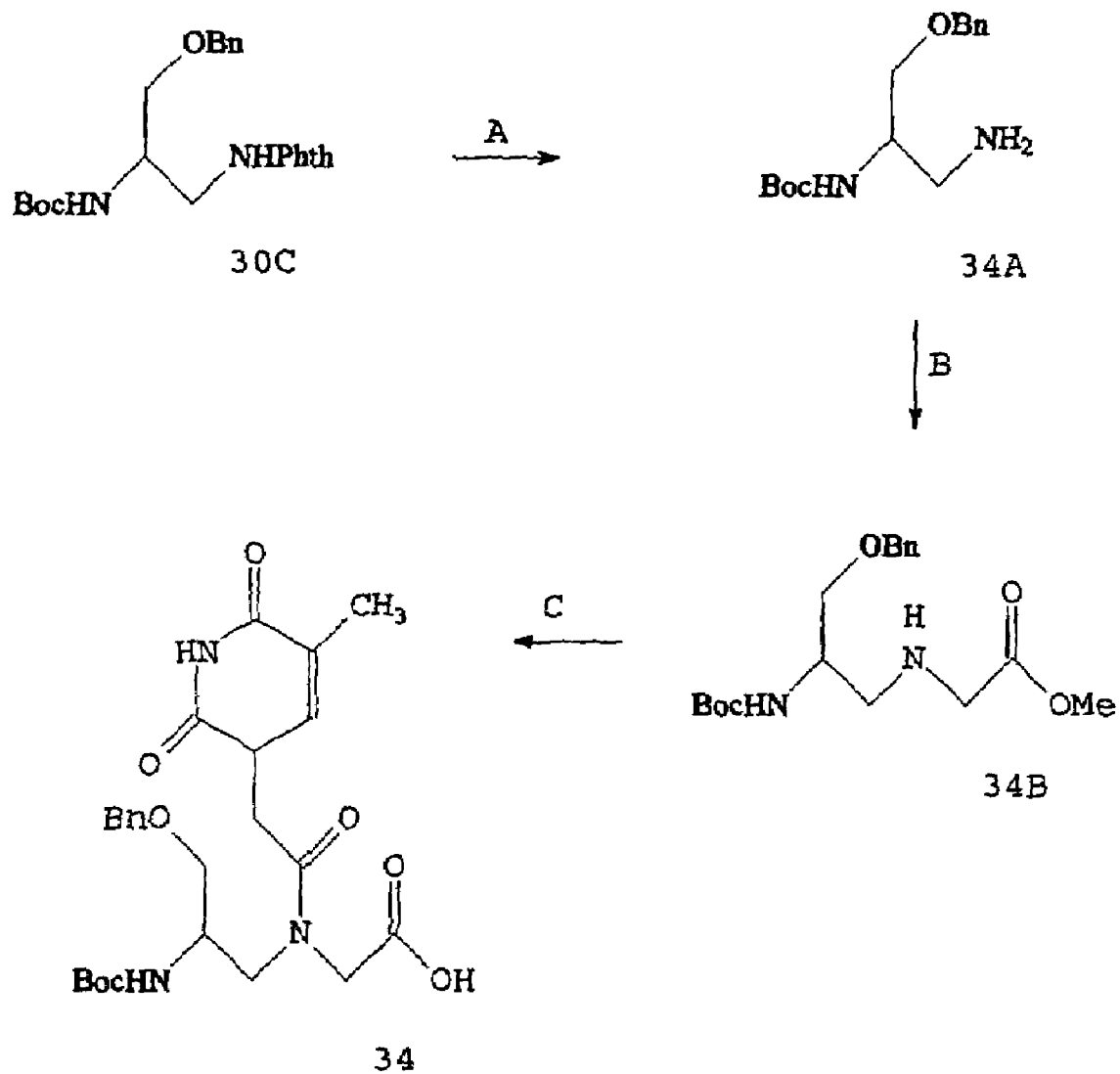
FIG. 2 is a reaction schematic depicting the exemplary functionalization of the 2-aminoethyl portion of a PNA backbone at the 2-position.

As used herein the term nucleobase includes naturally occurring heterocyclic bases such as adenine, guanine, thymine, cytosine and uracil, and also non-naturally occurring nucleobase analogs, homologs and modified nucleobases such as those bearing removable protecting groups. Some representative nucleobase ligands and illustrative synthetic ligands are shown in FIG. 2 of WO 92/20702.

Figure 4:
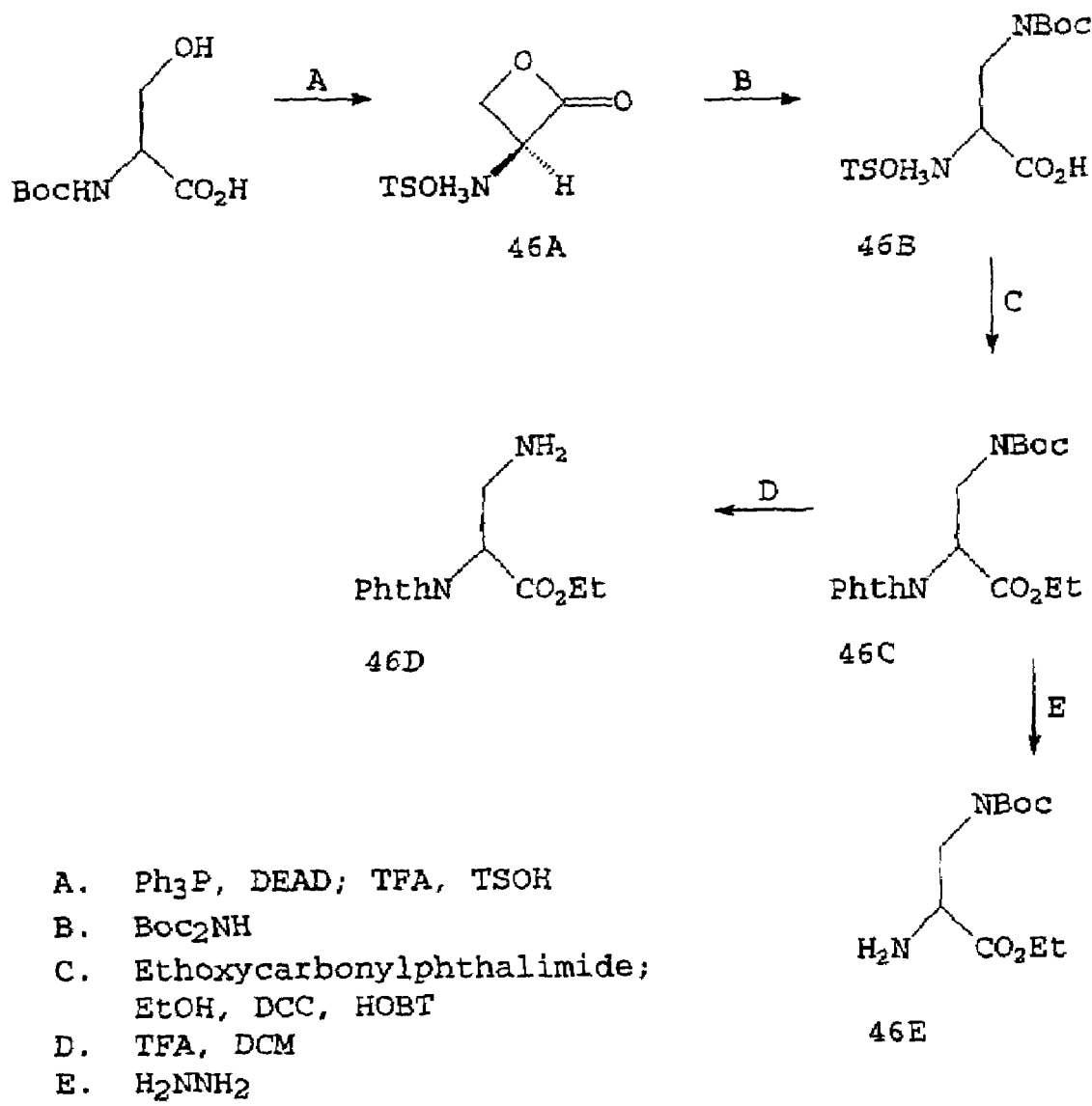
FIG. 4 is a reaction schematic depicting alternate exemplary routes useful in the practice of the invention.

As will be recognized, a variety of PNA conjugates can be prepared according to the present invention. Representative conjugates can be formed from homopolymeric PNA strands or heteropolymeric PNA strands (e.g., chimeras of PNA-DNA or PNA-RNA). Each PNA strand or PNA portion of a chimeric strand preferably includes a plurality of ligands, L (typically nucleobases) linked to a backbone via attachment at the position found in nature, i.e., position 9 for adenine or guanine, and position 1 for thymine or cytosine. Alternatively, the ligand can be a non-naturally occurring nucleobase (a nucleobase analog), another base-binding moiety, an aromatic moiety, $(C_1-C_4)$alkanoyl, hydroxy or hydrogen. L also can be further substituted with a conjugate attached through an optional linking group. In some preferred embodiments L is a conjugate. In monomer synthons, L can be blocked with protecting groups, as illustrated in FIG. 4 of WO 92/20702.

The term "conjugate" as used herein includes a reporter enzyme, a reporter molecule, a steroid, a carbohydrate, a terpene, a peptide, a protein, an aromatic lipophilic molecule, a non aromatic lipophilic molecule, a phospholipid, an intercalator, a cell receptor binding molecule, a crosslinking agent, a water soluble vitamin, a lipid soluble vitamin an RNA cleaving complex, a metal chelator, a porphyrin, an alkylator, and polymeric compounds such as polymeric amines, polymeric glycols and polyethers. PNAs of the present invention include at least one conjugate attached directly or through an optional linking moiety. When so derivatized, the PNA is useful, for example, as a diagnostic or therapeutic agent, to render other properties to a complementary nucleic acid in a test structure or to transfer a therapeutic or diagnostic agent across cellular membranes. Such a diagnostic or therapeutic agent is formed from an oligomeric compound of the invention wherein the oligomeric compound includes monomeric units bearing natural or non-natural occurring nucleobases in a sequence that is complementary to and will specifically hybridize with a region of an RNA or DNA of interest. Thus, an oligomeric compound of the invention is "functionalized" to include a conjugate attached to the oligomeric compound via an optional linking moiety. For the purpose of identification, such a functionalized oligomeric compound can be characterized as a substituent-bearing (e.g., steroid-bearing) oligomeric compound. Such oligomeric compounds will have at least one conjugate attached thereto to modulate their activity.

The oligomeric compounds of the present invention may be useful in binding to various other target molecules. Target molecules of the present invention can include any of a variety of biologically significant molecules. Target molecules can include but are not limited to nucleic acids, carbohydrates, glycoproteins or other proteins.

The PNA oligomers and monomer synthons of the invention are constructed such that conjugates may be covalently bound thereto. In one aspect of the invention conjugates are molecular entities appended to PNAs which serve to modulate, optimize, alter or otherwise affect the activity, transport, uptake or longevity of the desired PNA.

For the purposes of this invention the term "modify" shall mean to change properties by addition to, subtraction from, cleavage of or otherwise, such that which results is intrinsically different from that which is modified. The term "modulate" shall mean to change (i.e., increase or decrease) the magnitude of a property.

A PNA monomer can be functionalized and derivatized to include a conjugate, and the resulting conjugated monomer can be incorporated into a PNA oligomer. Alternatively, one or more conjugates can be incorporated into an oligomeric PNA that has been functionalized at predetermined positions. It will be apparent to those skilled in the art that a wide range of chemistries for the attachment of conjugates are amenable to the present invention.

Tether A can be a wide variety of groups such as

—$CR^1R^2C(O)$—, —$CR^1R^2C(S)$—, —$CR^1R^2C(Se)$—, —$CR^1R^2C(O)N(R^3)$—, —$CR^1R^2C(CH_2)$— and —$CR^1R^2C[C(CH_3)_2]$, where $R^1$, $R^2$ and $R^3$ are as defined above. Preferably, A is methylenecarbonyl (—$CH_2CO$—), amido (—$CONR^3$—), or, taken together with B when B is $R^3N^+$, ureido (—$N^+R^3CONR^3$—). A also can be a longer chain moiety such as propanoyl, butanoyl or pentanoyl, or a corresponding derivative wherein O is replaced by another moiety for X or the chain is substituted with $R^1R^2$, or contains Y where Y is a heteroatom. Further, A can be a $(C_2-C_6)$alkylene chain, a $(C_2-C_6)$alkylene chain substituted with $R^1R^2$ or contains Y where Y is a heteroatom. In some embodiments A is a single bond.

In one preferred embodiment B is a nitrogen atom, thereby presenting the possibility of an achiral backbone. B can also be CH or $R^3N^+$, where $R^3$ is as defined above.

In a preferred embodiment C is —$CR^6R^7$— or a two carbon unit, i.e. —$CHR^6CHR^7$— or —$CR^6R^7CH_2$—, where $R^6$ and $R^7$ are as defined above. $R^6$ and $R^7$ also can be a heteroaryl group such as, for example, pyrrolyl, furyl, thienyl, imidazolyl, pyridyl, pyrimidinyl, indolyl, or can be taken together to complete an alicyclic system such as, for example, 1,2-cyclobutanediyl, 1,2-cyclopentanediyl or 1,2-cyclohexanediyl. C can also be used as a point of attachment of a conjugate e.g. at $R^6$ and or $R^7$. In some preferred embodiments G is —$CONR^3$—. In monomeric embodiments F can be $NHR^3$ or $NPgR^3$ where Pg is an amino protecting group, and E can be CSOH, SOOH, $SO_2OH$ or an activated derivative thereof. In polymeric embodiments groups E and F are activated and chemically combined to produce group G, which therefore can be —$CSNR^3$—, —$SONR^3$— or —$SO_2NR^3$—. The activation can, for example, be achieved using an acid anhydride or an active ester derivative, wherein hydroxy in the groups represented by E is replaced by a leaving group suited for generating the growing backbone.

In some cases it may be useful to attach conjugates at either terminus (Q, I) to modulate the binding characteristics of the resulting PNAs. Representative conjugates include DNA intercalators, which improve dsDNA binding and increase cellular uptake, and basic groups such as lysine or polylysine, which strengthen the binding of the PNA by electrostatic interaction. Other moieties can be located on non-terminal positions. Oligonucleotides and/or oligonucleosides can be covalently bound to terminal positions Q or I to form chimeras containing PNA portions and oligonucleotide and/or oligonucleoside portions. Nucleosides and/or nucleotides (mono, di or tri-phosphates) also can be attached to the terminal positions.

Figure 1:
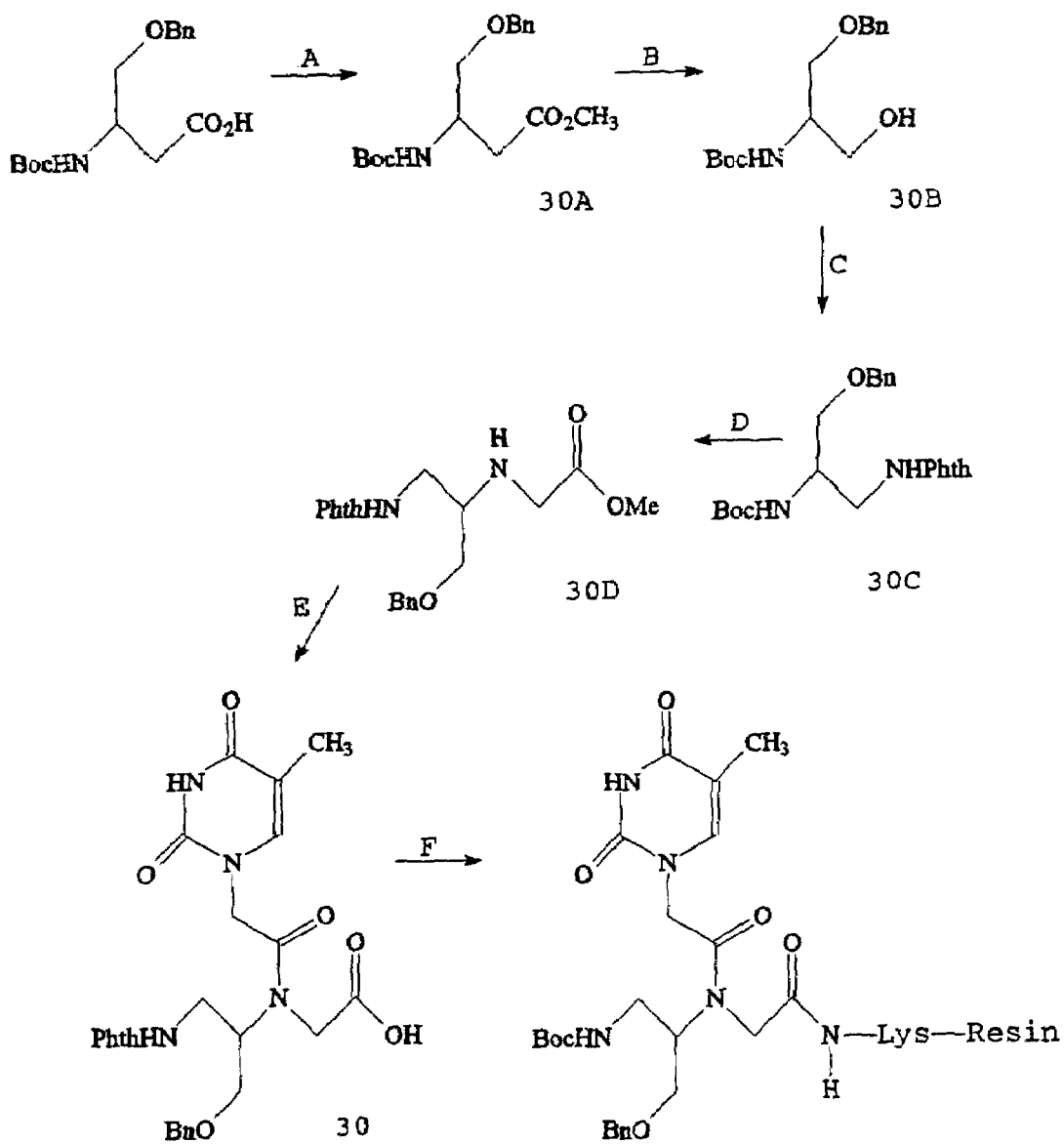
FIG. 1 is a reaction schematic depicting the exemplary functionalization of the 2-aminoethyl portion of a PNA backbone at the 1-position.

FIG. 1 is a reaction schematic depicting the exemplary functionalization of the 2-aminoethyl portion of a PNA backbone at the 1 position. Starting with the commercially available (O-benzyl)Boc-Serine, the acid is protected as the methyl ester using diazomethane and MeOH, yielding the fully protected Compound 30A. Compound 30A is reduced at the ester to give the Compound 30B having a free hydroxyl which is converted to the protected amine Compound 30C using standard Mitsunobo chemistry. Compound 30C is reacted with methyl bromoacetate to form a monomeric backbone unit which is further reacted with a chlorocarbonyl functionalized nucleobase or other ligand to form the functionalized monomer with side chain protected as an O-benzyl. The phthalimido group is removed and the free amine is protected with a BOC group, and the monomer is attached to MBHA Lysine resin to yield the initial monomer attached to the solid support. The support-bound monomer can then be deprotected using TFA, and reacted with a second functionalized monomer or unfunctionalized monomer to give the dimer. The process is repeated in an iterative fashion until the desired PNA is assembled.

FIG. 2 is a reaction schematic depicting the exemplary functionalization of the 2-aminoethyl portion of a PNA backbone at the 2-position. Compound 30C is deprotected with hydrazine and ethanol to give Compound 34A, which is further reacted with methyl bromoacetate to yield the functionalized backbone Compound 34B. Compound 34B is reacted with an acetyl chloride activated nucleobase or other ligand to form the functionalized monomer with the sidechain protected as a benzyl ether. Compound 34 results when 1-thyminyl-acetylchloride is used as the acetyl chlorocarbonyl functionalized nucleobase. Compound 34 is then attached to a suitable resin as shown in FIG. 1. The support-bound monomer is then deprotected with TFA, and reacted with additional monomers to yield the desired PNA chain.

Figure 3:
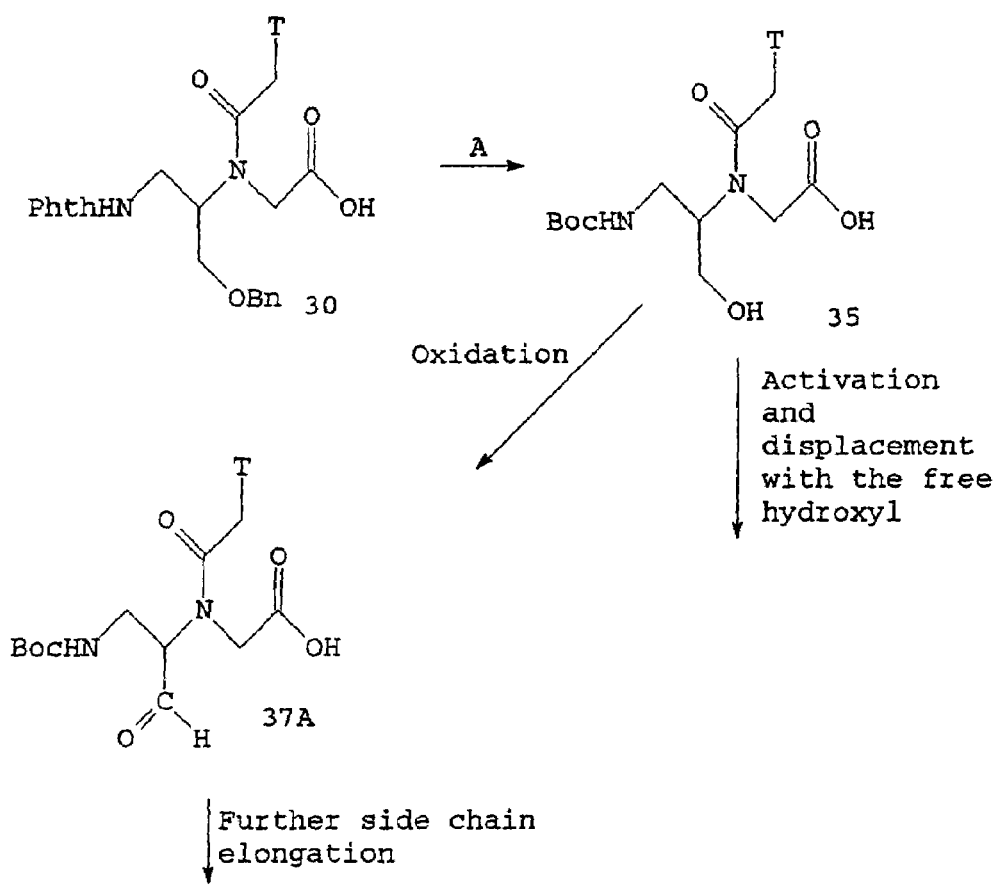
FIG. 3 depicts exemplary routes for chemical alteration of monomer synthons of the invention.

FIG. 3 depicts the transformation of PNA monomer sidechains. Compound 30 is converted from the phthalimido protected amine to the Boc protected amine using hydrazine and $Boc_2O$/NaOH, and the benzyl protected hydroxyl is deprotected by hydrogenolysis to yield Compound 35, which may participate in activation and displacement reactions typical of hydroxyl groups. Thus, PNA oligomer and monomer synthons of the invention may be functionalized with the many chemical species which are useful in the derivatization of DNA and RNA 2'- and 3'-hydroxyls.

Thus, linking moieties attached to PNA monomers of the invention can be modified through a variety of processes, and may participate in linkages with a wide variety of conjugates or conjugates that have themselves been functionalized with a linking moiety.

Compound 35 may also be oxidized to the carbonyl (aldehyde) compound 37A. Compound 37A may participate in Schiff's base linkages, which may be stabilized by reductive amination with, for example, sodium borohydride. Compound 37A may also be further functionalized via enolate condensations, organometallic reactions, stabilized Wittig reactions, and other reactions of active carbonyl groups which will be readily apparent to those skilled in the art.

FIG. 4 depicts an alternate route to the functionalized backbone. The commercially available BOC-serine is reacted with triphenylphosphine/DEAD and then TFA/TsOH to produce Compound 46A. Compound 46A is treated with Gabriel's reagent to give Compound 46B. Protection of the amine function as the phthalimide and esterification with ethanol gives Compound 46C. Deprotection with TFA gives Compound 46D, which can be used in the preparation of PNA monomers functionalized at the 2 position of the 2-aminoethyl portion of the monomer, as shown in FIG. 1. Deprotection with hydrazine 5 gives Compound 46E, which can be used in the preparation of PNA monomers functionalized at the 1 position of the 2-aminoethyl portion of the monomer, as shown in FIG. 2.

It will be seen that selective deprotection of Compound 46C with either hydrazine or TFA allows the synthesis of monomers functionalized at position 1 or 2 of the 2-aminoethyl portion of the monomer.

Figure 5:
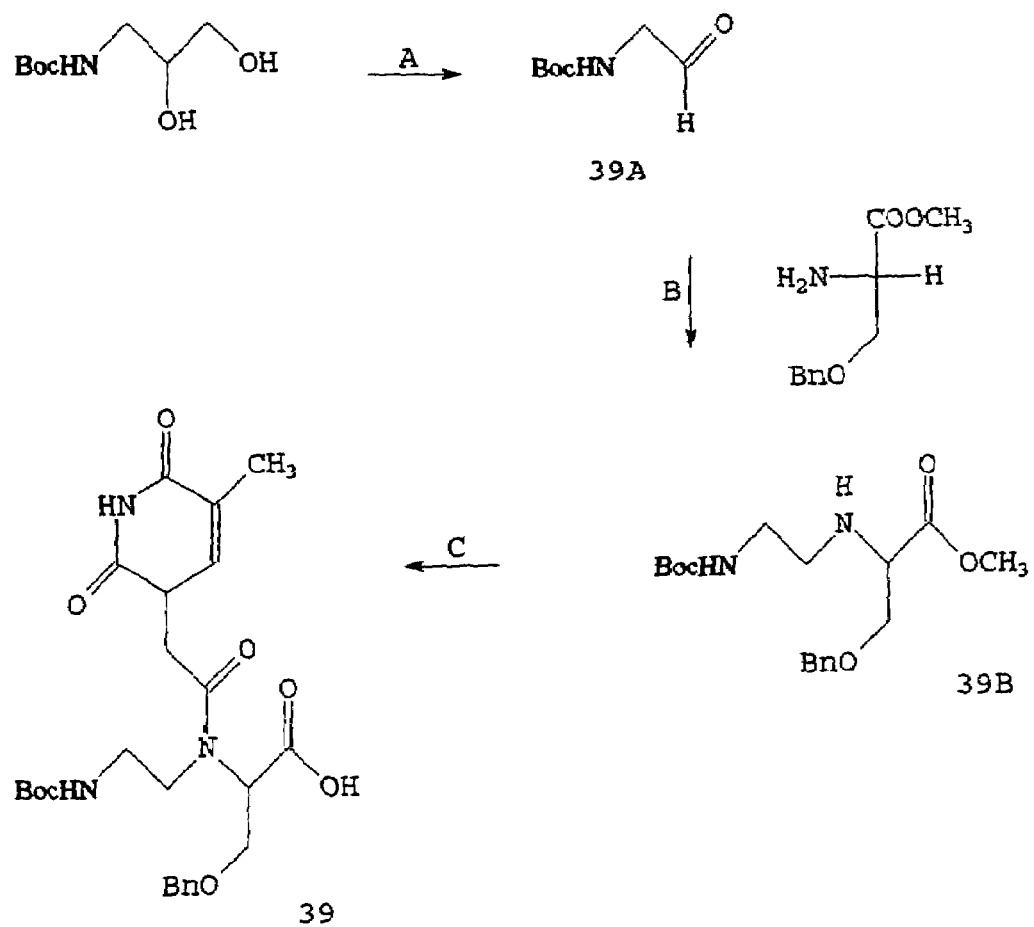
FIG. 5 is a reaction schematic depicting the exemplary functionalization of the OH group of an L-serine portion of a PNA backbone.

Functionalization of the backbone at another position is illustrated in FIG. 5. 3-(Boc-amino)-1,3-propanediol is converted to N-Boc-aminoacetaldehyde Compound 39A via periodate oxidation. Treatment of Compound 39A according to the procedures of Method A, with glacial acetic acid, and sodium triacetoxyborohydride will give the intermediate Compound 39B. Compound 39B can have a variety of different functionalities attached to the secondary amino group in a like manner to Compound 30D and 34B.

Compound 39B is further reacted with 1-carboxymethylthyminyl (compound 3) in 1N NaOH to give Compound 39. The benzyl-protected serine hydroxyl of compound 39 is deprotected according to the procedures of Example 42, and oxidized to a formyl group as per the procedures of Example 43. The formyl compound is further functionalized to yield the aminoethyl compound as per the procedures of Example 44. Compound 44 can be treated in a number of different ways to yield other compounds of the invention.

In one aspect of the present invention Compound 44 is treated with a protecting group, incorporated into a PNA oligomer, deprotected and further functionalized with a conjugate that may include an optional linking moiety. In another aspect of the present invention Compound 44 is functionalized with a tether and then incorporated into a PNA oligomer. After oligomerization the protecting group is removed and the tether is reacted with a conjugate that may include an optional linking moiety. In a further aspect of the invention the conjugate which may include an optional linking moiety is attached to Compound 44 prior to oligomerization. It will be understood by those skilled in the arts that many variations of the methods and techniques described above are amenable to the present invention.

It will also be seen that for the PNAs of the invention it may be advantageous to incorporate one or more functionalized monomers into the chain. The monomers may be independently functionalized at position 1 or 2 of the 2-aminoethyl portion of the monomer as illustrated above or at some other position e.g. O-lysine as illustrated above.

The term PNA oligomer as used herein means linked PNA monomers. The monomers that make up the oligomers are further referred to as synthons. A preferred linkage is an amide linkage between consecutive PNA monomers. Conjugates may be attached to a given PNA by a chemical bond to the PNA backbone as illustrated above, to ligand L, or to tether A. The term "PNA backbone" as used herein is intended to mean the linear polymeric chain of the PNA.

The amino acids which form the backbone can be identical or different. Those based on 2-aminoethylglycine are especially well suited to the purpose of the invention. Another backbone is the 2-aminoethylserine benzyl ether. Preferred are those backbones which are functionalized to include linking moieties capable of participating in linkages to conjugates, or to other linking moieties which are in turn attached to conjugates.

Thus, monomer synthons according to the invention may be prepared with linking moieties contained therein, and the desired conjugate group may be bound to the linking moiety either before or after assembly into a PNA oligomer. It will be seen that not every monomer synthon need be functionalized. However, if advantageous, all the monomers in a given PNA oligomer may be so functionalized.

Conjugates are attached to a linking moiety, a PNA monomer, or a PNA oligomer by the formation of a chemical bond from the reaction of two functional groups. Representative functional groups for formation of the chemical bond include but are not limited to hydroxy, formyl, carboxy or other active carbon species, amino, substituted amino, thio, sulfoxo, sulfono, sulfinic or sulfate ester, or other species similarly able to participate in a chemical linkage with a conjugate group. Functional groups also include those which are protected or "masked." Protecting groups are known per se as chemical functional groups that can be selectively appended to and removed from functionalities such as amine groups and thiol groups. These groups are present in a chemical compound to render such functionality inert to chemical reaction conditions to which the compound is exposed. See, e.g., Greene and Wuts, *Protective Groups in Organic Synthesis,* 2d ed, John Wiley & Sons, New York, 1991.

In some instances it is advantageous to link conjugate groups to PNA oligomers or monomer synthons through a linking moiety. Representative linking moieties useful in the practice of the invention are disclosed in U.S. application Ser. No. 08/116,801, filed Sep. 3, 1993, entitled "Thiol-Derivatized Nucleosides and Oligonucleosides" and United States application serial number 117,363, filed Sep. 3, 1993, entitled "Amine-Derivatized Nucleosides and Oligonucleosides", the disclosures of which are hereby incorporated by reference.

Thus, the monomer synthons (and therefore ultimately the PNA oligomers) of the invention may be constructed containing any one of several functionalities for the linking of conjugate groups, or linkers attached to conjugate groups (i.e., carboxy, formyl, thio, hydroxy, amino and the like). Those skilled in the art will appreciate that the PNA monomer and oligomers of the invention are capable of conjugation to a wide variety of linking functionalities. For example, to attach a conjugate containing a free amino group to a PNA monomer synthon or PNA oligomer, one may functionalize monomers to contain a carboxyl group, and create an amide linkage using standard chemistries. Similarly, in some instances it might be advantageous to attach the amino group through a PNA monomeric unit functionalized with a formyl moiety by reductive amination as described in the Example 85. In general, the choice of a particular functional group on a monomer synthon will be driven by the available functional groups on the conjugate group or linking molecule. Those skilled in the art will be able to determine the optimal match of functionalities by application of standard principles.

One aspect of the present invention is directed to PNAs that bear at least one thiol-containing linking moiety at a PNA backbone, tether or ligand position previously described. Representative thiol linking moieties useful for attaching a conjugate to PNA backbone, ligand or tether positions are —NH—$(CH_2)_6$—S—H and —$CH_2$—O—$(CH_2)_6$—S—H where H can be optionally replaced with a protecting group. It can readily be seen that a large number of variations on these linking moieties are possible. Numerous thiol protecting groups are known in the art, including, but not limited to, the triphenylmethyl (trityl; Tr) and S-t-butyl, S-p-nitrobenzyl, and S-p-methoxy-benzyl (see, e.g., Greene and Wuts, Protective Groups in Organic Synthesis, 2d edition, John Wiley & Sons, New York, 1991).

Preferred linker groups according to the invention include an alkyl moiety independently selected to having 1 to about 12 carbon atoms or alkyl groups interspaced with suitable heteroatoms including oxygen, sulfur and nitrogen to form polyethers, polythioethers or polyalkylamines. The term "alkyl" is intended to include straight chain and branched hydrocarbons. In such linkers, the preferred length of these hydrocarbons is 1 to about 7 carbon atoms. Other linkers include heterobifunctional and homobifunctional linkers.

For the purposes of this invention the terms "reporter molecule" and "reporter enzyme" are inclusive of those molecules or enzymes that have physical or chemical properties that allow them to be identified in gels, fluids, whole cellular systems, broken cellular systems and the like utilizing physical properties such as spectroscopy, radioactivity, colorimetric assays, fluorescence, and specific binding. Particularly useful as reporter molecules are biotin, rhodamine, coumarin and dye molecules including fluorescein dyes. Particularly useful as reporter enzymes are alkaline phosphatase and horseradish peroxidase.

Steroids include those chemical compounds that contain a perhydro-1,2-cyclopentanophenanthrene ring system. Particularly useful as steroid molecules are the bile acids including cholic acid, deoxycholic acid and dehydrocholic acid; steroids including cortisone, digoxigenin, testosterone and cholesterol and even cationic steroids such as cortisone having a trimethylaminomethyl hydrazide group attached via a double bond at the 3-position of the cortisone ring.

Proteins and peptides are utilized in their usual sense as polymers of amino acids. Normally peptides comprise such polymers that contain a smaller number of amino acids per unit molecule than do the proteins. Particularly useful as peptides and proteins are sequence-specific peptides and proteins including phosphodiesterase, peroxidase, phosphatase and nuclease proteins. Such peptides and proteins include but are not limited to SV40 peptide, RNase A, RNase H and Staphylococcal nuclease.

Lipophilic molecules include naturally-occurring and synthetic aromatic and non-aromatic moieties such as fatty acids, esters, alcohols and other lipid molecules, cage structures such as adamantane and buckminsterfullerenes, and aromatic hydrocarbons such as benzene, perylene, phenanthrene, anthracene, naphthalene, pyrene, chrysene, and naphthacene. Particularly useful as lipophilic molecules are alicyclic hydrocarbons, saturated and unsaturated fatty acids, waxes, terpenes and polyalicyclic hydrocarbons including adamantane and buckminsterfullerenes. Particularly useful as terpenoids are vitamin A, retinoic acid, retinal and dehydroretinol.

Alkylators according to the invention are moieties that can effect attachment of electrophilic groups to targeted molecular structures. Representative alkylators are disclosed by Meyer, et al., *J. Am. Chem. Soc.* 1989, 111, 8517.

Intercalators are polycyclic aromatic moieties that can insert between adjacent base pairs without affecting normal Watson-Crick base pairing. Representative intercalators are pyrene; phenanthroline, phenazine, phenanthridine, anthraquinone, acridine, and these and other examples are further disclosed by Manoharan, M., *Antisense Research and Applications*, Crooke and Lebleu, eds., CRC Press, Boca Raton, 1993. Pyrenes include pyrene and other pyrene-based carboxylic acids that can be conjugated using standard protocols. Intercalators of the present invention also include hybrid intercalators. One example of a hybrid intercalator is the photonuclease/intercalator 6-[[[9-[[6-(4-nitrobenzamido)hexyl]amino]acridin-4-yl]carbonyl]amino]hexanoyl-pentafluorophenyl ester. This compound has two noteworthy features: an acridine moiety that is an intercalator and a p-nitro benzamido group that is a photonuclease.

Cell receptor binding molecules according to the invention are vitamins and carbohydrate moieties for which specific receptors exist within a cell. Representative cell receptor binding molecules are disclosed by Application Serial No. PCT/US92/09196, filed Oct. 23, 1992, the contents of which are incorporated herein by reference.

Crosslinking agents are moieties that can effect intrastrand or interstrand covalent binding of RNA and/or DNA. Representative crosslinking agents are disclosed in International Patent Application Serial No. PCT/US93/02059, filed Mar. 5, 1993, which is incorporated herein by reference. Peptide nucleic acids are disclosed herein and by International Patent Application WO 92/20702, published Nov. 26, 1992.

Crosslinking agents of the present invention include photo-crosslinking agents. One group of photo-crosslinking agents is the aryl azides e.g. N-hydroxysuccinimidyl-4azidobenzoate (HSAB) and N-succinimidyl-6(–4'-azido-2'-nitrophenyl-amino)hexanoate (SANPAH). Aryl azides conjugated to PNA will effect crosslinking with nucleic acids and proteins upon irradiation. They will also crosslink with carrier proteins (such as KLH or BSA), raising an antibody against the oligonucleotides.

Vitamins according to the invention generally can be classified as water soluble or lipid soluble. Water soluble vitamins include thiamine, riboflavin, nicotinic acid or niacin, the vitamin $B_6$ pyridoxal group, pantothenic acid, biotin, folic acid, the $B_{12}$ cobamide coenzymes, inositol, choline and ascorbic acid. Lipid soluble vitamins include the vitamin A family, vitamin D, the vitamin E tocopherol family and vitamin K (and phytols). The vitamin A family, including retinoic acid-and retinol, are absorbed and transported to target tissues through their interaction with specific proteins such as cytosol retinol-binding protein type II (CRBP-II), Retinol-binding protein (RBP), and cellular retinol-binding protein- (CRBP). These proteins, which have been found in various parts of the human body, have molecular weights of approximately 15 kD. They have specific interactions with compounds of vitamin-A family, especially, retinoic acid and retinol.

The vitamin A family of compounds can be attached to PNA oligomers of the invention via acid or alcohol functionalities found in the various family members. For example, conjugation of an N-hydroxy succinimide ester of an acid moiety of retinoic acid to an amine function of a PNA or a linker attached to a PNA results in linkage of vitamin A to the PNA via an amide bond.

α-Tocopherol (vitamin E) and the other tocopherols (beta through zeta) can be conjugated to PNAs to enhance uptake because of their lipophilic character. Also, the lipophilic vitamin, vitamin D, and its ergosterol precursors can be attached to PNAs through their hydroxyl groups by first activating the hydroxyl groups to, for example, hemisuccinate esters. Conjugation then is effected to an aminolinker from the PNA, or to the PNA backbone through the other suitable functional groups described herein. Other vitamins that can be conjugated to PNAs or PNA aminolinkers through hydroxyl groups on the vitamins include thiamine, riboflavin, pyridoxine, pyridoxamine, pyridoxal, deoxypyridoxine. Lipid soluble vitamin K's and related quinone-containing compounds can be conjugated via carbonyl groups on the quinone ring. The phytol moiety of vitamin K may also serve to enhance binding of the PNA to cells.

Pyridoxal (vitamin $B_6$) has specific $B_6$-binding proteins. The role of these proteins in pyridoxal transport has been studied by Zhang and McCormick, *Proc. Natl. Acad. Sci. USA,* 1991 88, 10407. Zhang and McCormick also have shown that a series of N-(4'-pyridoxyl)amines, in which several synthetic amines were conjugated at the 4'-position of pyridoxal, are able to enter cells by a process facilitated by the B6 transporter. They also demonstrated the release of these synthetic amines within the cell. Other pyridoxal family members include pyridoxine, pyridoxamine, pyridoxal phosphate, and pyridoxic acid. Pyridoxic acid, niacin, pantothenic acid, biotin, folic acid and ascorbic acid can be conjugated to PNAs using N-hydroxysuccinimide esters that are reactive with the PNA or aminolinkers located on the PNA, as described above for retinoic acid.

Other groups for modifying properties of PNAs include RNA/DNA cleaving complexes. RNA/DNA cleavers include o-phenanthroline/metal complexes and 2+2+Ru(bipyridine)$_3^{2+}$ complexes. The Ru(bpy)$_3^{2+}$ complexes interact with nucleic acids and cleave nucleic acids photochemically. Metal chelators include EDTA, DTPA, nitrilo-triacetate (NTA), and o-phenanthroline. Porphyrins include porphine, its substituted forms, and metal complexes.

A polyamine or polymeric amine species as used herein refers to species that have a plurality of nitrogen atoms thereon. Polyamines include primary amines, hydrazines, semicarbazines, thiosemicarbazines and similar nitrogenous species. Such species can be symmetrical species such as polyamine containing polymers or they can be unsymmetrical wherein the amine functionalities of the polyamine are separated in space by different moieties. In addition to carbon atoms other atomic species such as nitrogen and sulfur may also be incorporated into the polyamine species. In some preferred embodiments of the invention, at least one nitrogen atom of the polyamine has a free electron pair.

Preferred as polyamines are species that range in length from about 3 to about 20 units. More preferably species having at least one nitrogen atom have the general formula $H_2N[(CH_2)_nNH]_m$- wherein n is an integer between 2 and 8 and m is an integer between 1 and 10. These species can be linear or cyclic. Cyclic amines would include crown amines and mixed crown amines/crown ethers.

Other suitable nitrogen-containing compounds suitable for the formation of polyamines include $C_1$–$C_{20}$ straight chain alkylamine, $C_1$–$C_{20}$ straight chain substituted alkylamine, $C_2$–$C_{50}$ branched chain alkylamine, $C_2$–$C_{50}$ branched chain substituted alkylamine, $C_3$–$C_{50}$ cyclic alkylamine, $C_3$–$C_{50}$ cyclic substituted alkyl amine, $C_2$–$C_{20}$ straight chain alkenylamine, $C_2$–$C_{20}$ straight chain substituted alkenylamine, $C_3$–$C_{50}$ branched chain alkenylamine, $C_3$–$C_{50}$ branched chain substituted alkenylamine, $C_3$–$C_{50}$ cyclic alkenylamine, $C_3$–$C_{50}$ cyclic substituted alkenylamine, $C_2$–$C_{20}$ straight chain alkynylamine, $C_2$–$C_{20}$ straight chain substituted alkynylamine, $C_3$–$C_{50}$ branched chain alkynylamine, $C_3$–$C_{50}$ branched chain substituted alkynylamine, $C_3$–$C_{50}$ cyclic alkynylamine, $C_3$–$C_{50}$ cyclic substituted alkynylamine, $C_1$–$C_{20}$ straight chain -alkylhydrazine, $C_1$–$C_{50}$ straight chain substituted alkylhydrazine, $C_2$–$C_{50}$ branched chain alkylhydrazine, $C_2$–$C_{50}$ branched chain substituted alkylhydrazine, $C_3$–$C_{50}$ cyclic hydrazoalkane, $C_3$–$C_{50}$ cyclic substituted hydrazoalkane, $C_2$–$C_{20}$ straight chain alkenylhydrazine, $C_2$–$C_{20}$ straight chain substituted alkenylhydrazine, $C_3$–$C_{50}$ branched chain alkenylhydrazine, $C_3$–$C_{50}$ branched chain substituted alkenylhydrazine, $C_3$–$C_{50}$ cyclic hydrazoalkene, $C_3$–$C_{50}$ cyclic substituted hydrazoalkene, $C_2$–$C_{20}$ straight chain alkynylhydrazine, $C_2$–$C_{20}$ straight chain substituted alkynylhydrazine, $C_3$–$C_{50}$ branched chain alkynylhydrazine, $C_3$–$C_{50}$ branched chain substituted alkynylhydrazine, $C_3$–$C_{50}$ cyclic hydrazoalkyne, $C_3$–$C_{50}$ cyclic substituted hydrazoalkyne, $C_1$–$C_{20}$ straight chain alkylhydroxyamine, $C_1$–$C_{20}$ straight chain substituted alkylhydroxyamine, $C_2$–$C_{50}$ branched chain alkylhydroxyamine, $C_2$–$C_{50}$ branched chain substituted alkylhydroxyamine, $C_3$–$C_{50}$ cyclic oxyalkylamine, $C_3$–$C_{50}$ cyclic substituted oxyalkylamine, $C_2$–$C_{20}$ straight chain alkenylhydroxyamine, $C_2$–$C_{20}$ straight chain substituted alkenylhydroxyamine, $C_3$–$C_{50}$ branched chain alkenylhydroxyamine, $C_3$–$C_{50}$ branched chain substituted alkenylhydroxyamine, $C_3$–$C_{50}$ cyclic oxyalkenylamine, $C_3$–$C_{50}$ cyclic substituted oxyalkenylamine, $C_2$–$C_{20}$ straight chain alkynylhydroxyamine, $C_2$–$C_{20}$ straight chain substituted alkynylhydroxyamine, $C_3$–$C_{50}$ branched chain alkynylhydroxyamine, $C_3$–$C_{50}$ branched chain substituted alkynylhydroxyamine, $C_3$–$C_{50}$ cyclic oxyalkynylamine, $C_3$–$C_{50}$ cyclic substituted oxyalkynylamine, $C_1$–$C_{20}$ straight chain alkylsemicarbazide, $C_1$–$C_{20}$ straight chain substituted alkylsemicarbazide, $C_2$–$C_{50}$ branched chain alkylsemicarbazide, $C_2$–$C_{50}$ branched chain substituted alkylsemicarbazide, $C_3$–$C_{50}$ cyclic alkylsemicarbazide, $C_3$–$C_{50}$ cyclic substituted alkylsemicarbazide, $C_2$–$C_{20}$ straight chain alkenylsemicarbazide, $C_2$–$C_{20}$ straight chain substituted alkenylsemicarbazide, $C_3$–$C_{50}$ branched chain alkenylsemicarbazide, $C_3$–$C_{50}$ branched chain substituted alkenylsemicarbazide, $C_3$–$C_{50}$ cyclic alkenylsemicarbazide, $C_3$–$C_{50}$ cyclic substituted alkenylsemicarbazide, $C_2$–$C_{20}$ straight chain alkynylsemicarbazide, $C_2$–$C_{20}$ straight chain substituted alkynylsemicarbazide, $C_3$–$C_{50}$ branched chain alkynylsemicarbazide, $C_3$–$C_{50}$ branched chain substituted alkynylsemicarbazide, $C_3$–$C_{50}$ cyclic alkynylsemicarbazide, $C_3$–$C_{50}$ cyclic substituted alkynylsemicarbazide, $C_1$–$C_{20}$ straight chain alkylthiosemicarbazide, $C_1$–$C_{20}$ straight chain substituted alkylthiosemicarbazide, $C_2$–$C_{50}$ branched chain alkylthiosemicarbazide, $C_2$–$C_{50}$ branched chain substituted alkylthiosemicarbazide, $C_3$–$C_{50}$ cyclic alkylthiosemicarbazide, $C_3$–$C_{50}$ cyclic substituted alkylthiosemicarbazide, $C_2$–$C_{20}$ straight chain alkenylthiosemicarbazide, $C_2$–$C_{20}$ straight chain substituted alkenylthiosemicarbazide, $C_3$–$C_{50}$ branched chain alkenylthiosemicarbazide, $C_3$–$C_{50}$ branched chain substituted alkenylthiosemicarbazide, $C_3$–$C_{50}$ cyclic alkenylthiosemicarbazide, $C_3$–$C_{50}$ cyclic substituted alkenylthiosemicarbazide, $C_2$–$C_{20}$ straight chain alkynylthiosemicarbazide, $C_2$–$C_{20}$ straight chain substituted alkynylthiosemicarbazide, $C_3$–$C_{50}$ branched chain alkynylthiosemicarbazide, $C_3$–$C_{50}$ branched chain substituted alkynylthiosemicarbazide, $C_3$–$C_{50}$ cyclic alkynylthiosemicarbazide, $C_3$–$C_{50}$ cyclic substituted alkynylthiosemicarbazide, $C_1$–$C_{20}$ straight chain alkylhydrazone, $C_1$–$C_{20}$ straight chain substituted alkylhydrazone, $C_2$–$C_{50}$ branched chain alkylhydrazone, $C_2$–$C_{50}$ branched chain substituted alkylhydrazone, $C_3$–$C_{50}$ cyclic hydrazoalkane, $C_3$–$C_{50}$ cyclic substituted hydrazoalkane, $C_2$–$C_{20}$ straight chain alkenylhydrazone, $C_2$–$C_{20}$ straight chain substituted alkenylhydrazone, $C_3$–$C_{50}$ branched chain alkenylhydrazone, $C_3$–$C_{50}$ branched chain substituted alkenylhydrazone, $C_3$–$C_{50}$ cyclic hydrazoalkene, $C_3$–$C_{50}$ cyclic substituted hydrazoalkene, $C_2$–$C_{20}$ straight chain alkynylhydrazone, $C_2$–$C_{20}$ straight chain substituted alkynylhydrazone, $C_3$–$C_{50}$ branched chain alkynylhydrazone, $C_3$–$C_{50}$ branched chain substituted alkynylhydrazone, $C_3$–$C_{50}$ cyclic hydrazoalkyne, $C_3$–$C_{50}$ cyclic substituted hydrazoalkyne, $C_1$–$C_{20}$ straight chain alkylhydrazide, $C_1$–$C_{20}$ straight chain substituted alkylhydrazide, $C_3$–$C_{50}$ branched chain alkylhydrazide, $C_3$–$C_{50}$ branched chain substituted alkylhydrazide, $C_3$–$C_{50}$ cyclic alkylhydrazide, $C_3$–$C_{50}$ cyclic substituted alkylhydrazide, $C_2$–$C_{20}$ straight chain alkenylhydrazide, $C_2$–$C_{20}$ straight chain substituted alkenylhydrazide, $C_3$–$C_{50}$ branched chain alkenylhydrazide, $C_3$–$C_{50}$ branched chain substituted alkenylhydrazide, $C_3$–$C_{50}$ cyclic alkenylhydrazide, $C_3$–$C_{50}$ cyclic substituted alkenylhydrazide, $C_2$–$C_{20}$ straight chain alkynylhydrazide, $C_2$–$C_{20}$ straight chain substituted alkynylhydrazide, $C_3$–$C_{50}$ branched chain alkynylhydrazide, $C_3$–$C_{50}$ branched chain substituted alkynylhydrazide, $C_3$–$C_{50}$ cyclic alkynylhydrazide and $C_3$–$C_{50}$ cyclic substituted alkynylhydrazide.

In accordance with preferred embodiments of the present invention polyamines are linear or cyclic non-aromatic polyamines. A useful class of cyclic non-aromatic polyamines are crown amines which are disclosed by Studer, et al., *Helv. Chim. Acta* 1986, 69, 2081 and Smith-Jones, et al., *Bioconjugate Chem.* 1991, 2, 415. In still more preferred embodiments of the present invention polyamines are linear or cyclic non-aromatic comprising non-amide nitrogen atoms. By non-amide is meant a nitrogen which is not adjacent to a carbonyl group (i.e. C=O or C=S).

Representative polyethylene glycol (PEG)-containing groups are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249. Polyethylene glycols and polyethers include both linear and cyclic compounds. The cyclic polyethers include crown ethers.

As used in this specification the term alkyl includes but is not limited to $C_1$–$C_{12}$ straight and branched chained alkyls such as methyl, ethyl, propyl, butyl, pentyl, hexyl, heptyl, octyl, nonyl, decyl, undecyl, dodecyl, isopropyl, 2-butyl, isobutyl, 2-methylbutyl, isopentyl, 2-methyl-pentyl, 3-methylpentyl, 2-ethylhexyl and 2-propylpentyl. Alkenyl groups include but are not limited to unsaturated moieties derived from the above alkyl groups including but not limited to vinyl, allyl and crotyl. Alkynyl groups include unsaturated moieties having at least one triple bond that are derived from the above alkyl groups including but are not limited to ethynyl and propargyl. Aryl groups include but are not limited to phenyl, tolyl, benzyl, naphthyl, anthracyl, phenanthryl, pyrenyl, and xylyl. Halogens include fluorine, chlorine, iodine and bromine. Suitable heterocyclic groups include but are not limited to imidazole, tetrazole, triazole, pyrrolidine, piperidine, piperazine and morpholine. Amines include amines of all of the above alkyl, alkenyl and aryl groups including primary and secondary amines and "masked amines" such as phthalimide. Alkanoyl compounds are those which contain an alkyl portion and are linked through a carbonyl group; i.e., groups which have the structure alkyl-C(O)—. Aralkyl groups have both aryl and alkyl portions, and are attached through their alkyl portions. A benzyl group is an example of an aralkyl group. Alkaryl groups also have both aryl and alkyl portions, but are attached through their aryl portions. Alkoxy groups are alkyl, alkenyl or alkynyl groups which are attached through an oxygen atom.

Heteroaryl groups are aromatic heterocycles, such as pyrrolyl, furyl, thienyl, imidazolyl, pyridyl, pyrimidinyl, and indolyl.

Terpenes are known in the art as oligomers of isoprene, particularly the dipentenes, pinenes, and myrcenes. Included within the definition of terpene molecules are terpene derivatives such as camphor and menthol.

The term phospholipid as used herein includes those compounds which upon hydrolysis yield phosphoric acid, an alcohol and one or more fatty acids. Representative examples of phospholipids include lecithin, cephalin and sphingomyelin.

Amines are also meant to include polyalkylamino compounds and aminoalkylamines such as aminopropylamine and further heterocyclo-alkylamines such as imidazol-1, 2 or 4-yl-propylamine.

Substituent groups for the above as well as for other moieties listed below include but are not limited to other alkyl, haloalkyl, alkenyl, alkynyl, alkoxy, thioalkoxy, haloalkoxy and aryl groups as well as halogen, hydroxyl, amino, azido, carboxy, cyano, nitro, mercapto, sulfides, sulfones, sulfoxides, keto, carboxy, nitrates, nitrites, nitroso, nitrile, trifluoromethyl, O-alkyl, S-alkyl, NH-alkyl, amino, silyl, amides, ester, ethers, carbonates, carbamates, ureas, imidazoles, intercalators, conjugates, polyamines, polyamides, polyethylene glycols, polyethers, groups that enhance the pharmacodynamic properties of oligonucleotides, and groups that enhance the pharmacokinetic properties of oligonucleotides. Other suitable substituent groups also include rhodamines, coumarins, acridones, pyrenes, stilbenes, oxazolo-pyridocarbazoles, anthraquinones, phenanthridines, phenazines, azidobenzenes, psoralens, porphyrins and cholesterols. One particularly preferred group is $CF_3$. Typical intercalators and conjugates include cholesterols, phospholipids, biotin, phenanthroline, phenazine, phenanthridine, anthraquinone, acridine, fluoresceins, rhodamines, coumarins, and dyes. Halogens include fluorine, chlorine, bromine, and iodine.

One method for preparing compounds according to the invention is to react PNA oligomers or monomeric units bearing at least one free hydroxyl group under basic conditions with a compound having formula $L_v$-$(CH_2)_n$—S-PG where $L_v$ is a leaving group, PG is a protecting group and n is from 1 to about 20. Displacement of the leaving group through nucleophilic attack of an oxygen anion produces the desired thiol derivative. Suitable leaving groups include but are not limited to halogen, alkylsulfonyl, substituted alkylsulfonyl, arylsulfonyl, substituted arylsulfonyl, hetercyclcosulfonyl, trichloroacetimidate, and pentafluorophenol. A more preferred group includes chloro, fluoro, bromo, iodo, p-(2,4-dinitroanilino)benzenesulfonyl, benzenesulfonyl, methylsulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazolesulfonyl, and 2,4,6-trichlorophenyl, with bromo being preferred.

In embodiments. wherein thiol-containing functionality is appended to PNA backbone hydroxyl positions, amine functionality in the base portion of the PNA oligomer or monomeric units preferably is protected under non-acidic conditions with protecting groups known in the art, including benzoyl and isobutyryl groups. Alternatively, base protection can precede reaction with thiol reagent $L_v\text{-}(CH_2)_n\text{—S-PG}$. Suitably protected PNA monomeric units can be assembled into a PNA oligomer according to techniques disclosed in Example 26 of this specification.

Compounds according to the invention can also be prepared by reacting 5-halogen substituted pyrimidine-bearing PNA monomer synthons or 2- or 8-halogen substituted purine PNA monomer synthons with an acetylenic reagent having formula $HC\equiv C\text{—}CH_2\text{-}Q_a\text{-}PG$ where $Q_a$ is O, S, or NH, under conditions effective to couple the pyrimidine or purine base with the acetylenic reagent and form a PNA monomer synthon bearing a substituent having formula $\text{—}C\equiv C\text{—}CH_2\text{-}Q_a\text{-}PG$ at the pyrimidine 5-position or at the purine 2- or 8-position. Numerous suitable protecting groups are known in the art, including, but not limited to: amine protecting groups such as trifluoroacetate, allyloxycarbonyl (Alloc), carbobenzyloxy (CBZ), chloroCbz, t-butyloxycarbonyl (Boc), fluorenylmethoxycarbonyl (Fmoc), isonicotinyloxycarbonyl (i-Noc) groups; hydroxyl protecting groups such as t-butyldiphenylsilyl, t-butyldimethylsilyl, and dimethoxytrityl groups; and thiol protecting groups such as S-trityl, S-p-methoxybenzylthioether, S-p-nitrobenzylthioether, and S-t-butylthioether. (see, e.g., Veber and Hirschmann, et al., *J. Org. Chem.* 1977, 42, 3286 and Atherton, et al., The Peptides, Gross and Meienhofer, Eds, Academic Press; New York, 1983; Vol. 9 pp. 1–38) Coupling preferably is mediated by a metal selected from palladium, nickel, platinum and iridium under conditions generally in accordance with Haralambidis, et al., *Nucleic Acids Research* 1987,15,4857. Once coupling is effected, the protecting group, is removed and the resultant free hydroxy, thio, or amino compound. is condensed with a suitable -thiol derivative having formula $R_4\text{—}(CH_2)_n\text{—S—}R_1$, where $R_4$ is $R_5OOC\text{—}$, HS, or —NCS where $R_5$ is H, chloro, alkyl having 1–12 carbon atoms, or an active ester.

Compounds according to the invention can also be prepared by reacting metal-substituted pyrimidine bearing PNA monomer synthons or purine bearing PNA monomer synthons with an acrylate having formula $H_2C=C\text{—}C(O)OR_6$ ($R_6$=alkyl having 1–12 carbon atoms) under conditions effective to couple the pyrimidine or purine base with the acrylate and form a PNA monomer synthon bearing a substituent having formula $\text{—CH}=CH\text{—}C(O)OH$ at the pyrimidine 5-position or at the purine 2- or 8-position. Coupling is effected under conditions generally in accordance with Dreyer, et al., *Proc. Natl. Acad. Sci. USA* 1985,82, 968. Once coupling is effected, the acid is condensed with an amino thiol derivative having formula $H_2N\text{—}(CH_2)_n\text{—S-PG}$.

Compounds according to the invention also can be prepared by reacting PNA monomer synthons bearing leaving groups, $L_v$ as defined above, at 5-pyrimidine positions or at 2-, 6-, or 8-purine positions with, for example, thiol derivatives having formula $HQ_a\text{-}(CH_2)_n\text{—S-PG}$ wherein $Q_a$ and PG are as described above, under conditions effective to displace the leaving group. Such displacement preferably occurs at room temperature in solvents such as dimethylformamide (DMF) or dimethylsulfoxide (DMSO).

PNA oligomers according to the invention can be prepared by assembling a PNA oligomer and appending thiol functionality thereto. For example, PNA oligomers having free hydroxyl groups can be assembled according to the techniques of Examples 26 and 31–37 of this specification, and then reacted with a reagent having formula $L_v\text{-}(CH_2)_n\text{—S-PG}$. As will be recognized, however, greater selectivity can be achieved in terms of placement of thiol functionality within a PNA oligomer by introducing such functionality, as discussed above, on selected PNA monomer synthons and then using both the selected PNA monomer synthons and other PNA monomer synthons to construct the desired PNA oligomer.

Once assembled a PNA bearing one or more linking moieties ending with -S-PG is treated with a Lewis acid under conditions to remove protecting group PG. Representative acids include silver cation and mercuric cation. Once deprotected, the PNA can be contacted with a thiol-containing steroid molecule, reporter molecule, lipophilic molecule, reporter enzyme, peptide, protein or other thiol containing conjugate in the presence of a thiol-based coupling reagent. Useful coupling reagents include 2,2'-dithiobis(5-nitropyridine) and other pyridyl disulfides or Ellman reagent.

Alternatively, a PNA bearing one or more linking moieties ending with —S—H can be contacted with electrophilic moieties having formula (maleimido)-conjugate or $L_v\text{—}CH_2C(O)\text{—}R_2$ where $L_v$ is a leaving group as defined above and $R_2$ is also defined above. As will be recognized, the sulfur atom on the PNA bonds with the former electrophilic moiety via 1,4-addition and with the latter via nucleophilic displacement. Preferred electrophilic moieties include phospholipid maleimide, o-phenanthroline-5-iodoacetamide, fluorescein maleimide, and pyrene maleimide however many alternative electrophilic moieties can be used.

Thus, in one aspect of the invention the desired PNA sequence is assembled using standard methods and techniques as set forth in Example 26. At least one PNA monomer including a masked or protected linking moiety is included in the sequence at a predetermined position. A conjugate is then chemically bonded to the linking moiety directly or via a linking moiety attached to the conjugate.

Additional representative thiol groups amenable to the present invention are cysteine, glutathione, penicillamine, 2-pyridylmercaptyl, $Br\text{—}CH_2\text{—}CO\text{—}NH\text{—}CH_2\text{—}CH_2\text{-}STr$, $SH\text{—}C\text{—}(CH_3)_2CH_2\text{—}NH\text{—}CH_2\text{—}CH_2\text{—}NH\text{—}CH_2\text{—}C\text{—}(CH_3)_2SH$, $HOOC\text{—}CH_2\text{—}CH_2\text{—}S\text{—}S\text{—}CH_3OOCS$, $CH_3\text{—}CO\text{—}S\text{—}C(CH_3)\text{—}CH_2\text{—}C\text{—}NH\text{—}(CH_2)_2\text{—}COOH$, (see, e.g., Dizio, et al., *Bioconjugate Chem.* 1991, 2, 353 and Greenfield, et al., *Bioconjugate Chem.* 1990, 1, 400).

Numerous amine protecting groups are known in the art, including, but not limited to: phthalimide (Phth), trifluoroacetate, allyloxycarbonyl (Alloc), carbobenzyloxy (CBZ), chloroCBZ, t-butyloxycarbonyl (Boc), fluorenylmethoxycarbonyl (Fmoc), and isonico-tinyloxycarbonyl (i-Noc) groups. (see, e.g., Veber and Hirschmann, et al., *J. Org. Chem.* 1977, 42, 3286 and Atherton, et al., The Peptides, Gross and Meienhofer, Eds, Academic Press; New York, 1983; Vol. 9 pp. 1–38).

Conjugate bearing PNA oligomers according to the invention may be prepared by either functionalizing the PNA monomeric synthons and assembly into the desired oligomer, or by assembly of PNA monomeric synthons which do not contain conjugate groups, and subsequently attaching the desired conjugate or conjugates thereto. For example, PNA monomer synthons bearing at least one free hydroxyl group may be reacted under basic conditions with a compound having formula $L_v\text{-}(CH_2)_n\text{—NH-PGA}$ where $L_v$ is a leaving group as defined above and PGA is an amine protecting group. Displacement of the leaving group through nucleophilic attack of an oxygen anion produces the desired amine derivative. Suitable leaving groups according to the invention include but are not limited to halogen, alkylsulfonyl, substituted alkylsulfonyl, arylsulfonyl, substituted arylsulfonyl, hetercycicosulfonyl or trichloroacetimidate. A more preferred group includes chloro, fluoro, bromo, iodo, p-(2,4-dinitroanilino)benzenesulfonyl, benzenesulfonyl, methylsulfonyl (mesylate), p-methylbenzenesulfonyl (tosylate), p-bromobenzenesulfonyl, trifluoromethyl-sulfonyl (triflate), trichloroacetimidate, acyloxy, 2,2,2-trifluoroethanesulfonyl, imidazolesulfonyl, and 2,4,6-trichlorophenyl, with bromo being preferred.

PNA oligomers according to the invention can also be prepared by assembling a PNA oligomer and appending alkylamino functionality thereto. For example, PNA oligomers having free hydroxyl groups can be assembled according to known techniques see Examples 26 and 31–37 and then reacted with a reagent having formula $L_v$-$(CH_2)_n$—NH-PGA. As will be recognized, however, greater selectivity can be achieved in terms of placement of alkylamino functionality within a PNA oligomer by introducing such functionality, as discussed above, on selected PNA monomeric synthons and then using both the selected PNA monomeric synthons and other PNA monomeric synthons to construct a desired PNA oligomer.

Once assembled, a PNA bearing one or more groups having a linking moiety ending with a protected amine group is treated with reagents effective to remove the protecting group. Once deprotected, the PNA can be contacted with electrophilic moieties such as, for example, succinimidyl esters and other activated carboxylic acids including C(=O)—O-succinimide and C(=O)—O-pentafluorophenyl, isothiocyanates, sulfonyl chlorides, haloacetamides, phospholipid carboxylic acid active esters, o=phenanthroline-5-iodoacetamide, fluorescein isothiocyanate, 1-pyrene butyric acid-N-hydroxy succinimide ester and carboxylic acid derivatives of peptide nucleic acids. Preferred electrophilic moieties include cholesteryl-3-hemisuccinate-N-hydroxy succinimide ester, pyrene-1-butyric acid-N-hydroxy succinimide ester and polyethylene glycol-propionic acid-N-hydroxy succimide ester.

In other aspects of the invention a conjugate is attached to at least one monomeric unit of a PNA in a diagnostic or therapeutic agent to assist in the transfer of therapeutic or diagnostic agent across cellular membranes. Such a diagnostic or therapeutic agent is formed from a plurality of linked PNA monomeric units bearing natural or non-natural occurring bases and including at least one conjugate which, can include an optional linking moiety, appended thereto, in a sequence that is complementary to and will specifically hybridize with a region of an RNA or DNA of interest. Thus, one or more of the linked PNA monomeric units are "functionalized" to include a conjugate linked to the PNA monomeric unit. This linkage may include an optional linking moiety. Linked PNA monomer units having at least one functionalized PNA monomer unit within their sequence are expected to demonstrate enhanced activity and transport across cellular membranes.

A variety of linking groups can be used to connect conjugates to PNA oligomers or monomer synthons. Certain linking groups, such as Ω-aminoalkoxy moieties and Ω-aminoalkylamino moieties, are particularly useful for linking steroid molecules or reporter molecules to PNA hydroxyl groups. Many linking groups are commercially available, including heterobifunctional and homobifunctional linking moieties available from the Pierce Co. (Rockford, Il). Heterobifunctional and homobifunctional linking moieties are particularly useful in conjunction with the Ω-aminoalkoxy and Ω-aminoalkylamino moieties to form extended linkers that connect peptides and proteins to PNA oligomers. It is intended that the PNA monomer synthons of the invention include adenine bearing PNA synthons functionalized with linkers on their N-6 purine amino groups, guanine bearing PNA monomer synthons functionalized with linkers at their exocyclic N-2 purine amino groups, and cytosine bearing PNA monomer synthons functionalized with linkers on either their N-4 pyrimidine amino groups or 5 pyrimidine positions. This type of linkage is cytosine in Example 47.

A PNA oligomer of the invention may be reacted with an active ester derivative of a conjugate (e.g., cholic acid). Active ester derivatives include N-hydroxysuccinimide esters, tetrafluorophenolic esters, pentafluorophenolic esters and pentachlorophenolic esters. For cholic acid, the reaction of the amino group and the active ester produces a PNA oligomer in which cholic acid is attached to the N-terminal position through a linking group. Cholic acid can be attached to the carboxy terminal of a PNA oligomer by conversion of the cholic acid to the N-hydroxysuccinimide ester thereof, and then by further reaction with the PNA of interest. Cholic acid can be attached to both ends of a PNA oligomer by applying both methods above. As will be seen by those skilled in the art, the above methods are applicable to a large number of conjugates of the present invention.

In further embodiments of the invention, a PNA oligomer bearing an aminolinker at one or more selected non-terminal monomeric units is prepared according to the procedures of Examples 26 and 65. A conjugate such as cholic acid is then attached using an active ester or an isothiocyanate thereof. This approach allows the introduction of a large number of conjugates into a single PNA oligomeric sequence. Indeed each of the PNA monomers in the oligomer can be so substituted.

Attachment of conjugates such as reporter enzymes, peptides, and proteins to PNAs is achieved by reaction of the enzyme, peptide or protein with the above-described amino linking group on the PNA by any of several methods. For example, a peptide or protein can be attached to a functionalized PNA monomer by treatment of the peptide or protein with EDC/sulfo-NHS (i.e., 1-ethyl-3(3-dimethylaminopropylcarbodiimide/N-hydroxysulfo-succinimide), which will facilitate linkage of the carboxyl end of the reporter enzyme, peptide, or protein to the amino terminal end of the PNA, or to an amine-containing linker bound to the PNA. Further, a PNA oligomeric conjugate can be prepared using EDC/sulfo-NHS to attach a carboxyl group of an aspartic or glutamic acid residue in the reporter enzyme, peptide or protein to the amino terminus of a PNA.

Preferably a reporter enzyme-, peptide- or protein-functionalized PNA can be prepared by treating the reporter enzyme, peptide or protein with the PNA oligomer functionalized with a heterobifunctional linker such as m-maleimidobenzoyl-N-hydroxysulfosuccinimide ester (MB S) or succinimidyl 4-(N-maleimidomethyl)cyclohexane-1-carboxylate (SMCC). Thus a thiol function on the reporter enzyme, peptide or protein is linked to the amino function of the PNA. A PNA oligomer-maleimide conjugate is formed by reaction of the amino group of the PNA-bound linker with the MBS or SMCC. maleimide linker. The resulting conjugate is then reacted with peptides or proteins having free sulfhydryl groups.

In a second preferred method, a reporter enzyme-, peptide- or protein-functionalized linked PNA oligomer can be prepared by treatment of the peptide or protein with the PNA using a homobifunctional: linker such as disuccinimidyl suberate (DSS) to link an amino function on the peptide or protein to the amino group of a linker on the PNA. By this mechanism, a succinimidyl functionality can be attached to a PNA oligomer by reaction of the amino group of the PNA-bound linker with a disuccinimidyl suberate linker. The disuccinimidyl suberate linker couples with the amine linker on the sequence to extend the size of the linker. The extended linker is then reacted with amine groups such as, for example, the amine of lysine or other available N-terminus amines on reporter enzymes, peptides and proteins.

PNA oligomers of the present invention may range in size from a dimer to a 200-mer. In preferred embodiments of the present invention the PNA oligomers range in size from a dimer to a 50-mer. In more preferred embodiments the PNA oligomers range in size from a dimer to about a 20-mer.

In further embodiments a 13- to 14-mer PNA is used following standard methods and techniques to identify a region of a DNA coding for a message that is present for the expression of a specific mRNA.

Although longer PNA molecules are envisioned by the present invention it can readily be seen that PNAs having from 1 to about 20 monomeric units will be useful for a number of diagnostic applications.

The compounds of the present invention also will be useful as research reagents for the modulation of the production of a protein by an organism. Modulation may be accomplished by contacting the organism with compounds of the present invention. Preferably the compounds are hybridizable with RNA/DNA coding for the proteins of interest.

The compounds of the present invention will additionally be useful as diagnostic reagents. Diagnostic applications include the detection of the presence or absence of a particular DNA or RNA in a sample. The sample of interest is contacted with a compound of the invention wherein the compound is specifically hybridizable with the RNA of interest. Methods of detecting the hybridization of the diagnostic reagent to the DNA or RNA of interest or alternatively the absence of such hybridization include but are not limited to detection by fluorescence, radiolabeling or capillary gel electrophoresis. PNAs of the present invention are labeled by attachment of the appropriate conjugate thereto. The sample of interest is contacted with the PNA having at least one conjugate attached thereto. The determination of the presence or absence of the nucleic acid of interest will be facilitated by the detection of the presence or absence of hybridization to the sample.

In a further aspect of the invention, the PNAs are conjugated to peptides or proteins, where the peptides have signaling activity and the proteins are, for example, enzymes, transcription factors or antibodies. Also, the PNAs can be attached to water-soluble or water-insoluble polymers.

In another aspect of the invention, the PNAs are conjugated to oligonucleotides or carbohydrates. When desired, a PNA oligomer can be synthesized onto a moiety (e.g., a peptide chain, reporter, intercalator or other type of ligand-containing group) which is attached to a solid support.

As a further aspect of the present invention, PNAs can be used to target RNA and ssDNA to produce hybridization probes for the identification and purification of nucleic acids. Furthermore, the PNAs can be modified to form strand displacement triple helices with dsDNA. Thus, these reagents may be used for research and in diagnostics for detection and isolation of specific nucleic acids.

Triple helix formation, wherein an oligonucleotide is triplexed to a dsDNA, is believed to be the only means known in the art for sequence-specific recognition of dsDNA. However, triple helix formation is largely limited to recognition of homopurine-homopyrimidine sequences. Triplexing with strand displacement using PNAs of this invention is superior to oligonucleotide-dsDNA triple helix recognition in that it may allow for recognition of any sequence by use of the four natural bases.

PNAs of the present invention may be useful as research and diagnostic reagents for the detection of a gene. PNAs are designed with a nucleobase sequence containing from about 12 to about 18 sub-units that are complementary to the regulatory region (the promoter) of the target gene. Samples (e.g. cells, tissue, or other) of interest are prepared following standard methods and techniques and are treated in vitro with a PNA (in a suitable carrier) of the present invention having a specific- sequence and at least one conjugate attached to at least one sub-unit. The PNA will bind to the promoter and block access thereto by RNA polymerase. Consequently, no mRNA, and thus no gene product (protein), is produced. If the target is within a vital gene for a virus, no viable virus particles will be produced. Alternatively, if the target is downstream from the promoter, RNA polymerase will terminate at this position, thus forming a truncated mRNA/protein which is nonfunctional.

Sequence-specific recognition of ssDNA by base complementary hybridization can be exploited to target specific genes and viruses. In this case, the target sequence is contained in the mRNA such that binding of the drug to the target hinders the action of ribosomes and, consequently, translation of the mRNA into protein. The peptide nucleic acids of the invention are superior to prior reagents in that they have significantly higher affinity for complementary ssDNA. Additionally, because PNAs do not possess a charged backbone, lysine or other similar charged moieties can be present without interfering with PNA activity. Additionally, PNAs are water soluble (which should facilitate cellular uptake), and contain amides of non-biological amino acids (which should make them biostable and resistant to enzymatic degradation by, for example, proteases), and are capable of triplex formation with mRNA.

Binding of PNA compounds to double-stranded DNA accompanied by strand displacement is shown in U.S. application Ser. No. 08/088,658, filed Jul. 2, 1993, entitled "Higher Order Structure and Binding of Peptide Nucleic Acids". Binding of PNA and bis PNA to double stranded DNA accompanied by strand invasion is also shown in U.S. application Ser. No. 08/275,951, filed Jul. 15, 1994, entitled "Linked Peptide Nucleic Acids". The illustrative examples therein show that PNA compounds bind via Watson-Crick binding to their complementary strand and extrudes the other strand in a virtually single-stranded conformation.

The chimeric structure between PNAs and DNA or RNA are used in place of, or in addition to a normal PNA strand to effect duplexing, triplexing, nucleic acid binding or protein binding. The RNA or DNA nucleic acid portion of such chimeric structures include but are not limited to a nucleic acid connected via phosphodiester, phosphorothioate, phosphorodithioate, alkyl phosphonate, hydrogen phosphonate, phosphotriester, phosphoramidite and other like phosphorus linkages. They further can include but are not limited to other substitutions such as substitution at the 2' position of a ribose sugar. Particularly preferred are 2'-fluoro's since they increase affinity of the nucleic acid portion of the chimera to other nucleic acids and 2'-O-alkyl, particularly 2'-O-propyl, 2'-O-allyl and the like since they confer nuclease resistance to the nucleic acid strand. The compounds of the present invention may be useful to bind to other target molecules. Target molecules of the present invention can include any of a variety of biologically significant molecules. Such other target molecules can be carbohydrates, glycoproteins or other proteins. In some preferred embodiments of the present invention, the target molecule is a protein such as an immunoglobulin, receptor, receptor binding ligand, antigen or enzyme and more specifically can be a phospholipase, tumor necrosis factor, endotoxin, interleukin, plasminogen activator, protein kinase, cell adhesion molecule, lipoxygenase, hydrolase or transacylase. In other embodiments of the invention the target molecules can be important regions of the human immunodeficiency virus, Candida, herpes viruses, papillomaviruses, cytomegalovirus, rhinoviruses, hepatitis viruses, or influenza viruses. In yet other embodiments of the present invention the target molecules can be regions of an oncogene. In still further embodiments, the target molecule is ras 47-mer stem loop RNA, the TAR element of human immunodeficiency virus, rev response element (RRE) or the gag-pol stem loop of human immunodeficiency virus (HIV). Still other targets can induce cellular activity. For example, a target can induce interferon.

In binding to transcription factors or other target molecules, the transcription factor or other target molecule need not be purified. It can be present, for example, in a whole cell, in a humoral fluid, in a crude cell lysate, in serum or in other humoral or cellular extract. Of course, purified transcription factor or a purified form of another target molecule is also useful in some aspects of the invention.

In still other embodiments of the present invention, synthetically prepared transcription factor or other target molecules can be useful. These synthetically prepared molecules need only contain at least one monomeric unit having a conjugate attached thereto. A transcription factor or other target molecule also can be modified, such as by biotinylation or radiolabeling. For example, synthetically prepared transcription factor can incorporate one or more biotin molecules during synthesis or can be modified post-synthesis.

Transcription factors, as the term is used herein, are DNA- or RNA-binding proteins that regulate the expression of genes. HIV tat and c-rel are examples of transcription factors which regulate the expression of genes. Also encompassed by the term are DNA and RNA binding proteins which are not strictly considered transcription factors, but which are known to be involved in cell proliferation. These transcription factors include c-myc, fos, and jun. Methods of the present invention are particularly suitable for use with transcription factor as target molecules since transcription factors generally occur in very small cellular quantities.

The utility of PNA-containing duplex structures can be illustrated by constructing PNA sequences which correspond to various sequences of the HIV TAR element that have the potential to form duplex structures either as stem-loop structures or two PNAs forming a duplex structure. In a competition assay, PNA structures that bind the tat transcription factor prevent binding of the competitor TAR sequence present in the incubation mixture. As the TAR RNA sequence is biotinylated only that proteins available to bind to TAR will remain on the microtiter plate after washing away unbound molecules and tat protein complexed to a PNA sequence. The concentration dependence of the competition between the TAR PNA structures and biotinylated TAR structure will serve to define those sequences capable of effectively competing for tat and thus useful as HIV modulatory agents.

Additional objects, advantages, and novel features of this invention will become apparent to those skilled in the art upon examination of the following examples thereof, which are not intended to be limiting.

EXAMPLE 1 tert-Butyl 4-nitrophenyl carbonate (1)

Sodium carbonate (29.14 g; 0.275 mol) and 4-nitrophenol (12.75 g; 91.6 mmol) were mixed with dioxane (250 ml). Boc-anhydride (20.0 g; 91.6 mmol) was transferred to the mixture with dioxane (50 ml). The mixture was refluxed for 1 h, cooled to 0° C., filtered and concentrated to ⅓, and then poured into water (350 ml) at 0° C. After stirring for ½ h., the product was collected by filtration, washed with water, and then dried over an appropriate drying agent, in vacuo. Yield 21.3 g (97%). M.p. 73.0-74.5° C. (litt. 78.5–79.5° C.). Anal. for $C_{11}H_{13}NO_5$ found(calc.) C: 55.20(55.23) H, 5.61 (5.48) N, 5.82(5.85).

EXAMPLE 2

(N-Boc-2-aminoethyl)glycine (2)

The title compound was prepared by a modification of the procedure by Heimer, et al. *Int. J. Pept.*, 1984, 23, 203-211 N-(2-Aminoethyl)glycine (3.00 g; 25.4 mmol) was dissolved in water (50 ml), dioxane (50 ml) was added, and the pH was adjusted to 11.2 with 2 N sodium hydroxide. tert-Butyl-4-nitrophenyl carbonate (1, 7.29 g; 30.5 mmol) was dissolved in dioxane (40 ml) and added dropwise over a period of 2 h, during which time the pH was maintained at 11.2 with 2 N sodium hydroxide. The pH was adjusted periodically to 11.2 for three more hours and then the solution was left overnight. The solution was cooled to 0° C. and the pH was carefully adjusted to 3.5 with 0.5 M hydrochloric acid. The aqueous solution was washed with chloroform (3×200 ml), the pH adjusted to 9.5 with 2N sodium hydroxide and the solution was evaporated to dryness, in vacuo (14 mm Hg). The residue was extracted with DMF (25+2×10 ml) and the extracts filtered to remove excess salt. This results in a solution of the title compound in about 60% yield and greater than 95% purity by tlc (visualized by ninhydrin, Rf=0.3). The solution was used in the following preparations of Boc-aeg (aeg=aminoethylglycine) derivatives without further purification.

EXAMPLE 3

N-1-Carboxymethylthymine (3)

This procedure is different from the literature synthesis, but is easier, gives higher yields, and leaves no unreacted thymine in the product. To a suspension of thymine (40.0 g; 0.317 mol) and potassium carbonate (87.7 g; 0.634 mmol) in DMF (900 ml) was added methyl bromoacetate (30.00 ml; 0.317 mmol). The mixture was stirred vigorously overnight under nitrogen. The mixture was filtered and evaporated to dryness, in vacuo.

The solid residue was treated with water (300 ml) and 4 N hydrochloric acid (12 ml), stirred for 15 min at 0° C., filtered, and washed with water (2×75 ml). The precipitate was treated with water (120 ml) and 2N sodium hydroxide (60 ml), and was boiled for 10 minutes. The mixture was cooled to 0° C., filtered, and the pure title compound was precipitated by the addition of 4 N hydrochloric acid (70 ml). Yield after drying, in vacuo over an appropriate drying agent: 37.1 g (64%). $^1$H-NMR: (90 MHz; DMSO-$d_6$): 11.33 ppm (s,1H,NH); 7.49(d,J=0.92 Hz,1H,ArH); 4.38 (s,2H,CH$_2$); 1.76 (d,J=0.92 Hz,T-CH$_3$).

EXAMPLE 4

N-1-Carboxymethylthymine pentafluorophenyl ester (4)

N-1-Carboxymethylthymine (3, 10.0g; 54.3 mmol) and pentafluorophenol (10.0 g; 54.3 mmol) were dissolved in DMF (100 ml) and cooled to 5C in ice water. DCC (13.45 g; 65.2 mmol) then was added. When the temperature passed below 5° C., the ice bath was removed and the mixture was stirred for 3 h at ambient temperature. The precipitated DCU was removed by filtration and washed twice with DMF (2×10 ml). The combined filtrate was poured into ether (1400 ml) and cooled to 0° C. Petroleum ether (1400 ml) was added and the mixture was left overnight. The title compound was isolated by filtration and was washed thoroughly with petroleum ether. Yield: 14.8 g(78%). The product was pure enough to carry out the next reaction, but an analytical sample was obtained by recrystallization from 2-propanol. M.p. 200.5–206° C. Anal. for $C_{13}H_7F_5N_2O_4$. Found(calc.) C: 44.79(44.59); H: 2.14(2.01) N: 8.13(8.00). FAB-MS: 443 (M+1+glycerol), 351 (M+1). $^1$H-NMR (90 MHz; DMSO-$d_6$): 11.52 ppm (s,1H,NH); 7.64 (s,1H,ArH); 4.99 (s,2H,CH$_2$); 1.76 (s,3H,CH$_3$).

EXAMPLE 5

N-(N-Boc-2-aminoethyl)-N-[(1-thyminyl)acetyl] glycine (5)

To the DMF-solution from Example 2 was added triethyl amine (7.08 ml; 50.8 mmol) followed by N-1-carboxymethylthymine pentafluorophenyl ester (4, 4.45 g; 12.7 mmol). The resultant solution was stirred for 1 h. The solution was cooled to 0° C. and treated with cation exchange material ("Dowex 50W X-8", 40 g) for 20 min. The cation exchange material was removed by filtration, washed with dichloromethane (2×15 ml), and dichloromethane (150 ml) was added. The resulting solution was washed with saturated sodium chloride, dried over magnesium sulfate, and evaporated to dryness, in vacuo, first by a water aspirator and then by an oil pump. The residue was shaken with water (50 ml) and evaporated to dryness. This procedure was repeated once. The residue then was dissolved in methanol (75 ml) and poured into ether (600 ml) and petroleum ether (1.4 L). After stirring overnight, the white solid was isolated by filtration and was washed with petroleum ether. Drying over an appropriate drying agent, in vacuo, gave 3.50 g (71.7%). M.p. 142–147° C. Anal. for $C_{16}H_{24}N_4O_7$. Found(calc.) C, 49.59(50.00) H: 6.34(6.29) N, 14.58(14.58). $^1$H-NMR (250 MHz, DMSO-$d_6$): Due to the limited rotation around the secondary amide bond several of the signals were doubled in the ratio 2:1,(indicated in the list by mj. for major and mi. for minor). 12.73 ppm (b,1H, —CO$_2$H); 11.27 ppm (s, mj., imide); 11.25 ppm (s, mi., imide); 7.30 ppm (s, mj., ArH); 7.26 ppm (s, mi., ArH); 6.92 (unres. t, mj., BocNH); 6.73 ppm (unres. t; mi., BocNH); 4.64 ppm (s, mj., T-CH$_2$—CO—); 4.47 ppm (s, mi., T-CH$_2$—CO—); 4.19 ppm (s, mi., CONRCH$_2$CO$_2$H); 3.97 ppm (s, mj., CONRCH$_2$CO$_2$H); 3.41-2.89 ppm (unres. m, —CH$_2$CH$_2$— and water); 1.75 ppm (s,3H, T-CH$_3$); 1.38 ppm (s, 9H, t-Bu). $^{13}$C-NMR: 170.68 ppm (CO); 170.34 (CO); 167.47 (CO); 167.08 (CO); 164.29 (CO); 150.9 (C5"); 141.92(C6"); 108.04(C2');77.95 and 77.68 (Thy-CH$_2$CO); 48.96, 47.45 and 46.70 (—CH2C H$_2$— and NCH$_2$CO$_2$H); 37.98 (Thy-CH$_3$); 28.07 (t-Bu). FAB-MS: 407 (M+Na$^+$); 385 (M+H$^+$).

EXAMPLE 6

N-(N-Boc- -aminoethyl)-N-[(1 thyminyl)acetyl] glycine pentafluorophenyl ester (6, Boc-Taeg.OPfp)

N-(N-Boc-2-aminoethyl)-N-[(1-thyminyl)acetyl]glycine (5) (2.00 g; 5.20 mmol) was dissolved in DMF (5 ml) and methylene chloride (15 ml) was added. Pentafluorophenol (1.05 g; 5.72 mmol) was added and the solution was cooled to 0° C. in an ice bath. DDC then was added (1.29 g; 6.24 mmol) and the ice bath was removed after 2 min. After 3 h with stirring at ambient temperature, the precipitated DCU was removed by filtration and washed with methylene chloride. The combined filtrate was washed twice with aqueous sodium hydrogen carbonate and once with saturated sodium chloride, dried over magnesium sulfate, and evaporated to dryness, in vacuo. The solid residue was dissolved in dioxane (150 ml) and poured into water (200 ml) at 0° C. The title compound was isolated by filtration, washed with water, and dried over an appropriate drying agent, in vacuo. Yield: 2.20 g (77%). An analytical sample was obtained by recrystallisation from 2-propanol. M.p. 174–175.5° C. Analysis for $C_{22}H_{23}N_4O_7F_5$, found(calc.): C, 48.22(48.01); H: 4.64(4.21); N: 9.67(10.18). $^1$H-NMR (250 MHz, CDCl$_3$): Due to the limited rotation around the secondary amide bond several of the signals were doubled in the ratio 6:1 (indicated in the list by mj. for major and mi. for minor). 7.01 ppm (s, mi., ArH); 6.99 ppm (s, mj., ArH); 5.27 ppm (unres. t, BocN H); 4.67 ppm (s, mj., T-CH$_2$—CO—); 4.60 ppm (s, mi., T-CH$_2$—CO—); 4.45 ppm (s, mj., CONRCH$_2$CO$_2$Pfp); 4.42 ppm (s, mi., CONRCH$_2$CO$_2$Pfp); 3.64 ppm (t,2H, BocNHCH$_2$CH$_2$-); 3.87 ppm ("q",2H,BocNHCH$_2$CH$_2$—); 1.44(s,9H,t-Bu). FAB-MS: 551 (10; M+1); 495 (10; M+1-tBu); 451 (80; -Boc).

EXAMPLE 7

N-(N-Boc-2-aminoethyl)-N-(Cbz)glycine (7)

Aminoethyl glycine (52.86 g; 0.447 mol) was dissolved in water (900 ml) and dioxane (900 ml) was added. The pH was adjusted to 11.2 with 2N NaOH. While the pH was kept at 11.2, tert-butyl-p-nitrophenyl carbonate (128.4 g; 0.537 mol) was dissolved in dioxane (720 ml) and added dropwise over the course of 2 hours. The pH was kept at 11.2 for at least three more hours and then left with stirring overnight. The yellow solution was cooled to 0° C. and the pH was adjusted to 3.5 with 2 N HCl. The mixture was washed with chloroform (4×100 ml), and the pH of the aqueous phase was readjusted to 9.5 with 2N NaOH at 0° C. Cbz chloride (73.5 ml; 0.515 mol) was added over half an hour, while the pH was kept at 9.5 with 2 N NaOH. The pH was adjusted frequently over the next 4 hours, and the solution was left with stirring overnight. On the following day the solution was washed with ether (3×600 ml) and the pH of the solution was afterwards adjusted to 1.5 with 2 N HCl at 0° C. The title compound was isolated by extraction with ethyl acetate (5×1000 ml). The ethyl acetate solution was dried over magnesium sulfate and evaporated to dryness, in vacuo. This afforded 138 g, which was dissolved in ether (300 ml) and precipitated by the addition of petroleum ether (1800 ml).

Yield 124.7 g (79%). M.p. 64.5-85° C. Anal. for $C_{17}H_{24}N_2O_6$ found(calc.) C, 58.40(57.94); H: 7.02(6.86); N: 7.94(7.95). $^1$H-NMR (250 MHz, CDCl$_3$) 7.33 & 7.32 (5H, Ph); 5.15 & 5.12 (2H, PhC$\underline{H}_2$); 4.03 & 4.01 (2H, NC$\underline{H}_2$CO$_2$H); 3.46 (b, 2H, BocNHCH$_2$C$\underline{H}_2$); 3.28 (b, 2H, BocNHC$\underline{H}_2$CH$_2$); 1.43 & 1.40 (9H, $^t$Bu). HPLC (260 nm) 20.71 min. (80.2%) and 21.57 min. (19.8%). The UV-spectra (200 nm -300 nm) are identical, indicating that the minor peak consists of Bis-Z-AEG.

EXAMPLE 8

N-(N-Boc-2-aminoethyl)glycine ethyl ester (8)

N-(N-Boc-2-aminoethyl)-N-(Cbz)glycine (7, 60.0 g; 0.170 mol) and N,N-dimethyl-4-aminopyridine (6.00 g) were dissolved in absolute ethanol (500 ml), and cooled to 0° C. 3 0 before the addition of DCC (42.2 g; 0.204 mol). The ice bath was removed after 5 minutes and stirring was continued for 2 more hours. The precipitated DCU (32.5 g dried) was removed by filtration and washed with ether (3×100 ml). The combined filtrate was washed successively with diluted potassium hydrogen sulfate (2×400 ml), diluted sodium hydrogencarbonate (2×400 ml) and saturated sodium chloride (1×400 ml). The organic phase was filtered, then dried over magnesium sulfate, and evaporated to dryness, in vacuo, which yielded 66.1 g of an oily substance which contained some DCU.

The oil was dissolved in absolute ethanol (600 ml) and was added 10% palladium on carbon (6.6 g) was added. The solution was hydrogenated at atmospheric pressure, where the reservoir was filled with 2 N sodium hydroxide. After 4 hours, 3.3 L was consumed out of the theoretical 4.2 L. The reaction mixture was filtered through celite and evaporated to dryness, in vacuo, affording 39.5 g (94%) of an oily substance. A 13 g portion of the oily substance was purified by silica gel (600 g SiO$_2$) chromatography. After elution with 300 ml 20% petroleum ether in methylene chloride, the title compound was eluted with 1700 ml of 5% methanol in methylene chloride. The solvent was removed from the fractions with satisfactory purity, in vacuo and the yield was 8.49 g. Alternatively 10 g of the crude material was purified by Kugel Rohr distillation. $^1$H-NMR (250 MHz, CD$_3$OD); 4.77 (b. s, NH); 4.18 (q, 2H, MeC$\underline{H}_2$-); 3.38 (s, 2H, NC$\underline{H}_2$CO$_2$Et); 3.16 (t, 2H, BocNHC$\underline{H}_2$CH$_2$); 2.68 (t, 2H, BocNHCH$_2$C$\underline{H}_2$); 1.43 (s, 9H, $^t$Bu) and 1.26 (t, 3H, CH$_3$) $^{13}$C-NMR 171.4 ($\underline{C}$OEt); 156.6 (CO); 78.3 ((CH$_3$)$_3\underline{C}$); 59.9 (CH$_2$); 49.0 (CH$_2$); 48.1 (CH$_2$); 39.0 (CH$_2$); 26.9 (CH$_2$) and 12.6 (CH$_3$).

EXAMPLE 9

N-(N-Boc-2-aminoethyl)glycine methyl ester (9)

The procedure of Example 8 was used, with methanol being substituted for ethanol. The final product was purified by flash column chromatography.

EXAMPLE 10

N-(N-Boc-2-aminoethyl)-N-[(1-thyminyl)acetyl] glycine ethyl ester (10)

N-(N-Boc-2-aminoethyl)glycine ethyl ester (8, 13.5 g; 54.8 mmol), DhbtOH (9.84 g; 30 60.3 mmol) and N-1-carboxymethyl thymine (4, 11.1 g; 60.3 mmol) were dissolved in DMF (210 ml). Methylene chloride (210 ml) then was added. The solution was cooled to 0° C. in an ethanol/ice bath and DCC (13.6 g; 65.8 mmol) was added. The ice bath was removed after 1 hour and stirring was continued for another 2 hours at ambient temperature. The precipitated DCU was removed by filtration and washed twice with methylene chloride 5 (2×75 ml). To the combined filtrate was added more methylene chloride (650 ml). The solution was washed successively with diluted sodium hydrogen carbonate (3×500 ml), diluted potassium hydrogen sulfate (2×500 ml), and saturated sodium chloride (1×500 ml). Some precipitate was removed from the organic phase by filtration, The organic phase was dried over magnesium sulfate and evaporated to dryness, in vacuo. The oily residue was dissolved in methylene chloride (150 ml), filtered and the title compound was precipitated by the addition of petroleum ether (350 ml) at 0° C. The methylene chloride/petroleum ether procedure was repeated once. This afforded 16.0 g (71%) of the title compound which was more than 99% pure by HPLC.

EXAMPLE 11

N-(N-Boc-2-aminoethyl)-N-[(1-thyminyl)acetyl] glycine (6a)

The material from Example 10 was suspended in THF (194 ml, gives a 0.2 M solution), and 1 M aqueous lithium hydroxide (116 ml) was added. The mixture was stirred for 45 minutes at ambient temperature and then filtered to remove residual DCU. Water (40 ml) was added to. the solution which was then washed with methylene chloride (300 ml). Additional water (30 ml) was added, and the alkaline solution was washed once more with methylene chloride (150 ml). The aqueous solution was cooled to 0° C. and the pH was adjusted to 2 by the dropwise addition of 1 N HCl (approx. 110 ml). The title compound was extracted with ethyl acetate (9×200 ml), the combined extracts +were dried over magnesium sulfate and were evaporated to dryness, in vacuo. The residue was evaporated once from methanol, which after drying overnight afforded a colorless glassy solid. Yield 9.57 g (64%). HPLC>98% $R_T$=14.8 min. Anal. for $C_{16}H_{24}N_4O_7/0.25H_2O$ Found (calc.) C: 49.29 (49.42); H: 6.52(6.35); N: 14.11(14.41). Due to the limited rotation around the secondary amide, several of the signals were doubled in the ratio 2:1 (indicated in the list by mj. for major and mi. for minor). $^1$H-NMR (250 MHz, DMSO-d$_6$): 12.75 (b.s., 1H, CO$_2$H); 11.28 (s, "1H", mj., imide NH); 11.26 (s, "1H", mi., imide NH); 7.30 (s, "1H", mj., T H-6); 7.26 (s, "1H", mi., T H-6); 6.92 (b.t., "1H", mj., BocNH); 6.73 (b.t., "1H", mi., BocNH); 4.64 (s, "2H", mj., C$\underline{H}_2$CON); 4.46 (s, "2H", mj., C$\underline{H}_2$CON); 4.19 (s, "2H", mi., C$\underline{H}_2$CO$_2$H); 3.97 (s, "2H", mj., C$\underline{H}_2$CO$_2$H); 3.63-3.01 (unresolved m, includes water, C$\underline{H}_2$C$\underline{H}_2$); 1.75 (s, 3H, C$\underline{H}_3$) and 1.38 (s, 9H, $^t$Bu).

EXAMPLE 12

N-4-Cbz cytosine (12)

Over a period of about 1 h, Cbz chloride (52 ml; 0.36 mol) was added dropwise to a suspension of cytosine(8, 20.0 g; 0.18 mol) in dry pyridine (1000 ml) at 0° C. under nitrogen in oven-dried equipment. The solution then was stirred overnight, after which the pyridine suspension was evaporated to dryness, in vacuo. Water (200 ml) and 4 N hydrochloric acid were added to reach pH ~1. The resulting white precipitate was filtered off, washed with water and partially dried by air suction. The still-wet precipitate was boiled with absolute ethanol (500 ml) for 10 min, cooled to 0° C., filtered, washed thoroughly with ether, and dried, in vacuo. Yield 24.7 g (54%). M.p.>250° C. Anal. for C12H11N3O3. Found(calc.); C: 58.59(58.77); H: 4.55(4.52); N: 17.17 (17.13). No NMR spectra were recorded since it was not possible to get the product dissolved.

EXAMPLE 13

N-4-Cbz-N-1-carboxymethyl cytosine (13)

In a three necked round bottomed flask equipped with mechanical stirring and nitrogen coverage was placed methyl bromacetate (7.82 ml;82.6 mmol) and a suspension of N-4-Cbz cytosine (12, 21.0 g;82.6 mmol) and potassium carbonate (11.4 g;82.6 mmol) in dry DMF (900 ml). The mixture was stirred vigorously overnight, filtered, and evaporated to dryness, in vacuo. Water (300 ml) and 4 N hydrochloric acid (10 ml) were added, the mixture was stirred for 15 minutes at 0° C., filtered, and washed with water (2×75 ml). The isolated precipitate was treated with water (120 ml), 2N sodium hydroxide (60 ml), stirred for 30 min, filtered, cooled to 0° C., and 4 N hydrochloric acid (35 ml) was added. The title compound was isolated by filtration, washed thoroughly with water, recrystallized from methanol (1000 ml) and washed thoroughly with ether. This afforded 7.70 g (31%) of pure compound. The mother liquor from the recrystallization was reduced to a volume of 200 ml and cooled to 0° C. This afforded an additional 2.30 g of a material that was pure by tlc but had a reddish color. M.p. 266–274° C. Anal. for $C_{14}H_{13}N_3O_5$. Found(calc.); C: 55.41 (55.45); H: 4.23(4.32); N: 14.04(13.86). $^1$H-NMR (90 MHz; DMSO-$d_6$): 8.02 ppm (d,J=7.32 Hz,1H,H-6); 7.39 (s,5H, Ph); 7.01 (d,J=7.32 Hz,1H,H-5); 5.19 (s,2H,PhC$\underline{H}_2$-); 4.52 (s,2H).

EXAMPLE 14

N-4-Cbz-N-1-carboxymethyl cytosine pentafluorophenyl ester (14)

N-4-Cbz-N-1-carboxymethyl-cytosine (13, 4.00 g; 13.2 mmol) and pentafluorophenol (2.67 g; 14.5 mmol) were mixed with DMF (70 ml), cooled to 0° C. with ice-water, and DCC (3.27 g; 15.8 mmol) was added. The ice bath was removed after 3 min and the mixture was stirred for 3 h at room temperature. The precipitated DCU was removed by filtration, washed with DMF, and the filtrate was evaporated to dryness, in vacuo (0.2 mmHg). The solid residue was treated with methylene chloride (250 ml), stirred vigorously for 15 min, filtered, washed twice with diluted sodium hydrogen carbonate and once with saturated sodium chloride, dried over magnesium sulfate, and evaporated to dryness, in vacuo. The solid residue was recrystallized from 2-propanol (150 ml) and the crystals were washed thoroughly with ether. Yield 3.40 g (55%). M.p. 241-245° C. Anal. for $C_{20}H_{12}N_3F_5O_5$. Found(calc.); C: 51.56(51.18); H: 2.77(2.58); N: 9.24(8.95). $^1$H-NMR (90 MHz; CDCl$_3$): 7.66 ppm (d,J=7.63 Hz,1H,H-6); 7.37 (s,5H,Ph); 7.31 (d,J=7.63 Hz,1H,H-5); 5.21 (s,2H,PhC$\underline{H}_2$—); 4.97 (s,2H,NC$\underline{H}_2$—). FAB-MS: 470 (M+1)

EXAMPLE 15

N-(N-Boc-2-aminoethyl)-N-[(N-4-Cbz-1-cytosinyl) acetyl]glycine (15)

To a solution of (N-Boc-2-aminoethyl)glycine 2, in DMF, prepared as described in Example 2, was added triethyl amine (7.00 ml; 50.8 mmol) and N-4-Cbz-N-1-carboxymethyl-cytosine pentafluorophenyl ester (14, 2.70 g; 5.75 mmol). After stirring the solution for 1 h at room temperature, methylene chloride (150 ml), saturated sodium chloride (250 ml), and 4 N hydrochloric acid to pH ~1 were added. The organic layer was separated and washed twice with saturated sodium chloride, dried over magnesium sulfate, and evaporated to dryness, in vacuo, first with a water aspirator and then with an oil pump. The oily residue was treated with water (25 ml) and was again evaporated to dryness, in vacuo. This procedure then was repeated. The oily residue (2.80 g) was then dissolved in methylene chloride (100 ml), petroleum ether (250 ml) was added, and the mixture was stirred overnight. The title compound was isolated by filtration and washed with petroleum ether. Tlc (system 1) indicated substantial quantities of pentafluorophenol, but no attempt was made to remove it. Yield: 1.72 g (59%). M.p. 156° C.(decomp.). $^1$H-NMR (250 MHz, CDCl$_3$): Due to the limited rotation around the secondary amide bond several of the signals were doubled in the ratio 2: 1,(indicated in the list by mj. for major and mi. for minor). 7.88 ppm (dd,1H,H-6); 7.39 (m,5H,Ph); 7.00 (dd,1H,H-5); 6.92 (b,1H,BocNH); 6.74 (b,1H,ZN$\underline{H}$)-?; 5.19 (s,2H,Ph-C$\underline{H}_3$); 4.81 ppm (s, mj., Cyt-CH$_2$—CO—); 4.62 ppm (s, mi., Cyt-CH$_2$—CO—); 4.23 (s, mi., CONRC$\underline{H}_2$CO$_2$H); 3.98 ppm (s, mj., CONRC$\underline{H}_2$CO$_2$H); 3.42-3.02 (unres. m, —CH$_2$CH$_2$— and water);1.37 (s,9H,tBu). FAB-MS: 504 (M+1); 448 (M+1-tBu).

EXAMPLE 16

N-(N-Boc-2-aminoethyl)-N-[(N-4-Cbz-1-cytosinyl) acetyl]glycine pentafluorophenyl ester (16)

N-(N-Boc-2-aminoethyl)-N-[(N-4-Cbz-1-cytosinyl) acetyl]glycine (15, 1.50 g; 2.98 mmol) and pentafluorophenol (548 mg; 2.98 mmol) was dissolved in DMF (10 ml) Methylene chloride (10 ml) was added, the reaction mixture was cooled to 0° C. in an ice bath, and DCC (676 mg; 3.28 mmol) was added. The ice bath was removed after 3 min and the mixture was stirred for 3 h at ambient temperature. The precipitate was isolated by filtration and washed once with methylene chloride. The precipitate was dissolved in boiling dioxane (150 ml) and the solution was cooled to 15° C., whereby DCU precipitated. The DCU was removed by filtration and the resulting filtrate was poured into water (250 ml) at 0° C. The title compound was isolated by filtration, was washed with water, and dried over an appropriate drying agent, in vacuo. Yield 1.30 g (65%). Analysis for $C_{29}H_{28}N_5O_8F_5$. Found(calc.); C: 52.63(52.02); H: 4.41(4.22); N: 10.55(10.46). $^1$H-NMR (250 MHz; DMSO-$d_6$): showed essentially the spectrum of the above acid, most probably due to hydrolysis of the ester. FAB-MS: 670 (M+1); 614 (M+1-tBu)

EXAMPLE 17

N-(N-Boc-2-aminoethyl)-N-[(N-4-Cbz-1-cytosinyl)acetyl]glycine (17)

N-(N-Boc-2-aminoethyl)glycine ethyl ester (8, 5.00 g; 20.3 mmol), DhbtOH (3.64 g; 22.3 mmol) and N-4-Cbz-N-1-carboxymethyl cytosine (13, 6.77 g; 22.3 mmol) were suspended in DMF (100 ml). Methylene chloride (100 ml) was then added. The solution was cooled to 0° C. and DCC (5.03 g;24.4 mmol) was added. The ice bath was removed after 2 h and stirring was continued for another hour at ambient temperature. The reaction mixture was evaporated to dryness, in vacuo. The residue was suspended in ether (100 ml). and stirred vigorously for 30 min. The solid material was isolated by filtration and the ether wash procedure was repeated twice. The material was then stirred vigorously for 15 min with dilute sodium hydrogencarbonate (aprox. 4% solution, 100 ml), filtered and washed. with water. This procedure was then repeated once, which after drying left 17.0 g. of yellowish solid material. The solid was then boiled with dioxane (200 ml) and filtered while hot. After cooling, water (200 ml) was added. The precipitated material was isolated by filtration, washed with water, and dried. According to HPLC (observing at 260 nm) this material has a purity higher than 99%, besides the DCU. The ester was then suspended in THF (100 ml), cooled to 0° C., and 1 N LiOH (61 ml) was added. After stirring for 15 minutes, the mixture was filtered and the filtrate was washed with methylene chloride (2×150 ml). The alkaline solution then was cooled to 0° C. and the pH was adjusted to 2.0 with 1 N HCl. The title compound was isolated by filtration and was washed once with water, leaving 11.3 g of a white powder after drying. The material was suspended in methylene chloride (300 ml) and petroleum ether (300 ml) was added. Filtration and wash afforded 7.1 g (69%) after drying. HPLC showed a purity of 99% $R_T$=19.5 min, and a minor impurity at 12.6 min (approx. 1%) most likely the Z-deprotected monomer. Anal. for $C_{23}H_{29}N_5O_8$ found(calc.) C, 54.16(54.87); H: 5.76(5.81) and N, 13.65(13.91). $^1$H-NMR (250 MHz, DMSO-$d_6$). 10.78 (b.s,1H,$CO_2\underline{H}$); 7.88 (2 overlapping doublets, 1H, Cyt H-5); 7.41-7.32 (m, 5H, Ph); 7.01 (2 overlapping doublets, 1H, Cyt H-6); 6.94 & 6.78 (unres. triplets, 1H, BocN$\underline{H}$); 5.19 (s, 2H, PhC$\underline{H}_2$); 4.81 & 4.62 (s, 2H, C$\underline{H}_2$CON); 4.17 & 3.98 (s, 2H, C$\underline{H}_2$CO$_2$

EXAMPLE 18

9-Carboxymethyl adenine ethyl ester (18)

Adenine (10.0 g, 74 mmol) and potassium carbonate (10.29 g, 74.0 mmol) were suspended in DMF and ethyl bromoacetate (8.24 ml, 74 mmol) was added. The suspension was stirred for 2.5 h under nitrogen at room temperature and then filtered. The solid residue was washed three times with DMF (10 ml). The combined filtrate was evaporated to dryness, in vacuo. The yellow-orange solid material was poured into water (200 ml) and 4 N HCl was added to pH≈6. After stirring at 0° C. for 10 min, the solid was filtered off, washed with water, and recrystallized from 96% ethanol (150 ml). The title compound was isolated by filtration and washed thoroughly with ether. Yield 3.4 g (20%). M.p. 215.5-220° C. Anal. for $C_9H_{11}N_5O_2$ found(calc.): C: 48.86 (48.65); H: 5.01(4.91); N: 31.66(31.42). $^1$H-NMR (250 MHz; DMSO-$d_6$): (s, 2H, H-2 & H-8), 7.25 (b. s., 2H, NH$_2$), 5.06 (s, 2H, NCH$_2$), 4.17 (q, 2H, J=7.11 Hz, OCH$_2$) and 1.21 (t, 3H, J=7.13 Hz, NCH$_2$). $^{13}$C-NMR. 152.70, 141.30, 61.41, 43.97 and 14.07. FAB-MS. 222 (MH+). IR: Frequency in cm$^{-1}$ (intensity). 3855 (54.3), 3274(10.4), 3246(14.0), 3117 (5.3), 2989(22.3), 2940(33.9), 2876(43.4), 2753(49.0), 2346 (56.1), 2106(57.1), 1899(55.7), 1762(14.2), 1742(14.2), 1742(1.0),1671(1.8),1644(10.9), 1606(0.6), 1582(7.1),1522 (43.8),1477(7.2),1445(35.8) and 1422(8.6). The position of alkylation was verified by X-ray crystallography on crystals, which were obtained by recrystallization from 96% ethanol.

Alternatively, 9-carboxymethyl adenine ethyl ester 18, can be prepared by the following procedure. To a suspension of adenine (50.0 g, 0.37 mol) in DMF (1100 ml) in 2 L three-necked flask equipped with a nitrogen inlet, a mechanical stirrer and a dropping funnel was added 16.4 g (0.407 mol) hexane washed sodium hydride- mineral oil dispersion. The mixture was stirred vigorously for 2 hours, then ethyl bromacetate 75 ml, 0.67 mol) was added dropwise over the course of 3 hours. The mixture was stirred for one additional hour, whereafter tlc indicated complete conversion of adenine. The mixture was evaporated to dryness at 1 mm Hg and water (500 ml) was added to the oily residue which caused crystallization of the title compound. the solid was recrystallized from 60% ethanol (600 ml). Yield after drying 53.7 (65.6%). HPLC (215 nm) purity>99.5%.

EXAMPLE 19

N-6-Cbz-9-carboxymethyl adenine ethyl ester (19)

9-Carboxymethyladenine ethyl ester (18, 3.40 g, 15.4 mmol) was dissolved in dry DMF (50 ml) by gentle heating, cooled to 20° C., and added to a solution of N-ethyl-Cbz-imidazole tetrafluoroborate (62 mmol) in methylene chloride (50 ml) over a period of 15 min with ice-cooling. Some precipitation was observed. The ice bath was removed and the solution was stirred overnight. The reaction mixture was treated with saturated sodium hydrogen carbonate (100 ml). After stirring for 10 min, the phases were separated and the. organic phase was washed successively with one volume of water, dilute potassium hydrogen sulfate (twice), and with saturated sodium chloride. The solution was dried over magnesium sulfate and evaporated to dryness, in vacuo, which afforded 11 g of an oily material. The material was dissolved in methylene chloride (25 ml), cooled to 0° C., and precipitated with petroleum ether (50 ml). This procedure was repeated once to give 3.45 g (63%) of the title compound. M.p. 132-35° C. Analysis for $C_{17}H_{17}N_5O_4$ found (calc.): C: 56.95(57.46); H: 4.71(4.82); N: 19.35(19.71). $^1$H-NMR (250 MHz; CDCl$_3$): 8.77 (s, 1H, H-2 or H-8); 7.99 (s, 1H, H-2 or H-8); 7.45-7.26 (m, 5H, Ph); 5.31 (s, 2H, N—C$\underline{H}_2$); 4.96 (s, 2H, Ph-C$\underline{H}_2$); 4.27 (q, 2H, J=7.15 Hz, C$\underline{H}_2$CH$_3$) and 1.30 (t, 3H, J=7.15 Hz, CH$_2$C$\underline{H}_3$). $^{13}$C-NMR: 153.09; 143.11; 128.66; 67.84; 62.51; 44.24 and 14.09. FAB-MS: 356 (MH+) and 312 (MH+–CO$_2$). IR: frequency in cm$^{-1}$ (intensity). 3423 (52.1); 3182 (52.8); 3115(52.1); 3031(47.9); 2981(38.6); 1747(1.1); 1617(4.8); 15.87(8.4); 1552(25.2); 1511(45.2); 25 1492(37.9); 1465(14.0) and 1413(37.3).

EXAMPLE 20

N-6-Cbz-9-carboxymethyl adenine (20)

N-6-Cbz-9-carboxymethyladenine ethyl ester (19, 3.20 g; 9.01 mmol) was mixed with methanol (50 ml) cooled to 0° C. Sodium Hydroxide Solution (50 ml; 2N) was added, whereby the material quickly dissolved. After 30 min at 0° C., the alkaline solution was washed with methylene chloride (2×50 ml). The aqueous solution was brought to pH 1.0 with 4 N HCl at 0° C., whereby the title compound precipitated. The yield after filtration, washing with water, and drying was 3.08 g (104%). The product contained salt and elemental analysis reflected that. Anal. for $C_{15}H_{13}N_5O_4$ found(calc.): C: 46.32(55.05); H: 4.24(4.00); N: 18.10(21.40) and C/N, 2.57(2.56). $^1$H-NMR(250 MHz; DMSO-$d_6$): 8.70 (s, 2H, H-2 and H-8); 7.50-7.35 (m, 5H, Ph); 5.27 (s, 2H, N—C$\underline{H}_2$); and 5.15 (s, 2H, Ph-C$\underline{H}_2$). $^{13}$C-NMR. 168.77, 152.54, 151.36, 148.75, 145.13, 128.51, 128.17, 127.98, 66.76 and 44.67.IR (KBr) 3484(18.3); 3109 (15.9); 3087(15.0); 2966(17.1); 2927(19.9); 2383(53.8); 1960(6.27); 1739(2.5); 1688(5.2); 1655(0.9); 1594(11.7); 1560(12.3); 1530(26.3); 1499(30.5); 1475(10.4); 1455(14.0); 1429(24.5) and 1411(23.6). FAB-MS: 328 (MH+) and 284 (MH+—$CO_2$). HPLC (215 nm, 260 nm) in system 1: 15.18 min, minor impurities all less than 2%.

EXAMPLE 21

N-(N-Boc-2-aminoethyl)-N-[(N-6-Cbz-9-adeninyl) acetyl]glycine ethyl ester (21)

N-(N-Boc-2-aminoethyl)glycine ethyl ester (8, 2.00 g; 8.12 mmol), DhbtOH (1.46 g; 8.93 mmol) and N-6-Cbz-9-carboxymethyl adenine (20, 2.92 g; 8.93 mmol) were dissolved in DMF (15 ml). Methylene chloride (15 ml) then was added. The solution was cooled to 0° C. in an ethanol/ice bath. DCC (2.01 g; 9.74 mmol) was added. The ice bath was removed after 2.5 h and stirring was continued for another 1.5 hour at ambient temperature. The precipitated DCU was removed by filtration and washed once with DMF (15 ml), and twice with methylene chloride (2×15 ml). To the combined filtrate was added more methylene chloride (100 ml). The solution was washed successively with dilute sodium hydrogen carbonate (2×100 ml), dilute potassium hydrogen sulfate (2×100 ml), and saturated sodium chloride (1×100 ml). The organic phase was evaporated to dryness, in vacuo, which afforded 3.28 g (73%) of a yellowish oily substance. HPLC of the raw product showed a purity of only 66% with several impurities, both more and less polar than the main peak. The oil was dissolved in absolute ethanol (50 ml) and activated carbon was added. After stirring for 5 minutes, the solution was filtered. The filtrate was mixed with water (30 ml) and was left with stirring overnight. The next day, the white precipitate was removed by filtration, washed with water, and dried, affording 1.16 g (26%) of a material with a purity higher than 98% by HPLC. Addition of water to the mother liquor afforded another 0.53 g with a purity of approx. 95%. Anal. for $C_{26}H_{33}N_7O_7.H_2O$ found (calc.) C: 55.01(54.44; H: 6.85(6.15) and N, 16.47(17.09). $^1$H-NMR (250 MHz, CDCl$_3$) 8.74 (s, 1H, Ade H-2); 8.18 (b. s, 1H, ZNH); 8.10 & 8.04 (s, 1H, H-8); 7.46-7.34 (m, 5H, Ph); 5.63 (unres. t, 1H, BocNH); 5.30 (s, 2H, PhC$\underline{H}_2$); 5.16 & 5.00 (s, 2H, CH$_2$CON); 4.29 & 4.06 (s, 2H, C$\underline{H}_2$CO$_2$H); 4.20 (q, 2H, OC$\underline{H}_2$CH$_3$); 3.67-3.29 (m, 4H, C$\underline{H}_2$C$\underline{H}_2$); 1.42 (s, 9H, $^t$Bu) and 1.27(t, 3H, OCH$_2$C$\underline{H}_3$). The spectrum shows traces of ethanol and DCU.

EXAMPLE 22

N-(N-Boc-2-aminoethyl)-N-[(N-6-Cbz-9-adeninyl) acetyl]glycine (22)

N-(N-Boc-2-aminoethyl)-N-[(N-6-Cbz-9-adeninyl) acetyl]glycine ethyl ester (21, 1.48 g; 2.66 mmol) was suspended in THF (13 ml) and the mixture was cooled to 0° C. Lithium hydroxide (8 ml; 1 N) was added. After 15 min of stirring, the reaction mixture was filtered, extra water (25 ml) was added, and the solution was washed with methylene chloride (2×25 ml). The pH of the aqueous solution was adjusted to pH 2.0 with 1 N HCl. The precipitate was isolated by filtration, washed with water, and dried, affording 0.82 g (58%). The product reprecipitated twice with methylene chloride/ petroleum ether, 0.77 g (55%) after drying. M.p. 119° C. (decomp.) Anal. for $C_{24}H_{29}N_7O_7.H_2O$ found(calc.) C, 53.32(52.84); H: 5.71(5.73); N: 17.68(17.97). FAB-MS. 528.5 (MH$^+$). $^1$H-NMR (250 MHz, DMSO-$d_6$). 12.75 (very b, 1H, CO$_2$H); 10.65 (b. s, 1H, ZNH); 8.59 (d, 1H, J=2.14 Hz, Ade H-2); 8.31 (s, 1H, Ade H-8); 7.49-7.31 (m, 5H, Ph); 7.03 & 6.75 (unresol. t, 1H, BocNH); 5.33 & 5.16 (s, 2H, CH$_2$CON); 5.22 (s, 2H, PhC$\underline{H}_2$); 4.34-3.99 (s, 2H, CH$_2$CO$_2$H); 3.54-3.03 (m's, includes water, C$\underline{H}_2$C$\underline{H}_2$) and 1.39 & 1.37 (s, 9H, $^t$Bu). $^{13}$C-NMR. 170.4; 166.6; 152.3; 151.5; 149.5; 145.2; 128.5; 128.0; 127.9; 66.32; 47.63; 47.03; 43.87 and 28.24.

EXAMPLE 23

2-Amino-6-chloro-9-carboxymethylpurine (23)

To a suspension of 2-amino-6-chloropurine (5.02 g; 29.6 mmol) and potassium carbonate (12.91 g; 93.5 mmol) in DMF (50 ml) was added bromoacetic acid (4.70 g; 22.8 mmol). The mixture was stirred vigorously for 20 h. under nitrogen. Water (150 ml) was added and the solution was filtered through Celite to give a clear yellow solution. The solution was acidified to a pH of 3 with 4 N hydrochloric acid. The precipitate was filtered and dried, in vacuo, over an appropriate drying agent. Yield (3.02 g; 44.8%). $^1$H-NMR (DMSO-$d_6$): d=4.88 ppm (s,2H); 6.95 (s,2H); 8.10 (s,1H).

EXAMPLE 24

2-Amino-6-benzyloxy-9-carboxymethylpurine (24)

Sodium (2.0 g; 87.0 mmol) was dissolved in benzyl alcohol (20 ml) and heated to 130° C. for 2 h. After cooling to 0° C., a solution of 2-amino-6-chloro-9-carboxymethylpurine (23, 4.05 g; 18.0 mmol) in DMF (85 ml) was slowly added, and the resulting suspension stirred overnight at 20° C. Sodium hydroxide solution (1N, 100 ml) was added and the clear solution was washed with ethyl acetate (3×100 ml). The water phase then was acidified to a pH of 3 with 4-N hydrochloric acid. The precipitate was taken up in ethyl acetate (200 ml), and the water phase was extracted with ethyl acetate (2×100 ml). The combined organic phases were washed, with saturated sodium chloride solution (2 ×75 ml), dried with anhydrous sodium sulfate, and taken to dryness by evaporation, in vacuo. The residue was recrystallized from ethanol (300 ml). Yield after drying, in vacuo, over an appropriate drying agent: 2.76 g (52%). M.p. 159-65° C. Anal. (calc., found) C(56.18; 55.97), H(4.38; 4.32), N(23.4; 23.10). $^1$H-NMR (DMSO-$d_6$): 4.82 ppm.(s,2H); 5.51 (s,2H); 6.45 (s,2H); 7.45 (m,5H); 7.82 (s,1H).

EXAMPLE 25

N-(N-Boc-2-aminoethyl)-N-[(2-Amino-6-benzyloxy-purine-9-yl)acetyl]glycine [BocGaeg monomer] (25)

2-Amino-6-benzyloxy-9-carboxymethyl-purine (24, 0.50 g; 1.67 mmol), N-Boc-aminoethyl glycine methyl ester (0.65 g; 2.80 mmol), diisopropylethyl amine (0.54 g; 4.19 mmol), and bromo-tris-pyrrolidino-phosphonium-hexafluoro-phosphate (PyBroP®) (0.798 g; 1.71 mmol) were stirred in DMF (2 ml) for 4 h. The clear solution was poured into an ice-cooled solution of sodium hydrogen carbonate (1 N; 40 ml) and extracted with ethyl acetate (3×40 ml). The organic layer was washed with potassium hydrogen sulfate solution (1 N; 2×40 ml), sodium hydrogen carbonate (1 N; 1×40 ml) and saturated 5 sodium chloride solution (60 ml). After drying with anhydrous sodium sulfate -and evaporation, in vacuo, the solid residue was recrystallized from ethyl acetate/hexane (20 ml (2:1)) to give the methyl ester in 63% yield (MS-FAB 514 (M+1). Hydrolysis was accomplished by dissolving the ester in ethanol/water (30 ml (1:2)) containing conc. sodium hydroxide (1 ml). After stirring for 2 h, the solution was filtered and acidified to a pH of 3, by the addition of 4 N hydrochloric acid. The title compound was obtained filtration. Yield: 370 mg (72% for the hydrolysis). Purity by HPLC was more than 99%. Due to the limited rotation around the secondary amide several of the signals were doubled in the ratio 2:1 (indicated in the list by mj. for major and mi. for minor). $^{1}$H-NMR(250, MHz, DMSO-d$_6$): d=1.4 ppm. (s,9H); 3.2 (m,2H); 3.6 (m,2H); 4.1 (s, mj., CONRC$\underline{H}_2$COOH); 4.4(s, mi., CONRC$\underline{H}_2$COOH); 5.0 (s, mi., Gua-C$\underline{H}_2$CO-); 5.2 (s, mj., Gua-C$\underline{H}_2$CO); 5.6 (s,2H); 6.5 (s,2H); 6.9 (m, mi., BocNH); 7.1 (m, mj., BocNH); 7.5 (m.,3H); 7.8 (s,1H); 12,8 (s;1H). $^{13}$C-NMR. 170.95; 170.52; 167.29; 166.85; 160.03; 159.78; 155.84; 154.87; 140.63; 136.76; 128.49; 128.10; 113.04; 78.19; 77.86; 66.95; 49.22; 47.70; 46.94; 45.96; 43.62; 43.31 and 28.25.

EXAMPLE 26

Synthesis of PNA Oligomers by Solid Phase, General Procedure

The functionalized resin is measured out to typically provide 0.1-1.0 millimoles of functionality, (functionalities attached to resins are commercially available through various sources e.g. Peptides International, Kentucky). This weight of resin is suspended in a 1:1 (v:v) dichloromethane: dimethylformamide solution (30mL/1 g of resin) and allowed to swell for a period of time if desired. The solvent is then removed by filtration and the resin resuspended in trifluoroacetic acid (1 mL/1 gm of resin) and shaken for 3 minutes. The trifluoroacetic acid is removed by filtration and this step is repeated twice. The resin is washed three times with a solution of 1:1 (v:v) dichloromethane:dimethylfomammide. The resulting resin is resuspended in pyridine solution (5 mL/100 mg of resin) and vacuum filtered to remove the pyridine. This step is repeated twice. The resin is suspended in 1:1 (v:v) pyridine:dimethylformamide and to this suspension is added the desired PNA monomer (2-10 molar equivalents), TBTU (1.9-9.9 molar equivalents), and di-isopropylethylamine (5–20 molar equivalents) such that the final concentration of PNA monomer is 0.2M. The suspension is shaken for 15-60 minutes and the spent coupling solution is removed by filtration. The resin is washed with pyridine three times, and any unreacted amines are capped using Rapoport's Reagent, 5 equivalents in DMF for 5 minutes. The resin is then washed three times with pyridine followed by three washes with a solution of 1.1 (v:v) dichloromethane: dimethylformamide (5 ml/100 mg of resin). At this point, the resin is ready for the next coupling reaction and this procedure is repeated until the desired PNA is assembled on the resin.

Specific Examples of Amino Ethyl Glycine (aeg-) PNAs and aeg-PNA Derivatives Prepared by this General Method

| Resin Employed | aeg-PNA/aeg-PNA Derivative Prepared |
|---|---|
| Merrifield | H$_2$N-GCAT-COOH (SEQ ID NO:1) |
| Lys Substituted Merrifield | H$_2$N-GCAT-Lys-COOH (SEQ ID NO:2) |
| MBHA | H$_2$N-GCAT-CONH$_2$ (SEQ ID NO:3) |
| Lys Substituted MBHA | H$_2$N-GCAT-Lys-CONH$_2$ (SEQ ID NO:4) |

EXAMPLE 27

Capping of the PNA

PNA can be capped by a non-PNA moiety on the N terminus by following the procedures described in Example 26 and substituting a desired carboxylic acid-based capping reagent for the PNA monomer in the final coupling step.

Specific Examples of aeg-PNAs and aeg-PNA Derivatives Prepared by this General Method

| Resin Employed | aeg-PNA/aeg-PNA Derivative Prepared |
|---|---|
| Capping Reagent = Acetyl | |
| Merrifield | CH$_3$CONH-GCAT-COOH (SEQ ID NO:5) |
| Lys Substituted Merrifield | CH$_3$CONH-GCAT-Lys-COOH (SEQ ID NO:6) |
| MBHA | CH$_3$CONH-GCAT-CONH$_2$ (SEQ ID NO:7) |
| Lys Substituted MBHA | CH$_3$CONH-GCAT-Lys-CONH$_2$ (SEQ ID NO:8) |
| Capping Reagent = N-Boc glycine | |
| Merrifield | BocGly-GCAT-COOH (SEQ ID NO:9) |
| Lys Substituted Merrifield | BocGly-GCAT-Lys-COOH (SEQ ID NO:10) |
| MBHA | BocGly-GCAT-CONH$_2$ (SEQ ID NO:11) |
| Lys Substituted MBHA | BocGly-GCAT-Lys-CONH$_2$ (SEQ ID NO:12) |
| Capping Reagent = 1. Glycine; 2. Cholic Acid (ChA) | |
| Merrifield | ChA-GlyGCAT-COOH (SEQ ID NO:13) |
| Lys Substituted Merrifield | ChA-GlyGCAT-Lys-COOH (SEQ ID NO:14) |
| MBHA | ChA-GlyGCAT-CONH$_2$ (SEQ ID NO:15) |
| Lys Substituted MBHA | ChA-GlyGCAT-Lys-CONH$_2$ (SEQ ID NO:16) |
| Capping Reagent = Fluorescein (Fluor) | |
| Merrifield | Fluor-GCAT-COOH (SEQ ID NO:17) |
| Lys Substituted Merrifield | Fluor-GCAT-Lys-COOH (SEQ ID NO:18) |
| MBHA | Fluor-GCAT-CONH$_2$ (SEQ ID NO:19) |
| Lys Substituted MBHA | Fluor-GCAT-Lys-CONH$_2$ (SEQ ID NO:20) |
| Capping Reagent = 1. Glycine, 2. Fluorescein (Fluor) | |
| Merrifield | Fluor-GlyGCAT-COOH (SEQ ID NO:21) |
| Lys Substituted Merrifield | Fluor-GlyGCAT-Lys-COOH (SEQ ID NO:22) |
| MBHA | Fluor-GlyGCAT-CONH$_2$ (SEQ ID NO:23) |
| Lys Substituted MBHA | Fluor-GlyGCAT-Lys-CONH$_2$ (SEQ ID NO:24) |
| Capping Reagent = Adipic Acid t-butyl ester (tBuOOC(CH$_2$)$_4$CO) | |
| Merrifield | tBuOOC(CH$_2$)$_4$CONH-GCAT-COOH (SEQ ID NO:25) |
| Lys Substituted Merrifield | tBuOOC(CH$_2$)$_4$CONH-GCAT-Lys-COOH (SEQ ID NO:26) |

-continued

| Resin Employed | aeg-PNA/aeg-PNA Derivative Prepared |
|---|---|
| MBHA | tBuOOC(CH$_2$)$_4$CONH-GCAT-CONH$_2$ (SEQ ID NO:27) |
| Lys Substituted MBHA | tBuOOC(CH$_2$)$_4$CONH-GCAT-Lys-CONH$_2$ (SEQ ID NO:28) |
| Capping Reagent = Cholic Acid (ChA) | |
| Merrifield | ChA-GCAT-COOH (SEQ ID NO:29) |
| Lys Substituted Merrifield | ChA-GCAT-Lys-COOH (SEQ ID NO:30) |
| MBHA | ChA-GCAT-CONH$_2$ (SEQ ID NO:31) |
| Lys Substituted MBHA | ChA-GCAT-Lys-CONH$_2$ (SEQ ID NO:32) |

EXAMPLE 28

General Cleavage Reaction

The completed PNA or PNA derivative may be cleaved from the resin and isolated via the following. The resin is washed twice with trifluoroacetic acid, then suspended in a mixture of thioanisole, m-cresol, trifluoromethanesulfonic acid, and trifluoroacetic acid in a ratio of 1:1:2:6, 200 µl/1 µmole, for 1 hour at room temperature. The cleavage solution is then drained into ether, 1 ml/µmole, and the above process is repeated. The precipitate is then collected by either filtration or centrifugation.

EXAMPLE 29

General Purification Procedure

The isolated PNA or PNA derivative is purified by preparative reverse phase HPLC using a Waters µBondapak Phenyl-C18 column (19 mm×50 mm) and eluting with a gradient comprised of a solution of 9:1 acetonitrile:0.050M NH$_4$OAc, pH 6, 0.1% hexafluoroisopropanol added to a solution of 0.050M NH$_4$OAc, pH 6, 0.1% hexafluoroisopropanol. The eluent can be adjusted for the particular PNA or PNA derivative being purified.

EXAMPLE 30

N-[(N-phthaloyl)(1-methyl-O-benzyl)-2-aminoethyl]-N-[(1-thyminyl)acetyl]glycine (30)

A. (O-Benzyl) Boc Serine methyl ester (30A)

(O-benzyl) Boc Serine 2.00 g (6.8 mmoles) was dissolved in 50 ml of ether. To this solution was added an ether solution containing freshly prepared diazomethane prepared from 5 g of Diazald using the procedure from Aldrich Technical Bulletin number AL-180. After stirring the solution for 30 minutes, glacial acetic acid was added dropwise until the solution became clear. The resulting solution was concentrated in vacuo to yield 2.00 g, 95% as a clear oil. $^1$H: (CDCl$_3$); 7.3 (d, 5H), 5.5 (bs, 1H), 4.5 (s, 2H), 3.8 (m, 2H), 3.7 (s, 3H), 1.4 (s, 9H)

B. 1-O-Benzyl-2-N-Boc-2,3-propandiol (30B)

Compound 30A was dissolved in 50 ml of methanol and cooled to 0° C. To this was added 300 mg of lithium borohydride in small portions, waiting for the gas evolution to cease between additions. When all of the hydride had been added the reaction was refluxed for 1 hour. It was then cooled to 0° C., and quenched by the dropwise addition of saturated sodium bicarbinate. The solution was extracted twice with 50 ml portions of chloroform. The combined organic extracts were washed again with saturated sodium bicarbonate, followed by saturated sodium chloride solutions. The chloroform solution was dried over magnesium sulfate and concentrated to an oil. The oil was chromatographed over silica gel eluting with 7% methanol in dichloromethane, isolating 1.30 g as a clear oil. 1H: (CDCl$_3$); 7.3 (s, 5H), 5.2 (bs, 1H), 4.5 (s, 2H), 3.9-3.5 (m, 5H), 1.4 (s, 9H)

C. 1-O-benzyl-2-N-Boc-3-phthaloyl-2,3-diaminopropanol (30C)

Compound 30B was dissolved in 100 ml of freshly distilled THF. To this solution was added the following reagents; triphenyl phosphine, (1.26 g 4.82 mmol), diethyl azodicarboxylate (0.839 g 4.82 mmol), and phthalimide (0.710 g 4.82 mmol), and the 5 reaction stirred overnight at room temperature. After stirring the solution was concentrated to a yellow solid and chromatographed over silica gel using 30% ethyl acetate in hexanes. The product was isolated as a white solid weighing 1.60 g, 97%. 1,H: (CDCl$_3$); 7.9 (m, 2H), 7.7 (m, 2H), 7.3 (s, 5H), 5.1 (d, 1H), 4.5 (s, 2H), 4.0-3.5 (m, 5H), 1.3 (s, 9H).

D. N-[(N-phthaloyl)(1-methyl-O-benzyl)-2-aminoethyl] glycine methyl ester

Compound 30C (1.00 g, 2.9 mmol) is dissolved in 20 ml dichloromethane and cooled to 0° C. To this is added 20 ml TFA and the reaction is allowed to warm to room temperature. Upon completion, the reaction is concentrated in vacuo and then redissolved in dichloromethane and washed with 1 N NaOH and brine, the organic solution is dried and concentrated to give the free amine. This amine is then dissolved in anhydrous THF with 2 eq of triethylamine and cooled to 0° C. Methyl bromoacetate (0.500 g, 3.2 mmol) is added and the reaction is allowed to stir at room temperature until complete. Standard aqueous workup and chromatography yields the title compound.

E. N-[(N-phthaloyl)(1-methyl-O-benzyl)-2-aminoethyl]-N-[(1-thymin-yl)acetyl]glycine (30)

The functionalized backbone monomer of Example 30D is dissolved in THF and treated with 3 eq of triethyl amine. To this 1 eq of 1-chlorocarbonylmethyl thymine is added dropwise as a THF solution over 30 min. The resulting solution is stirred overnight or until complete. Standard acidic workup and chromatography yield the title compound.

EXAMPLE 31

N-[(N-phthaloyl)(1-methyl-O-benzyl)-2-aminoethyl]-N-[(9-adeninyl)acetyl]glycine (31)

A. 9-Carboxymethyl adenine ethyl ester (31A)

Adenine (10.0 g, 74 mmol) and potassium carbonate (10.29 g, 74.0 mmol) were suspended in DMF and ethyl bromoacetate (8.24 ml, 74 mmol) was added. The suspension was stirred for 2.5 h under nitrogen at room temperature and then filtered. The solid residue was washed three times with DMF (10 ml). The combined filtrate was evaporated to dryness, in vacuo. The yellow-orange solid material was poured into water (200 ml) and 4 N HCl was added to pH≈6. After stirring at 0° C. for 10 min, the solid was filtered off, washed with water, and recrystallized from 96% ethanol (150 ml). The title compound was isolated by filtration and washed thoroughly with ether. Yield 3.4 g (20%). M.p. 215.5-220° C. Anal. for C$_9$H$_{11}$N$_5$O$_2$ found(calc.): C, 48.86 (48.65); H: 5.01(4.91); N: 31.66(31.42). $^1$H-NMR (250

MHz; DMSO-d$_6$): (s, 2H, H-2 & H-8), 7.25 (b. s., 2H, NH$_2$), 5.06 (s, 2H, NCH$_2$), 4.17 (q, 2H, J=7.11 Hz, OCH$_2$) and 1.21 (t, 3H, J=7.13 Hz, NCH$_2$). $^{13}$C-NMR. 152.70, 141.30, 61.41, 43.97 and 14.07. FAB-MS. 222 (MH+) IR: Frequency in cm$^{-1}$ (intensity). 3855 (54.3), 3274(10.4), 3246(14.0), 3117 (5.3), 2989(22.3), 2940(33.9), 2876(43.4), 2753(49.0), 2346 (56.1), 2106(57.1), 1899(55.7), 1762(14.2), 1742(14.2), 1742(1.0),1671(1.8),1644(10.9), 1606(0.6),1582(7.1),1522(43.8),1477(7.2),1445(35.8) and 1422(8.6). The position of alkylation was verified by X-ray crystallography on crystals, which were obtained by recrystallization from 96% ethanol.

Alternatively, 9-carboxymethyl adenine ethyl ester can be prepared by the following procedure. To a suspension of adenine (50.0 g, 0.37 mol) in DMF (1100 ml) in 2 L three-necked flask equipped with a nitrogen inlet, a mechanical stirrer and a dropping funnel was added 16.4 g (0.407 mol) hexane washed sodium hydride- mineral oil dispersion. The mixture was stirred vigorously for 2 hours, whereafter ethyl bromacetate 75 ml, 0.67 mol) was added dropwise over the course of 3 hours. The mixture was stirred for one additional hour, whereafter tlc indicated complete conversion of adenine. The mixture was evaporated to dryness at 1 mmHg and water (500 ml) was added to the oily residue which caused crystallization of the title compound. The solid was recrystallized from 96% ethanol (600 ml). Yield after drying 53.7 (65.6%). HPLC (215 nm) purity>99.5%.

B. N-6-Cbz-9-carboxymethyl adenine ethyl ester (31B)

9-Carboxymethyladenine ethyl ester (31A, 3.40 g, 15.4 mmol) was dissolved in dry DMF (50 ml) by gentle heating, cooled to 20° C., and added to a solution of N-ethyl-Cbz-imidazole tetrafluoroborate (62 mmol) in methylene chloride (50 ml) over a period of 15 min with ice-cooling. Some precipitation was observed. The ice bath was removed and the solution was stirred overnight. The reaction mixture was treated with saturated sodium hydrogen carbonate (100 ml). After stirring for 10 min, the phases were separated and the organic phase was washed successively with one volume of water, dilute potassium hydrogen sulfate (twice), and with saturated sodium chloride. The solution was dried over magnesium sulfate and evaporated to dryness, in vacuo, which afforded 11 g of an oily material. The material was dissolved in methylene chloride (25 ml), cooled to 0° C., and precipitated with petroleum ether (50 ml). This procedure was repeated once to give 3.45 g (63%) of the title compound. M.p. 132-35° C. Analysis for C$_{17}$H$_{17}$N$_5$O$_4$ found (calc.): C: 56.95(57.46); H: 4.71(4.82); N: 19.35(19.71). $^1$H-NMR (250 MHz; CDCl$_3$): 8.77 (s, 1H, H-2 or H-8); 7.99(s, 1H, H-2 or H-8), 7.45-7.26 (m, 5H, Ph); 5.31 (s, 2H, N-CH$_2$); 4.96 (s, 2H, Ph-CH$_2$); 4.27 (q, 2H, J=7.15 Hz, CH$_2$CH$_3$) and 1.30 (t, 3H, J=7.15 Hz, CH$_2$CH$_3$). $^{13}$C-NMR: 153.09; 143.11; 128.66; 67.84; 62.51; 44.24 and 14.09. FAB-MS: 356 (MH$^+$) and 312 (MH+—CO$_2$). IR: frequency in cm$^{-1}$ (intensity). 3423 (52.1); 3182 (52.8); 3115(52.1); 3031(47.9); 2981(38.6); 1747(1.1); 1617(4.8); 15.87(8.4); 1552(25.2); 1511(45.2); 1492(37.9); 1465(14.0) and 1413 (37.3).

C. N-6-Cbz-9-carboxymethyl adenine (31C)

N-6-Cbz-9-carboxymethyladenine ethyl ester (31B, 3.20 g; 9.01 mmol) was mixed with methanol (50 ml) cooled to 0° C. Sodium hydroxide solution (50 ml; 2N) was added, whereby the material quickly dissolved. After 30 min at 0° C., the alkaline solution was washed with methylene chloride (2×50 ml). The aqueous solution was brought to pH 1.0 with 4 N HCl at 0° C., whereby the title compound precipitated. The yield after filtration, washing with water, and drying was 3.08 g (104%). The product contained salt and elemental analysis reflected that. Anal. for C$_{15}$H$_{13}$N$_5$O$_4$ found(calc.): C, 46.32(55.05); H: 4.24(4.00); N: 18.10(21.40) and C/N, 2.57(2.56). $^1$H-NMR(250 MHz; DMSO-d$_6$): 8.70 (s, 2H, H-2 and H-8); 7.50-7.35 (m, 5H, Ph); 5.27 (s, 2H, N—CH$_2$); and 5.15 (s, 2H, Ph-CH$_2$). $^{13}$C-NMR. 168.77, 152.54, 151.36, 148.75, 145.13, 128.51, 128.17, 127.98, 66.76 and 44.67.1R (KBr) 3484(18.3); 3109(15.9); 3087(15.0); 2966(17.1); 2927(19.9); 2383(53.8); 1960(62.7); 1739(2.5); 1688(5.2); 1655(0.9); 1594(11.7); 1560(12.3); 1530(26.3); 1499(30.5); 1475(10.4); 1455(14.0); 1429(24.5) and 1411(23.6). FAB-MS: 328 (MH$^+$) and 284 (MH+—CO$_2$). HPLC (215 nm, 260 nm) in system 1: 15.18 min, minor impurities all less than 2%.

D. N-[(N-phthaloyl)(1-methyl-O-benzyl)-2-aminoethyl]-N-[(9-adenin-yl)acetyl]glycine (31)

N-6-Cbz-9-carboxymethyl adenine (31C) is converted to the acid chloride using 5 standard techniques, and treated according to the procedure of Example 30D to yield the title compound.

EXAMPLE 32

N-[(N-phthaloyl)(1-methyl-O-benzyl)-2-aminoethyl]-N-[(1-cytosinyl)acetyl]glycine (32)

A. N-4-Cbz cytosine (32A)

Over a period of about 1 h, Cbz chloride (52 ml; 0.36 mol) was added dropwise to a suspension of cytosine (8, 20.0 g; 0.18 mol) in dry pyridine (1000 ml) at 0° C. under nitrogen in oven-dried equipment. The solution then was stirred overnight, after which the pyridine suspension was evaporated to dryness, in vacuo. Water (200 ml) and 4 N hydrochloric acid were added to reach pH 1. The resulting white precipitate was filtered off, washed with water and partially dried by air suction. The still-wet precipitate was boiled with absolute ethanol (500 ml) for 10 min, cooled to 0° C., filtered, washed thoroughly with ether; and dried, in vacuo. Yield 24.7 g (54%). M.p.>250° C. Anal. for C$_{12}$H$_{11}$N$_3$O$_3$. Found(calc.); C: 58.59(58.77); H: 4.55(4.52); N: 17.17 (17.13). No NMR spectra were recorded since it was not possible to get the product dissolved.

B. N-4-Cbz-N-1-carboxymethyl cytosine (32B)

In a three necked round bottomed flask equipped with mechanical stirring and nitrogen coverage was placed methyl bromacetate (7.82 ml;82.6 mmol) and a suspension of N-4-Cbz-cytosine (32A, 21.0 g;82.6 mmol) and potassium carbonate (11.4 g;82.6 mmol) in dry DMF (900 ml). The mixture was stirred vigorously overnight, filtered, and evaporated to dryness, in vacuo. Water (300 ml) and 4 N hydrochloric acid (10 ml) were added, the mixture was stirred for 15 minutes at 0° C., filtered, and washed with water (2×75 ml). The isolated precipitate was treated with water (120 ml), 2N sodium hydroxide (60 ml), stirred for 30 min, filtered, cooled to 0° C., and 4 N hydrochloric acid (35 ml) was added. The title compound was isolated by filtration, washed thoroughly with water, recrystallized from methanol (1000 ml) and washed thoroughly with ether. This afforded 7.70 g (31%) of pure compound. The mother liquor from the recrystallization was reduced to a volume of 200 ml and cooled to 0° C. This afforded an additional 2.30 g of a material that was pure by tlc but had a reddish color. M.p. 266-274° C. Anal. for C$_{14}$H$_{13}$N$_3$O$_5$. Found(calc.); C: 55.41

(55.45); H: 4.23(4.32); N: 14.04(13.86). $^1$H-NMR (90 MHz; DMSO-d$_6$): 8.02 ppm (d,J=7.32 Hz,1H,H-6); 7.39 (s,5H, Ph); 7.01 (d,J=7.32 Hz,1H,H-5); 5.19 (s,2H,PhCH$_2$—); 4.52 (s,2H).

C. N-[(N-phthaloyl)(1-methyl-O-benzyl)-2-aminoethyl]-N-[(1-cytosinyl-)acetyl]glycine (32)

N-4-Cbz-N-1-carboxymethyl cytosine is converted to the acid chloride according to standard techniques, and treated according to the procedure of Example 30D to yield the title compound.

EXAMPLE 33

N-[(N-phthaloyl)(1-methyl-O-benzyl)-2-aminoethyl]-N-[(2-Amino-6-benzyloxy-purine-9-yl)acetyl] glycine (33)

A. 2-Amino-6-chloro-9-carboxymethylpurine (33A)

To a suspension of 2-amino-6-chloropurine (5.02 g; 29.6 mmol) and potassium carbonate (12.91 g; 93.5 mmol) in DMF (50 ml) was added bromoacetic acid (4.70 g; 22.8 mmol). The mixture was stirred vigorously for 20 h under nitrogen. Water (150 ml) was added and the solution was filtered through Celite to give a clear yellow solution. The solution was acidified to a pH of 3 with 4 N hydrochloric acid. The precipitate was filtered and dried, in vacuo, over an appropriate drying agent. Yield (3.02 g; 44.8%). $^1$H-NMR (DMSO-d$_6$): d=4.88 ppm (s,2H); 6.95 (s,2H); 8.10 (s,1H).

B. 2-Amino-6-benzyloxy-9-carboxymethylpurine (33B)

Sodium (2.0 g; 87.0 mmol) was dissolved in benzyl alcohol (20 ml) and heated to 130° C. for 2 h. After cooling to 0° C., a solution of 2-amino-6-chloro-9-carboxymethylpurine (33A, 4.05 g; 18.0 mmol) in DMF (85 ml) was slowly added, and the resulting suspension stirred overnight at 20° C. Sodium hydroxide solution (IN, 100 ml) was added and the clear solution was washed with ethyl acetate (3×100 ml). The water phase then was acidified to a pH of 3 with 4 N hydrochloric acid. The precipitate was taken up in ethyl acetate (200 ml), and the water phase was extracted with ethyl acetate (2×100 ml). The combined organic phases were washed with saturated sodium chloride solution (2×75 ml), dried with anhydrous sodium sulfate, and taken to dryness by evaporation, in 5 vacuo. The residue was recrystallized from ethanol (300 ml). Yield after drying, in vacuo, over an appropriate drying agent: 2.76 g (52%). M.p. 159-65° C. Anal. (calc., found) C(56.18; 55.97), H(4.38; 4.32), N(23.4; 23.10). $^1$H-NMR (DMSO-d$_6$): 4.82 ppm.(s,2H); 5.51 (s,2H); 6.45 (s,2H); 7.45 (m,5H); 7.82 (s,1H).

C. N-[(N-phthaloyl)(1-methyl-O-benzyl)-2-aminoethyl]-N-[(2-Amino-6-benzyloxy-purine-9-yl)acetyl] glycine (33)

2-Amino-6-benzyloxy-9-carboxymethyl-purine (33B, 1.67 mmol), Compound 31D (2.80 mmol), diisopropylethyl amine (4.19 mmol), and bromo-tris-pyrrolidinb-phosphonium-hexafluoro-phosphate (PyBroP®) (1.71 mmol) are stirred in DMF (2 ml) for4 h. The clear solution is poured into an ice-cooled solution of sodium hydrogen carbonate (1 N; 40 ml) and extracted with ethyl acetate (3×40 ml). The organic layer is washed with potassium hydrogen sulfate solution (1 N; 2×40 ml), sodium hydrogen carbonate (1 N; 1×40 ml) and saturated sodium chloride solution (60 ml). The organic layer is separated, dried with anhydrous sodium sulfate and concentrated in vacuo. The solid residue is recrystallized from ethyl acetate/hexane (20 ml (2:1)) to give the methyl ester. Hydrolysis is accomplished by dissolving the ester in ethanol/water (30 ml (1:2)) containing conc. sodium hydroxide (1 ml). After stirring for 2 h, the solution is filtered and acidified to a pH of 3, by the addition of 4 N hydrochloric acid. The title compound is obtained by filtration. Purity is judged by HPLC.

EXAMPLE 34

N-[(N-Boc)(2-methyl-O-benzyl)-2-aminoethyl]-N-[(1-thyminyl)acetyl]glycine (34)

A. (O-benzyl)$_2$-N-Boc-diaminopropanol (34A)

Compound 30C is dissolved in 200 ml ethanol in a 500 ml flask. Hydrazine is added to the stirring reaction mixture. The mixture is heated to 60-65° in an oil bath and refluxed 14 hours. Solvent is evaporated in vacuo. The residue is dissolved in dichloromethane (250 ml) and extracted twice with an equal volume of NH$_4$OH. The organic layer is evaporated to yield the crude compound 34A. The product may be used without further purification or can be further purified by HPLC. NMR is used to assay product purity.

B. N-[(N-Boc)(2-methyl-O-benzyl)-2-aminoethyl]-N-glycine methyl ester (34B)

Compound 34A is treated with methyl bromoacetate according to the procedure of Example 30B to yield the title compound.

C. N-[(N-Boc)(2-methyl-O-benzyl)-2-aminoethyl]-N-[(1-thyminyl)-acetyl]glycine (34)

Compound 34B is treated with chlorocarbonylmethylthymine according to the procedure of Example 30C to yield the title compound.

EXAMPLE 35

N-[(N-Boc)(1-hydroxymethyl)-2-aminoethyl]-N-[(1-thyminyl)-acetyl]glycine (35)

Compound 30 is treated with hydrazine according to the procedure of Example 34A 1 5 to convert the phthalimido group to the free amine, which is then treated with Boc$_2$O/NaOH to yield the N-Boc intermediate which is then treated with H$_2$/Pd/C to yield the title compound.

EXAMPLE 36

N-[(N-Boc)(2-hydroxymethyl)-2-aminoethyl]-N-[(1-thyminyl)-acetyl]glycine (36)

Compound 34 is treated according to the procedures of Example 35 to yield the title compound.

EXAMPLE 37

N-[(N-Boc)(1-formyl)-2-aminoethyl]-N-[(1-thyminyl)acetyl]glycine (37A) and N-[(N-Boc)(2-formyl)-2-aminoethyl-N-[(1-thyminyl)acetyl]glycine (37B)

Compound 35 or 36 is treated with oxalyl chloride/DMSO according to the procedure of Omura and Swem, Tetrahedron 34 1651 (1978) to yield the respective title compound.

EXAMPLE 38

N-[(N-Boc)(1-aminomethyl)-2-aminoethyl]-N-[(1-thyminyl-acetyl]glycine (38A) and N-[(N-Boc)(2-aminomethyl)-2-aminoethyl]-N-[(1-thyminyl)acetyl]glycine (38B)

Compound 37A or 37B is dissolved in 4 ml methanol. Sodium acetate pH 4.0 (2 ml), sodium cyanoborohydride (0.02 grams, 0.3 mmol) and ammonia in water (300 µl) are added to the reaction mixture, which is stirred 2 hours, after which it is concentrated in vacuo. The residue is dissolved in dichloromethane (50 mL) and washed with an equal volume saturated $NaHCO_3$. The aqueous layer is washed with dichloromethane and the combined organic extracts washed with an equal volume saturated NaCl. The aqueous layer is washed with dichloromethane and the combined organic layers dried over $MgSO_4$ and concentrated. The residue is chromatographed on a silica gel column, eluting with a gradient of 50% ethyl acetate in hexanes to 100% ethyl acetate. The desired product (0.15 grams, 80%) elutes with 10% Methanol/90% ethyl acetate.

EXAMPLE 39

Synthesis of N-(N-Boc-2-aminoethyl)-N-[(1-thyminyl)acetyl]-L-serine(OBn) (39)

A. N-Boc-aminoacetaldehyde (39A)

3-(Boc-amino)-1,2-propanediol (21g, 110 mmol) was dissolved in water (200 ml) and stirred with potassium m-periodate (25.3g, 110 mmol) at room temperature under argon for 2h. The reaction mixture was filtered and washed with methylene chloride (100 ml). The aqueous layer was extracted with methylene chloride (3×150 ml). The organic extract was washed with brine (50ml), dried and evaporated to dryness to give a light pink oil. This oil was purified by flash column chromatography using silica gel and $CH_2Cl_2$/ethyl acetate as the eluent. Yield was 14g (80%). $^1$HNMR ($CDCl_3$) d 1.45 (s, 9H, t-Butyl), 4.08 (d, 2H, $CH_2$), 5.24 (bs, 1H, NH) and 9.67 (s, 1H, CHO).

B. N-(N-Boc-2-aminoethyl)-L-serine(O-benzyl) methyl ester (39B)

Method A: L-Serine(OBn) methyl ester (16.93g, 81 mmol) and N-Boc-aminoacetaldehyde (39A) (12.88g, 81 mmol) were dissolved in dry $CH_2Cl_2$ (200 ml) and allowed to stir at room temperature under an atmosphere of argon. Glacial acetic acid (1 ml) was added and the mixture was stirred for an additional 15 minutes. Sodium triacetoxyborohydride (18.99g, 90 mmol) was added at room temperature in one lot. After stirring for 3h under argon, the reaction was diluted with $CH_2Cl_2$ (100 ml). The organic layer was washed first with sat. $NaHCO_3$ (100 ml) to pH 7 followed by washing with water (50 ml) and then brine (50ml). The organic extract was dried and evaporated to dryness. The residue was purified by flash chromatography using $CH_2Cl_2$/acetone as the eluent. The fractions having the required product were collected and evaporated to dryness to give 8.0g (28%) of pure product as foam. $^1$HNMR ($CDCl_3$) δ 1.38 (s, 9H, t-Butyl), 1.95 (bs, 1H, NH), 2.60 (m, 1H, $CH_2$), 2.80 (m, 1H, $CH_2$), 3.18 (m, 2H, $CH_2$), 3.42 (t, 1H), 3.65 (m, 2H, $CH_2$), 3.72 (s, 3H, $OCH_3$), 4.50 (s, 2H, $OCH_2$), 5.04 (bs, 1H, NH) and 7.30 (m, 5H, ArH). Anal. Calcd for $C_{11}H_{22}N_2O_5$: C, 50.37; H, 8.45; N, 10.68. Found: C, 50.60; N, 10.83.

Method B: L-Serine(OBn) methyl ester (2.6g, 12.44 mmol) and N-Boc-aminoacetaldehyde (39A) (2.07g, 13 mmol) were dissolved in dry $CH_3OH$ (35 ml) and placed in a parr bottle. To this solution anhydrous NaOAc (1.77g, 13 mmol) and Pd/C (10%, 0.6g) were added under an atmosphere of argon. The reaction mixture was hydrogenated at 3 psi of hydrogen for 2h. The catalyst was filtered, washed with methanol (20 ml) and the combined filtrate was evaporated to dryness. The residue was partitioned between $CH_2Cl_2$ (150 ml) and sat. $NaHCO_3$ (100 ml) and extracted with $CH_2Cl_2$. The organic extract was washed with water (100 ml) and brine, dried and evaporated to dryness. The residue was purified by flash column chromatography using $CH_2Cl_2$/acetone as the eluent. The pure fractions were collected and evaporated to dryness to give 3.9g(89%) of the product as foam.

C. N-(N-Boc-2-aminoethyl)-N-[(1-thyminyl)acetyl]-L-serine(OBn) methyl ester (39C)

The substrate 39B (7.0g, 20 mmol) and N-1-carboxymethylthymine (3, 3.68g, 20 mmol) were dissolved in dry $DMF/CH_2Cl_2$ (1:1; 200 ml) and cooled to 0° C. in an ice bath under an atmosphere of argon. To this cold solution was added DhbtOH (3.62g, 20 mmol) followed by EDC (4.20g, 22 mmol). The reaction mixture was stirred at room temperature under argon overnight and evaporated to dryness. The residue was dissolved in a mixture of $CH_2Cl_2$ (200 ml) and water (100 ml) and extracted in $CH_2Cl_2$. The organic extract was washed with 5% $NaHCO_3$ (100 ml), water (100 ml) and brine(100 ml). The $CH_2Cl_2$ layer was dried over anhydrous $Na_2SO_4$ and evaporated to dryness. The residue was purified by flash column chromatography over silica gel using $CH_2Cl_2$/MeOH as the eluent. The pure fractions were collected and evaporated to give 9g (87%) of the product as a foam. $^1$HNMR ($CDCl_3$) d 1.42 (s, 9H, t-Butyl), 1.90 (s, 3H, $CH_3$), 3.32 (m, 2H, $CH_2$), 3.55 (m, 2H, $CH_2$), 3.72 (s, 3H, $OCH_3$), 4.00 (m, 2H, $CH_2$), 4.32 (m, 1H, CH), 4.50 (s, 2H, $OCH_2$), 4.52 (m, 2H, $CH_2$), 5.46 (t, 1H, NH), 6.85 (s, 1H, $C_6H$), 7.30 (m, 5H, ArH) and 8.8 (s, 1H, NH). Anal. Calcd for $C_{25}H_{34}N_4O_8$: C, 57.90; H: 6.61; N, 10.80. Found: C, 57.83; H, 6.68; N, 10.65.

D. N-(N-Boc-2-aminoethyl)-N-[(1-thyminyl)acetyl]-L-serine(OBn)(39)

The substrate 39C (0.52g, 1 mmol) was dissolved in THF (10 ml) and cooled to 0° C. in an ice bath. To this cold stirred solution NaOH (1N, 5 ml, 5 mmol) was added all at once. The reaction mixture was stirred at 0° C. for 1 h and evaporated to dryness. The residue was dissolved in water (10 ml) and the pH was adjusted to 3-4 with solid citric acid. The aqueous solution was extracted with EtOAc (3×30 ml). The organic extract was washed with brine, dried and evaporated to dryness to give a foam. The residue was dried over solid NaOH and checked by HNMR. Yield 0.25g (49%). $^1$HNMR (DMSO-$d_6$) d 1.38 (s, 9H, t-Butyl), 1.72 (s, 3H, $CH_3$), 3.00 to 4.00 (m, 4H, $2CH_2$), 4.40 (m, 5H, CH, $CH_2$, & $OCH_2$), 6.80 (t, 1H, NH), 7.22 (m, 6H, $C_6H$ & ArH) and 11.25 (m, 1H, COOH).

EXAMPLE 40

N-(N-Boc-2-Aminoethyl)-N-(2,2,2-trichloro-1,1-dimethyl-1-ethyoxycarbonyl)-L-serine[(α-methoxy-α-trifluoromethyl-α-phenyl)-O-acetate] methyl ester (40)

A. N-(N-Boc-2-aminoethyl)-L-serine(OH) methyl ester (40a)

The substrate 39b (0.7g, 2 mmol) was dissolved in methanol (20 ml) and treated with Pd/C (10%, 0.2g). The reaction mixture was hydrogenated for 12h at 50 psi $H_2$. The catalyst was filtered and washed with MeOH (20 ml). The combined filtrate was evaporated to dryness. The residue was purified by flash column chromatography over silica gel using $CH_2Cl_2$/MeOH as the eluent. The pure fractions were collected and evaporated to give 0.9g (95%) of the product as a foam. $^1$HNMR (CDCl$_3$) d 1.42 (s, 9H, t-Butyl), 2.70 (m, 1H, $CH_2$), 2.88 (m, 1H, $CH_2$), 3.20 (m, 2H, $CH_2$), 3.45 (m, 1H), 3.62 to 3.90 (m, 6H, $CH_2$, $OCH_3$), 5.15 (bs, 1H, NH).

B. N-(2-Boc-Aminoethyl)-N-(2,2,2-trichloro-1,1-dimethyl-1-ethyoxycarbonyl)-L-serine(OH) methyl ester (40b)

The substrate 40a (2.62g, 10 mmol) was dissolved in ether (30 ml) and mixed with 2N NaHCO$_3$ solution (20 ml). To this stirred solution was added 1,1-dimethyl-2,2,2-trichloroethyl chloroformate (2.39g, 10 mmol, dissolved in 20 ml of ether) slowly during 15 min period at room temperature. After the addition of TecBocCl, the reaction was stirred for 12h and concentrated to dryness. The residue was suspended in water (5OmI) and extracted in $CH_2Cl_2$ (2×75 ml). The organic extract was washed water (50 ml) and brine(50 ml). The $CH_2Cl_2$ layer was dried over anhydrous $Na_2SO_4$ and evaporated to dryness. The residue was purified by flash column chromatography over silica gel using $CH_2Cl_2$/acetone as the eluent. The pure fractions were collected and evaporated to give 3.9 g(85%) of an oily product. $^1$HNMR (CDCl$_3$) d 1.42 (s, 9H, t-Butyl), 1.90 (s, 6H, $2CH_3$), 3.35 (m, 2H, $CH_2$), 3.50 (m, 2H, $CH_2$), 3.75 (s, 3H, $OCH_3$), 3.90 to 4.30 (m, 3H, OH & $CH_2$), 4.45 (m, 1H, CH), 5.06 (m, 1H, NH).

C. N-(N-Boc-2-Aminoethyl)-N-(2,2,2-trichloro-1,1-dimethyl-1-ethyoxycarbonyl)-L-serine[(α-methoxy-α-trifluoromethyl-α-phenyl)-O-acetate]methyl ester (40)

The substrate 40b (0.3g, 0.65 mmol) was dissolved in dry $CH_2Cl_2$ (30 ml) and cooled to 0° C. under argon. To this cold stirred solution was added dry pyridine (1 ml) followed by a-methoxy-a-trifluoromethyl-a-phenyl acetyl chloride (0.18g, 0.7 mmol). After addition of the acid chloride, the reaction was allowed to stir for 12h. The reaction mixture was diluted with $CH_2Cl_2$ (75 ml) and washed with 5% NaHCO$_3$ (100 ml), water (5OmI) and brine(50 ml). The $CH_2Cl_2$ layer was dried over anhydrous $Na_2SO_4$ and evaporated to dryness. The residue was loaded on a column loaded with silica gel using $CH_2Cl_2$. The excess Moser's acid was eluted first with $CH_2Cl_2$. Then the column was eluted with $CH_2Cl_2$/acetone (8:2) to give the product. The product was checked by $^{19}$F for chiral purity. The $^{19}$F showed two peaks at 20° C. for the rotamer around the amide bond. But the two peaks became a single peak at 80° C. No raceimization was observed. $^1$H NMR (CDCl$_3$) d 1.42 (s, 9H, t-Butyl), 1.88 (s, 6H, $2CH_3$), 3.00 (m, 2H, $CH_2$), 3.50 (s, 3H, $OCH_3$), 3.75 (s, 3H, $OCH_3$), 4.28 (m, 1H, CH), 4.80 (m, 2H, $CH_2$), 5.10 (m, 1H, NH) and 7.45 (m, 5H, ArH). $^{19}$F NMR (DMSO-$d_6$) ppm −72.699 & −72.78(20° C.), −71.15(80° C.) with TFA (−76.53 ppm) as internal standard.

EXAMPLE 41

N-(N-Boc-2-Aminoethyl)-N-(2,2,2-trichloro-1,1-dimethyl-1-ethyoxycarbonyl)-L-serine[(α-methoxy-α-trifluoromethyl-α-phenyl)-O-acetate] methyl ester (41)

A. N-(N-Boc-2-aminoethyl)-D-serine(O-benzyl) methyl ester (41a)

The titled compound was prepared by following the method B Example 39, described for the preparation of L isomer 39b. The reactants used: Boc-aminoacetaldehyde (8.27g, 52 mmol), D-serine(0Bn) methyl ester (11.0 g, 52.63 mmol), NaOAc (7.07g, 52 mmol), Pd/C (2g) and dry MeOH (100 ml). The crude product was purified by flash chromatography using $CH_2Cl_2$/ethyl acetate as the eluent. Yield 12 g (66%). $^1$HNMR (CDCl$_3$) δ 1.44 (s, 9H, t-Butyl), 1.95 (bs, 1H, NH), 2.60 (m, 1H, $CH_2$), 2.80 (m, 1H, $CH_2$), 3.18 (m, 2H, $CH_2$), 3.44 (t, 1H), 3.68 (m, 2H, $CH_2$), 3.72 (s, 3H, $OCH_3$), 4.50 (s, 2H, $OCH_2$), 5.06 (bs, 1H, NH) and 7.26 (m, 5H, ArH). Anal. Calcd for $C_{18}H_{28}N_2O_5$: C, 61.34; H, 8.01; N, 7.95. Found: C, 61.31; H, 8.12; N, 7.85.

B. N-(2-Boc-Aminoethyl)-D-serine methyl ester (41b)

The titled compound was prepared by following the procedure described for the preparation of L-isomer 40a, Example Y. The reactants used were: The substrate 41a, (0.71g, 2 mmol), Pd/C (10%, 0.2g) and dry MeOH (20 ml). The crude product was purified by flash chromatography using $CH_2Cl_2$/MeOH as the eluent. Yield 0.9g (95%). $^1$HNMR (CDCl$_3$) δ 1.42 (s, 9H, t-Butyl), 2.70 (m, 1H, $CH_2$), 2.88 (m, 1H, $CH_2$), 3.20 (m, 2H, $CH_2$), 3.45 (m, 1H), 3.62 to 3.90 (m, 6H, $CH_2$, $OCH_3$), 5.15 (bs, 1H, NH).

C. N-(N-Boc-2-aminoethyl)-N-(2,2,2-trichloro-1,1-dimethyl-1-ethyoxycarbonyl)-D-serine(OH) methyl ester (41c)

The titled compound was prepared by following the procedure described for the preparation of L-isomer 40b. The reactants used were: The substrate 41b, (0.5g, 1.91 mmol), 1,1-dimethyl-2,2,2-trichloroethyl chloroforamate (0.72g, 3 mmol), 1N NaHCO$_3$ (5 ml, 5 mmol) and ether (10 ml). The crude product was purified by flash chromatography using $CH_2Cl_2$/acetone as the eluent. Yield 0.5g (56%). $^1$HNMR (CDCl$_3$) δ 1.42 (s, 9H, t-Butyl), 1.90 (s, 6H, $2CH_3$), 3.35 (m, 2H, $CH_2$), 3.50 (m, 2H, $CH_2$), 3.75 (s, 3H, $OCH_3$), 3.90 to 4.30 (m, 3H, OH & $CH_2$), 4.45 (m, 1H, CH), 5.06 (m, 1H, NH).

D. N-(N-Boc-2-Aminoethyl)-N-(2,2,2-trichloro-1,1-dimethyl-1-ethyoxycarbonyl)-L-serine[α-methoxy-α-trifluoromethyl-α-phenyl)-O-acetate]methyl ester (41d)

The substrate 41c 15 (0.3g, 0.65 mmol) was dissolved in dry $CH_2Cl_2$ (30 ml) and cooled to 0° C. under argon. To this cold stirred solution was added dry pyridine (1 ml) followed by α-methoxy-α-trifluoromethyl-α-phenyl acetic acid chloride (0.18 g, 0.7 mmol). After the addition of acid chloride, the reaction was allowed to stir for 12h. The reaction mixture was diluted with $CH_2Cl_2$ (75 ml) and washed with 5% $NaHCO_3$ (100 ml), water (SOmI) and brine (50 ml). The $CH_2Cl_2$ layer was dried over anhydrous $Na_2SO_4$ and evaporated to dryness. The residue was loaded on a column silica gel using $CH_2Cl_2$. The excess Moser's acid was eluted first with $CH_2Cl_2$. Then the column was eluted with $CH_2Cl_2$/acetone (8:2) to give the product. The product was checked by19F for chiral purity. The $^{19}F$ showed two peaks at 20° C. for rotamer around the amide bond. But the two peaks became single peak at 80° C. No raceimization was observed. The L-isomer (40) and D-isomer (41d) were mixed and checked by $^{19}F$ NMR. The mixture showed a triplet (ppm, -70.772, -70.856 & -70.947) at 20° C., but at 80° C. a triplet became a doublet (ppm, -70.679 & -70.758). This accounts for the DL mixture and rotamer at 20° C. On the other hand at 80° C. they exist only as the DL isomer. $^1H$ NMR (DMSO-$d_6$) δ 1.38 (s, 9H, t-Butyl), 1.80 (m, 6H, 2$CH_3$), 3.00 (m, 2H, $CH_2$), 3.32 (m, 2H, $CH_2$), 3.42 (s, 3H, $OCH_3$), 3.64 (s, 3H, $OCH_3$), 4.76 (m, 3H, CH & $CH_2$), 6.64 (m, 1H, NH) and 7.45 (s, 5H, ArH). $^{19}F$ NMR (DMSO-$d_6$) ppm -70.86 & -70.96(20° C.), -70.75(80° C.) with TFA (-76.53 ppm) as internal standard.

E. N-(N-Boc-2-aminoethyl)-N-[(1-thyminyl)acetyl]-D-serine(OBn) methyl ester (41e)

The titled compound was prepared by following the procedure described for the preparation of L-isomer 39c. The reactants used were: The substrate 41a (10.3g, 29.3 mmol), thymin-1-ylacetic acid (6.07g, 33 mmol), DhbtOH (5.4g, 33 mmol), EDC (6.3g, 33 mmol), dry $CH_2Cl_2$ (150 ml) and dry DMF (50 ml). The crude product was purified by flash chromatography using $CH_2Cl_2$/acetone as the eluent. Yield 13.2g (87%). $^1HNMR$ (CDCl$_3$) δ 1.42 (s, 9H, t-Butyl), 1.90 (s, 3H, $CH_3$), 3.32 (m, 2H, $CH_2$), 3.55 (m, 2H, $CH_2$), 3.72 (s, 3H, $OCH_3$), 4.00 (m, 2H, $CH_2$), 4.32 (m, 1H, CH), 4.50 (s, 2H, $OCH_2$), 4.52 (m, 2H, $CH_2$), 5.46 (t, 1H, NH), 6.85 (s, 1H, $C_6$), 7.30 (m, 5H, ArH) and 8.8 (s, 1H, NH). Anal. Calcd for $C_{25}H_{34}N_4O_8$: C, 57.90; H, 6.61; N, 10.80. Found: C, 57.82; H, 6.67; N, 10.67.

EXAMPLE 42

N-(N-Boc-2-aminoethyl)-N-[(1-thyminyl)acetyl]-L (or D)-serine methyl ester (42)

Compound 39 (0.5g) is dissolved in ethanol and palladium on carbon (50 mg) is added. The mixture is shaken on a Parr hydrogenation apparatus for 24h. The reaction mixture is filtered and concentrated. The residue is purified by flash column chromatography to give the title compound.

EXAMPLE 43

N-(N-Boc-2-aminoethyl)-N-[(1-thyminyl)acetyl]-L (or D)-serine methyl ester (43)

Compound 42 is converted to the title compound using the procedures of Example 37.

EXAMPLE 44

N-(N-Boc-2-aminoethyl)-N-[(1-thyminyl)acetyl]-L-serine methyl ester (44)

Compound 43 is converted to the title compound using the procedures of Example 38.

EXAMPLE 45

N-Methyl PNA Monomers, General Procedures for Synthesis and Oligomerization

1. Method A

A. N-Methyl-1-amino-2,3-propandiol (45A)

Methylamine (172 ml of a 40% solution in water, 2 mol) was cooled to 0° C. and 2,3-epoxy-1-propanol (25g, 0.34 mol) was added at a rate to maintain the temperature at or below 10° C. The mixture was stirred for 3 hours at 0° C. Excess methylamine and water was evaporated in vacuo and the product was purified by distillation at 103-105° C., at 0.5 mm Hg, to give 25.6g (76%) of the title compound.

B. N-Boc-N-methyl-1-amino-2,3-propandiol (45B)

To a solution of N-methyl-1-amino-2,3-propandiol (21g, 0.2 mol) in water (340 ml) maintained at 0° C. was added Boc-anhydride (52.3g, 0.24 mol). The mixture was allowed to equilibrate to room temperature. The pH was adjusted to and maintained at 10.5 with 4N NaOH. NaOH (2 eq.) is added and the reaction mixture was kept at room temperature under an atmosphere of nitrogen overnight. The reaction mixture is cooled to 0° C. and the pH is adjusted to 2.5 with 4N HCl. The acidic mixture is extracted with ethylacetate (6×100 ml). The ethylacetate extracts were combined, washed with half-saturated $KHSO_4$ (3×150 ml) and saturated brine (1×150 ml), dried over $MgSO_4$ and evaporated to dryness. The title compound was isolated as an oil (bp 110-112° C. at 0.5 mm Hg). The yield of the title compound was 31.3g (81%).

C. N-Boc-N-methyl-2-amino-acetaldehyde (45C)

To a solution of N-Boc-N-methyl-1-amino-2,3-propandiol (20g, 0.097 mol) in water (100 ml) was added $KIO_4$ (24.68g, 0.108 mol). The reaction mixture was stirred for 2.5 hr under an atmosphere of nitrogen and then filtered. The filtrate was extracted with chloroform (5×50 ml). The resulting chloroform extracts are dried over $MgSO_4$, filtered, and evaporated to dryness. The title compound 13.26g (79%) was isolated as a clear oil (bp 76-80° C. at 0.5 mm Hg).

D. N-[(N-Boc-N-methyl)-2-aminoethyl]glycine ethyl ester (45D)

Glycine ethyl ester hydrochloride (0.58 mol) was dissolved in absolute ethanol (100 ml) and added dropwise to a solution of N-Boc-N-methyl-2-amino-acetaldehyde (10 g, 0.058 mol) and NaOAc (9.32g, 0.114 mol) dissolved in absolute ethanol (130 ml) at 0° C. This solution was hydrogenated using palladium on carbon (1.65g) and hydrogen (1 eq) overnight. The reaction mixture was filtered and water (80 ml) was added. The pH was adjusted to 8 with 2N NaOH and extracted with dichloromethane (5×60 ml). The organic phase was dried over $MgSO_4$ and evaporated to dryness. The residue was purified by kugelrohr distillation (100° C., 0.5 mm Hg) to give 10.6g (74.3%) of the title compound as a clear oil.

E. General Procedure for synthesis and deprotection of the Monomers (A, C, G, T)

The monomers containing the four natural bases attached via an acetyl linker were synthesized using N-Boc-N-methyl-1-aminoethylglycine ethyl ester (X). To a solution of N-Boc-N-methyl-1-aminoethylglycine ethyl ester (X, 1.82g, 7 mmol) in dry DMF (30 ml) was added DHBT-OH (1.26 g, 7.7 mmol)and the carboxymethyl derivative of the base. Dichloromethane (30 ml) was added and the solution was cooled to 0° C. DCC (1.73g, 0.84 mmol, 1.2 eq) was added and the mixture was stirred for 1 hr. The reaction mixture was allowed to warm to room temperature and stirred for 3 hr and then filtered.

The protected A monomer, N-[(N-Boc-N-methyl)-2-aminoethyl]-N-[(9-adeninyl)acetyl]glycine ethyl ester, was synthesized using the above procedures. The reaction mixture was evaporated, redissolved in dichloromethane (300 ml), washed with half-saturated aqueous $NaHCO_3$ (3×100 ml), half-saturated aqueous $KHSO_4$, (2×100 ml) and saturated brine (1×100 ml). The organic phase was dried over $MgSO_4$ and evaporated to dryness. Absolute ethanol (60 ml) and water (30 ml) was added to the residue and the mixture was stirred overnight. The resulting precipitate was filtered and dried to afford the protected A monomer.

The protected A monomer is dissolved in THF and cooled to 0° C. LiOH (25 ml) was added and the reaction mixture was stirred for 30 min. The pH was adjusted to 1 with HCl (2N). The resulting precipitate was filtered and dried to afford N-[(N-Boc-N-methyl)-2-aminoethyl]-N-[(9-adeninyl)acetyl]glycine.

The protected C monomer, N-[(N-Boc-N-methyl)-2-aminoethyl]-N-[(1-cytosinyl)acetyl]glycine ethyl ester, was synthesized using the above procedures. The reaction mixture was evaporated to dryness. Ether (50 ml) was added to the residue and the mixture was stirred for 2 hr and filtered. This was repeated two times and then followed by addition of half-saturated aqueous $NaHCO_3$, filtered and dried. The resulting residue was dissolved in boiling dioxane (60 ml) and precipitated with water (60 ml), filtered and dried. The precipitate was purified by silica gel column chromatography using methanol/dichloromethane 5/95 to afford the protected C monomer.

The protected C monomer is dissolved in THF and cooled to 0° C. LiOH (60 ml) was added and the reaction mixture was stirred for 30 min. The pH was adjusted to 2 with HCl (2N). The mixture was extracted with dichloromethane and the organic phase dried over $MgSO_4$ and evaporated to afford 0.72 g (27%) N-[(N-Boc-N-methyl)-2-aminoethyl]-N-[(1-cytosinyl)acetyl]glycine (mp 181–184° C.).

The protected G monomer, N-[(N-Boc-N-methyl)-2-aminoethyl]-N-[(9-guaninyl)acetyl]glycine ethyl ester, was synthesized using the above procedures. The reaction mixture was evaporated, redissolved in dichloromethane (80 ml), washed with half-saturated aqueous $KHSO_4$, (3×40 ml), dried over $MgSO_4$, and evaporated to dryness. The precipitate was recrystallized in ethylacetate and dried to give the protected G monomer.

The protected G monomer is dissolved in methanol (40 ml) NaOH (40 ml, 2N) was added. The mixture was stirred at room temperature for 1 hr and then cooled to 0° C. The pH was adjusted to 2 with HCl (2N). The resulting precipitate was filtered, dried and recrystalized from absolute ethanol to afford 1.27g (43%) of N-[(N-Boc-N-methyl)-2-aminoethyl]-N-[(9-guaninyl)acetyl]glycine (mp 189-192° C.).

The protected T monomer, N-[(N-Boc-N-methyl)-2-aminoethyl]-N-[(1-thyminyl)acetyl]glycine ethyl ester, was synthesized using the above procedures. Dichloromethane (60 ml) was added to the reaction mixture and the resulting mixture was washed with half-saturated $NaHCO_3$ (3×30 ml), half-saturated aqueous $KHSO_4$ (2×30 ml), and saturated brine (1×30 ml). The organic phase was dried over $MgSO_4$ and evaporated. The residue was redissolved in dichloromethane, cooled to 0° C. and precipitated by slow addition of petroleum ether with vigorous stirring. Filtration of the mixture gave the protected T monomer as a white solid.

The protected T monomer is dissolved in methanol (45 ml) and cooled to 0° C. NaOH (45 ml, 2N) was added and the mixture was stirred at room temperature for 2 hrs. The pH was adjusted to 2 with HCl (2N) and the organic phase was extracted with ethylacetate. The organic phase was dried over $MgSO_4$ and evaporated to dryness to afford 1.45g (52%) of N-[(N-Boc-N-methyl)-2-aminoethyl]-N-[(1-thyminyl)acetyl]-glycine (mp 114-118° C.).

F. General Procedures for Oligomerization

The prepared monomers were used for oligomerization by solid phase peptide synthesis on MBHA-resin.

Using the above procedures the following oligomers were prepared:

H-GT*AGAT*CACT*Lys-$CONH_2$ (SEQ ID NO:33)

H-Gly-G*T*A*G*A*T*C*A*C*T*-Lys-$CONH_2$ (SEQ ID NO:34)

H-TTTTTT*TTTT-Lys-$CONH_2$ (SEQ ID NO:35)

H-TTTT*TT*TTT-Lys-$CONH_2$ (SEQ ID NO:36)

H-TTTT*TT*TT*TT-Lys-$CONH_2$ (SEQ ID NO:37)

H-Gly-T*T*T*T*T*T*T*T*T*T*-Lys-$CONH_2$ (SEQ ID NO:38)

wherein a * denotes a monomer functionalized to have an N-methyl group on the 2-aminoethyl portion of the monomer.

2. Method B

A. N-Boc sarcosylglycine methyl ester

To a suspension of Boc-sarcosine (9.0 g, 048 mol) in 70 ml of $CH_2Cl_2$ at −20° C. was added isobutyl chlorofomate (7.1 g, 0.052 mol) and N-Methylmorpholine (4.8 g, 0.047 mol). After 2 min glycine methyl ester, hydrochloride (7.19g, 0.057 mol) and N-methylmorpholine (5.76g, 0.057 mol) in $CH_2Cl_2$ (60 ml) was added. The reaction was stirred at −10° C. for 1 h and allowed to warm to room temperature. After 4h at room temperature, the reaction was filtered and washed with salt. $NaHCO_3$ (100 ml), 1N $NaHCO_3$ 100 ml, twice with 1N $KHSO_4$ (100 ml), water (100 ml) and brine (70 ml). The organic phase was dried with $Na_2SO_4$ and evaporated. The yield of Boc sarcosyl-glycine methyl ester was 89%.

B. N-[(N-Boc)(N-methyl)(1-thiocarbonyl)-2-aminoethyl]-glycine methyl ester

A suspension of the N-Boc-sarcosylglycine methyl ester (10.0 g, 0.041 mol) and Lawessons reagent (9.87 g, 0.024 mol) in toluene (90 ml), was heated to 80° C. for 1 h and then evaporated to dryness. The product was purified by column chromatography ($CH_2Cl_2$/MeOH 95:5) on silica gel to give 63% of the title compound.

C. N-[(N-Boc)(N-methyl)-2-aminoethyl]-glycine methyl ester

To a suspension of the N-[(N-Boc)(N-methyl)(1-thiocarbonyl)-2-aminoethyl]-glycine methyl ester (2.67 g, 0.0097 mol) and $NiCl_2 6H_2O$ (18.39 g, 0.077 mol) in THF:MeOH 1:1 (100 ml) at −20° C., $NaBH_4$ (8.78 g, 0.23 mol) was slowly added so that the temperature did not exceed 0° C. After addition of the $NaBH_4$, the reaction was allowed to go to room temperature. The reaction mixture was filtered several times through celite and evaporated to dryness. The product was isolated by column chromatography on silica gel with $CH_2CL_2$/MeOH 90:10 eluent. The yield of the title compound was 60%.

D. N-[(N-Boc)(N-methyl)-2-aminoethyl]-N-[(1-thyminyl)acetyl] glycine methyl ester To a suspension of N-[(N-Boc)(N-methyl)-2-aminoethyl]-glycine methyl ester (0.9 g, 0.0037 mol) and DHBT-OH (0.65 g, 0.004 mol) in $CH_2Cl_2$ 10 ml was added N-1-carboxymethylthymine (0.74 g, 0.04 mol) dissolved in DMF (6 ml). The solution was cooled in an ice bath and DCC (0.905, 0.049 mol) was added. The reaction mixture was stirred for 1 hour and the ice bath was removed. The reaction mixture was left for 16 hours at room temperature. The reaction mixture was filtered and washed twice with 1N $KHSO_4$ (15 ml) and three times with $NaHCO_3$ (15 ml), brine (10 ml) and water (10 ml) and dried with $Na_2SO_4$. The product was purified by column chromatography on silica gel with $CH_2Cl_2$/MeOH 95:5 eluent. The yield of the title compound was 55%.

E. N-[(N-Boc)(N-methyl)-2-aminoethyl]-N-[(1-thyminyl)acetyl] glycine

N-[(N-Boc)(N-methyl)-2-aminoethyl]-N-[(1-thyminyl)acetyl] glycine methyl ester was dissolved in 1N NaOH in MeOH/$H_2O$ 1:1 for 2 hours. The pH was adjusted to 2 with 2N HCl and extracted with ethyl acetate (50 ml). The organic phase was dried with $Na_2SO_4$ and evaporated to dryness. The yield of the title compound was 77%.

F. Oligomerization of N-methyl monomers

MBHA resin was adjusted to a loading of 0.1 mmol/mg by applying N-Boc N'-2-chloro-Z-lysine and DIC in $CH_2Cl_2$/DMF 1:1 24 hours. Coupling of the monomers including the N-methyl derivative follows the normal protocol for coupling of PNA monomers to the solid support (see Example 26). Coupling of the monomer following the N-methylated monomer follows this protocol: 3 eq. of the monomer and 3 eq. of PyBorP was dissolved in $CH_2Cl_2$/DMF and added to the solid phase. Diisoproylethylamine (9 eq.) was added. The reaction mixture was left for 24 hours. The reaction mixture was washed twice with DMF for a few seconds and once with DMF for two minutes. Then it was washed four times with $CH_2Cl_2$. This was repeated four times and the standard protocol for PNA oligomerization was then followed again.

EXAMPLE 46

Alternative Synthetic Route for Production of Functionalized PNA Monomers

A. (S)-3-Amino-2-oxetanone p-toluenesulfonate (46A)

Boc serine is treated with $Ph_3P$, DEAD, and TFA, followed by TsOH to give the title compound.

B. [(2-N-Tosyl)-3-N-Boc]propionic acid (46B)

Compound 46A is treated with $Boc_2NH$ to give the title compound.

C. Ethyl (2-N-phthaloyl)-(3-N-Boc)-2,3-diaminopropionate (46C)

Compound 46B is treated with ethoxycarbonylphthalimide followed by ethanol, DCC and HOBT to give the title compound.

D. Ethyl-(2-N-phthaloyl)-2,3-diaminopropionate (46D), ethyl-(3-N-Boc)-2,3-diaminopropionate (46E)

Compound 46C is either deprotected at the C-3 Boc group to give the amino group by treatment with TFA/dichloromethane to give Compound 46D, or deprotected at the C-2 amino group by treatment with hydrazine to give 46E.

The compounds ethyl-(2-N-phthaloyl)-2,3-diaminopropionate and ethyl-(3-N-Boc)-2,3-diaminopropionate are used directly in the syntheses of functionalized PNA backbones as described in Examples 30-38.

EXAMPLE 47

Incorporation of Biotin into an Aminoethyl Glycine-PNA Oligomer
H-TTC(Biotin)-TT-Lys-$NH_2$ (SEQ ID NO:39)

The protected aminoethyl glycine-PNA oligomer is assembled on a Boc-Lys(CIZ) modified MBHA resin with a substitution of approximately 0.10 mmol/g. The synthesis is initiated on 100 mg (dry weight) of t-Boc-Lys(CIZ)-MBHA resin, preswollen in dichloromethane. The aminoethyl glycine-PNA-oligomer is synthesized as per the procedures of Example 26. In step (3) an aeg-cytosine monomer from Examples 10 thru 17 which has been further derivatized following the procedures of Sproat B.S., et al., *Nucleic Acids Research*, 1989, 17, 3373-3386, to include an N-4 (5-trifluoroacetylaminopentyl) protected linking moiety. The procedure of Sproat is modified for use with a PNA monomer by simply using an aminoethyl glycine cytosine monomer having the N-4 exocyclic amino group deprotected and the amino and the carboxyl group of the aminoethyl glycine protected. The aminoethyl glycine-PNA was cleaved from the resin as per the procedures of Example 28. Yield: 5.8 mg (purity 90%), purified by RP-HPLC, (µBondapak C18). MS(FAB+) m/z:(found/calcd) 2702/2701

EXAMPLE 48

N-Terminal Conjugation of Biotin to a PNA

The N-terminal Boc-blocked PNA containing resin is measured out to typically provide 0.1-1.0 millimoles of PNA. This weight of resin is suspended in a 1:1 (v:v) dichloromethane:dimethylformamide solution (5 mL/100 mg of resin) and allowed to swell for a period of time if desired. The solvent is then removed by filtration and the resin resuspended in trifluoroacetic acid (3 mL/100 mg of resin) and shaken for 2 minutes. The trifluoroacetic acid is removed by filtration and this is repeated one time. The resulting resin is resuspended in pyridine (1 mL/10 µmoles of resin) and vacuum filtered to remove the pyridine. This is repeated. This washing step is repeated twice. The resin is suspended in 1:1 (v:v) pyridine:dimethylformamide and to this suspension is added the biotin (2-10 molar equivalents), TBTU (1.9-9.9 molar equivalents), and di-isopropylethlamine (5-20 molar equivalents) such that the final concentration of PNA monomer is 0.2M. The suspension is shaken for 15-60 minutes and the spent coupling solution is removed by filtration. The resin is then washed three times with 1:1 (v:v) dichloromethane:dimethylformamide solution (5 mL/100 mg of resin) giving the N-terminal biotin-attached PNA. This can be cleaved from the resin as described in Example 28. Starting with BocGly-GCAT-CO-Merrifield resin one obtains Biotin-Gly-GCAT-COOH and starting with BocGly-GCAT-Lys-CO-Merrifield resin one gets Biotin-Gly-GCAT-COOH.

EXAMPLE 49

N-Terminal Conjugation of Pteroic Acid to a PNA

An N-Boc-O-Benzyl-Blu-blocked PNA containing resin is measured out to typically provide 0.1-1.0 millimoles of PNA. This weight of resin is suspended in a 1:1 (v:v) dichloromethane:dimethylformamide solution (5 mL/100 mg of resin) and allowed to swell for a period of time if desired. The solvent is then removed by filtration and the resin resuspended in trifluoroacetic acid (1 mL/100 mg of resin) and shaken for 2 minutes. The trifluoroacetic acid is removed by filtration and this is repeated one time. The resulting resin is resuspended in pyridine solution (1 mL/1 gm of resin) and vacuum filtered to remove the pyridine. This is repeated. This is followed by resuspension followed by filtration (designated "washing") using 1:1 (v:v) dichloromethane:dimethylformamide solution (5 mL/1 gm of resin). This washing step is repeated twice. The resin is suspended in 1:1 (v:v) pyridine:dimethylformamide and to this suspension is added the N-Boc pteroic acid (prepared from pteroic acid, Aldrich Chem Co., 2-10 molar equivalents), TBTU (1.9-9.9 molar equivalents), and diisopropylethylamine (5-20 molar equivalents) such that the final concentration of PNA monomer is 0.2 m. The suspension is shaken for 15-60 minutes and the spent coupling solution is removed by filtration. The resin is then washed three times with 1:1 (v:v) dichloromethane:dimethylformamide solution (5 mL/100 mg of resin) giving the N-terminal folic acid-attached PNA. This can be cleaved from the resin as described in Example 28. Starting with N-Box-O-Benzyl-Glu-GCAT-CO-Merrifield resin one obtains Boc-folate-GCAT-COOH and starting with N-Boc-O-Benzyl-Glu-GCAT-Lys-COMerrifield resin one gets N-Boc-folate-GCAT-COOH.

EXAMPLE 50

Coupling to a Free COOH of a PNA or PNA Derivative

A PNA or PNA derivative having a single free COOH such as $CH_3CONH$-GCAT-COOH is dissolved in tetrahydrfuran:water to provide a solution that is 0.1 M in PNA and to this is added 1-(3-dimethylaminopropyl)-3-ethylcarbodimide hydrochloride [EDCI] and Rhodamine 123 hydrate to give a solution which is 0.1-1.0 molar in both EDCI and Rhodamine. The solution is stirred for 0.1-2 hours, then evaporated to a solid and purified by preparative HPLC as described in Example 29.

By this method one can prepare the following compounds.

Rhodamine=Rhod
  $CH_3CONH$-GCAT-CONHrhod (SEQ ID NO:40)
  $CH_3CONHY$-GCAT-Asp(Rhod)-$CONH_2$ (SEQ ID NO:41)
  Chol-GlyGCAT-Asp(Rhod-$CONH_2$ (SEQ ID NO:42)
  Chol-GCAT-Asp(Rhod)-$CONH_2$ (SEQ ID NO:43)
  RhodNHOC$(CH_2)_4$CONH-GCAT-Lys-$CONH_2$ (SEQ ID NO:44)
  RhodNHOC$(CH_2)_4$CONH-GCAT-$CONH_2$ (SEQ ID NO:45)
  $H_2N$-GCAT-CONHRhod (SEQ ID NO:46)
  $H_2N$-Gly-GCAT-CONHRhod (SEQ ID NO:47)
  $H_2N$-GCAT-Lys-CONHRhod (SEQ ID NO:48)
  $H_2N$-Gly-GCAT-Lys-CONHRhod (SEQ ID NO:49)
  Fluor-GCAT-CONRhod (SEQ ID NO:50)
  Fluor-GyGCAT-CONHRhod (SEQ ID NO:51)
  Fluor-GCAT-Gly-CONHRhod (SEQ ID NO:52)
  $CH_3CONH$-GCAT-Lys(Fluor)-CONRhod (SEQ ID NO:53)
  Chol-GlyGCAT-Lys(Fluor)-CONHRhod (SEQ ID NO:54)
  Chol-GCAT-Lys(Fluor)-CONRhod (SEQ ID NO:55)
  RhodNHOC$(CH_2)_4$ACONH-GCAT-Lys(Fluor)-$CONH_2$ (SEQ ID NO:56)
  Fluor-GlyGCAT-Lys(Fluor)-CONHRhod (SEQ ID NO:57)
  Fluor-GCAT-Lys(Fluor)-CONHRhod (SEQ ID NO:58)

EXAMPLE 51

6-S-Tritylthiohexylbronide (51), 6-S-tritylthiohexanoic acid (51A), 6-S-tritylthiohexylamine (51B), 6-S-tritylthiohexylmercaptan (51C)

To a solution of triphenylmethanethiol (Fluka; 69 g, 250 mmol) in 500 mL 95% ethanol (EtOH) was added 11 grams of sodium hydroxide dissolved in 75 mL of water (275 mmol). After stirring for about 15 minutes under an atmosphere of argon, using an addition funnel, 1,6-dibromohexane (91.5 g, 375 mmol, 58 mL) dissolved in 100 mL of 95% EtOH was added dropwise over a period of 1 hour with vigorous stirring. After about 15 minutes of stirring, a brown white solid separates out from the reaction mixture. After stirring for an additional 4 hours, the reaction mixture was filtered. The filtrate was evaporated under high vacuum and the oily residue was combined with the filtered residue and dissolved in 500 mL $CH_2Cl_2$, and filtered again. The filtrate was washed once with water (200 mL) and once with saturated NaCl solution. After drying the $CH_2Cl_2$ layer over $MgSO_4$, it was concentrated to 200 mL in volume. About 200 mL of hexane was added and the solution was left in the freezer. Three crops of cream white product was isolated to give 81 g of 6-S-Tritylthiohexylbromide (51), mp 91-92° C.

Portions of the product are independently treated with sodium cyanide followed by hydrolysis to give the corresponding acid, 6-S-tritylthiohexanoic acid (Compound 51A), with lithium azide followed by triphenylphosphine reduction to give the corresponding amine, 6-S-tritylthiohexylamine (Compound 51B), and with sodium hydrogen sulfide to give the corresponding thiol, 6-S-tritylthiohexylmercaptan (Compound 51C).

EXAMPLE 52

N-[(N-Boc)(1-(6-S-tritylhexyloxymethyl))2-aminoethyl]-N-[(1-thyminly)acetyl]glycine ethyl ester (52A) and N-[(N-Boc)(2-(6-S-tritylhexyloxymethyl))2-aminoethyl]-N-[(1-thyminly)acetyl]glycine ethyl ester (52B)

The free carboxyl group of compound 35 or 36 is protected as the ethyl ester according to standard procedures (see, e.g., Greene and Wuts, Protective Groups in Organic Synthesis, 2d edition, John Wiley & Sons, New York, 1991). The resulting ethyl aminoethylglycinate is alkylated with S-trityl-6-mercaptohexylbromide in the presence of DMF and sodium hydride to yield the title compounds.

EXAMPLE 53

N-[((N-Boc-)(1-{(6-thio)hexyloxymethyl})2-aminoethyl]-N-[(1-thyminly)acetyl]glycine ethyl ester (Compound 53A) and N-[((N-Boc-)(2-{(6-thio)hexyloxymethyl})2-aminoethyl]-N-[(1-thyminly)acetyl]glycine ethyl ester (Compound 53B)

Compound 52A or 52B (0.19 mmol) is dissolved in 4 mL chloroform. Silver Nitrate (8 mM) in EtOH (12 mL) is added and the reaction mixture is stirred for 45 minutes. Dithiothreitol (0.35 M) in chloroform (3 mL) is added and the reaction is stirred overnight. The white precipitate is filtered off and the solvent removed in vacuo. The residue is dissolved in dichloromethane, extracted once with saturated NaHCO$_3$ and saturated NaCl and dried over MgSO$_4$. The solvent is removed in vacuo. The product is purified on a silica gel column or by HPLC. The product is analyzed by $^1$H, $^{13}$C, and $^{13}$C-APT NMR and mass spectroscopy.

EXAMPLE 54

Attachment of Thiol Linker at Position 2 and 8 of Purines a. 2-Fluorohypoxanthene is treated with ethyl bromoacetate as per the procedures of Example 18 to give 9-carboxymethyl-2-fluorohypoxanthene ethyl ester which is further reacted with N-(N-Boc-2-aminoethyl) glycine ethyl ester as per the procedures of Examples 20 and 21 to give N-(N-Boc-2-aminoethyl)-N-[(2-fluorohypo-xanthene-9-yl)acetyl]glycine. N-(N-Boc-2-aminoethyl)-N-[(2-fluorohypoxanthene)-acetyl]glycine is reacted with 6-S-tritylthiohexylamine following the procedures of Harris, et al., *J. Am. Chem. Soc.* 1991, 113, 4328. The resulting purine C-2 thiol linker, PNA monomer is incorporated into PNA oligomers.

b. 8-Bromoadenine is treated with ethyl bromoacetate as per the procedures of Example 18 to give 9-carboxymethyl-8-bromoadenine ethyl ester. 9-Carboxymethyl-8-bromoadenine ethyl ester is treated as per the procedures of Example 19 to put a Cbz protection group on the N-6 exocyclic amino group. The resulting N-6-Cbz-9carboxymethyl adenine ethyl ester is further reacted with N-(N-Boc-2-aminoethyl) glycine ethyl ester as per the procedures of Examples 20 and 21 to give N-(N-Boc-2-aminoethyl)-N-[({N-6-Cbz-8-bromo}-9-adenyl)acetyl]glycine ethyl ester. N-(N-Boc-2-aminoethyl)-N-[({N-6-Cbz-8-bromo}-9-adenyl)acetyl]glycine ethyl ester is further reacted with 6-S-tritylthiohexylamine following the procedures of Harris, et al., *J. Am. Chem. Soc.* 1991, 113, 4328. The resulting purine C-8 thiol linker, PNA monomer is incorporated into PNA oligomers.

EXAMPLE 55

Attachment Of Amino Linker At 6-Position of Purines b. N-(N-Boc-2-aminoethyl)-N-[((N-2-trifluoroacetyl)N-6-trifluoroacetyl-aminohexylamino-9-guaninyl)acetyl]glycine (55A)

Guanine is dissolved in pyridine and treated with trifluoroacetic anhydride. The resultant 2(trifluoroacetamido)—6-O-pyrilyl-guanine intermediate is further reacted with pentafluorophenol to give 6-pentafluorophenyloxy-2-trifluoroacetamido guanine. A similar reaction scheme has been previously described for 2'-deoxy guanosine by Gao, et.al., *J. Org. Chem.*, 1992, 57, 6954.

The 2-(protected)functionalized 6-protected nucleobase is further reacted with 2-bromoethylacetate as per the procedures of Example 18 to give a protected acetyl tether at the 9 position. The compound is treated with N-6-trifluoroacetyl-hexane-1,6-diamine resulting in the replacement of the O—C$_6$F$_5$ with a bifunctional linking group (NH(CH$_2$)$_6$NHCOCF$_3$). This monoprotected diamine linker has been described by Agrawal, et al., *Tetrahedron Lett.*, 1990, 31, 1543. After the protected linking group is attached the resulting compound is treated via the procedures of Example 22 to give the title compound. The final compound having a protected linking moiety is further incorporated into oligomers using standard methods. The protected linking moiety is deprotected and functionalized with a further functional group e.g. fluorescein or biotin.

b. N-(N-Boc-2-aminoethyl)-N-[(N-6-trifluoroacetylaminohexylamino-9-adeninyl)acetyl]glycine (55B)

Hypoxanthine (6-hydroxypurine) is dissolved in pyridine and treated with pentafluorophenol to give 6-pentafluorophenyloxy-purine. The modified nucleobase is further treated with 2-bromoethylacetate as per the procedures of Example 18 to give the protected acetyl tether at the 9 position. The compound is treated with N-6-trifluoroacetyl-hexane-1,6-diamine resulting in the replacement of the O—C$_6$F$_5$ with a bifunctional linking group (NH(CH$_2$)$_6$NH-COCF$_3$). After the protected linking group is attached the resultant functionalized adenine nucleobase is treated via the procedures of Example 22 to give the title compound. The final compound having a protected linking moiety is further incorporated into oligomers using standard methods. The protected linking moiety is deprotected and functionalized with a further functional group e.g. fluorescein or biotin.

EXAMPLE 56

Coupling of Cholesterol to Thiol Containing PNA Monomer via Disulfide Bridge Compound 53A or 53B is treated with 2,2'-dithiobis(5-nitropyridine) in methylene chloride overnight. The precipitated 5-nitro pyridine-2-thione is removed by filtration, and the filtrate is concentrated. The resultant product (56C or 56D, respectively) is treated with thiocholesterol in $CH_2Cl_2$ and shaken overnight to give the compound (56A or 56B, respectively) with cholesterol attached through a disulfide link. The resulting compounds are further used in PNA synthesis.

EXAMPLE 57

Conversion of the Thiol Linker with a Trityl Protecting Group into a Thiol Linker Protected by Disulfide Linkage Compound 56C or 56D is treated with propylmercaptan in $CH_2Cl_2$ and stirred overnight. The resulting disulfide compound (57A and 57B, respectively), which has a $CH_2$—O—$(CH_2)_6$—S—S—$CH_2$—$CH_2$—$CH_3$ linkage, is further derivatized and incorporated into PNA oligomers. The free thiol group is liberated, before conjugation, by the addition of dithiothreitol (DTT).

EXAMPLE 58

Conversion to a Base Labile Thiol Linker

Compound 56C or 56D is treated with CBzCl (carbobenzyloxy chloride) in triethylamine. The resulting compound 58A or 58B, which contains a protected thiol group is used in the synthesis of PNA oligomers. The free thiol group may be regenerated from the monomer before or after the monomer is used for incorporation into a PNA oligomer by treatment with ammonia followed by DTT.

EXAMPLE 59

Conjugation Reactions of PNA-O-hexylthiol Linker

To illustrate the conjugation potential of the PNA-O—thiol tether, PNA $H_2N$-GCA*T-COOH (SEQ ID NO: 113) is synthesized as per the procedures of Example 26. The asterisk (*) denotes the incorporation of a disulfide protected thiolhexyloxymethyl linker attached at the C-1 position of the 2-aminoethyl portion of the monomer in the oligomer, synthesized as per the procedures of Example 58. The PNA is treated with 0.1M $AgNO_3$ in TEAA buffer followed by DTT treatment to generate a free thiol group. The thiol-PNA is then reacted with four classes of compounds each having a haloacetamide or a maleimide group and the desired functionality at the other end. The following compounds are employed: (1) a phospholipid maleimide, which can offer cell signaling and trafficking properties to PNAs; (2) 5-iodoacetamido-O-phenanthroline, which is a nucleic acid cleaving agent; this particular conjugation offers an added advantage of optimal placement for the cleaving agent as this reagent when complexed to cuprous ion reacts via a minor groove attack at the C-1 position; (3) pyrene-maleimide, which may stabilize a PNA-PNA, PNA-DNA or PNA-RNA duplex via intercalation; and (4) fluorescein maleimide, which is used as a general diagnostic tool, allowing the monitoring of PNA uptake. The conjugations are carried out in phosphate buffer (pH 8.0). Completion of reaction is monitored by HPLC analysis using a C-18 column and a linear 1% increase of $CH_3CN$ concentration for every minute. The conjugates are purified by size exclusion and reverse phase HPLC and characterized by their UV-VIS spectra (where applicable). Fluorescein maleimide, pyrene maleimide and phospholipid maleimide are purchased from Molecular Probes (Eugene, Oreg.). O-Phenanthroline-5-iodoacetamide is synthesized according to the published procedure of Sigman, *Biochemistry* 1990, 29, 9097.

EXAMPLE 60

N-[(N-Boc)-1-(5-phthaloylpentyloxymethyl)-2-aminoethyl]-N-[(1-thyminyl)acetyl]glycine Ethyl ester (57) and N-[(N-Boc)-2-(5-phthaloylpentyloxymethyl)-2-aminoethyl]-N-[(1-thyminyl)acetyl]glycine Ethyl ester (57A)

Compounds 35 and 36 are independently treated with ethanol/DCC to produce the ethyl ester which is then treated with 5-bromopentylphthalimide to yield the title compounds.

EXAMPLE 61

N-[(N-Boc)-1-(5-phthaloylpentyloxymethyl)-2-aminoethyl]-N-[(9-adeninyl)-acetyl]glycine Ethyl ester (61) and N-[(N-Boc)-2-(5-phthaloylpentyloxymethyl)-2-aminoethyl]-N-[(9-adeninyl)-acetyl]glycine Ethyl ester (61A)

Compounds 61 and 61A, are prepared using the general procedures of Examples 1 thru 6, 35 and 36, and further treated according to the procedures of Example 60, to yield the intermediate ethyl esters and the title compounds.

EXAMPLE 62

N-[(N-Boc)-1-(5-aminopentyloxymethyl)-2-aminoethyl]-N-[(9-adeninyl)-acetyl]glycine Ethyl ester (62) and N-[(N-Boc)2-(5-aminopentyloxymethyl)-2-aminoethyl]-N-[(9-adeninyl)-acetyl]glycine Ethyl ester (62A)

Compound 61 or 61A is dissolved in 200 ml methanol in a 500 ml flask. Hydrazine is added to the stirring reaction mixture. The mixture is heated to 60-65° in an oil bath and refluxed 14 hours. Solvent is evaporated in vacuo. The residue is dissolved in dichloromethane (250 ml) and extracted twice with an equal volume $NH_4OH$. The organic layer is evaporated to yield the crude product. NMR is used to assay product purity. The products are used in subsequent reactions without further purification.

EXAMPLE 63

N-[(N-Boc)-1-(5-phthaloylpentyloxymethyl)-2-aminoethyl]-N-[(1-thyminyl)-acetyl]glycine methyl ester (63)

Substrate 42 is converted to the title compound as per the procedures of Example 60.

EXAMPLE 64

N-[(N-Boc)-1-(5-aminopentyloxymethyl)-2-amino-ethyl]-N-[(1-thyminyl)-acetyl]glycine methyl ester (64)

Substrate 63 is converted to the title compound as per the procedures of Example 62.

EXAMPLE 65

Synthesis of PNA Oligomer Having Amine Containing Functionalities

The following PNA oligomers having aminoethylglycine backbones are synthesized according to the procedures of Examples 26 et seq.:

H$_2$N-GCA TGCAT-COOH (SEQ ID NO:60),
H$_2$N-GCA TGC AT-COOH (SEQ ID NO:61),
H$_2$N-GCA T*GCA *T-COOH (SEQ ID NO:62)
H$_2$N-CTG TCT CCA* TCC TCT TCA CT-COOH (SEQ ID NO:63)
H$_2$N-CTG TCT CCA* TCC TCT TCA* CT-COOH (SEQ ID NO:64)
H$_2$N—CCA A**GC CUC AGA-COOH (SEQ ID NO:65)
H$_2$N—CCA GGC UCA GA*T-COOH (SEQ ID NO:66)

wherein a *, , or * represents a PNA monomer functionalized to incorporate a pentyl-N-phthalimido functionality at a position having a hydroxy methyl group. A * indicates a pentyl-N-phthalimido functionality attached to the hydroxy methyl group at the C-1 carbon of the 2-aminoethyl portion of the monomer as synthesized in Examples 60 and 61. A  indicates a pentyl-N-phthalimido functionality attached to the hydroxy methyl group at the C-2 carbon of the 2-aminoethyl portion of the monomer as synthesized in Examples 60 and 61. A * indicates a pentyl-N-phthalimido functionality at serine-O of the serine portion of the monomer as synthesized in Example 63. PNA Oligomers SEQ ID NO:63 and 64 are compounds complementary to the E2 region of the bovine papilloma virus-i (BPV-1). PNA oligomers SEQ ID NO:65 and 66 are compounds complementary to the HIV-1 TAR region.

EXAMPLE 66

Conjugation Of PNA Oligomers Through a Hydroxyl Group

A. Functionalization with Biotin
1. Single Site Modification

About 10 O.D. units (A$_{260}$) of PNA oligomer SEQ ID NO:63 is treated as per the procedures of Example 62 to remove the phthaloyl protecting group. The resulting oligomer (see, Example 65) is dried in a microfuge tube. The PNA oligomer is dissolved in 200 µl of 0.2 M NaHCO$_3$ buffer and D-biotin-N-hydroxysuccinimide ester (2.5 mg, 7.3 µmols) (Sigma, St. Louis, Mo.) is added followed by 40 µl DMF. The solution is allowed to stand overnight. The solution is then applied to a Sephadex G-25 column (0.7×15 cm) and the PNA oligomer fractions are combined. Analytical HPLC is used to determine the percentage conversion to the product. The product is purified by HPLC (Waters 600E with 991 detector, Hamilton PRP-1 column 0.7×15 cm; solvent A: 50 mM TEAA pH 7.0; B: 45 mM TEAA with 80% acetonitrile: 1.5 ml flow rate: Gradient: 5% B for first 5 minutes, linear (1%) increase in B every minute thereafter) and further desalted on Sephadex G-25 to give the PNA oligomer:

CTG TCT CCA* TCC TCT TCA CT (SEQ ID NO:67)

wherein A* represents a PNA monomer functionalized to incorporate a biotin functionality linked via a pentylamino linking group attached to the C-1 hydroxymethyl group of the PNA monomer.

2. Multiple Site Modification

About 10 O.D. units (A$_{260}$) of PNA oligomer SEQ ID NO:64 is treated as per the procedures of Example 62 to remove the phthaloyl protecting group. The resulting oligomer (see, Example 65) is treated utilizing the method of Example 61(A)(1) above with D-biotin-N-hydroxysuccinimide ester (5 mg) in 300 µl of 0.2 M NaHCO$_3$ buffer/50 µl DMF. Analytical HPLC is used to monitor progress of the reaction. HPLC and Sephadex G-25 purification give the PNA oligomer:

CTG TCT CCA* TCC TCT TCA* CT (SEQ ID NO:68)

wherein A* represents a PNA monomer functionalized to incorporate a biotin functionality linked via a pentylamino linking group to the hydroxyl group of the serine portion of the PNA.

B. Functionalization with Fluorescein
1. Single Site Modification

A 1M Na$_2$CO$_3$/1M NaHCO$_3$ buffer (pH 9.0) is prepared by adding 1M NaHCO$_3$ to 1M Na$_2$CO$_3$. A 200 µl portion of this buffer is added to 10 O.D. units of PNA oligomer SEQ ID NO:63 (which is first treated to remove the phthaloyl protecting group as above) (see, Example 65) in a microfuge tube. A 10 mg portion of fluorescein-isothiocyanate in 500 µl DMF is added to give a 0.05 M solution. A 100 µl portion of the fluorescein solution is added to the solution of PNA oligomer in the microfuge tube. The tube is covered with aluminum foil and allowed to stand overnight. The reaction mixture is applied to a Sephadex G-25 column (0.7×20 cm) that has been equilibrated with 25% (v/v) ethyl alcohol in water. The column is eluted with the same solvent. Product migration can be seen as a yellow band well separated from dark yellow band of the excess fluorescein reagent. The fractions showing absorption at 260 nm and 485 nm are combined and purified by HPLC as per the purification procedure of Example 66(A)(1). The product is lyophilized and desalted on Sephadex to give the PNA oligomer:

CTG TCT CCA* TCC TCT TCA CT (SEQ ID NO:69)

wherein A* represents a PNA monomer functionalized to incorporate a fluorescein functionality linked via a pentylamino linking group to the hydroxymethyl group at the C-1 position of the 2-aminoethyl portion of the PNA.

2. Multiple Site Modification

About 10 O.D. units (A$_{260}$) of PNA oligomer SEQ ID NO:64 is treated as per the procedures of Example 62 to remove the phthaloyl protecting group. The resulting oligomer (see Example 60) is dissolved in 300 µl of the 1M Na$_2$HCO$_3$/1M Na$_2$CO$_2$ buffer of Example 61(B)(1) and 200 µl of the fluorescein-isothiocyanate stock solution of Example 61(B)(1) is added. The resulting solution is treated as per Example 61(B)(1). Analytical HPLC is used to indicate the percent of doubly labeled product. Work up of the reaction gives the PNA oligomer:

CTG TCT CCA* TCC TCT TCA* CT (SEQ ID NO:70)

wherein A* represents a PNA monomer functionalized to incorporate a fluorescein functionality linked via an pentylamino linking group to the hydroxyl group of the serine portion of the PNA.

C. Functionalization with Cholic Acid

1. Cholic Acid N-Hydroxysuccinimide Ester (Compound 61(C)(1)(A))

Anhydrous DMF (150 ml) was added to a mixture of cholic acid (4.09g, 15 mmol) and N-hydroxysuccinimide (5.25g, 45 mmol). The mixture was stirred in the presence of nitrogen. EDAC (4 ml, 25 mmol) was then added and the mixture was stirred overnight. The solution was then evaporated to a gum and partitioned between 1:1 ethyl acetate and 4% $NaHCO_3$ solution (pH 7.9) (100 ml each). The organic layer was washed with saturated NaCl solution, dried over anhydrous $Na_2SO_4$ and evaporated to yield the title compound as a pale yellow foam (4.6g, 91%). $^{13}C$ NMR (DMSO-$d_6$) δ 12.27, 16.71, 22.58, 22.80, 25.42, 26.19, 27.20, 28.49, 30.41, 30.56, 34.36, 34.82, 34.82, 35.31, 39.09, 39.09, 41.38, 41.53, 45.84, 46.05, 66.25, 70.45, 71.03, 169.28 and 170.16.

2. Single Site Modification

About 10 O.D. units ($A_{260}$) of PNA oligomer SEQ ID NO:63 is treated as per the procedures of Example 62 to remove the phthaloyl protecting group. The resulting oligomer (see, Example 60) is treated with cholic acid-NHS ester (Compound 1 in application Ser. No. 782,374, 5 mg, 9.9 μmols) in 200 μl of 0.2 M $NaHCO_3$ buffer/40 μl DMF. The reaction mixture is heated for 16 hours at 45° C. Analytical HPLC is used to determine the percent of product formation. Work up of the reaction gives the PNA oligomer:

CTG TCT CCA* TCC TCT TCA CT (SEQ ID NO:71)

wherein A* represents a PNA monomer functionalized to incorporate a cholic acid functionality linked via a pentylamino linking group to the hydroxymethyl group at the C-1 position of the 2-aminoethyl portion of the PNA.

3. Multiple Site Modification

About 10 O.D. units ($A_{260}$) of PNA oligomer SEQ ID NO:64 is treated as per the procedures of Example 62 to remove the phthaloyl protecting group. The resulting oligomer (see, Example 65) is treated with cholic acid-NHS ester (Compound 1 in application Ser. No. 782,374, 10 mg, 19.8 μmols) in 300 μl of 0.2 M $NaHCO_3$ buffer/50 μl DMF. The reaction mixture is heated for 16 hours at 45° C. The product is isolated according to the method of Example 66(A)(1). Analytical HPLC is used to determine the percentages of doubly and singly labeled products. Work up according to the procedure of Example 66(A)(1) gives the PNA oligomer:

CTG TCT CCA* TCC TCT TCA* CT (SEQ ID NO:72)

wherein A* represents a PNA monomer functionalized to incorporate a cholic acid functionality linked via a pentylamino linking group to the hydroxyl group of the serine portion of the PNA.

D. Functionalization with Digoxigenin

1. Single Site Modification

About 10 O.D. units ($A_{260}$) of PNA oligomer SEQ ID NO:63 is treated as per the procedures of Example 62 to remove the phthaloyl protecting group. The resulting oligomer (see, Example 65) is treated with digoxigenin-3-O-methylcarbonyl-ε-aminocaproic N-hydroxy succinimide ester (Boehringer Mannheim Corporation, Indianapolis, Ind.) in 200 μl of 0.1 M borate pH 8.3 buffer/40 μl DMF. The reaction mixture is allowed to stand overnight. The product is isolated according to the method of Example 66(A)(1). Work up of the reaction gives the PNA oligomer:

CTG TCT CCA* TCC TCT TCA CT (SEQ ID NO:73)

wherein A* represents a PNA monomer functionalized to incorporate a digoxigenin functionality linked via an pentylamino linking group to the hydroxymethyl group at the C-1 position of the 2-aminoethyl portion of the PNA.

2. Multiple Site Modification

About 10 O.D. units ($A_{260}$) of PNA oligomer SEQ ID NO:64 is treated as per the procedures of Example 62 to remove the phthaloyl protecting group. The resulting oligomer (see, Example 30) is treated with digoxigenin-3-O-methylcarbonyl-ε-aminocaproic N-hydroxy succinimide ester (Boehringer Mannheim Corporation, Indianapolis, Ind.) in 300 μl of 0.1 M borate pH 8.3 buffer/50 μl DMF. The reaction mixture was allowed to stand overnight. The product was isolated according to the method of Example 66(A)(1). Work up as per Example 66(A)(1) gives the PNA oligomer:

CTG TCT CCA* TCC TCT TCA* CT (SEQ ID NO:74)

wherein A* represents nucleotides functionalized to incorporate a cholic acid functionality linked via a pentylamino linking group to the hydroxyl group of the serine portion of the PNA.

EXAMPLE 67

Functionalization of PNA Monomers with Pyrene
N-[(N-Boc)-1-{(5-{4-(1-pyrenyl)
butanoylamino}pent-1-yl)oxymethyl}-2-aminoethyl]-N-[(uracil-1-yl)acetyl]glycine ethyl ester (67)
and N-[(N-Boc)-2-{(5-{4-(1-pyrenyl)
butanoylamino}pent-1-yl)oxymethyl}-2-aminoethyl]-N-[(uracil-1-yl)acetyl]glycine ethyl ester (67A)

A. Preparation of N-[(N-Boc)-1-(5-aminopentyloxymethyl)-2-aminoethyl]-N-[(uracil-1-yl)acetyl] glycine ethyl ester (67a) and N-[(N-Boc)-2-(5-aminopentyl-oxymethyl)-2-aminoethyl]-N-[(uracil-1-yl) acetyl]glycine ethyl ester (67b)

The title compounds are synthesized as per the procedures of Examples 1 thru 11, 35, 39, 60, and 62.

B. Preparation of N-[(N-Boc)-1-{(5-{4-(1-pyrenyl) butanoylamino}pent-1-5 μl)oxymethyl}-2-aminoethyl]-N-[(uracil-1-yl)acetyl]glycine ethyl ester (67)

Compound 67a or 67b (0.78 mmol), are dissolved in anhydrous DMF (15 mL). 1-Hydroxybenzotriazole (1.17 mmol) and 1-pyrene-butyric acid pentafluorophenyl ester (1.17 mmol) are added to the reaction mixture. The mixture is stirred under argon at room temperature for 2 hours, after which it is concentrated in vacuo. Residual DMF is coevaporated with toluene. The residue is dissolved in dichlorormethane (50 mL) and washed with an equal volume saturated $NaHCO_3$. The aqueous layer is washed with dichloromethane and the combined organic extracts are washed with an equal volume saturated NaCl. The aqueous layer is washed with dichloromethane and the combined organic layers dried over $MgSO_4$ and concentrated. The residue is purified by silica gel column chromatography to yield the respective product.

EXAMPLE 68

A. Preparation of N-[[(N-Boc)-1-[(5-(5-fluoroscenylthioureido)-pent-1-yl)oxymethyl]-2-aminoethyl]-N-[(uracil-1-yl)acetyl]glycine ethyl ester (68)

Fluorescein isothiocyanate (Isomer I, available from Cal Biochem, La Jolla, Calif.) was treated with 12 equivalents of pivaloyl chloride in Et$_3$N/THF to give di-O-pivaloyl fluorescein isothiocyanate. This compound was purified using a silica gel column with 3:1 hexane:ethyl acetate. Compound 67a is then condensed with dipivaloyl fluorescein isothiocyanate in CH$_2$Cl$_2$/pyrimidine. The protecting groups are removed by treatment with dilute acid. The title compound is then purified by elution from a silica column using ethyl acetate hexane as the eluent.

B. Preparation of N-[[(N-Boc)-2-[(5-(5-fluoresceinylthioureido)-pent-1-yl)oxymethyl]-2-aminoethyl]-N-[(uracil-1-yl)acetyl]glycine ethyl ester (68A)

Substituting 67b for 67a into the above procedure will give the title compound.

EXAMPLE 69

A. Preparation of N-[(N-Boc)-1-[1-({N-(cholesterol-O-carboxy)-5-aminopentyl}oxymethyl)-2-aminoethyl]-N-[(uracil-1-yl)acetyl]]glycine ethyl ester (69)

Compound 67a (6.0 mmol) is dissolved in anhydrous pyridine/dichloromethane 50/50 (v/v) (20 mL). Cholesteryl chloroformate (Fluka, 6.68 mmol) is dissolved in anhydrous dichloromehthane (20 ml) and added slowly under argon with a syringe to the stirring reaction mixture. The mixture is stirred under argon at room temperature for 2 h after which it is concentrated in vacuo. Residual DMF is coevaporated with toluene. The residue is dissolved in dichloromethane (50 mL) and washed with an equal volume of saturated NaHCO$_3$. The aqueous layer is washed with dichloromethane and the combined organic extracts washed with an equal volume of saturated NaCl. The aqueous layer is washed with dichloromethane and the combined organic layers dried over MgSO$_4$ and concentrated. The residue is chromatographed on a silica gel column with a gradient of 25% ethyl acetate in hexanes to 100% ethyl acetate. The desired product elutes with 100% ethyl acetate and is assayed for purity by TLC.

B. Preparation of N-[(N-Boc)-2-[1-({N-(cholesterol-O-carboxy)-5-aminopentyl}oxymethyl)-2-aminoethyl]-N-[(uracil-1-yl)acetyl]]glycine ethyl ester (69a)

Substituting 67b for 67a into the above procedure will give the title compound.

EXAMPLE 70

A. Preparation of N-[(N-Boc)-1-[{N-(2,4-dinitrophenyl)-5-aminopentyl}-oxymethyl]-2-aminoethyl]-N-[(uracil-1-yl)acetyl]glycine ethyl ester (70)

Compound 67a (1.37 mmol) is dissolved in methanol (20 mL). 2,4-Dinitrofluorobenzene (DNFB, 0.25 grams, 1.37 mmol) is added and the mixture shaken on a mechanical shaker. The reaction is monitored by TLC. After 90 min, another 0.25 grams of DNFB is added and the reaction mixture shaken an additional 30 min, followed by addition of another 0.25 grams of DNFB. After shaking 2.5 hours, the mixture is concentrated in vacuo and chromatographed on a silica gel column, eluting with a gradient of 25% ethyl acetate in hexanes to 100% ethyl acetate. The desired product elutes with 100% ethyl acetate and is assayed for purity by TLC.

B. Preparation of N-[(N-Boc)-2-[{N-(2,4-dinitrophenyl)-5-aminopentyl}-oxymethyl]-2-aminoethyl]-N-[(uracil-1-yl)acetyl]glycine ethyl ester (70A)

Substituting 67b for 67a into the above procedure will give the title compound.

EXAMPLE 71

A. Preparation of N-[(N-Boc)-1-[(N-(Na-Nim-Di-FMOC-L-histidinyl)-5-aminopentyl)oxymethyl]-2-aminoethyl]-N-[(uracil-1-yl)acetyl]glycine ethyl ester (71)

Compound 67a (1.51 mmol) is dissolved in dichloromethane (25 mL) and cooled to 0° C. in an ice bath. Na, Nim-Di-FMOC-L-histidine pentafluorophenyl ester (3.1 mmol, purchased from Sigma) and 1-hydroxybenzotriazole (0.24 mmol, purchased from Fluka) are added to the stirred reaction mixture stirred under argon. After 15 minutes, the ice bath is removed and the mixture stirred under argon at room temperature for 72 h. The mixture is concentrated in vacuo and chromatographed on a silica gel column, eluting with a gradient of 50% ethyl acetate in hexanes to 70% ethyl acetate in hexanes. The desired product elutes with 70% ethyl acetate.

B. Preparation of N-[(N-Boc)-2-[(N-(Na-Nim-Di-FMOC-L-histidinyl)-5-aminopentyl)oxymethyl]-2-aminoethyl]-N-[(uracil-1-yl)acetyl]glycine ethyl ester (71A)

Substituting 67b for 78a into the above procedure will give the title compound.

EXAMPLE 72

A. Preparation of N-[[(N-Boc)-1-[(N-(Ω-methyl-polyethylene glycol-propionoyl)-5-aminopentyl)oxymethyl]]-2-aminoethyl]-N-[(uracil-1-yl)acetyl]glycine ethyl ester (72)

Compound 67a, (1.55 mmol) is dissolved in anhydrous DMF (15 mL). 1-Hydroxybenzotriazole (1.75 mmol) and polyethylene glycol-propionic acid-NHS-ester (1.75 mmol) are added to the reaction mixture. The mixture is stirred under argon at room temperature for 2 hours after which it is concentrated in vacuo. Residual DMF is coevaporated with toluene. The residue is dissolved in dichloromethane (50 mL) and then washed with an equal volume saturated NaHCO$_3$. The aqueous layer is washed with dichloromethane and the combined organic extracts washed with an equal volume saturated NaCl. The aqueous layer is washed with dichloromethane and the combined organic layers dried over MgSO$_4$ and concentrated. The residue is chromatographed on a silica gel column, eluting with a gradient of 50% ethyl acetate in hexanes to 100% ethyl acetate.

B. Preparation of N-[[(N-Boc)-2-[(N-(Ω-methyl-polyethylene glycol-propionoyl)-5-aminopentyl)oxymethyl]]-2-aminoethyl]-N-[(uracil-1-yl)acetyl]glycine ethyl ester (72a)

Substituting 67b for 67a into the above procedure will give the title compound.

EXAMPLE 73

A. Preparation of Macrocycle Derivatized PNA Monomer

Compound 67a, (1.55 mmol) is treated according to the procedures of Example 67 with the macrocycle 4-{1,4,8,11-tetraza-[tri-(trifluoroacetyl)cyclotetradec-1-yl]}methyl benzoic acid-N-hydroxy succinimide ester (prepared according to Simon Jones, et. al., *Bioconjugate Chem.* 1991, 2, 416) to yield the product.

Substituting 67b for 67a into the above procedures will give the 2 substituted compound.

EXAMPLE 74

Functionalization with Folic Acid

A. Preparation of N-[(N-Boc)-1-[(5-(N-folate)aminopentyl)oxymethyl]-2-aminoethyl]-N-[(uracil-1-yl)acetyl]glycine ethyl ester (74a)

Compound 67a, is treated according to the procedures of Example 67 with folic acid pentafluorophenyl ester (protected with an isobutyryl protecting group) to yield the product.

B. Preparation of N-[(N-Boc)-2-[(5-(N-folate)aminopentyl)oxymethyl]-2-aminoethyl]-N-[(uracil-1-yl)acetyl]glycine ethyl ester (74b)

Substituting 67b for 67a into the above procedures will give 2 substituted compound.

EXAMPLE 75

A. N-[(N-Boc)-1-[(N-(2-methoxy-6-chloro-9-(6-aminohexanoyl)acridine)-5-aminopentyl)oxymethyl]-2-aminoethyl]-N-[(uracil-1-yl)acetyl]glycine ethyl ester (75)

6,9-Dichloro-2-methoxyacridine (Aldrich, 36 mmol) and phenol (2.5 g) were placed together on a round-bottom flask with a stirring bar and to this 6-amino-hexanoic acid (9.3 g, 71 mmol) was added and the flask was heated to 100° (oil bath) for 2 hours. TLC (10% methanol in methylene chloride) showed complete disappearance of starting material. The reaction mixture was cooled and poured into 200 mL of methanol. The. product isolates out as a yellow solid (about 10 g). This compound was then converted into its pentafluorophenol ester.

Compound 67a (78 mmol) is dissolved in anhydrous DMF (15 mL). 1-Hydroxy-benzotriazole (1.17 mmol) and 2-methoxy-6-chloro-9-(6-aminohexanoyl)acridine pentafluorophenyl ester (1.17 mmol) are added to the reaction mixture. The mixture is stirred under argon at room temperature for 2 h, after which it is concentrated in vacuo. Residual DMF is coevaporated with toluene. The residue is dissolved in dichloromethane (50 mL) and washed with an equal volume of saturated NaHCO$_3$. The aqueous layer is washed with dichloromethane and the combined organic extracts washed with an equal volume of saturated NaCl. The aqueous layer is then washed with dichloromethane and the combined organic layers dried over MgSO$_4$ and concentrated. The residue is purified by silica gel column chromatography.

B. Preparation of N-[(N-Boc)-2-[(N-(2-methoxy-6-chloro-9-(6-aminohexanoyl)acridine)-5-aminopentyl)oxymethyl]-2-aminoethyl]-N-[(uracil-1-yl)acetyl] glycine ethyl ester (75a)

Substituting 62b for 62a into the above procedures will give 2 substituted compound.

EXAMPLE 76

A. Preparation of N-[(N-Boc)-1-{(-5-(N,N-dimethylamino)pentyl)-oxymethyl}-2-aminoethyl]-N-[(uracil-1-yl)acetyl]glycine ethyl ester (76)

Compound 67a (0.29 mmol) is dissolved in 4 ml methanol. Sodium acetate pH 4.0 (2 ml), sodium cyanoborohydride (0.3 mmol) and 37% formaldehyde in water (300 µl) are added to the reaction mixture, which is stirred 2 hours, after which it is concentrated in vacuo. The residue is dissolved in dichloromethane (50 mL) and washed with an equal volume saturated NaHCO$_3$. The aqueous layer is washed with dichloromethane and the combined organic extracts washed with an equal volume saturated NaCl. The aqueous layer is washed with dichloromethane and the combined organic layers dried over MgSO$_4$ and concentrated. The residue is chromatographed on a silica gel column, eluting with a gradient of 50% ethyl acetate in hexanes to 100% ethyl acetate. The desired product elutes with 10% Methanol-90% ethyl acetate.

A. Preparation of N-[(N-Boc)-2-{(-5-(N,N-dimethylaniino)pentyl)-15 oxymethyl}-2-aminoethyl]-N-[(uracil-1-yl)acetyl]glycine ethyl ester (76a)

Substituting 67b for 67a into the above procedures will give 2 substituted compound.

EXAMPLE 77

Functionalization of PNA Oligomer with Reporter Enzymes, Peptides and Proteins A. Use of Heterobifunctional Linker 1. Synthesis of PNA-Maleimide Conjugate PNA oligomer SEQ ID NO:63 is treated as per the procedures of Example 62 to remove the phthaloyl protecting group. The resulting oligomer is lyophilized in a 5 ml pear-shaped flask. Sulfo-SMCC reagent, Pierce Chemical Co. (Rockford, II) (46 µmols) is dissolved in phosphate buffer (800 µl, 0.1M, pH 7.0) and added to the PNA oligomer bearing flask. An additional 200 µl of buffer are used to wash the reagent and transfer it to the flask containing the PNA oligomer. The contents of the flask are stirred overnight and loaded on to a Sephadex G-25 column (1×40 cm) equipped with a fraction collector. The PNA oligomer-maleimide conjugate containing fractions are collected and tested by analytical HPLC for separation from other NHS type products.

2. Synthesis of PNA oligomer-Peptide-Conjugate

An aliquot of the PNA oligomer-maleimide conjugate of Example 77(A)(1) (300 nmols) is lyophilized in a microfuge tube. SV40 peptide (pro-asp-lys-lys-arg-lys-cys)(about 2.5 [mols) is taken up in phosphate buffer (800 µl, 0.1 M, pH 7.0) and added to the PNA oligomer-maleimide conjugate containing tube. The contents of the tube are stirred overnight under an argon atmosphere. The reaction mixture is passed through a Sephadex G-25 column and the PNA-peptide conjugate fractions are identified by HPLC. Isolation of the product from product-bearing fractions via HPLC and desalting on Sephadex G-25 will yield a PNA oligomer of the sequence:

CTG TCT CCA* TCC TCT TCA CT SEQ ID NO:75 wherein A* represents a PNA monomer functionalized to incorporate a SV40 peptide functionality linked via a pentyl-amino-sulfo-SMCC (sulfosuccinimidyl-4-(N-maleimidomethyl)cyclohexane-1-carboxylate) linking group to the hydroxymethyl group of the designated PNA monomer.

B. Use of Homobifunctional Linker

1. Synthesis of PNA Oligomer-Disuccinimidyl Suberate Conjugate

PNA oligomer SEQ ID NO:63 is treated as per the procedures of Example 62 to remove the phthaloyl protecting group. The resulting oligomer is evaporated to dryness and dissolved in freshly prepared 0.1 M NaHCO$_3$/50 mM EDTA (100 µl, pH 8.25). The solution is then treated with a solution of DSS, Pierce Chemical Co. (Rockford, Il) (7 µmol) in 200 µl DMSO. The solution is stored at room temperature for 15 minutes and then immediately applied to a Sephadex G-25 column (1×40 cm) which has been previously packed and washed with water at 4° C. The PNA oligomer fractions are combined immediately in a 25 ml pear-shaped flask and are rapidly frozen in dry ice/isopropyl alcohol and lyophilized to a powder.

2. Synthesis of PNA Oligomer-Protein Conjugate

A solution of calf intestinal alkaline phosphatase (Boehringer Mannheim) (2.06 ml, 147 nmol) is spun at 4° C. in a Centricon microconcentrator at 6000 rpm until the volume is less than 50 µl. It is then redissolved in 1 ml of cold Tris buffer (pH 8.5, 0.1M containing 0.1 NaCl and 0.05 M MgCl$_2$) and concentrated twice more. Finally the concentrate is dissolved in 400 µl of the same buffer. This solution is added to the activated PNA oligomer from Example 77(B)(1) and the solution stored for 18 hrs at room temperature. The product is diluted to approximately 30 ml and applied to a Sephadex G-25 column (1×20 cm, chloride form) maintained at 4° C. The column is eluted with 50 nM Tris-Cl pH 8.5 until the UV absorbance of the fractions eluted, reach near zero values. The column is then eluted with a NaCl salt gradient 0.05 M to 0.75 M (150 ml each). The different peaks are assayed for both PNA oligomer presence and alkaline phosphatase activity and the product-bearing fractions are combined. Typically the first peak will be excess enzyme, the second peak the PNA oligomer-protein conjugate and the third peak unreacted PNA oligomer. Isolation of the product from the product-bearing fractions via HPLC and desalting on Sephadex G-25 will yield a PNA oligomer of the sequence:

CTG TCT CCA* TCC TCT TCA CT SEQ ID NO:76 wherein A* represents a PNA monomer functionalized to incorporate an alkaline phosphatase functionality linked via a DSS linking group to the aminopentyl oxymethyl of the designated PNA monomer.

EXAMPLE 78

Retinoic Acid Conjugated PNA oligomers

A. Retinoic Acid N-Hydroxysuccinimide Ester

Anhydrous DMF (150 ml) was added to a mixture of retinoic acid (15 mmol, Fluka) and N-hydroxysuccinimide (45 mmol). The mixture was stirred in the presence of argon. EDAC [ethyl-3-(3-dimethylamino)propyl carbodiimide] (4 ml, 25 nmol) was then added and this mixture was then stirred overnight. The solution was then evaporated to a yellow gum and dissolved in 200 ml ethylacetate and washed successively with 4% NaHCO$_3$ Solution (200 ml) followed by a saturated NaCl solution, dried over anhydrous MgSO$_4$ and evaporated to yield the desired compound as a yellow solid in nearly 90% yield.

B. Retinoic Acid Functionalized PNA Monomers

Compound 67a, 67b, 62, or 62A is dissolved in 200 µl of 0.2 M NaHCO$_3$ buffer and retinoic acid N-hydroxysuccinimide ester (7.3 µmols) is added followed by 40 µl DMF. The solution is allowed to stand overnight. The solution is then applied to a Sephadex G-25 column (0.7×15 cm) and the PNA oligomer fractions are combined. Analytical HPLC is used to determine the percentage conversion to the product. The product is purified by HPLC (Waters 600E with 991 detector, Hamilton PRP-1 column 0.7×15 cm; solvent A: 50 mM TEAA pH 7.0; B: 45 mM TEAA with 80% acetonitrile: 1.5 ml flow rate: Gradient: 5% B for first 5 minutes, linear (1%) increase in B every minute thereafter) and further desalted on Sephadex G-25 to give the retinoic acid-PNA monomer conjugate.

C. Retinoic Acid Functionalized PNA Oligomers

The retinoic acid-PNA monomer conjugates of Example 78B may be incorporated into PNA oligomers by deprotection of the PNA monomer carboxyl group and insertion of the resulting monomer into the synthetic procedures of Example 26.

EXAMPLE 79

Folic Acid Conjugated Oligonucleotide

A mixture of folic acid (30 mg, 68 µmols) and 1-hydroxybenzotriazole (30 mg, 222 µmols) is dissolved in 9 ml of dry DMF. To this solution, 50 µL of EDAC (312 µmols) is added. The resultant yellow viscous material is vortexed well and 500 µL from the solution is transferred into a 0.2M NaHCO$_3$ buffer solution containing PNA oligomer SEQ ID NO:63 which has previously been treated according to the procedure of Example 62 to convert the NPHTH group to the free amine. The solution is vortexed, covered with aluminum foil and allowed to react for 16 hrs. The mixture is then loaded onto a Sephadex G-25 column (1×40 cm). The PNA oligomer fraction is collected, concentrated and passed one more time through a Sephadex G-25 column. Isolation of the product from the product-bearing fractions via HPLC and desalting on Sephadex G-25 will yield a PNA oligomer of the sequence:

CTG TCT CCA* TCC TCT TCA CT SEQ ID NO:77 wherein A* represents a PNA monomer functionalized to incorporate a folic acid functionality linked to the aminopentyloxymethyl of the designated PNA monomer.

EXAMPLE 80

Methyl Folate Conjugated PNA Oligomer

In a like manner to Example 79, 5-methyl folate is conjugated to deprotected PNA oligomers SEQ ID NO:63 and SEQ ID NO:64 to give the conjugated methyl folate group tethered to the C—I position of the 2-aminoethyl portion of the PNA oligomer and to the Serine O portion when SEQ ID NO:64 is used which also has multiple sites for conjugation.

EXAMPLE 81

Pyridoxal Conjugated PNA Oligomer

PNA oligomer SEQ ID NO:63 or PNA oligomer SEQ ID NO:64 is treated according to the procedure of Example 62 to convert the N—PHTH group to the free amine. The resulting PNA oligomer is dissolved in 100 microliters of water, and 100 ml of 1M NaOAc buffer (pH 5.0) is added followed by 5 mg of pyridoxal hydrochloride (24 µmols) and 50 µl of 60 mM NaCNBH$_3$ solution. The solution is vortexed, left overnight, and is then passed through a Sephadex G-25 column and further purified in an analytical HPLC column.

EXAMPLE 82

Tocopherol Conjugated PNA Oligomer

A. Vitamin E (Tocopherol)-hemisuccinate-NHS ester

α-Tocopherolhemisuccinate (Sigma, 5 g, 9.4 mmols) was treated with 3 equivalents of N-hydroxysuccinimide and 2 equivalents of EDAC as described above in Example 78A. The work-up is the same as for Example 51, and yields the title compound as a light brown wax-like solid.

B. Tocopherol Conjugated PNA Oligomer α-Tocopherol-hemisuccinate-NHS ester is treated according to the procedure of Example 78B and 78C above to obtain tocopherol attached via a tether to the desired PNA oligomer.

EXAMPLE 83

Conversion of a PNA Oligomer Having an Alkyl Aminolinker to a PNA Oligomer Having a Thiolinker A. PNA Oligomer SEQ ID NO:78

PNA oligomer (SEQ ID NO:63) H$_2$N-CTG TCT CCA* TCC TCT TCA CT-COOH wherein * represents a pentyl N-phthaloyl oxymethyl group attached at the C-1 position of the 2-aminoethyl portion of the designated monomer in the oligomer, is treated with hydrazine/ethanol followed by 5 mg SATA (N-succinimidyl-S-acetylthio-acetate) in 0.2M NaHCO$_3$ buffer. The reaction mixture is passed through a Sephadex G-25 column, and the PNA oligomer fraction is concentrated and treated with 200 mM hydroxylamine hydrochloride solution in water (1 ml). The resulting PNA oligomer (SEQ ID NO:78) H$_2$N-CTG TCT CCA* TCC TCT TCA CT-COOH has a CH$_2$—O—(CH$_2$)$_5$—N—C(O)—CH$_2$—SH group attached to the C-1 position of the 2-aminoethyl portion of the designated (*) monomer in the oligomer.

B. PNA Oligomer SEQ ID NO:79

PNA oligomer (SEQ ID NO:64) H$_2$N-CTG TCT CCA* TCC TCT TCA* CT-COOH wherein represents a pentyl N-phthaloyl oxymethyl group attached at the serine O— portion of the designated monomer in the oligomer, is treated with hydrazine/ethanol followed by 5 mg SATA (N-succinimidyl-S-acetylthioacetate) in 0.2M NaHCO$_3$ buffer. The reaction mixture is passed through a Sephadex G-25 column, and the PNA oligomer fraction is concentrated and treated with 200 mM hydroxylamine hydrochloride solution in water (1 ml) to give PNA oligomer (SEQ ID NO:79) H$_2$N-CTG TCT CCA TCC TCT TCA* CT-COOH having a CH$_2$—O—(CH$_2$)$_5$—N—C(O)—CH$_2$—SH group attached to the serine O— portion of the designated (*) monomer in the oligomer.

EXAMPLE 84

Conjugation of o-Phenanthroline to PNA Oligomers

A. PNA Oligomer SEQ ID NO:80

PNA oligomer (SEQ ID NO:78) H$_2$N-CTG TCT CCA* TCC TCT TCA CT-COOH from Example 83(A) is treated with 2 mg of 5-(iodoacetamide)-o-phenanthroline reagent followed by shaking overnight. The oligomer is purified by a size exclusion column and reverse phase HPLC to yield;

CTG TCT CCA* TCC TCT TCA CT-COOH PNA Oligomer SEQ ID NO:80 wherein * represents a PNA monomer functionalized with phenanthroline via a thiol linker of the structure —CH$_2$—O—(CH$_2$)$_5$—NH—C(=O)—CH$_2$—S—CH$_2$—C(=O)—NH— at the C-1 position of the 2-aminoethyl portion of the designated monomer in the oligomer.

B. PNA Oligomer SEQ ID NO:81

PNA oligomer (SEQ ID NO:79) H$_2$N-CTG TCT CCA* TCC TCT TCA* CT-COOH from Example 83B having a CH$_2$—O—(CH$_2$)$_5$—N—C(O)—CH$_2$—SH group attached to the serine O— portion of the designated (*) monomer in the oligomer is treated with 2 mg of 5-(iodoacetamide)-α-phenanthroline reagent followed by shaking overnight. The oligomer is purified by a size exclusion column and reverse phase HPLC to yield H$_2$N-CTG TCT CCA* TCC TCT TCA*** CT-COOH PNA oligomer SEQ ID NO:81 wherein *** represents a PNA monomer functionalized at the serine O— position with phenanthroline via a thiol linker of the structure —CH$_2$—O—(CH$_2$)$_5$—NH—C(=O)—CH$_2$—S—CH$_2$—C(=O)—NH—.

EXAMPLE 85

Conjugation of Pyrene to PNA Oligomers

A. Single site modification

PNA oligomer (SEQ ID NO:63) H$_2$N-CTG TCT CCA* TCC TCT TCA CT-COOH, where * denotes a pentyl N-phthaloyl oxymethyl group at the C-1 position of the 2-aminoethyl portion of the designated monomer, (approximately 60 nmols) is treated with hydrazine/ethanol to give the free amine. The free amine is dried in a microfuge tube and is dissolved in 200 µl of 0.2 M NaHCO$_3$ buffer. Pyrene-1-butyric acid N-hydroxysuccinimide ester (i.e., succinimidyl-1-pyrene butyrate, 3 mg, 7.79 µmols, Molecular Probes, Eugene, Oreg.) is added followed by 400 µl of DMF. The mixture is incubated at 37° C. overnight, and the solution is applied to a Sephadex G-25 column (1×40 cm). The PNA oligomer fractions are combined, and the product is purified by HPLC to give PNA oligomer (SEQ ID NO:82) H$_2$N-CTG TCT CCA* TCC TCT TCA CT-COOH, where * denotes a pyrene attached via a CH$_2$—O—(CH$_2$)$_5$—NHC(=O)—(CH$_2$)3-linking group at the C-1 position of the 2-aminoethyl portion of the designated monomer.

B. Multiple site modifications

PNA oligomer (SEQ ID NO:64) H$_2$N-CTG TCT CCA* TCC TCT TCA* CT-COOH, where denotes a pentyl N-phthaloyl oxymethyl group at the serine —O portion of the designated monomer, is treated with hydrazine/ethanol to give the free amine. The free amini is further treated with two equivalents of pyrene-1-butyric acid N-hydroxysuccinimide (6 mg in 400 µl DMF) and worked up in the same fashion as Example 85(A). Sephadex G-25 purification followed by HPLC purification gives the doubly pyrene-conjugated PNA oligomer SEQ ID NO:83H$_2$N-CTG TCT CCA* TCC TCT TCA* CT-COOH where denotes a pyrene attached via a CH$_2$—O—(CH$_2$)$_5$—NHC(=O)—(CH$_2$)$_3$— linking group at the serine —O portion of the designated monomers in the oligomer. The oligomer is further purified as per the procedures of 85(A).

EXAMPLE 86

Conjugation of Acridine to PNA Oligomers

A. Single site modification

PNA oligomer SEQ ID NO:63 (2 μmol) is treated with hydrazine/ethanol to give the free amine. The free amine is dried and dissolved in 1M NaHCO$_3$/Na$_2$CO$_3$ buffer, pH 9.0, 200 μl. 9-Acridinyl-isothiocyanate, (5 mg, 2.1 μmols, Molecular Probes, Eugene, Oreg.) is dissolved in 200 μl DMF. This solution is added to the PNA oligomer, and the mixture is vortexed, covered with aluminum foil and left at 37° C. overnight. The reaction mixture is purified by passing through a Sephadex G-25 column (1×40 cm), concentrated and further purified by HPLC to give PNA oligomer SEQ ID NO:84H$_2$N-CTG TCT CCA* TCC TCT TCA CT-COOH where * denotes a 9-acridinyl group attached via a CH$_2$—O—(CH$_2$)$_5$—NHSCN-linking moiety to the C-1 position of the 2-aminoethyl portion of the indicated (*) monomer.

B. Multiple site modifications

PNA oligomer SEQ ID NO:84H$_2$N-CTG TCT CCA* TCC TCT TCA* CT-COOH is treated with hydrazine/ethanol to give the free amine. The free amine is treated with 400 μl of 1M Na$_2$CO$_3$/NaHCO$_3$ buffer (pH 9.0) and further treated with 10 mg of 9-acridinyl-isothiocyanate in 400 μl of DMF. The reaction mixture is vortexed, covered with aluminum foil and left at 37° C. overnight. The reaction mixture is purified as for the single site reaction of Example 85(A). The doubly conjugated acridine-oligonucleotide elutes as the last peak in the HPLC following single-modification products to give PNA oligomer SEQ ID NO:85H$_2$N-CTG TCT CCA* TCC TCT TCA* CT-COOH where *** denotes a 9-acridinyl group attached via a CH$_2$—O—(CH$_2$)$_5$—NHSCN-linking moiety to the serine O— position on the designated monomers in the oligomer.

EXAMPLE 87

Conjugation of Porphyrin to PNA Oligomers

Methylpyroporphyrin XXI ethyl ester (Aldrich) is condensed with aminocaproic acid using N-hydroxysuccinimide and EDAC. The resultant carboxylic acid is then activated again with N-hydroxy succinimide and EDAC and treated with PNA oligomer SEQ ID NO:63 according to the procedure of Example 85(A) to give PNA oligomer 5 SEQ ID NO:86H$_2$N-CTG TCT CCA TCC TCT TCA CT-COOH wherein * denotes a 2-porphyrin group tethered to the C-1 position of the 2-aminoethyl portion of the designated PNA oligomer.

EXAMPLE 88

Conjugation of Hybrid Intercalator-Ligand to PNA Oligomers

A. Photonuclease/intercalator ligand

The photonuclease/intercalator ligand 6-[[[9-[[6-(4-nitrobenzamido)hexyl]amino]acridin-4-yl]carbonyl]amino]hexanoyl-pentafluorophenyl ester is synthesized according to the procedure of Egholm et al., *J. Am. Chem. Soc.* 1992, 114, 1895.

B. Single site modification

10 O.D. units of PNA oligomer SEQ ID NO: 63 is treated with hydrazine/ethanol to deblock the amino group. The resultant material is dissolved in 100 μl of 0.1 M borate buffer (pH 8.4) and treated with 330 μl of DMF solution (10 mg in 1 ml of DMF) of 6-[[[9-[[6-(4-nitrobenzamido)hexyl]amino]acridin-4-yl]carbonyl]amino]hexanoyl-pentafluorophenyl ester. The solution is covered with aluminum foil and allowed to react overnight. The reaction mixture is purified by Sephadex G-25 and HPLC purification to give PNA oligomer SEQ ID NO:87H$_2$N-CTG TCT CCA* TCC TCT TCA CT-COOH wherein * denotes a photonuclease/intercalator ligand attached with a tether to the C-1 position of the 2-aminoethyl portion of the designated monomer in the oligomer.

C. Multiple site modification

10 O.D. units A$_{260}$ of PNA oligomer SEQ ID NO:64 is treated with hydrazine/ethanol to deblock the protected amino positions. The resultant material is dissolved in 200 μl of 0.1 M borate buffer (pH 8.4) and treated with 660 μl of the DMF solution of 6-[[[9-[[6-(4-nitrobenzamido)hexyl]amino]acridin-4-yl]carbonyl]amino]-hexanoylpentafluorophenyl ester (10 mg in 1 ml solution) and the solution is covered with aluminum foil and left aside overnight. The solution is purified by Sephadex G-25 and reverse phase HPLC to give PNA oligomer SEQ ID NO:88H$_2$N-CTG TCT CCA* TCC TCT TCA* CT-COOH wherein denotes a photonuclease/intercalator ligand attached with a tether to the serine O-position of the designated monomers in the oligomer.

EXAMPLE 89

Conjugation of Bipyridine Complex to PNA Oligomers

A. Bipyridine complex

Succinimidyl-4-carboxyl-4'-methyl-2,2'-bipyridine is synthesized according to the procedure of Telser, et al., *J. Am. Chem. Soc.* 1989, 111, 7221.

B. Single site Modification

10 O.D. A$_{260}$ units of PNA oligomer SEQ ID NO:63 is treated with hydrazine/ethanol to deblock the protected amino group. The resultant material is reacted with a 200 fold molar excess of succinimidyl-4-carboxyl-4'-methyl-2, 2'-bipyridine in 0.1 M borate buffer pH 8.5/DMF. The solution is purified by Sephadex G-25 and reverse phase HPLC to yield PNA oligomer SEQ ID NO:89H$_2$N-CTG TCT CCA* TCC TCT TCA CT-COOHH$_2$N-CTG TCT wherein * denotes a bipyridinyl complex attached via a linker to the C—1 position of the 2-aminoethyl portion of the designated monomer in the oligomer.

EXAMPLE 90

Conjugation of Aryl Azide Photocrosslinkers to PNA Oligomers

A. Conjugation of N-hydroxysuccinimidyl-4-azidobenzoate (HSAB)

PNA oligomer SEQ ID NO:63 is treated with hydrazine/ethanol to give the free-amine containing PNA oligomer:
CTG TCT CCA* TCC TCT TCA CT-COOH SEQ ID NO:90 wherein * denotes a pentylamino oxymethyl group attached at the C-1 of the 2-aminoethyl portion of the designated monomer in the oligomer.

PNA oligomer SEQ ID NO:90 (approx. 50 nmols) is dried, dissolved in 500 ml of 0.2M NaHCO₃ buffer pH 8.1 and treated with 25 mg of N-hydroxysuccinimidyl-4-azidobenzoate (HSAB, 96 μmols, available both from Pierce & Sigma) dissolved in 500 μl of DMF. The mixture is stirred overnight at 37° C. and passed twice over Sephadex G-25 column (1×40 cm). The PNA oligomer fraction is purified by reverse-phase HPLC (5%-40% CH₃CN in 60 min) on a reverse phase column to give PNA oligomer SEQ ID NO:91 CTG TCT CCA* TCC TCT TCA CT-COOH wherein * denotes an HSAB group attached via a tether to the C—I position of the 2-aminoethyl portion of the designated monomer in the oligomer.

B. Conjugation of N-succinimidyl-6(4'-azido-2'-nitrophenyl-amino)hexanoate

PNA oligomer SEQ ID NO:90 is dissolved in 500 ml of NaHCO₃ buffer (0.2M, pH 8.1) and treated with 500 μL of DMF containing 500 mg of N-succinimidyl-6(4'-azido-2'-nitrophenyl-amino)hexanoate (SANPAH, 128 μmols, available both from Pierce and Sigma). The reaction vial is wrapped with aluminum foil and heated at 37° C. overnight. The reaction mixture is passed twice over a Sephadex G-25 column (1×40 cm). The PNA oligomer fraction is purified by reverse-phase HPLC (5%–40% CH₃CN in 60 min.) on a reverse phase column to give PNA oligomer SEQ ID NO:92 CTG TCT CCA* TCC TCT TCA CT-COOH wherein * denotes a 6(4'-azido-2'-nitrophenyl-amino)hexanoate group attached via a tether to the C-1 position of the 2-aminoethyl portion of the designated monomer in the oligomer.

EXAMPLE 91

Conjugation of Imidazole-4-acetic acid to PNA Oligomers

A. Activated imidazole-4-acetic acid

Imidazole-4-acetic acid was reacted with 2,4-dinitrofluoro benzene. The resulting imidazole-N-(DNP)-4-acetic acid was converted to its N-hydroxy succinimide ester by treating with NHS/EDAC according to the procedure of Example 78.

B. PNA conjugation

10 O.D. $A_{260}$ units of PNA oligomer SEQ ID NO:90. is reacted with a 100 fold molar excess of imidazole-N-(DNP)-4-acetic acid NHS ester in 0.1M borate buffer pH 8.5/DMF (200 μL each). The mixture is stirred overnight and further treated with 200 μL of mercaptoethanol to cleave off the DNP protecting group. The resulting reaction mixture is purified by passing through a Sephadex G-25 column followed by reverse phase HPLC to give PNA oligomer SEQ ID NO 93 CTG TCT CCA* TCC TCT TCA CT-COOH wherein * denotes an imidazolyl group attached via a tether to the C-1 position of the 2-aminoethyl portion of the designated monomer in the oligomer.

EXAMPLE 92

Conjugation of Metal Chelating Agents to PNA Oligomers

A. EDTA Complex

To form an EDTA Fe(II) complex for coupling to a PNA oligomer as a nucleic acid cleaving agent, tricylohexyl ester of EDTA, is synthesized according to the procedure of Sluka, et al., *J. Am. Chem. Soc.* 1990, 112, 6369.

B. PNA Oligomer Modification

The tricyclohexyl ester of EDTA (1.25 mg, 1.94 mmol) and hydroxybenzotriazole (HOBt, 1 mg, 6.6 mmol) are dissolved in DMF (50 μL) and EDAC. 10 μL is added. To this solution, PNA oligomer SEQ ID NO:90 (10 OD units) in 100 μL 0.1M borate buffer is added and left overnight. The solution is passed through a Sephadex G-25 column and the PNA oligomer fraction is treated with conc. NH₃ (100 μL) for 1 hr. to cleave off the acid protecting groups. Finally purification is effected by size exclusion chromatography and HPLC.

C. DTPA Site Modification

PNA oligomer SEQ ID NO:90 is treated with diethylene triamine pentaacetic anhydride (DTPA) in 0.1M NaHCO₃/ DMF to offer single-site modification. The conjugate is complexed with Gadolinium ion (Gd III) to form a contrasting agent, which is useful as, inter alia, an uptake measuring agent. The resulting PNA oliogmer SEQ ID NO:94 CTG TCT CCA* TCC TCT TCA CT-COOH wherein * denotes the complexed Gadolinium ion attached via a tether to the C-1 position of the 2-aminoethyl portion of the designated monomer in the oligomer.

EXAMPLE 93

Conjugation of Cholesterol To PNA Oligomers

A. Method 1- via aminolinker

Cholesterol-hemisuccinate is first converted to its N-hydroxy succinimide ester, which is then conjugated to PNA oligomer SEQ ID NO:90 according to the procedure of Example 85(A) to give PNA oligomer SEQ ID NO:95 CTG TCT CCA* TCC TCT TCA CT-COOH wherein * denotes cholesterol attached via a tether to the C—I position of the 2-aminoethyl portion of the designated monomer in the oligomer or PNA oligomer SEQ ID NO:64 which is first treated with hydrazine/ethanol to free the amine and then further treated as per the procedures of Example 85(A) to give PNA oligomer SEQ ID NO:96H₂N-CTG TCT CCA *TCC TCT TCA CT-COOH wherein denotes a cholesterol attached via a tether to the serine O— position of the designated monomers in the oligomer.

B. Method 2- Conjugation of Cholesterol via a Disulfide Bridge

1. S-(2-thio-5-nitropyridyl)-thio cholesterol

Thiocholesterol (1.4 g, 3.5 mmol) is added to a stirred solution of 2,2'-dithiobis(5-nitropyridine) (1.4 g 4 mmol) in chloroform (20 mL) containing glacial acetic acid (400 μL) under an argon atmosphere. The reaction is allowed to continue overnight at room temperature, after which the precipitated 5-nitropyridine-2-thione is removed and the solution evaporated and purified on a silica column to give S-(2-thio-5-nitropyridyl)-thio cholesterol.

2. Conjugation to PNA Oligomer

PNA oligomer SEQ ID NO:89H₂N-GCA*T-COOH, wherein * denotes a disulfide protected thiohexyloxymethyl linking group attached to the C-1 position of the 2-aminoethyl portion of the monomer in the oligomer, is reacted with an excess of S-(2-thio-5-nitropyridyl)-thiocholesterol to attach the cholesterol moiety to the thiol group of the PNA oligomer via a disulfide bridge to give PNA oligomer SEQ ID NO:97H$_2$N-GCA*T-COOH wherein * denotes a cholesterol group attached via a tether to the C-1 position of the 2-aminoethyl portion of the monomer in the oligomer.

EXAMPLE 94

Coupling of Conjugate Groups to Primary Amino Groups of a PNA or a PNA Derivative PNAs and PNA derivatives having primary amino groups can have a conjugate group attached thereto including terminal amine groups and those "masked" during PNA oligomer synthesis and later regenerated.

Amino hexanoic acid (AHA) groups are added to PNA oligomers during solid phase synthesis as N-t-butyloxycarbonyl-ε-amino-hexanoic acid following the standard protocols.

I. General Synthesis of PNA Conjugates via an Amino Group

A. Coupling to Primary Amino Groups of H-PNA-NH$_2$, H-PNA-Lys-NH$_2$ and AHA-PNA-NH$_2$ (AHA=-NH—(CH$_2$)$_5$—C=(O)O—)

The three 2-aminoethylglycine-based PNA structures below were synthesized such that each has at least one free amino group:

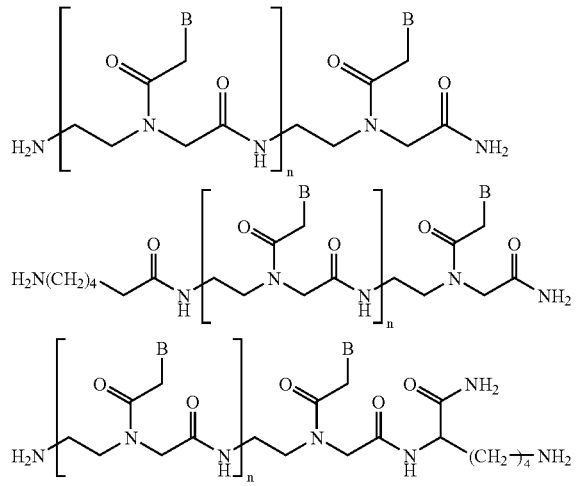

where B is a nucleobase or a derivative thereof.

B. Coupling of D-biotin-N-hydroxysuccinimide Ester (BAE)

H-PNA-NH$_2$, H-PNA-Lys-NH$_2$, or AHA-PNA-NH$_2$ (0.2 μL, 2.5 μg/μL in DMF) is added to a reaction flask containing 0.2M Na$_2$CO$_3$ (2.5 μL), 0.2M NaHCO$_3$ (2.5 μL), and CH$_3$CN (5 μL). BAE (0.2 μL, 20 μg/μL in DMF) is added to the reaction flask in three portions, while shaking the flask. The reaction is allowed to proceed at room temperature for 15 minutes after each addition. Fifteen minutes after the last addition following two-buffer gradient system:

| Time (min) | % Buffer A | % Buffer B |
|---|---|---|
| 0 | 100 | 0 |
| 10 | 100-r | r |
| 40 | 100-q | q |
| 50 | 100 | 0 |

Buffer A = 0.1% TFA in H$_2$O.
Buffer B = 0.1% TFA; 60% CH$_3$CN; 40% H$_2$O

C. Coupling of Acridine-N-hydroxysuccinimide Ester (AAE)

H-PNA-NH$_2$, H-PNA-Lys-NH$_2$, or AHA-PNA-NH$_2$ (27.5 μg) is added to a reaction flask containing 0.2M Na$_2$CO$_3$ (2.5 μL), 0.2M NaHCO$_3$ (2.5 μL), and CH$_3$CN (5 μL). AAE (0.7 μL, 20 μg/μL in DMF) is added to the reaction flask in three portions, while shaking the flask. The reaction is allowed to proceed at room temperature for 15 minutes after each addition. Fifteen minutes after the last addition the reaction mixture is separated by HPLC according to the procedure of Example 44(B).

D. Coupling of Azidobenzoyl Chloride (ABC)

H-PNA-NH$_2$, H-PNA-Lys-NH$_2$, or AHA-PNA-NH$_2$ (1.3 μL, 2.5 μg/μL in DMF) is added to a reaction flask containing 0.2M Na$_2$CO$_3$ (10 μL), and CH$_3$CN (10 μL). Azidobenzoyl chloride (30% g) is added to the reaction flask, which is allowed to remain at room temperature for fifteen minutes. Orthophosphoric acid (0.5 μl, 85% solution) is added, and the solution is extracted with chloroform five times. The aqueous phase is then separated on the HPLC according to the procedure of Example 94(B).

E. Coupling of Alkanoyl Chloride

H-PNA-NH$_2$, H-PNA-Lys-NH$_2$, or AHA-PNA-NH$_2$ (1.3 μL, 2.5 μg/μL DMF) is added to a reaction flask containing 0.2M Na$_2$CO$_3$ (2.5 μL), NaHCO$_3$ (2.5 μL), and CH$_3$CN (5 μL). One microliter of the alkanoyl chloride is added to the reaction flask with shaking, and the reaction is allowed to proceed at 37° C. for 15 minutes. The aqueous solution is extracted with hexane three times, and the resulting aqueous phase is separated by HPLC according to the procedure of Example 94(B).

F. Coupling of Cholesteryl Chloroformate (CC)

H-PNA-NH$_2$, H-PNA-Lys-NH$_2$, or AHA-PNA-NH$_2$ (1.3 μL, 2.5 μg/μL in DMF) is added to a reaction flask containing 0.2M Na$_2$CO$_3$ (2.5 μL), and CHCl$_3$ (2.5 μL). Cholesteryl chloroformate (30 μg) is added to the reaction flask, which is shaken at room temperature for five days and nights. The aqueous phase is then separated on the HPLC according to the procedure of Example 94(B).

G. Coupling of Dansyl Chloride (DC)

Dansyl chloride (0.16 μL of a 1 μg/μL in CH$_3$CN) is added to a reaction flask containing 0.2M Na$_2$CO$_3$ (0.5 μL) and 0.2M NaHCO$_3$ (0.5 μL). H-PNA-NH$_2$, H-PNA-Lys-NH$_2$, or AHA-PNA-NH$_2$ (3.34 μL, 2.5 μg/μL DMF) is then added, and the reaction is allowed to proceed in the dark at room temperature for 1.5 hours. The reaction mixture is then separated by HPLC according to the procedure of Example 94(B).

H. Coupling of Folic Acid (FA)

H-PNA-NH$_2$, H-PNA-Lys-NH$_2$, or AHA-PNA-NH$_2$ (1.3 µL, 2.5 µg/µL DMF) is placed in a reaction flask containing folic acid (0.5 µL of 1 µg/µL in DMSO), EDC (0.16 µL, 10 µg/µL in DMSO) and DMSO (3.34 µL). The reaction is allowed to proceed overnight in the dark at room temperature, and then folic acid (0.5 µL, 1 µg/µL in DMSO) and EDC (0.16 µL, 10 µg/µL in DMSO) are added to the flask. The reaction is allowed to proceed another six hours in the dark at room temperature, followed by another addition of folic acid (0.5 µL, 1 µg/µL in DMSO) and EDC (0.16 µL, 10 µg/µL in DMSO). The reaction is allowed to continue overnight in the dark at room temperature. Water (16.26 µL) is added, and the reaction mixture is lyophilized, taken up in water, and separated by HPLC according to the procedure of Example 94(B).

I. Coupling of Maleimido Active Ester (N-Maleimidopropionic Acid N-hydroxysuccinide Ester) (MAE)

H-PNA-NH$_2$, H-PNA-Lys-NH$_2$, or AHA-PNA-NH$_2$ (1.3 µL, 2.5 µg/µL in DMF) is added to a reaction flask containing 0.2M Na$_2$CO$_3$ (1.25 µL), 0.2M NaHCO$_3$ (1.25 µL), and CH$_3$CN (6.9 µL). MAE (0.2 µL, 20 µg/µL in DMF) is added to the reaction flask in three portions, while shaking the flask. The reaction is allowed to proceed at room temperature for 15 minutes after each addition. Fifteen minutes after the last addition the reaction mixture is separated by HPLC according to the procedure of Example 94(B) except that TFA is omitted from the gradient, and the product is collected.

J. Coupling of Quinone active ester (anthraquinone-2 carboxylic acid-ODhbt ester) (QAE)

H-PNA-NH$_2$, H-PNA-Lys-NH$_2$, or AHA-PNA-NH$_2$ (1.3 µL, 2.5 µg/µL in DMF) is added to a reaction flask containing 0.2M Na$_2$CO$_3$ (1.3 µL), 0.2M NaHCO$_3$ (1.3 µL), and CH$_3$CN (5.2 µL). QAE (0.9 µL, 5 µg/µL in DMF) is added to the reaction flask in three portions, while shaking the flask. The reaction was allowed to proceed at room temperature for 15 minutes after each addition. Fifteen minutes after the last addition the reaction mixture is separated by HPLC according to the procedure of Example 94(B).

K. Coupling of Fluorescein

A PNA or PNA derivative having a single free NH$_2$ such as H$_2$N-GCAT-COOH is dissolved in tetrahydrofuran:water to provide a solution that is 0.1 M in PNA and to this is added fluorescein isothiocyanate to give a solution which is 0.1-1.0 M in fluorescein isothiocyanate. The solution is. stirred for 0.1-2 hours, then evaporated to a solid and purified by preparative HPLC.

L. Coupling of EDTA

EDTA conjugates are prepared from EDTA-tribenzyl ester by standard solid phase synthesis. Purification is by HPLC.

M. Coupling of Nitrillo Triacetic Acid (NTA)

NTA conjugates are prepared as dibenzylesters from glycine-tert-butylester using standard solid phase synthesis. Purification is by HPLC.

N. Coupling of 5-Amino-1,10-phenanthroline-glutaramide (Phen$_1$)

1. 5-Amino-1,10-phenanthroline-glutarimide

5-Amino-1,10-phenanthroline (350 mg, 1.8 mmol) was refluxed with glutaric anhydride (2.0g, 17.5 mmol) in pyridine (3 mL) and triethylamine (3 mL) for 2 hours. The reaction mixture was reduced to a viscous oil by rotary evaporation. Column purification on silica with 10% methanol in methylene chloride (product produced bright red spots with Fe(II) on TLC) gave the crude product (320 mg 1.1 mmol). Further purification of the crude product was by recrystallization once from 30 mL boiling water to give the title compound (250 mg, 0.85 mmol) as centimeter long transparent needles.

2. 5-Amino-1,10-phenanthroline-glutaramide

The purified title compound from 94(I)N(1) above (250 mg, 0.85 mmol) was refluxed in water (3 mL) and triethylamine (3 mL) for 10 minutes. The material was evaporated on a rotary evaporator and further coevaporated with 3, 10 mL portions of water. This afforded the title compound in a quantitative yield with a trace of triethylamine as a contaminant. The material was recrystallized from water (30 mL) to give after drying the purified title compound (200 mg, 0.61 mmol) (72%) as a white macrocrysaline monohydrate.

3. Coupling to PNA

The triethylammonium salt of 5-Amino-1,10-phenanthroline-glutaramide (60 mg, 0.14 mmol) from Example 94(I) N(2) above was dissolved in DMF (1 mL) and pyridine (0.5 mL). HBTU (45 mg, 0.12 mmol) was added followed by diisopropylethylamine (0.05 mL, 0.3 mmol). This solution is then added to an N-terminal end of a growing PNA or can be used to functionalize gel.

O. Coupling of piperazine-N-acetic acid-N'-acetic acid-(5'-phenanthryl)-amide (Phen$_2$)

1. piperazine-N-acetic acid-tert-butylester-N'-acetic acid-(5'-phenanthryl)-amide Iodoacetamido-phenanthroline (150 mg, 0.41 mmol) and piperazineacetic acid-tert-butylester (90 mg, 0.48 mmol) were mixed in DMF (1 mL) and triethylamine (0.5 mL). The reagents were stirred for 1 hour at room temperature and then the solvents were removed by rotary evaporator. The product was purified by silica gel column chromatography with pyridine (15%) in DMF as the eluent (product produced bright red spots with Fe(II) on TLC) to give the title compound in a 70% yield (120 mg, 0.29 mmol).

2. piperazine-N-acetic acid-N'-acetic acid-(5'-phenanthryl)-amide

Piperazine-N-acetic acid-tert-butylester-N'-acetic acid-(5'-phenanthryl)-amide (120 mg, 0.29mmol) was dissolved-in dichloromethane (3 mL) and trifluoroacetic acid (3 mL).

The mixture was stirred at room temperature for 3 hours and then the solvent was removed in vacuo at 0.1 mmHg. This gave the title compound (with traces of starting material) in a quantitative yield as a trifluoroacetate.

3. Coupling to PNA

Piperazine-N-acetic acid-N'-acetic acid-(5'-phenanthryl)-amide (150 mg, 0.25 mmol) as a trifluoroacetate was dissolved in DMF (2 mL) and diisopropylethylamine. (1 mL). To the resulting solution (1.5 mL) was added HBTU (38 mg, 0.1 mmol) and this solution is then added to an N-terminal end of a growing PNA or can be used to functionalize gel.

P. Coupling of $Fluor_{phet}$ and $Fluor_{met}$

1. Fluorescein-(2-phenyl)ethylester-O-acetic acid-tert-butylester

Fluorescein-(2-phenyl)ethylester (3 g, 6.9 mmol) was dissolved in DMF (10 mL) and triethylamine (2.5 mL). The mixture was heated to 70° C., and bromoacetic acid tert-butylester (2 g, 10 mmol) was added. The reaction mixture was maintained at 70° C. for 2 hours and then cooled to room temperature. Dichloromethane (40 ml) was added and the resulting solution was extracted with 5% $NaHCO_3$ (2×10 mL). The organic phase was dried over $Na_2CO_3$, filtered and evaporated in vacuo. The residue was purified twice using silica gel column chromatography with methanol (3-15%) in dichloromethane as the eluent. The title was obtained in a 53% yield (2.0g, 3.6 mmol).

2. Fluorescein-(2-phenyl)ethylester-O-acetic acid

Fluorescein-(2-phenyl)ethylester-O-acetic acid-tert-butylester (2.0g, 3.6 mmol) was dissolved in dichloromethane (10 ml) and trifluoroacetic acid (10 mL). The mixture was stirred overnight and then evaporated to a viscous oil. Following 2 column purifications with methanol (10%) in dichloromethane as the eluent the title compound precipitated from the last eluate, and was dissolved in warm ethanol (96%, 150 mL). The ethanol was evaporated to leave approximately 30 mL and upon cooling the title compound precipitated. The title compound was isolated as a microcrystaline red powder in a 78% yield (1.4g, 2.8 mmol).

3. Fluorescein-monomer-ethylester

Fluorescein-(2-phenyl)ethylester-O-acetic acid (1.08 g, 2.0 mmol) and Compound 8, N-Boc-aminoethyl glycine ethyl ester (500 mg, 2.0 mmol) was dissolved in DMF (15 mL) and dichloromethane (5 mL), HDBTU (324 mg) and DCC (480 mg) were added. The mixture was heated to 50° C. for 1 hour and then allowed to stand at room temperature overnight. DCU was filtered off and ether (50 mL) was added followed by washing with 5% $NaHCO_3$ (20 mL) and 5% $NaHSO_4$ (20. mL). The organic phase was dried and evaporated to dryness. Purification was by silica gel column chromatography using methanol (0-15%) in dichloromethane as eluent. The title compound was isolated in a 67% yield (0.98g, 13.5 mmol).

4. Fluorescein-monomers $Fluor_{phet}$ and $Fluor_{met}$

Fluorescein-(2-phenyl)ethylester (300 mg, 41 mmol) was dissolved in THF (20 mL) and LiOH (1 M, 5 mL) was added. The mixture was stirred for 35 minutes at room temperature, poured onto ice/dilute $NaHSO_4$ and was extracted with ethyl acetate. The organic phase was dried and evaporated to dryness. Purification was by silica gel column chromatography using DMF as eluent. The title compound $Fluor_{phet}$ was isolated as a dark red oil in a 30% yield (100 mg, 1.4 mmol). The monomers are incorporated into PNA oligomers using standard protocols. (The transesterification product $Fluor_{met}$ was also observed in one synthesis and used to form a PNA conjugate.)

Q. PNA-Staphylococcal Nuclease Conjugate

Maleimido-PNA derivative (3 μg) from 94(I) above was dissolved in 10 mM $NaPO_4$ buffer (100 μL, pH 7.0) and was incubated with SH-straphylococcal nuclease mutant Lys116-Cys (10 μg) (Corey, et.al., *Science*, 1987, 238, 1401), for 2 hours at room temperature. The PNA-nuclease conjugate was separated from excess maleimido-PNA by chromatography on a Sephadex G-50 in 10 mM $NaPO_4$ pH 7.0.

II. Coupling of Conjugates to AHA-$T_2CT_2CT_4$-$NH_2$

A. Acridine-AHA-$T_2CT_2CT_4$-$NH_2$

PNA AHA-$T_2CT_2CT_4$-$NH_2$ (SEQ ID NO:98) was synthesized using standard methods and techniques as per Example 26. 3300 μg of PNA (SEQ ID NO:98) was dissolved in 0.2M $Na_2CO_3$ (300 μL), 0.2M $NaHCO_3$ (300 μL) and $CH_3CN$ (600 μL). Acridine-N-hydroxy-succinimide-ester (AAE) (100 μL, 20 μg/μL DMF) was added in 5 portions while shaking the reaction vessel. The mixture was left for 15 minutes at room temperature after each portion of AAE. The reaction was monitored by HPLC using a reversed phase spherisorp S50DS1 C-18 column (250×4.6 mm) and a gradient of varying concentrations of Buffer A (0.1% TFA in H2O) and Buffer B (0.1% TFA, 60% $CH_3CN$, 40% $H_2O$). The retention time of the starting material PNA AHA-$T_2CT_2CT_4$-$NH_2$ (SEQ ID NO:98) was approximately 15 minutes and that of the final PNA, acridine-AHA-$T_2CT_2CT_4$-$NH_2$ was 23 minutes.

After completion of the reaction, the PNA was precipitated with 12 ml of isobutanol, lyophilized and then redissolved in 1 ml $H_2O$. The acridine-PNA was purified by HPLC using a reversed phase C-18 column and the same conditions as above.

In a subsequent binding assay of the acridine-PNA to dsDNA the Kd shows that there is a 10-100 fold increase in the binding compared to that of unmodified PNA and that it binds to dsDNA at 150 mM salt at μmolar (6.5) concentrates.

B. Anthraquinone-AHA-$T_2CT_2CT_4$-$NH_2$

115 μg of PNA AHA-$T_2CT_2CT_4$-$NH_2$ (SEQ ID NO:98) was dissolved in 0.2M $Na_2CO_3$ (111 μL), 0.2M $NaHCO_3$ (111 μL) and $CH_3CN$ (444 μL). Anthraquinone-DHBT-ester (QAE) (79.5 μL, 5 μg/μL $CH_3Cl$) was added in 3 portions while shaking the reaction vessel. The mixture was left for 10 minutes at room temperature after each portion of QAE was added. The reaction was monitored by HPLC using a reversed phase spherisorp S50DS1 C-18 column (250×4.6 mm) and a gradient of varying concentrations of Buffer A (0.1% TFA in H2O) and Buffer B (0.1% TFA, 60% $CH_3CN$, 40% $H_2O$). The retention time of the starting material PNA AHA-$T_2CT_2CT_4$-$NH_2$ (SEQ ID NO:98) was approximately 21 minutes and that of the final PNA, acridine-AHA-T$_2$CT$_2$CT$_4$-NH$_2$ was 30 minutes.

After completion of the reaction, the H$_2$O phase with the PNA was lyophilized and then redissolved in 1 ml H$_2$O. The Quinone-PNA was purified by HPLC using a reversed phase C-18 column and the same conditions as above.

C. Biotin-AHA-T$_2$CT$_2$CT$_4$-NH$_2$

78 µL, 2.5 µg/µL of PNA AHA-T$_2$CT$_2$CT$_4$-NH$_2$ (SEQ ID NO:98) was dissolved in 0.2M Na$_2$CO$_3$ (150 µL), 0.2M NaHCO$_3$ (150 µL) and CH$_3$CN (300 µL). Biotin-N-hydroxy-succinimide-ester (BAE) (120 µL, 2 µg/µL DMF) was added in 4 portions while shaking the reaction vessel. The mixture was left for 15 minutes at room temperature after each portion of BAE was added.-The reaction was monitored by HPLC using a reversed phase spherisorp S50DS1 C-18 column (250×4.6 mm) and a gradient of varying concentrations of Buffer A (0.1% TFA-in H2O) and Buffer B (0.1% TFA, 60% CH$_3$CN, 40% H$_2$O). The retention time of the starting material PNA AHA-T$_2$CT$_2$CT$_4$-NH$_2$ (SEQ ID NO:98) was approximately 15 minutes and that of the final PNA, acridine-AHA-T$_2$CT$_2$CT$_4$-NH$_2$ was 41 minutes.

After completion of the reaction, the H$_2$O phase with the PNA was lyophilized and then redissolved in 0.45 ml H$_2$O. The biotin-PNA was purified by HPLC using a reversed phase C-18 column and the same conditions as above.

D. Folic Acid-AHA-T$_2$CT$_2$CT$_4$-NH$_2$

400 µL 2.5 µg/µL of PNA AHA-T$_2$CT$_2$CT$_4$-NH$_2$ (SEQ ID NO:98) was mixed with 154 µL 1.0 µg/µL DMSO folic acid, 50 µL 10 µg/µL of DMSO EDC, and 1228 µL DMSO. The mixture was left overnight in the dark at room temperature. The next day 150 µL 1.0 µg/µL DMSO folic acid plus 50 µL 10 µg/µL DMSO EDC was added and the mixture was left for 6 hours in the dark at room temperature. Then 150 µL 1.0 µg/µL DMSO folic acid plus 50 µL 10 µg/H$_2$O DMSO EDC was added and the mixture was left overnight in the dark at room temperature. The following day H$_2$O (5 mL) was added and the H$_2$O-phase was lyophilized and then redissolved in 400 µL 1:1 mixture of H$_2$O and DMSO. The reaction was monitored by HPLC using a reversed phase spherisorp S50DS1 C-18 column (250×4.6 mm) and a gradient of varying concentrations of Buffer A (0.1% TFA in H2O) and Buffer B (0.1% TFA, 60% CH$_3$CN, 40% H$_2$O). The retention time of the starting material PNA AHA-T$_2$CT$_2$CT$_4$-NH (SEQ ID NO:98) was approximately 24 minutes and that of the final PNA, folic acid-AHA-T$_2$CT$_2$CT$_4$-NH was 34 minutes.

The folic acid PNA was purified by HPLC using a reversed phase C-18 column and the same conditions as above.

E. Octanoyl-AHA-T$_2$CT$_2$CT$_4$-NH$_2$

370 µL, 2.0 µg/µL of PNA AHA-T$_2$CT$_2$CT$_4$-NH$_2$ (SEQ ID NO:98) was dissolved in 0.2M Na$_2$CO$_3$ (340 µL), 0.2M NaHCO$_3$ (340 µL) and CH$_3$CN (680 µL). 80 µL CH$_3$(CH$_2$)$_6$COCl was added in 4 portions while shaking the reaction vessel. The mixture was left for 15 minutes at room temperature after each portion of CH$_3$(CH$_2$)$_6$COCl was added. The reaction was monitored by HPLC using a reversed phase spherisorp S50DS1 C-18 column (250×4.6 mm) and a gradient of varying concentrations of Buffer A (0.1% TFA in H2O) and Buffer B (0.1% TFA, 60% CH$_3$CN, 40% H$_2$O). The retention time of the starting material PNA AHA-T$_2$CT$_2$CT$_4$-NH (SEQ ID NO:98) was approximately 21 minutes and that of the final PNA, acridine-AHA-T$_2$CT$_2$CT$_4$-NH was 30 minutes.

After completion of the reaction, the H$_2$O phase with the PNA was lyophilized and then redissolved in 0.45 ml H$_2$O. The octanoyl-PNA was purified by HPLC using a reversed phase C-18 column and the same conditions as above.

F. Psoralen-AHA-T$_2$CT$_2$CT$_4$-NH$_2$

4600 µg of PNA AHA-T$_2$CT$_2$CT$_4$-NH (SEQ ID NO:98) was dissolved in H$_2$O (920 µL), 0.2M NaHCO$_3$ (230 µL), and 1917 µL DMF. 552 µL 10 µg/µL DMF psoralene-N-hydroxy-succinimide-ester (PAE) was added in 4 portions while shaking the reaction vessel. The mixture was left for 15 minutes at room temperature after each portion of PAE was added. The reaction was monitored by HPLC using a reversed phase spherisorp S50DS1 C-18 column (250×4.6 mm) and a gradient of varying concentrations of Buffer A (0.1% TFA in H2O) and Buffer B (0.1% TFA, 60% CH$_3$CN, 40% H$_2$O). The retention time of the starting material PNA AHA-T$_2$CT$_2$CT$_4$-NH (SEQ ID NO:98) was approximately 20 minutes and that of the final PNA, psoralen-AHA-T$_2$CT$_2$CT$_4$-NH was 30 minutes.

After completion of the reaction, the H$_2$O phase with the PNA was lyophilized and then redissolved in 1 mL H$_2$O. The psoralen-PNA was purified by HPLC using a reversed phase C-18 column and the same conditions as above (SEQ ID NO:99) Acridine-AHA-T$_2$CT$_2$CT$_4$-NH$_2$ (SEQ ID NO:100) AnthraQuinone-AHA-TTC TTC TTT T-NH2

(SEQ ID NO:101) Biotin-AHA-TTC TTC TTT T-NH2

(SEQ ID NO:102) Folic acid-AHA-TTC TTC TTT T-NH2

(SEQ ID NO:103) Octanoyl-AHA-TTC TTC TTT T-NH2

(SEQ ID NO:104) Psoralen-AHA-T$_2$CT$_2$CT$_4$-NH$_2$ (SEQ ID NO:105) H-TTT TTT TTT T-Lys-Biotin (SEQ ID NO:106) Biotin-H-TTT TTT TTT T-Lys-Biotin (SEQ ID NO:107) H-TTT TTT TTT T-Lys-Hexyl-Biotin (SEQ ID NO:108) Biotin-AHA-Tyr-TTC TTC TTT T-Lys-NH$_2$ (SEQ ID NO:109) Biotin-AHA-CTC TTT TTT T-NH$_2$ (SEQ ID NO:110) Biotin-TTT CTT CTC ACT TCT T-NH$_2$ (SEQ ID NO:111) Biotin-Hexyl-TTT CTT CTC ACT TCT T-NH$_2$ (SEQ ID NO:112) H-TTT TTT TTT T-Lys-Maleimide (SEQ ID NO:113) Maleimide-H-TTT TTT TTT T-Lys-Maleimide (SEQ ID NO:114) H-Tyr-TTT TTT TTT T-Lys-Maleimide (SEQ ID NO:115) Maleimide-AHA-TTC TTC TTT T-NH$_2$ (SEQ ID NO:116) Maleimide-AHA-Tyr-TTC TTC TTT T-NH$_2$ (SEQ ID NO:117) Maleimide-TTT Tr-NH$_2$ (SEQ ID NO:118) Quinone-AHA-TTC TTC TTT T-NH$_2$ (SEQ ID NO:119) Quinone-AHA-Tyr-TTC TTC TTT T-NH$_2$ (SEQ ID NO:120) Acridine-AHA-TTC TTC TTT T-NH$_2$ (SEQ ID NO:121) Acridine-AHA-TTT TGG TGT GGG TCT-NH$_2$ (SEQ ID NO:122) N$_3$-Benzoyl-AHA-TTC TTC TTT T-NH$_2$ (SEQ ID NO:123) N$_3$-Benzoyl-TTT CTT CTC ACT TCT T-NH$_2$ (SEQ ID NO:124) H-GTA GAT CAC T-Lys-Benzoyl-N$_3$ (SEQ ID NO:125) H-AGT CAT CTA C-Lys-Benzoyl-N$_3$ (SEQ ID NO:126) Dodecanoyl-AHA-TTC TTC TTT T-NH$_2$ (SEQ ID NO:127) Dodecanoyl-AHA-CTC TTT TTT T-NH$_2$ (SEQ ID NO:128) Myristoyl-AHA-CTC TTT TTT T-NH$_2$ (SEQ ID NO:129) Cholesteryl-formyl-AHA-TTC TTC TTT T-NH$_2$ (SEQ ID NO:130) Cholic Acid-FLUO$_{phet}$-CTC TTT TTT T-NH$_2$ (SEQ ID NO:131) Dansyl-TTT TT-NH$_2$ (SEQ ID NO:132) PHEN$_1$-AHA-TGT ACG TCA CAA CTA-NH$_2$ (SEQ ID NO:133) EDTA-AHA-TGT ACG TCA CAA CTA-NH$_2$ (SEQ ID NO:134) EDTA-AHA-TTC TTC TTT T-NH$_2$ (SEQ ID NO:135) EDTA-AHA-Lys$_2$-TTC TTC TTT T-Lys$_2$NH$_2$ (SEQ ID NO:136) PHEN$_2$-AHA-TTC TTC TTT T-NH$_2$ (SEQ ID NO:137) PHEN$_2$-AHA-Lys-Lys-TTC TTC TTT T-NH$_2$ (SEQ ID NO:138) NTA-AHA-TTC TTC TTT T-NH$_2$ (SEQ ID NO:139) NTA-AHA-Lys$_2$-TTC TTC TTT T-Lys$_2$-NH$_2$ (SEQ ID NO:140) FLUO$_{met}$-AHA-CTC TTT TTT T-NH$_2$ where Lys is lysine, Tyr is tyrosine, AHA is amino hexanoic acid, NTA is nitrillo triacetic acid, PHEN$_1$ is a substituted phenathroline as reported by Jenkins, Y. and Barton, J. K., *JACS* 1992, 114, 8736-38. PHEN$_2$ is a similar compound that incorporates a piperazine linker. FLUO$_{phet}$ is a partially deprotected flourescein monomer while FLUO$_{met}$ is a transeterified flourescein product.

EXAMPLE 95

N-Terminal Polyamine End Labeled PNA Oligomers

Polyamines are attached to the N-terminal end of PNA oligomer having the sequence H$_2$N-GCA TGC AT-C(O)OCH$_3$ SEQ ID NO:141 synthesized as per standard methods and techniques, wherein the polyamine is one of the following:

TABLE III

| | |
|---|---|
| 1,6 Diaminohexane | PNA Oligomer SEQ ID NO:142 |
| Diethylenetriamine | PNA Oligomer SEQ ID NO:143 |
| Triethylenetetramine | PNA Oligomer SEQ ID NO:144 |
| Spermine | PNA Oligomer SEQ ID NO:145 |
| Pentaethylenehexamine | PNA Oligomer SEQ ID NO:146 |

A. Preparation of the PNA Oligomer

PNA oligomer SEQ ID NO:141 having the terminal carboxyl group protected as a methyl ester and having a free amino terminal group is prepared in accordance with Examples 26–28, and standard protection protocols.

B. Preparation of Polyamine Functionalized PNA Oligomer

The PNA oligomer from Example 95(A) above is dissolved in freshly prepared NaHCO$_3$ buffer (0.2 M, pH 8.1) and treated with a solution of disuccinimidyl suberate (DSS) (approximately 5 mgs) dissolved in 150 ul of methyl sulfoxide (DMSO). The reaction mixture is left to react for 20 minutes at room temperature. The mixture is then passed over a Sephadex G-25 column (0.7×45 cm) to separate the activated PNA oligomer-DSS from the excess DSS. The PNA oligomer-DSS is then frozen immediately and lyophilized to dryness. A solution of polyamine in 0.33 M NaOAc (approximately 6 mg polyamine in 300 ul 0.33 M NaOAc, pH 5.2, final solution pH 6-8.0) is added to the dried PNA oligomer-DSS, and this mixture is allowed to react overnight at room temperature. The resulting polyamine-PNA oligomer conjugate is characterized by reverse phase HPLC and a 20% denaturing gel. Solvent A is 50 mM TEAA, solvent B is CH$_3$CN. The HPLC gradient is from 0-10 mins, 95% solvent A, 5% solvent B; linear increase to 40% solvent B in the next 50 minutes using a Water's Delta-Pak C-18 reverse phase column.

HPLC analysis shows progressively faster migration times for the larger amines.

C. Preparation of Biotin Functionalized PNA Oligomer Polyamine Conjugate

To further characterize the PNA-oligomer polyamine conjugate, biotin is attached to the free amines made available by the polyamines attached in the above Examples. About 10 O.D. units (A$_{260}$) of PNA oligomers SEQ ID NO:142 and SEQ ID NO:114, (approximately 58 nmoles) are dried in a microfuge tube.

The PNA oligomer polyamine conjugate is rehydrated in 400 ul of 0.2 M NaHCO$_3$ (pH 8.1) buffer and D-biotin-N-hydroxysuccinimide ester (approximately 5.0 mgs biotin for the 1,6 Diaminohexane conjugate, 8.0 mgs for the diethylenetriamine) (Sigma) is added followed by 200 ul of DMF. The solution is left to react overnight at room temperature. The solution is then passed over a NAP-25 column and analyzed by reverse phase HPLC. Solvent is 50 mM TEAA and solvent B is CH$_3$CN. The HPLC gradient wis 0-10 mins, 95% A, 5% B; linear increase to 40% B in the next 50 minutes using a Water's Delta-Pak C-18, reverse phase column.

EXAMPLE 96

Internal Polyamine Labeled PNA Oligomer: linkage to formyl-functionalized monomer 1. N-[(N-Boc-1-formyl)-2-amin6ethyl]-N-[(1-thyminyl)-acetyl]glycine ethyl ester (97A)

Compound 35 is converted to the ethyl ester by standard techniques. The resulting compound is then treated according to the procedure of Example 37 to yield the title compound.

2. N-[(N-Boc){1-(6-aminohexyl)aminomethyl}-2-aminoethyl]-N-[(1-thyminyl)-acetyl]glycine ethyl ester (97B)

Compound 97A is dissolved in 100 microliters of water, and 100 ml of 1M NaOAc buffer (pH 5.0) is added followed by 1,6 diaminohexane hydrochloride (24 μmols) and 50 μl of 60 mM $NaCNBH_3$ solution. The solution is vortexed, left overnight and purified in an analytical HPLC column. The product is then deprotected at the carboxyl group to yield the title compound (97B).

3. Incorporation of N-[(N-Boc){1-(6-aminohexyl)aminomethyl}-2-aminoethyl]-N-[(1-thyminyl)-acetyl]glycine ethyl ester (97B) into PNA oligomers The free amino group of compound 97B is Boc-protected using standard techniques. The protected monomer is then incorporated into PNA oligomers according to the procedure of Example 26.

EXAMPLE 97

C-8 Purine and C-5 Pyrimidine conjugation

The C-8 position of purines and the C-5 position of pyrimidines are modified as per the procedures outlined in Ruth, J. L., Oligonucleotides with reporter groups attached to the base, *in Oligonucleotides and Analogues, A Practical Approach*, Eckstein, F., IRL Press, New York.

A. N-(N-Boc-2-aminoethyl)-N-[(N-6-Cbz)(8-[N-(6-trifluoroacetylaminohexyl)-3-(E)acrylamido]-9-adeninyl)acetyl]glycine (Compound 97A)

Compound 97A is synthesized using the procedures of the above reference. A purine substituted protected PNA monomer is used in place of a nucleoside. N-(N-Boc-2-aminoethyl)-N-[(6-Cbz-9-adeninyl)acetyl]glycine ethyl ester (21) is used as the starting material instead of adenosine. After the protected linking group is attached the resulting compound is treated via the procedures of Example 22 to give the title compound. The final compound having a protected linking moiety is further incorporated into oligomers using standard methods. The protected linking moiety is deprotected and functionalized with a further functional group e.g. fluorescein or biotin.

B. N-(N-Boc-2-aminoethyl)-N-[(N-4-Cbz)(5-[N-(6-trifluoroacetylaminohexyl)-3-(E)acrylamido]-1-cytosinyl)acetyl]glycine (Compound 97B)

Compound 97B is synthesized using the procedures of the above reference except that Compound 16 is used as the starting material instead of cytidine. After the protected linking group is attached the resulting compound is treated via the procedures of Example 17. The final compound having a protected linking moiety is further incorporated into oligomers using standard methods. The protected linking moiety is deprotected and functionalized with a further functional group e.g. fluorescein or biotin.

EXAMPLE 98

5-Propynyl Pyrimidines (Cytosine and Uracil)

A. N-(N-Boc-2-aminoethyl)-N-[(N-4-Cbz)(5-propynyl)-1-cytosinyl)-acetyl]glycine (Compound 98A)

Compound 98A is synthesized using the procedures of Wagner, W. W., et. al., *Science*, 1993, 260, 1510-1513, except that Compound 16 is used as the starting material instead of cytidine. After the 5-propynyl group is attached to the protected N-1acetylcytosine the resulting compound is treated via the procedures of Example 17. The final compound having a 5-propynyl group is further incorporated into oligomers using standard methods.

B. N-(N-Boc-2-aminoethyl)-N-[(5-propynyl)-1-urasinyl)acetyl]glycine (Compound 98B)

Compound 98B is synthesized analogously to Compound 98A except that the protection step for the exocyclic amino group is omitted and uracil is substituted for cytosine in the applicable examples e.g. Examples 13-17. After the 5-propynyl group is attached to N-1-acetyluracil the resulting compound is treated via the procedures of Example 17. The final compound having a 5-propynyl group is further incorporated into oligomers using standard methods.

EXAMPLE 99

N-Fmoc-3-Aminopropionic Acid

Sodium bicarbonate (2.52 g, 30 mmol) and 3-aminopropionic acid (1.00 g, 11.2 mmol) were dissolved in 50 ml water and 50 ml dioxane was added. A solution of fluorenylmethyl chloroformate (3.10 g, 12.0 mmol) in 50 ml dioxane was added dropwise with stirring. After 6 hours the solution was diluted with water (100 ml) and saturated bicarbonate solution (50 ml), extracted once with diethyl ether, and the aqueous layer acidified to pH 2 with concentrated HCl. The cloudy solution was extracted with ethyl acetate (2×100 ml), washed with brine and dried with $MgSO_4$. After evaporation a mixture of the title product and the peptide dimer was obtained. The pure product was obtained by flash chromatography. $^1$H NMR: ($CDCl_3$, 200 MHz) δ 7.95-7.26 (8H, m, ArH), 7.40-7.15 (3H, m, $CHCH_2O$),3.20 (2H, t, J=8 Hz, $CH_2N$), 2.40 (2H, t, J=8 Hz, $HOOCCH_2$).

EXAMPLE 100

N-(N-Boc-2-aminoethyl)-N-(N-Fmoc-3-aminopropionoyl)glycine (100)

This compound is prepared as per the procedures described in Examples 10 and 11 substituting N-Fmoc-3-aminopropionic Acid (99) in place of N-1-carboxymethyl thymine. The final compound is further incorporated into oligomers using standard methods.

EXAMPLE 101

N-Imidazolyl-2-Acetic acid

Imidazole (3.7 g, 54 mmol) was added to a suspension of sodium hydride (2.6 g of a 60% dispersion in oil, 60 mmol) in 50 ml dry THF. Bromoacetic acid (3.4 g, 24 mmol) was then added and the mixture stirred overnight. Water (1 ml) was then added and the solvent removed under reduced pressure. The residue was taken up in water (50 ml, pH>10), extracted with ether and the organic layer discarded. The aqueous layer was acidified to pH 1 with concentrated HCl and extracted again with ether. The aqueous layer was evaporated to dryness. The oily residue was dissolved in absolute ethanol (EtOH) to precipitate NaCl, and recrystallized from acetone/methanol to give 1.22 g (7.5 mmol, 30%) pure product as the hydrochloride. $^1$H NMR: (DMSO-d6, 200 MHz) δ 9.20 (s, H$_2$), 7.76 (d, J=1.5 Hz), 7.69 (d, J=1.5 Hz), 5.20 (s, CH$_2$).0

EXAMPLE 102

N-(N-Boc-2-aminoethyl)-N-(N-Imidazolyl-2-Acetyl) glycine (102)

This compound is prepared as per the procedures described in Examples 10 and 11 substituting N-imidazolyl-2-acetic acid (101) in place of N-1-carboxymethyl thymine. The final compound is further incorporated into oligomers using standard methods.

EXAMPLE 103

Benzyl 3,6,9,12-Tetraoxatridecanoate (103)

Triethyleneglycol monomethyl ether (10 mmol) and benzyl bromoacetate (11 mmol) are added to a suspension of anhydrous K$_2$CO$_3$ (15 mmol) in 50 ml anhydrous DMF. The suspension is stirred at room temperature overnight. Water is added and the emulsion is extracted with ethyl acetate (3×200 ml), washed with water, brine, and dried with MgSO$_4$. The solvent is evaporated and the residual oil purified by flash chromatography to give the title compound.

EXAMPLE 104

3,6,9,12-Tetraoxatridecanoic Acid (104)

Benzyl-3,6,9,12-Tetraoxatridecanoate (103, 5 mmol) is dissolved in methanol (50 ml) and 10% palladium on carbon is added (100 mg catalyst/mmol). The suspension. is shaken under 30 psi H$_2$ until the starting material is consumed. The suspension is filtered through a short pad of Celite, washed thoroughly with methanol, and the solvent evaporated. The product is used directly without purification.

EXAMPLE 105

N-(N-Boc-2-aminoethyl)-N-(3,6,9,12-Tetraoxatridecanoyl)glycine (105)

This compound is prepared as per the procedures described in Examples 10 and 11 substituting 3,6,9,12-tetraoxatridecanoic Acid (104) in place of N-1-carboxymethyl thymine. The final compound is further incorporated into oligomers using standard methods.

EXAMPLE 106

N-α-(FMOC)-glutamic acid γ-benzyl ester (106)

To a solution of γ-benzyl glutamate (10 mmol) in 50 ml dioxane and 50 ml water is added triethylamine (25 mmol), followed by a solution of fluorenylmethyl chloroformate (11 mmol) in 50 ml dioxane. The mixture is vigorously stirred until the starting material is consumed. The solution is acidified to pH 2 with concentrated HCl, extracted with ethyl acetate (2×250 ml), washed with brine, dried with MgSO$_4$ and evaporated. The product is used without purification.

EXAMPLE 107

N-α-(FMOC)-γ-benzyl-L-glutamic acid fluorenylmethyl ester (107)

N-α-(FMOC)-glutamic acid γ-benzyl ester (106, 5 mmol), fluorenylmethanol (5.5 mmol) and dimethylaminopyridine (0.5 mmol) are dissolved in 50 ml CH$_2$Cl$_2$. Dimethylaminopropyl ethyl carbodiimide (EDC, 6.0 mmol) is added, and the solution stirred at room temperature. After complete consumption of the starting material the solution is diluted with CH$_2$Cl$_2$, washed with 1% HCl, water and brine, dried with MgSO$_4$ and evaporated. The residue is purified by flash chromatography using ethyl acetate and hexane as eluant.

EXAMPLE 108

N-α-(FMOC)-L-glutamic acid α-fluorenylmethyl ester (108)

N-α-(FMOC)-γ-benzyl-L-glutamic acid fluorenylmethyl ester (107, 5 mmol) is dissolved in methanol (50 ml) and 10% Palladium on carbon is added (100 mg catalyst/mmol). The suspension is shaken under 30 psi H$_2$ until the starting material is consumed. The suspension is filtered through a short pad of Celite, washed thoroughly with methanol, and the solvent evaporated. The product is used directly without purification.

EXAMPLE 109

N-(N-Boc-2-aminoethyl)-N-[N-α-(FMOC)-L-glutamoyl-α-fluorenylmethyl ester]-glycine (109)

This compound is prepared as per the procedures described in Examples 10 and 11 substituting N-α-(FMOC)-L-glutamic acid α-fluorenylmethyl ester (108) in place of N-1-carboxymethyl thymine. The final compound is further incorporated into the N-terminus of PNA oligomers using standard methods.

EXAMPLE 110

N-(N-Boc-2-aminoethyl)-N-(1-methyl-2-pyrroleacetyl)glycine (110)

This compound is prepared as per the procedures described in Examples 10 and 11 substituting 1-methyl-2-pyrrolecarboxylic acid (Aldrich) in place of N-1-carboxymethyl thymine. The final compound is further incorporated into oligomers using standard methods.

EXAMPLE 111

Cleavage of Plasmid-DNA by NTA-Lys$_2$-T$_2$CT$_2$CT$_4$-Lys$_2$-NH$_2$

A mixture of 2.0 µL 5.9 µM PNA NTA-Lys$_2$-T$_2$CT$_2$CT$_4$-Lys$_2$-NH$_2$ and 0.2 µL 5.9 µM Fe$^{2+}$ was incubated for 10 minutes at room temperature. Buffer (100 mM PO$_4$, pH 6.5 or 100 mM PO$_4$, pH 6.5, 10 mM EDTA, 9.5 µL H$_2$O and 0.5 µL $^{32}$P-labeled targeted DNA, pA8G2 was added and the incubation was continued for 1 hour at 37° C. 1 µL of 40 mM DTT was added and the incubation continued for 1 hour at 37° C. Samples were analyzed on an 8% polyacrylamide sequencing gel according to the following scheme:

| nr. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| PNA | + | + | + | + | + | + | + | + |   | + | + | + | + | + |   |   |
| $Fe^{2+}$ | + |   |   | + |   |   | + | + |   | + | + | + | + |   |   |   |
| PNA/$Fe^{2+}$ | 10 |   |   | 10 |   |   | 10 | 10 |   | 0.5 | 1 | 4 | 10 |   |   |   |
| EDTA |   |   |   | + | + | + |   | + |   |   |   |   |   |   |   |   |
| 5'* | + | + | + | + | + | + | + | + | + |   |   |   |   |   |   |   |
| 3'* |   |   |   |   |   |   |   |   |   | + | + | + | + | + | + | + |
| DTT | + | + |   | + | + |   |   |   |   | + | + | + | + |   |   |   |
| DMS |   |   |   |   |   |   | + | + | + |   |   |   |   |   |   |   |
| $KMnO_4$ |   |   |   |   |   |   |   |   |   |   |   |   |   | + | + |   |
| seq. |   |   |   |   |   |   |   |   |   |   |   |   |   |   |   | + |

5'* denotes that the EcoR1/Pvu 11 fragment of pA8G2 was labeled at the 5'-end and 3'* that this fragment was labeled at the 3'end. DMS denotes probing with dimethylsulphate and $KMnO_4$.

Figure 6:
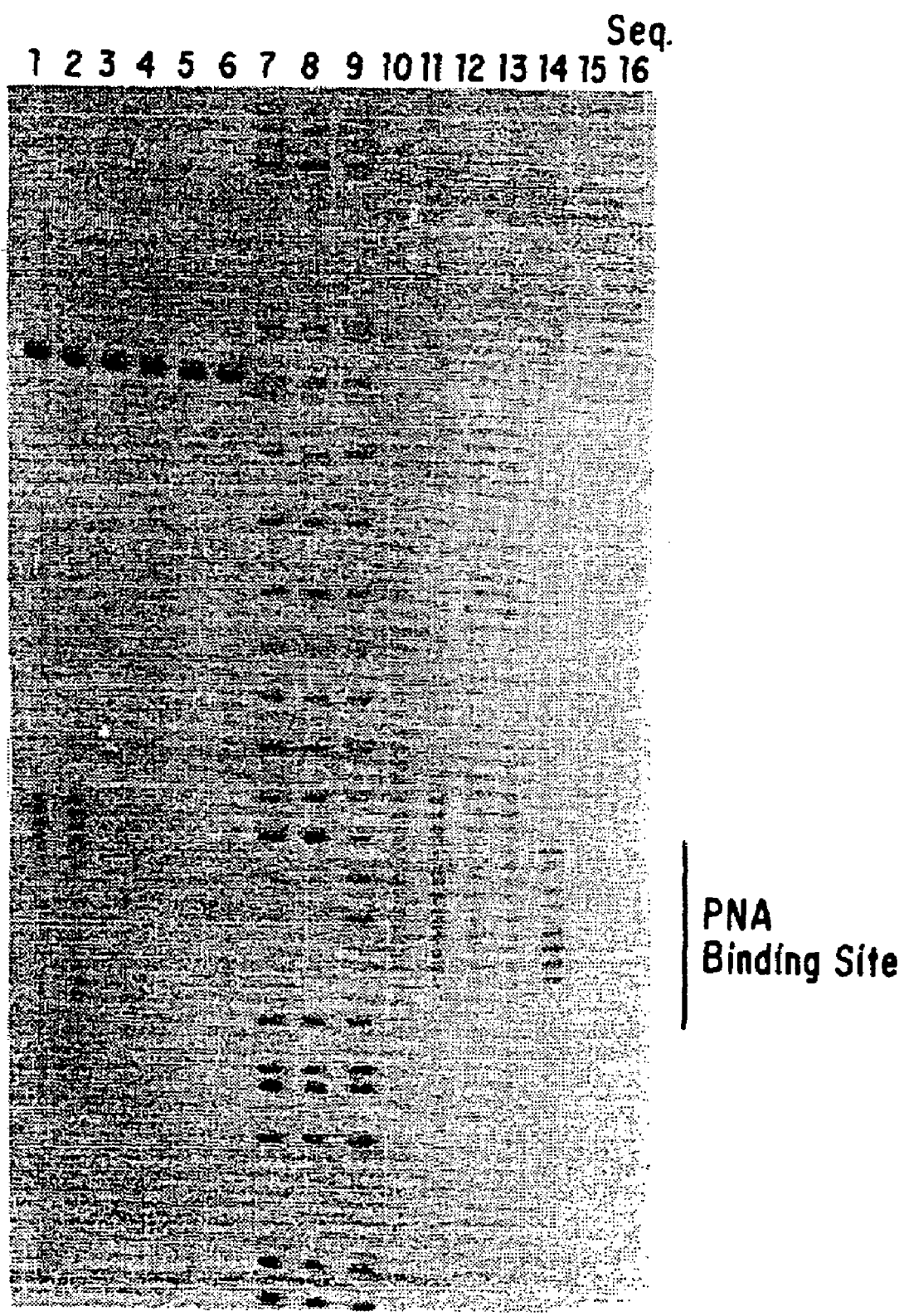
FIG. 6 is a reproduction of an electrophoresis gel pertinent to Example 111, showing that PNA NTA $Fe^{2+}$ is an effective oligonucleotide cleavage agent.

When the experimental results were analyzed by gel electrophoresis (see FIG. 6) it was shown that PNA NTA $Fe^{2+}$ was an effective oligonucleotide cleavage agent. A comparison of lane 1 to lane 4 where EDTA was employed to competitively bind available $Fe^{2+}$ shows that the $Fe2^+$-NTA complex was necessary and effective at cleaving the DNA strand. A comparison of lane 13 to lane 14 shows that the cleaving pattern has been extended beyond the PNA binding site as mapped by $KMnO_4$ cleavage of the strand displaced by the PNA which is consistent with the $Fe2^+$-NTA complex being oriented at that end.

EXAMPLE 112

Binding of PNA conjugates to double stranded DNA targets

A mixture of 200 cps $^{32}$P-labeled EcoRI-PvuII fragment (the large fragment labeled at the 3'-end of the EcoRI site) of the indicated plasmid, 0.5 µg carrier calf thymus DNA, and 300 ng PNA having an appropriate conjugate attached thereto in 100 µl buffer (10 mM Na-phosphate, 1 mM EDTA pH 7) are incubated at 37° C. for 60 min. 5 µl 20 mM $KMnO_4$ is added and incubated at 20° C. for 15 seconds. The reaction is stopped by addition of 3 µl 10.5 M 2-mercaptoethanol, 1M NaOAc and the DNA is precipitated by addition of 250 µl 2% potassium acetate in ethanol. The DNA is treated with hot (50° C.) 1M piperidine and is analyzed by electrophoresis in 10% polyacrylamide sequencing gels and the radiolabeled DNA bands visualized by autoradiography.

The target plasmids are prepared by cloning of the appropriate oligonucleotides into pUC19. Target A10: oligonucleotides GATCCA10G & GATCCT10G cloned into the BamHI site (plasmid designated pT10). Target A5GA4: oligonucleotides TCGACT4CT5G & TCGACA5GA4G cloned into the SalI site (plasmid pT9C). Target A2GA2GA4: oligonucleotides GA2GA2GA4TGCA & GT4CT2CT2CTGCA into the PstI site (plasmid pT8C2). The positions of the targets in the gel are indicated by bars to the left. A/G is an A+G sequence ladder of target P10.

EXAMPLE 113

A. Determination of Cellular Uptake and Activity of Thiol Linker Containing PNA Oligomers This is determined by the inhibition of ICAM-1 (Intra Cellular Adhesion Molecule-1) utilizing the method of Chiang, et al., *J. Biol. Chem.* 1991, 266 18162.

ICAM-1 Assay: ICAM-1 expression on the cell surface is determined by ELISA using cells grown to confluence in 96-well plates. Cells are washed three times with Dulbecco's phosphate-buffered saline and fixed for 20 minutes in 2% formaldehyde diluted in Dulbecco's PBS. The cells are washed three times with Dulbecco's PBS, blocked for 1 hour at 37° C. with 2% bovine serum albumin in Dulbecco's PBS, and incubated with ICAM-1 monoclonal antibody $84H_{10}$ (0.5 µg/ml) for 1 hour at 37° C. Antibody bound to the cells is determined by incubation with a 1:1000 dilution of biotinylated goat anti-mouse IgG followed by incubation with a 1: 1000 dilution of β—galactosidase-conjugated streptavidin. The plates are developed with 100 µl of 3.3 mM chlorophenolred-β-D-galactopyranoside in 50-mM sodium phosphate, 1.5 mM $MgCl_2$, pH 7.0. Product formed is detected by absorbance at 575 nm. The data are expressed as percent control activity, which is calculated as described by Chiang, et al., in the above reference.

PNA Oligomer Treatment of Cells: Cells are washed three times with Opti-MEM prewarmed to 37° C. Opti-MEM containing either 10 µg/ml DOTMA solution (HUVEC) or 20 mg/ml DOTMA solution (A549 cells) is added to each well of the plate (100 µl). PNA oligomers were sterilized by centrifugation through 0.2 µM Centrex cellulose acetate filters. PNA oligomers are added as 20x stock solution to the wells and incubated for 4 hours at 37° C. and then stimulated with the appropriate cytokine for 14-16 hours as indicated. ICAM-1 expression is determined as described above.

The following PNA oligomers having aminoethylglycine backbones are synthesized according to the procedures of the foregoing Examples: $H_2$N-TGG GA*G CCA TAG CGA GCC-COOH (SEQ ID NO:147), ICAM PNA; and $H_2$N-TCT GAG TAG CAG AGG AGC TA*A G (SEQ ID NO:148); a sequence in the 5'-cap region of ICAM. The asterisk (*) denotes the incorporation of a monomeric unit containing a protected thiol functionality according to Example 58. PNA oligomer having SEQ ID NO:117 serves to evaluate the tritylthioether group in uptake experiments and to determine its ability to inhibit ICAM protein expression. PNA oligomer SEQ ID NO:118 is conjugated to O-phenanthroline and targeted against the 5'-cap-messenger RNA of the ICAM system to cleave the target RNA. The PNA oligomer is used in the above assay to assess its effect on ICAM expression.

B. RNA Cleavage Assay Using Oligonucleotide Containing Thiol Linker

PNA oligomer SEQ ID NO:118 is thiol deprotected and conjugated to O-phenanthroline reagent. The conjugate is targeted against 5'-capped RNA of the ICAM system. The hybrid is incubated at 37° C. over a 48 hour period in the presence of excess Cu(II) salt under buffered conditions. Analysis of the reaction by gel electrophoresis (as described by Baker, *J. Am. Chem. Soc.* 1993, 115, 3378) demonstrates that the 15 oligonucleotide-O-phenanthroline-Cu complex cleaves the target RNA strand.

EXAMPLE 114

Inhibition of restriction enzyme cleavage by PNA-conjugate

A 2 µg portion of plasmid pT10 is mixed with the indicated amount of PNA conjugate in 20 µl TE buffer (10 mM Tris-HCl, 1 mM EDTA, pH 7.4) and incubated at 37° C. for 120 min. 2 µl 10× buffer (10 mM Tris-HCl, pH 7.5, 10 mM, $MgCl_2$, 50 mM NaCl, 1 mM DTT). PvuII (2 units) and BamHI (2 units) are added and the incubation is continued for 60 min. The DNA is analyzed by gel electrophoresis in 5% polyacrylamide and the DNA is visualized by ethidium bromide staining.

EXAMPLE 115

Kinetics of PNA conjugate—dsDNA strand displacement complex formation

A mixture of 200 cps $^{32}P$-labeled EcoRI-PvuII fragment of pT10 (the large fragment labeled at the 3'-end of the EcoRI site), 0.5 µg carrier calf thymus DNA, and 300 ng of PNA conjugate in 100 µl buffer (200 mM NaCl, 50 mM Na-acetate, pH 4.5, 1 mM $ZnSO_4$) are incubated at 37° C. Periodically, 50 U of $S_1$ nuclease is added to each of 7 samples and incubation is continued for 5 min at 20° C. The DNA is then precipitated by addition of 250 µl 2% K-acetate in ethanol and analyzed by electrophoresis in a 10% polyacrylamide sequencing gel. The amount of strand displacement complex is calculated from the intensity of the $S_1$-cleavage at the target sequence, as measured by densitometric scanning of autoradiographs.

EXAMPLE 116

Stability of PNA-dsDNA complexes

A mixture of 200 cps $^{32}P$-pT10 fragment, 0.5 µg calf thymus DNA and 300 ng of the desired PNA conjugate is incubated in 100 µl 200 mM NaCl, 50 mM Na-acetate, pH 4.5, 1 mM $ZnSO_4$ for 60 min at 37° C. A 2 µg portion of oligonucleotide $GATCCA_{10}G$ is added and each sample is heated for 10 min at the temperature indicated, cooled in ice for 10 min and warmed to 20° C. A 50 U portion of $S_1$ nuclease is added and the samples treated and analyzed and the results quantified.

EXAMPLE 117

Inhibition of Transcription by PNA

A mixture of 100 ng plasmid DNA (cleaved with restriction enzyme PvuII (see below) and 100 ng of PNA conjugate in 15 µl 10 mM Tris-HCl, 1 mM EDTA, pH 7.4 is incubated at 37° C. for 60 min. Subsequently, 4 µl 5× concentrated buffer (0.2 M Tris-HCl (pH 8.0), 40 mM $MgCl_2$, 10 mM spermidine, 125 mM NaCl) are mixed with 1 µl NTP-mix (10 mM ATP, 10 mM CTP, 10 mM GTP, 1 mM UTP, 0.1 µCi/µl $^{32}P$-UTP, 5 mM DTT, 2 µg/ml tRNA, 1 µg/ml heparin) and 3 units RNA polymerase. Incubation is continued for 10 min at 37° C. The RNA is then precipitated by addition of 60 µl 2% potassium acetate in 96% ethanol at −20° C. and analyzed by electrophoresis in 8% polyacrylamide sequencing gels. RNA transcripts are visualized by autoradiography. The following plasmids are used: pT8C2-KS/pA8G2-KS: oligonucleotides $GA_2GA_2GA_4GTGAC$ & $GT_4CT_2CT_2CTGCA$ cloned into the PstI site of pBluescript-$KS^+$; pT10-KS/pA10-KS (both orientations of the insert were obtained). pT10UV5: oligonucleotides $GATCCA_{10}G$ & $GATCCT_{10}G$ cloned into the BamHI site of a pUC18 derivative in which the lac UV5 *E. coli* promoter had been cloned into the EcoRI site (Jeppesen, et al., *Nucleic Acids Res.*, 1988, 16, 9545).

EXAMPLE 118

Biological stability of PNA

A mixture of PNA conjugate (10 µg) and a control, "normal" peptide (10 µg) in 40 µl 50 mM Tris-HCl, pH 7.4 is treated with varying amounts of peptidase from porcine intestinal mucosa or protease from *Streptomyces caespitosus* for 10 min at 37° C. The amount of PNA and peptide is determined by HPLC analysis (reversed phase C-18 column: 0-60% acetonitrile, 0.1% trifluoroacetic acid or other appropriate solvent system).

EXAMPLE 119

Inhibition of Gene Expression

A preferred assay to test the ability of peptide nucleic acids to inhibit expression of the E2 mRNA of papillomavirus is based on the well-documented transactivation properties of E2. Spalholtz, et al., *J. Virol.*, 1987, 61, 2128-2137. A reporter plasmid (E2RECAT) is constructed to contain the E2.responsive element, which functions as an E2 dependent enhancer. E2RECAT also contains the SV40 early promoter, an early polyadenylation signal, and the chloramphenicol acetyl transferase gene (CAT). Within the context of this plasmid, CAT expression is dependent upon expression of E2. The dependence of CAT expression on the presence of E2 is tested by transfection of this plasmid into C127 cells transformed by BPV-1, uninfected C127 cells and C127 cells cotransfected with E2RECAT and an E2 expression vector.

A. Inhibition of BPV-1 E2 Expression

BPV-1 transformed C127 cells are plated in 12 well plates. Twenty four hours prior to transfection with E2RE1, cells are pretreated by addition of complementary PNA conjugates to the growth medium at final concentrations of 5, 15 and 30 mM. The next day cells are transfected with 10 µg of E2RE1CAT by calcium phosphate precipitation. Ten micrograms of E2RE1 CAT and 10 µg of carrier DNA (PUC 19) are mixed with 62 µl of 2 M $CaCl_2$ in a final volume of 250 µl of $H_2O$, followed by addition of 250 µl of 2×HBSP (1.5 mM $Na_2PO_2$. 10 mM KCl, 280 mM NaCl, 12 mM glucose and 50 mM HEPES, pH 7.0) and incubated at room temperature for 30 minutes. One hundred microliters of this solution is added to each test well and allowed to incubate for 4 hours at 37° C. After incubation, cells are glycerol shocked for 1 minute at room temperature with 15% glycerol in 0.75 mM $Na_2PO_2$, 5 mM KCl, 140 mM NaCl, 6 mM glucose and 25 mM HEPES, pH 7.0. After shocking, cells are washed 2 times with serum free DMEM and refed with DMEM containing 10% fetal bovine serum and oligonucleotide at the original concentration. Forty eight hours after transfection cells are harvested and assayed for CAT activity.

For determination of CAT activity, cells are washed 2 times with phosphate buffered saline and collected by scraping. Cells are resuspended in 100 µl of 250 mM Tris-HCl, pH 8.0 and disrupted by freeze-thawing 3 times. Twenty four microliters of cell extract is used for each assay. For each assay the following are mixed together in an 1.5 ml Eppendorf tube and incubated at 37° C. for one hour: 25 µl of cell extract, 5 µl of 4 mM acetyl coenzyme A, 18 µl H$_2$O and 1 µl $^{14}$C-chloramphenicol, 40-60 mCi/mM. After incubation, chloramphenicol (acetylated and nonacetylated forms) is extracted with ethyl acetate and evaporated to dryness. Samples are resuspended in 25 µl of ethyl acetate, spotted onto a TLC plate and chromatographed in chloroform:methanol (19:1). Chromatographs are analyzed by autoradiography. Spots corresponding to acetylated and nonacetylated $^{14}$C-chloramphenicol are excised from the TLC plate and counted by liquid scintillation for quantitation of CAT activity. Peptide nucleic acids that depress CAT activity in a dose dependent fashion are considered positives.

B. Inhibition of HPV E2 Expression

The assay for inhibition of human papillomavirus (HPV) E2 by peptide nucleic acids is essentially the same as that for BPV-1 E2. For HPV assays appropriate HPVs are co-transfected into either CV-1 or A431 cells with PSV2NEO using the calcium phosphate method described above. Cells which take up DNA are selected for by culturing in media containing the antibiotic G418. G418-resistant cells are then analyzed for HPV DNA and RNA. Cells expressing E2 are used as target cells for complementary studies. For each PNA, cells are pretreated as above, transfected with E2RE1CAT, and analyzed for CAT activity as above. Peptide nucleic acid conjugates are considered to have a positive effect if they can depress CAT activity in a dose dependent fashion.

EXAMPLE 120

Iodination Procedure

A 5 µg portion of a PNA having a conjugate attached thereto is dissolved in 40 µl 100 mM Na-phosphate, pH 7.0, and 1 mCi Na$^{125}$I and 2 µl chloramine-T (50 mM in CH$_3$CN) are added. The solution is left at 20° C. for 10 min and then passed through a 0.5+5 cm Sephadex G10 column. The first 2 fractions (100 µl each) containing radioactivity are collected and purified by HPLC: reversed phase C-18 using a 0-60% CH$_3$CN gradient in 0.1% CF$_3$COOH in H$_2$O, or other suitable solvent system. The $^{125}$I-PNA elutes right after the PNA peak. The solvent is removed under reduced pressure.

EXAMPLE 121

Detection of mutant β-amyloid precursor protein gene expression (βAPP)

Point mutations in the gene encoding β-amyloid have been implicated in familial. Alzheimer's disease (FAD). PNA oligomers are labeled after synthesis with fluorescein or other fluorescent tag as illustrated above. Alternatively, oligomers can be labeled with other reporter molecules before or after oligomer synthesis. Labeled PNA oligomers are contacted with tissue or cell samples suspected of abnormal βAPP expression under conditions in which specific hybridization can occur, and the sample is washed to remove unbound PNA oligomers. Label remaining in the sample indicates bound oligonucleotide and is quantitated using a fluorimeter, fluorescence microscope or other routine means.

Tissue or cell samples suspected of expressing a point mutation in the βAPP gene are incubated with a fluorescein-labeled PNA oligomer which is targeted to the mutant codon 717, codon 670 or codon 671 of βAPP mRNA. An identical sample of cells or tissues is incubated with a second labeled PNA oligomer which is targeted to the same region of normal βAPP mRNA, under conditions in which specific hybridization can occur, and the sample is washed to remove unbound PNA oligomer. Label remaining in the sample indicates bound PNA oligomer and can be quantitated using a fluorimeter or other routine means. The presence of mutant βAPP is indicated if the first sample binds labeled PNA oligomer and the second sample does not bind fluorescent label.

Double labeling can also be used with PNA oligomers and methods of the invention to specifically detect expression of mutant βAPP. A single tissue sample is incubated with a rhodamine-labeled PNA oligomer which is targeted to codon 717, codon 670 or codon 671 of mutant βAPP mRNA and a fluorescein-labeled PNA oligomer which is targeted to the translation initiation site of mutant βAPP mRNA, under conditions in which specific hybridization can occur. The sample is washed to remove unbound PNA oligomer and labels are detected by and fluorimetry with appropriate filters. The presence of mutant βAPP is indicated if the sample does not bind rhodamine-labeled PNA oligomer but does retain the fluorescein label.

EXAMPLE 122

Detection of Mutant H-ras Gene Expression

Point mutations in the H-ras gene have been implicated in numerous aberrations of the Ras pathway. PNA oligomers are labeled after synthesis with fluorescein or other fluorescent tag as illustrated above. Alternatively, oligomers can be labeled with other reporter molecules before or after oligomer synthesis. Labeled PNA oligomers are contacted with tissue or cell samples suspected of abnormal ras expression under conditions in which specific hybridization can occur, and the sample is washed to remove unbound PNA oligomer. Label remaining in the sample indicates bound PNA oligomer and is quantitated using a fluorimeter, fluorescence microscope or other routine means.

Tissue or cell samples suspected of expressing a point mutation in the H-ras gene are incubated with a fluorescein-labeled PNA oligomer which is targeted to the mutant codon 12, codon 13 or codon 61 of H-ras mRNA. An identical sample of cells or tissues is incubated with a second labeled PNA oligomer which is targeted to the same region of normal H-ras mRNA, under conditions in which specific hybridization can occur, and the sample is washed to remove unbound PNA oligomer. Label remaining in the sample indicates bound PNA oligomer and can be quantitated using a fluorimeter or other routine means. The presence of mutant H-ras is indicated if the first sample binds labeled PNA oligomer and the second sample does not bind fluorescent label.

Double labeling can also be used with PNA oligomers and methods of the invention. to specifically detect expression of mutant ras. A single tissue sample is incubated with a rhodamine-labeled PNA oligomer which is targeted to codon 12, codon 13 or codon 61 of mutant H-ras mRNA and a fluorescein-labeled PNA oligomer which is targeted to the translation initiation site of ras mRNA, under conditions in which specific hybridization can occur. The sample is washed to remove unbound PNA oligomer and labels are detected by and fluorimetry with appropriate filters. The presence of mutant ras is indicated if the sample does not bind rhodamine-labeled PNA oligomer but does retain the fluorescein label.

What is claimed is:

1. A peptide nucleic acid of the formula:

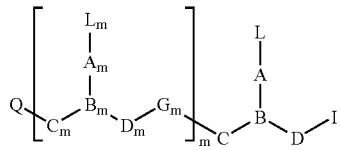

wherein:

m is an integer from 1 to about 50;

L and $L_m$ independently are naturally occurring nucleobases;

C and $C_m$ are $(CR^6R^7)_y$; wherein:

$R^6$ and $R^7$ are hydrogen;

$R^3$ is hydrogen;

D and $D_m$ are $(CR^6R^7)_z$;

y is 1 and z is 2;

$G_m$ is —$NR^3CO$— in either orientation;

each pair of A-$A_m$ and B-$B_m$ are >N—C(O)—$CH_2$—;

I is —$NR^8R^9$ or —$NR^{10}C(O)R^{11}$; wherein:

$R^8$, $R^9$, $R^{10}$ and $R^{11}$ independently are hydrogen, alkyl, an amino protecting group, a reporter ligand, an intercalator, a chelator, a peptide, a protein, a carbohydrate, a lipid, a steroid, a nucleoside, a nucleotide, a nucleotide diphosphate, a nucleotide triphosphate, an oligonucleotide, an oligonucleoside, a soluble polymer, a non-soluble polymer, a reporter enzyme, a reporter molecule, a terpene, a phospholipid, a cell receptor binding molecule, a water soluble vitamin, a lipid soluble vitamin, an RNA/DNA cleaving complex, a porphyrin, or a polymeric compound selected from polymeric amines, polymeric glycols and polyethers; and Q is —$CO_2H$, —$CO_2R^8$, or —$CONR^8R^9$.

2. The peptide nucleic acid of claim 1 wherein $R^8$, $R^9$, $R^{10}$ and $R^{11}$ independently are hydrogen, alkyl, a peptide, a protein, a carbohydrate, a nucleoside, a nucleotide, a nucleotide diphosphate, a nucleotide triphosphate, an oligonucleotide, or an oligonucleoside.

3. The peptide nucleic acid of claim 1 wherein $R^8$, $R^9$, $R^{10}$ and $R^{11}$ independently are a nucleoside, a nucleotide, an oligonucleotide, or an oligonucleoside.

* * * * *

```
                         SEQUENCE LISTING (1) GENERAL INFORMATION:

(iii) NUMBER OF SEQUENCES: 148

(2) INFORMATION FOR SEQ ID NO:1:

(i) SEQUENCE CHARACTERISTICS:
         (A) LENGTH: 4 base pairs
         (B) TYPE: nucleic acid
         (C) STRANDEDNESS: single
         (D) TOPOLOGY: linear (ii) MOLECULE TYPE: nucleic acid (xi) SEQUENCE DESCRIPTION: SEQ ID NO:1:

GCAT                                                                       4

(2) INFORMATION FOR SEQ ID NO:2:

(i) SEQUENCE CHARACTERISTICS:
         (A) LENGTH: 4 base pairs
         (B) TYPE: nucleic acid
         (C) STRANDEDNESS: single
         (D) TOPOLOGY: linear (ii) MOLECULE TYPE: nucleic acid (xi) SEQUENCE DESCRIPTION: SEQ ID NO:2:

GCAT                                                                       4

(2) INFORMATION FOR SEQ ID NO:3:

(i) SEQUENCE CHARACTERISTICS:
         (A) LENGTH: 4 base pairs
         (B) TYPE: nucleic acid
         (C) STRANDEDNESS: single
         (D) TOPOLOGY: linear (ii) MOLECULE TYPE: nucleic acid (xi) SEQUENCE DESCRIPTION: SEQ ID NO:3:

GCAT                                                                       4

(2) INFORMATION FOR SEQ ID NO:4:

(i) SEQUENCE CHARACTERISTICS:
         (A) LENGTH: 4 base pairs
         (B) TYPE: nucleic acid
         (C) STRANDEDNESS: single
         (D) TOPOLOGY: linear (ii) MOLECULE TYPE: nucleic acid (xi) SEQUENCE DESCRIPTION: SEQ ID NO:4:

GCAT                                                                       4

(2) INFORMATION FOR SEQ ID NO:5:

(i) SEQUENCE CHARACTERISTICS:
         (A) LENGTH: 4 base pairs
         (B) TYPE: nucleic acid
```

```
        (C) STRANDEDNESS: single
        (D) TOPOLOGY: linear (ii) MOLECULE TYPE: nucleic acid (xi) SEQUENCE DESCRIPTION: SEQ ID NO:5:

GCAT                                                                            4

(2) INFORMATION FOR SEQ ID NO:6:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:6:

GCAT                                                                            4

(2) INFORMATION FOR SEQ ID NO:7:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:7:

GCAT                                                                            4

(2) INFORMATION FOR SEQ ID NO:8:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:8:

GCAT                                                                            4

(2) INFORMATION FOR SEQ ID NO:9:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:9:

GCAT                                                                            4

(2) INFORMATION FOR SEQ ID NO:10:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid
```

```
       (xi) SEQUENCE DESCRIPTION: SEQ ID NO:10:

GCAT                                                                    4

(2) INFORMATION FOR SEQ ID NO:11:

(i) SEQUENCE CHARACTERISTICS:
          (A) LENGTH: 4 base pairs
          (B) TYPE: nucleic acid
          (C) STRANDEDNESS: single
          (D) TOPOLOGY: linear (ii) MOLECULE TYPE: nucleic acid (xi) SEQUENCE DESCRIPTION: SEQ ID NO:11:

GCAT                                                                    4

(2) INFORMATION FOR SEQ ID NO:12:

(i) SEQUENCE CHARACTERISTICS:
          (A) LENGTH: 4 base pairs
          (B) TYPE: nucleic acid
          (C) STRANDEDNESS: single
          (D) TOPOLOGY: linear (ii) MOLECULE TYPE: nucleic acid (xi) SEQUENCE DESCRIPTION: SEQ ID NO:12:

GCAT                                                                    4

(2) INFORMATION FOR SEQ ID NO:13:

(i) SEQUENCE CHARACTERISTICS:
          (A) LENGTH: 4 base pairs
          (B) TYPE: nucleic acid
          (C) STRANDEDNESS: single
          (D) TOPOLOGY: linear (ii) MOLECULE TYPE: nucleic acid (xi) SEQUENCE DESCRIPTION: SEQ ID NO:13:

GCAT                                                                    4

(2) INFORMATION FOR SEQ ID NO:14:

(i) SEQUENCE CHARACTERISTICS:
          (A) LENGTH: 4 base pairs
          (B) TYPE: nucleic acid
          (C) STRANDEDNESS: single
          (D) TOPOLOGY: linear (ii) MOLECULE TYPE: nucleic acid (xi) SEQUENCE DESCRIPTION: SEQ ID NO:14:

GCAT                                                                    4

(2) INFORMATION FOR SEQ ID NO:15:

(i) SEQUENCE CHARACTERISTICS:
          (A) LENGTH: 4 base pairs
          (B) TYPE: nucleic acid
          (C) STRANDEDNESS: single
          (D) TOPOLOGY: linear (ii) MOLECULE TYPE: nucleic acid (xi) SEQUENCE DESCRIPTION: SEQ ID NO:15:

GCAT                                                                    4
```

(2) INFORMATION FOR SEQ ID NO:16:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:16:

GCAT                                                            4

(2) INFORMATION FOR SEQ ID NO:17:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:17:

GCAT                                                            4

(2) INFORMATION FOR SEQ ID NO:18:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:18:

GCAT                                                            4

(2) INFORMATION FOR SEQ ID NO:19:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:19:

GCAT                                                            4

(2) INFORMATION FOR SEQ ID NO:20:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:20:

GCAT                                                            4

(2) INFORMATION FOR SEQ ID NO:21:

```
    (i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:21:

GCAT                                                                    4

(2) INFORMATION FOR SEQ ID NO:22:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:22:

GCAT                                                                    4

(2) INFORMATION FOR SEQ ID NO:23:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:23:

GCAT                                                                    4

(2) INFORMATION FOR SEQ ID NO:24:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:24:

GCAT                                                                    4

(2) INFORMATION FOR SEQ ID NO:25:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:25:

GCAT                                                                    4

(2) INFORMATION FOR SEQ ID NO:26:

(i) SEQUENCE CHARACTERISTICS:
        (A) LENGTH: 4 base pairs
        (B) TYPE: nucleic acid
        (C) STRANDEDNESS: single
```

```
        (D) TOPOLOGY: linear (ii) MOLECULE TYPE: nucleic acid (xi) SEQUENCE DESCRIPTION: SEQ ID NO:26:

GCAT                                                                    4

(2) INFORMATION FOR SEQ ID NO:27:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:27:

GCAT                                                                    4

(2) INFORMATION FOR SEQ ID NO:28:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:28:

GCAT                                                                    4

(2) INFORMATION FOR SEQ ID NO:29:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:29:

GCAT                                                                    4

(2) INFORMATION FOR SEQ ID NO:30:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:30:

GCAT                                                                    4

(2) INFORMATION FOR SEQ ID NO:31:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid
```

(xi) SEQUENCE DESCRIPTION: SEQ ID NO:31:

GCAT                                                                            4

(2) INFORMATION FOR SEQ ID NO:32:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:32:

GCAT                                                                            4

(2) INFORMATION FOR SEQ ID NO:33:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:33:

GTAGATCACT                                                                     10

(2) INFORMATION FOR SEQ ID NO:34:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:34:

GTAGATCACT                                                                     10

(2) INFORMATION FOR SEQ ID NO:35:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:35:

TTTTTTTTTT                                                                     10

(2) INFORMATION FOR SEQ ID NO:36:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:36:

TTTTTTTTTT                                                                     10

(2) INFORMATION FOR SEQ ID NO:37:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:37:

TTTTTTTTTT                                      10

(2) INFORMATION FOR SEQ ID NO:38:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:38:

TTTTTTTTTT                                      10

(2) INFORMATION FOR SEQ ID NO:39:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:39:

TTCTT                                          5

(2) INFORMATION FOR SEQ ID NO:40:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:40:

GCAT                                            4

(2) INFORMATION FOR SEQ ID NO:41:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:41:

GCAT                                            4

(2) INFORMATION FOR SEQ ID NO:42:

(i) SEQUENCE CHARACTERISTICS:

```
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:42:

GCAT                                                            4

(2) INFORMATION FOR SEQ ID NO:43:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:43:

GCAT                                                            4

(2) INFORMATION FOR SEQ ID NO:44:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:44:

GCAT                                                            4

(2) INFORMATION FOR SEQ ID NO:45:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:45:

GCAT                                                            4

(2) INFORMATION FOR SEQ ID NO:46:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:46:

GCAT                                                            4

(2) INFORMATION FOR SEQ ID NO:47:

(i) SEQUENCE CHARACTERISTICS:
        (A) LENGTH: 4 base pairs
        (B) TYPE: nucleic acid
        (C) STRANDEDNESS: single
        (D) TOPOLOGY: linear
```

(ii) MOLECULE TYPE: nucleic acid (xi) SEQUENCE DESCRIPTION: SEQ ID NO:47:

GCAT 4

(2) INFORMATION FOR SEQ ID NO:48:

(i) SEQUENCE CHARACTERISTICS:
      (A) LENGTH: 4 base pairs
      (B) TYPE: nucleic acid
      (C) STRANDEDNESS: single
      (D) TOPOLOGY: linear (ii) MOLECULE TYPE: nucleic acid (xi) SEQUENCE DESCRIPTION: SEQ ID NO:48:

GCAT 4

(2) INFORMATION FOR SEQ ID NO:49:

(i) SEQUENCE CHARACTERISTICS:
      (A) LENGTH: 4 base pairs
      (B) TYPE: nucleic acid
      (C) STRANDEDNESS: single
      (D) TOPOLOGY: linear (ii) MOLECULE TYPE: nucleic acid (xi) SEQUENCE DESCRIPTION: SEQ ID NO:49:

GCAT 4

(2) INFORMATION FOR SEQ ID NO:50:

(i) SEQUENCE CHARACTERISTICS:
      (A) LENGTH: 4 base pairs
      (B) TYPE: nucleic acid
      (C) STRANDEDNESS: single
      (D) TOPOLOGY: linear (ii) MOLECULE TYPE: nucleic acid (xi) SEQUENCE DESCRIPTION: SEQ ID NO:50:

GCAT 4

(2) INFORMATION FOR SEQ ID NO:51:

(i) SEQUENCE CHARACTERISTICS:
      (A) LENGTH: 4 base pairs
      (B) TYPE: nucleic acid
      (C) STRANDEDNESS: single
      (D) TOPOLOGY: linear (ii) MOLECULE TYPE: nucleic acid (xi) SEQUENCE DESCRIPTION: SEQ ID NO:51:

GCAT 4

(2) INFORMATION FOR SEQ ID NO:52:

(i) SEQUENCE CHARACTERISTICS:
      (A) LENGTH: 4 base pairs
      (B) TYPE: nucleic acid
      (C) STRANDEDNESS: single
      (D) TOPOLOGY: linear (ii) MOLECULE TYPE: nucleic acid (xi) SEQUENCE DESCRIPTION: SEQ ID NO:52:

```
GCAT                                                          4
```

(2) INFORMATION FOR SEQ ID NO:53:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:53:

```
GCAT                                                          4
```

(2) INFORMATION FOR SEQ ID NO:54:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:54:

```
GCAT                                                          4
```

(2) INFORMATION FOR SEQ ID NO:55:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:55:

```
GCAT                                                          4
```

(2) INFORMATION FOR SEQ ID NO:56:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:56:

```
GCAT                                                          4
```

(2) INFORMATION FOR SEQ ID NO:57:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:57:

```
GCAT                                                          4
```

(2) INFORMATION FOR SEQ ID NO:58:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:58:

GCAT                                                                                                                       4

(2) INFORMATION FOR SEQ ID NO:59:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:59:

GCAT                                                                                                                       4

(2) INFORMATION FOR SEQ ID NO:60:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:60:

GCATGCAT                                                                                                    8

(2) INFORMATION FOR SEQ ID NO:61:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:61:

GCATGCAT                                                                                                    8

(2) INFORMATION FOR SEQ ID NO:62:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:62:

GCATGCAT                                                                                                    8

(2) INFORMATION FOR SEQ ID NO:63:

(i) SEQUENCE CHARACTERISTICS:
        (A) LENGTH: 20 base pairs

```
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:63:

CTGTCTCCAT CCTCTTCACT                                              20

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:64:

CTGTCTCCAT CCTCTTCACT                                              20

(2) INFORMATION FOR SEQ ID NO:65:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:65:

CCAAGCCUCA GA                                                      12

(2) INFORMATION FOR SEQ ID NO:66:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:66:

CCAGGCUCAG AT                                                      12

(2) INFORMATION FOR SEQ ID NO:67:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:67:

CTGTCTCCAT CCTCTTCACT                                              20

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: nucleic acid (xi) SEQUENCE DESCRIPTION: SEQ ID NO:68:

CTGTCTCCAT CCTCTTCACT                                                  20

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:69:

CTGTCTCCAT CCTCTTCACT                                                  20

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:70:

CTGTCTCCAT CCTCTTCACT                                                  20

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:71:

CTGTCTCCAT CCTCTTCACT                                                  20

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:72:

CTGTCTCCAT CCTCTTCACT                                                  20

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:73:

```
CTGTCTCCAT CCTCTTCACT                                               20

(2) INFORMATION FOR SEQ ID NO:74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:74:

CTGTCTCCAT CCTCTTCACT                                               20

(2) INFORMATION FOR SEQ ID NO:75:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:75:

CTGTCTCCAT CCTCTTCACT                                               20

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:76:

CTGTCTCCAT CCTCTTCACT                                               20

(2) INFORMATION FOR SEQ ID NO:77:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:77:

CTGTCTCCAT CCTCTTCACT                                               20

(2) INFORMATION FOR SEQ ID NO:78:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:78:

CTGTCTCCAT CCTCTTCACT                                               20

(2) INFORMATION FOR SEQ ID NO:79:
```

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: nucleic acid (xi) SEQUENCE DESCRIPTION: SEQ ID NO:79:

CTGTCTCCAT CCTCTTCACT                                            20

(2) INFORMATION FOR SEQ ID NO:80:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:80:

CTGTCTCCAT CCTCTTCACT                                            20

(2) INFORMATION FOR SEQ ID NO:81:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:81:

CTGTCTCCAT CCTCTTCACT                                            20

(2) INFORMATION FOR SEQ ID NO:82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:82:

CTGTCTCCAT CCTCTTCACT                                            20

(2) INFORMATION FOR SEQ ID NO:83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:83:

CTGTCTCCAT CCTCTTCACT                                            20

(2) INFORMATION FOR SEQ ID NO:84:

(i) SEQUENCE CHARACTERISTICS:
        (A) LENGTH: 20 base pairs
        (B) TYPE: nucleic acid

```
            (C) STRANDEDNESS: single
            (D) TOPOLOGY: linear (ii) MOLECULE TYPE: nucleic acid (xi) SEQUENCE DESCRIPTION: SEQ ID NO:84:

CTGTCTCCAT CCTCTTCACT                                              20

(2) INFORMATION FOR SEQ ID NO:85:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: nucleic acid (xi) SEQUENCE DESCRIPTION: SEQ ID NO:85:

CTGTCTCCAT CCTCTTCACT                                              20

(2) INFORMATION FOR SEQ ID NO:86:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: nucleic acid (xi) SEQUENCE DESCRIPTION: SEQ ID NO:86:

CTGTCTCCAT CCTCTTCACT                                              20

(2) INFORMATION FOR SEQ ID NO:87:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: nucleic acid (xi) SEQUENCE DESCRIPTION: SEQ ID NO:87:

CTGTCTCCAT CCTCTTCACT                                              20

(2) INFORMATION FOR SEQ ID NO:88:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: nucleic acid (xi) SEQUENCE DESCRIPTION: SEQ ID NO:88:

CTGTCTCCAT CCTCTTCACT                                              20

(2) INFORMATION FOR SEQ ID NO:89:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: nucleic acid
```

(xi) SEQUENCE DESCRIPTION: SEQ ID NO:89:

CTGTCTCCAT CCTCTTCACT                                       20

(2) INFORMATION FOR SEQ ID NO:90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:90:

CTGTCTCCAT CCTCTTCACT                                       20

(2) INFORMATION FOR SEQ ID NO:91:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:91:

CTGTCTCCAT CCTCTTCACT                                       20

(2) INFORMATION FOR SEQ ID NO:92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:92:

CTGTCTCCAT CCTCTTCACT                                       20

(2) INFORMATION FOR SEQ ID NO:93:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:93:

CTGTCTCCAT CCTCTTCACT                                       20

(2) INFORMATION FOR SEQ ID NO:94:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:94:

CTGTCTCCAT CCTCTTCACT                                       20

(2) INFORMATION FOR SEQ ID NO:95:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:95:

CTGTCTCCAT CCTCTTCACT                                    20

(2) INFORMATION FOR SEQ ID NO:96:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:96:

CTGTCTCCAT CCTCTTCACT                                    20

(2) INFORMATION FOR SEQ ID NO:97:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:97:

GCAT                                                                          4

(2) INFORMATION FOR SEQ ID NO:98:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:98:

TTCTTCTTTT                                                 10

(2) INFORMATION FOR SEQ ID NO:99:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:99:

TTCTTCTTTT                                                 10

(2) INFORMATION FOR SEQ ID NO:100:

```
    (i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:100:

TTCTTCTTTT                                                                10

(2) INFORMATION FOR SEQ ID NO:101:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:101:

TTCTTCTTTT                                                                10

(2) INFORMATION FOR SEQ ID NO:102:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:102:

TTCTTCTTTT                                                                10

(2) INFORMATION FOR SEQ ID NO:103:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:103:

TTCTTCTTTT                                                                10

(2) INFORMATION FOR SEQ ID NO:104:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:104:

TTCTTCTTTT                                                                10

(2) INFORMATION FOR SEQ ID NO:105:

(i) SEQUENCE CHARACTERISTICS:
        (A) LENGTH: 10 base pairs
        (B) TYPE: nucleic acid
        (C) STRANDEDNESS: single
```

(D) TOPOLOGY: linear (ii) MOLECULE TYPE: nucleic acid (xi) SEQUENCE DESCRIPTION: SEQ ID NO:105:

TTTTTTTTTT                                                              10

(2) INFORMATION FOR SEQ ID NO:106:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: nucleic acid (xi) SEQUENCE DESCRIPTION: SEQ ID NO:106:

TTTTTTTTTT                                                              10

(2) INFORMATION FOR SEQ ID NO:107:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: nucleic acid (xi) SEQUENCE DESCRIPTION: SEQ ID NO:107:

TTTTTTTTTT                                                              10

(2) INFORMATION FOR SEQ ID NO:108:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: nucleic acid (xi) SEQUENCE DESCRIPTION: SEQ ID NO:108:

TTCTTCTTTT                                                              10

(2) INFORMATION FOR SEQ ID NO:109:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: nucleic acid (xi) SEQUENCE DESCRIPTION: SEQ ID NO:109:

CTCTTTTTTT                                                              10

(2) INFORMATION FOR SEQ ID NO:110:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: nucleic acid (xi) SEQUENCE DESCRIPTION: SEQ ID NO:110:

TTTCTTCTCA CTTCTT                                                    16

(2) INFORMATION FOR SEQ ID NO:111:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:111:

TTTCTTCTCA CTTCTT                                                    16

(2) INFORMATION FOR SEQ ID NO:112:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:112:

TTTTTTTTTT                                                           10

(2) INFORMATION FOR SEQ ID NO:113:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:113:

TTTTTTTTTT                                                           10

(2) INFORMATION FOR SEQ ID NO:114:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:114:

TTTTTTTTTT                                                           10

(2) INFORMATION FOR SEQ ID NO:115:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:115:

TTCTTCTTTT                                                           10

(2) INFORMATION FOR SEQ ID NO:116:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:116:

TTCTTCTTTT                                                            10

(2) INFORMATION FOR SEQ ID NO:117:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:117:

TTTTT                                                                 5

(2) INFORMATION FOR SEQ ID NO:118:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:118:

TTCTTCTTTT                                                            10

(2) INFORMATION FOR SEQ ID NO:119:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:119:

TTCTTCTTTT                                                            10

(2) INFORMATION FOR SEQ ID NO:120:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:120:

TTCTTCTTTT                                                           10

(2) INFORMATION FOR SEQ ID NO:121:

(i) SEQUENCE CHARACTERISTICS:

```
        (A) LENGTH: 15 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:121:

TTTTGGTGTG GGTGC                                                    15

(2) INFORMATION FOR SEQ ID NO:122:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:122:

TTCTTCTTTT                                                          10

(2) INFORMATION FOR SEQ ID NO:123:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:123:

TTTCTTCTCA CTTCTT                                                   16

(2) INFORMATION FOR SEQ ID NO:124:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:124:

GTAGATCACT                                                          10

(2) INFORMATION FOR SEQ ID NO:125:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:125:

AGTCATCTAC                                                          10

(2) INFORMATION FOR SEQ ID NO:126:

(i) SEQUENCE CHARACTERISTICS:
        (A) LENGTH: 10 base pairs
        (B) TYPE: nucleic acid
        (C) STRANDEDNESS: single
        (D) TOPOLOGY: linear
```

(ii) MOLECULE TYPE: nucleic acid (xi) SEQUENCE DESCRIPTION: SEQ ID NO:126:

TTCTTCTTTT                                                           10

(2) INFORMATION FOR SEQ ID NO:127:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:127:

CTCTTTTTTT                                                           10

(2) INFORMATION FOR SEQ ID NO:128:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:128:

CTCTTTTTTT                                                           10

(2) INFORMATION FOR SEQ ID NO:129:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:129:

TTCTTCTTTT                                                           10

(2) INFORMATION FOR SEQ ID NO:130:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:130:

CTCTTTTTTT                                                           10

(2) INFORMATION FOR SEQ ID NO:131:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:131:

TTTTT                                                          5

(2) INFORMATION FOR SEQ ID NO:132:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:132:

TGTACGTCAC AACTA                                               15

(2) INFORMATION FOR SEQ ID NO:133:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:133:

TGTACGTCAC AACTA                                               15

(2) INFORMATION FOR SEQ ID NO:134:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:134:

TTCTTCTTTT                                                     10

(2) INFORMATION FOR SEQ ID NO:135:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:135:

TTCTTCTTTT                                                     10

(2) INFORMATION FOR SEQ ID NO:136:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:136:

TTCTTCTTTT                                                     10

(2) INFORMATION FOR SEQ ID NO:137:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:137:

TTCTTCTTTT                                                            10

(2) INFORMATION FOR SEQ ID NO:138:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:138:

TTCTTCTTTT                                                            10

(2) INFORMATION FOR SEQ ID NO:139:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:139:

TTCTTCTTTT                                                            10

(2) INFORMATION FOR SEQ ID NO:140:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:140:

CTCTTTTTTT                                                            10

(2) INFORMATION FOR SEQ ID NO:141:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:141:

GCATGCAT                                                               8

(2) INFORMATION FOR SEQ ID NO:142:

(i) SEQUENCE CHARACTERISTICS:
        (A) LENGTH: 8 base pairs

```
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:142:

GCATGCAT                                                              8

(2) INFORMATION FOR SEQ ID NO:143:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:143:

GCATGCAT                                                              8

(2) INFORMATION FOR SEQ ID NO:144:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:144:

GCATGCAT                                                              8

(2) INFORMATION FOR SEQ ID NO:145:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:145:

GCATGCAT                                                              8

(2) INFORMATION FOR SEQ ID NO:146:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:146:

GCATGCAT                                                              8

(2) INFORMATION FOR SEQ ID NO:147:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

```
        (ii) MOLECULE TYPE: nucleic acid (xi) SEQUENCE DESCRIPTION: SEQ ID NO:147:

TGGGAGCCAT AGCGAGCC                                                 18

(2) INFORMATION FOR SEQ ID NO:148:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: nucleic acid (xi) SEQUENCE DESCRIPTION: SEQ ID NO:148:

TCTGAGTAGC AGAGGAGCTA AG                                            22
```